US012593765B2

(12) United States Patent
Que et al.

(10) Patent No.: US 12,593,765 B2
(45) Date of Patent: Apr. 7, 2026

(54) SIMULTANEOUS GENE EDITING AND HAPLOID INDUCTION

(71) Applicant: Syngenta Participations AG, Basel (CH)

(72) Inventors: Qiudeng Que, Research Triangle Park, NC (US); Timothy Kelliher, Research Triangle Park, NC (US)

(73) Assignee: SYNGENTA CROP PROTECTION AG, Basel (CH)

( * ) Notice: Subject to any disclaimer, the term of this patent is extended or adjusted under 35 U.S.C. 154(b) by 382 days.

(21) Appl. No.: 16/465,644

(22) PCT Filed: Dec. 4, 2017

(86) PCT No.: PCT/US2017/064512
§ 371 (c)(1),
(2) Date: May 31, 2019

(87) PCT Pub. No.: WO2018/102816
PCT Pub. Date: Jun. 7, 2018

(65) Prior Publication Data
US 2019/0376075 A1      Dec. 12, 2019

Related U.S. Application Data

(60) Provisional application No. 62/429,260, filed on Dec. 2, 2016.

(51) Int. Cl.

| | |
|---|---|
| *A01H 1/08* | (2006.01) |
| *C07K 14/415* | (2006.01) |
| *C12N 9/22* | (2006.01) |
| *C12N 15/11* | (2006.01) |
| *C12N 15/82* | (2006.01) |
| *C12Q 1/68* | (2018.01) |
| *C12Q 1/6895* | (2018.01) |

(52) U.S. Cl.
CPC ............ *A01H 1/08* (2013.01); *C07K 14/415* (2013.01); *C12N 9/22* (2013.01); *C12N 15/11* (2013.01); *C12N 15/8213* (2013.01); *C12N 15/8216* (2013.01); *C12N 15/8238* (2013.01); *C12N 15/8241* (2013.01); *C12N 15/8287* (2013.01); *C12Q 1/6895* (2013.01); *C12N 2310/20* (2017.05); *C12N 2800/80* (2013.01); *C12Y 301/01032* (2013.01)

(58) Field of Classification Search
CPC .................................................... C12N 15/82
See application file for complete search history.

(56) References Cited

U.S. PATENT DOCUMENTS

| | | | | |
|---|---|---|---|---|
| 7,135,615 | B2 | 11/2006 | Kato | |
| 8,269,061 | B2 | 9/2012 | Williams | |
| 9,677,082 | B2 | 6/2017 | Chintamanani et al. | |
| 10,285,348 | B2 * | 5/2019 | Kelliher | C07K 14/415 |
| 10,448,588 | B2 * | 10/2019 | Chintamanani | C12N 9/18 |
| 10,487,336 | B2 | 11/2019 | Michelmore | |
| 10,519,456 | B2 * | 12/2019 | Que | C12N 15/8213 |
| 11,193,131 | B2 | 12/2021 | Campbell et al. | |
| 2003/0005479 | A1 | 1/2003 | Kato | |
| 2008/0216198 | A1 | 9/2008 | Zhao et al. | |
| 2009/0297495 | A1 | 12/2009 | Kerovuo et al. | |
| 2013/0198893 | A1 | 8/2013 | Zhao et al. | |
| 2015/0067922 | A1 | 3/2015 | Yang et al. | |
| 2015/0307889 | A1 | 10/2015 | Petolino et al. | |
| 2017/0240912 | A1 | 8/2017 | Chintamanani et al. | |
| 2018/0245090 | A1 * | 8/2018 | Campbell | C12N 9/22 |
| 2019/0136250 | A1 | 5/2019 | Que et al. | |

FOREIGN PATENT DOCUMENTS

| | | |
|---|---|---|
| CN | 102487816 | 6/2012 |
| CN | 104737757 | 7/2015 |
| EP | 2574234 | 4/2013 |
| EP | 1602717 B1 | 12/2014 |
| EP | 3037540 | 6/2016 |
| RU | 2349642 C2 | 3/2009 |
| RU | 2551313 C2 | 5/2015 |
| RU | 2560599 C2 | 8/2015 |
| RU | 2636344 C2 | 11/2017 |
| RU | 2658437 C2 | 6/2018 |
| WO | 0185969 | 11/2001 |
| WO | 2009089928 A1 | 7/2009 |

(Continued)

OTHER PUBLICATIONS

Puchta The Plant Journal 87:5-15, 2015 (Year: 2015).*
Ryu et al (2005 Biochimica et Biophysica Acta (BBA)—Molecular and Cell Biology of Lipids 1736:144-151 (Year: 2005).*
Puchta, Holger, Using CRISPR/Cas in three dimensions: towards syntheticplant genomes, transcriptomes and epigenomes, The Plant Journal 87: pp. 5-15, 2015.
Mao, Yanfei, et al., Development of germ-line-specific CRISPR-case 9 systems to improve the production of heritable gene modifications in *Arabidopsis*, Plant Biotechnolgy Journal, 14.2, 2016, pp. 519-532.
Luca Comai, Genome Elimination: Translating Basic Research into a Future Tool for Plant Breeding, PLOS Biol. 12(6):1-4 (2014).

(Continued)

*Primary Examiner* — Brent T Page
(74) *Attorney, Agent, or Firm* — Kilpatrick Townsend & Stockton LLP

(57) ABSTRACT

The presently disclosed subject matter relates to using a haploid inducing line (whether existing or created) and transforming the haploid line so that it encodes cellular machinery capable of editing genes. The transformed haploid inducing line is used as a parent in a cross between two plants. During pollination, the parental gametes fuse to form an embryo; and the gene editing machinery is also delivered to the embryo at this time. During embryonic development, one set of parental chromosomes are lost, and the gene editing machinery operates on the remaining set of chromosomes. Thus, at least one haploid progeny with edited genes is produced from the cross.

10 Claims, 24 Drawing Sheets
Specification includes a Sequence Listing.

(56) References Cited

FOREIGN PATENT DOCUMENTS

| | | | |
|---|---|---|---|
| WO | 2011044132 A1 | 4/2011 |
| WO | 2011072246 A2 | 6/2011 |
| WO | 2014110274 A2 | 7/2014 |
| WO | 2015171894 A1 | 11/2015 |
| WO | 2016/075255 A1 | 5/2016 |
| WO | 2016106121 A1 | 6/2016 |
| WO | 2016149352 | 9/2016 |
| WO | 2016177887 A1 | 11/2016 |
| WO | 2017/004375 A1 | 5/2017 |
| WO | 2017/087682 A1 | 5/2017 |
| WO | 2018/015956 A1 | 1/2018 |
| WO | 2018/015957 A1 | 1/2018 |
| WO | 2018/052919 A1 | 3/2018 |
| WO | 2021252619 A1 | 12/2021 |

OTHER PUBLICATIONS

Kelliher, et al., One-step genome editing of elite crop germplasm during haploid induction, Nature Biotech. 37:287-292 (2019).

Gu, et al., Study on the culture of cut plants in wheat haploid embryo induction by a wheat × maize cross, Front. Agric. China 2(4):391-395 (2008).

Rines, H.W., Oat Haploids from Wide Hybridization, Doubled Haploid Production in Crop Plants, pp. 155-159, 2003.

Gurushidze, et al., True-Breeding Targeted Gene Knock-Out in Barley Using Designer TALE-Nuclease in Haploid Cells, PLOS One 9(3):1-9 (2014).

Chen, et al., Wide Hybridization of Hordeum )× Zea mays, Genome 34(4):603-605 (1991).

Laurie, et al. The production of haploid wheat plants from wheat x maize crosses, Theor. Appl. Genet. 76:393-397 (1988).

Li et al., Multiplex and homologous recombination-mediated genome editing in Arabidopsis and Nicotiana benthamiana using guide RNA and Cas9, Nat. Biotechnol., 31(8):688-691, Aug. 2013.

Makarova et al., "Evolution and classification of the CRISPR-Cas systems," Nat. Rev. Microbial., 9(6):467-477, Jun. 2011.

Prigge and Melchinger, "Production of haploids and doubled haploids in maize," Methods Mol Biol., 877: 161-72, 2012.

Voytas, "Plant genome engineering with sequence-specific nucleases," Annu. Rev. Plant Biol., 64:327-350, May 2013.

Shukla et al., "Precise genome modification in the crop species Zea mays using zinc-finger nucleases," Nature, 459(7245):437-441, May 2009.

Liang et al., "Targeted mutagenesis in Zea mays using TALENs and the CRISPR/Cas system," J. Genet. Genomics., 41(2):63-68, Feb. 2014.

Huang, Shihshieh, et al., "Cloning of an Arabidopsis Patatin-Like Gene, STURDY, by Activation T-DNA Tagging," Plant Physiology, vol. 125, issue 2, 2001, pp. 573-584.

Rietz, eta l., "Roles of Arabidopsis Patatin-Related Phospholipases a in Root Development are Related to Auzin Responses and Phosphate Deficiency.", Molecular Plant 3.3, 2010, pp. 524-538.

Scherer, et al., "Patatin-Related Phospholipase A: Nomenclature, Subfamilies and Functions in Plants," Trends in Plant Science 15:12, 2010, pp. 693-700.

Hahn, Florian, et al. "An Efficient Visual Screen for C RISPR/Cas9 Activity in Arabidopsis thaliana" Frontiers in Plant Science 8, 2017, 39.

Ravi, et al., "Haploid Plants Produced by Centromere-Mediated Genome Elimination." Nature 464. 7228. 2015, 615.

Muiruri et al., "Expressed Centromere Specific Histone 3 (CENH) Variants in Cultivated Triploid and Wield Diploid Bananas (Musa spp.)" Frontiers in plant science 8, 2017, 1034.

International Search Report mailed in application No. PCT/US2017/064512 mailed on Mar. 7, 2018.

Gilles et al., "Loss of Pollen-Specific Phospholipase Not Like Dad triggers gynogenesis in Maize", The EMBO Journal, pp. 1-11, 2017.

Lui et al., "A 4bp Insertion at ZmPLA1 Encoding a Putative Phospholipase A Generates Haploid Induction in Maize", Accepted Manuscript, Molecular Plant, pp. 1-8, Jan. 31, 2017.

Nair et al., "Dissection of a Major QTL qhirl Conferring Maternal Haploid Induction Ability in Maize", Theoretical Applied Genetics, Dec. 8, 2016.

Kelliher et al., "MATRILINEAL, A Sperm-Specific Phospholipase, Triggers Maize Hapliod Induction", Feb. 2, 2017, Nature, vol. 542, pp. 105-122.

Begheyn, Rachel et al: "Haploid and Doubled Haploid Techniques in Perennial Ryegrass (Lolium perenne L.) to Advance Research and Breeding", in: Agronomy. vol. 6. No. 4. Nov. 28, 2016, p. 60. XP055695804. DOI: 10.3390/agronomy6040060.

Shen, Yaou et al.: "Haploid Strategies for Functional Validation of Plant Genes" in: Trends in Biotechnology, vol. 33 No. 10. Oct. 1, 2015, pp. 611-620. XP029279685. ISSN: 0167-7799. DOI: 10.1016/J.TIBTECH.2015.07.005.

Xing, Hui-Li et al: "A CRISPR/Cas9 toolkit for multiplex genome editing in plants" in: BMC Plant Biology. Biomed Central. London, vol. 14. No. 1. Nov. 29, 2014, p. 327. XP021205803. ISSN: 1471-2229. DOI: 10.1186/S12870-014-0327-Y.

Bakos et al., Regeneration of Haploid Plants After Distant Pollination of Wheat Via Zygote Rescue, Acta Biologica Cracoviensia, vol. 47, No. 1, 2005, pp. 167-171.

Brazauskas et al., Improved Approaches in Wheat × Maize Crossing for Wheat Doubled Haploid Production, Biologija, vol. 51, No. 4, Oct. 1, 2005, pp. 15-18.

Chen et al., A Comparison of Hordeum Bulbosum-Mediated Haploid Production Efficiency in Barley Using In Vitro Floret and Tiller Culture, Theoretical and Applied Genetics, vol. 77, No. 5, May 1989, pp. 701-704.

Devaux, The Hordeum bulbosum (L.) Method, Doubled Haploid Production in Crop Plants, 2003, pp. 15-19.

Haberer et al., Structure and Architecture of the Maize Genome, Plant Physiology, vol. 139, No. 4, Dec. 9, 2005, pp. 1612-1624.

Inagaki, Doubled Haploid Production in Wheat Through Wide Hybridization, In Doubled Haploid Production in Crop Plants: A Manual, 2003, pp. 53-58.

Kasha et al., High Frequency Haploid Production in Barley (Hordeum vulgare L.), Nature, vol. 225, No. 5235, Feb. 28, 1970, pp. 874-876.

Knox et al., Dicamba and Growth Condition Effects on Doubled Haploid Production in Durum Wheat Crossed with Maize, Plant Breeding, vol. 119, No. 4, Aug. 2000, pp. 289-298.

Laurie et al., Chromosome Behavior in Wheat X Maize, Wheat X Sorghum and Barley X Maize Crosses, In Kew Chromosome Conference Proceedings III, 1988, pp. 167-177.

Riera-Lizarazu et al., Cytological and Molecular Characterization of Oat X Maize Partial Hybrids, Theoretical and Applied Genetics, vol. 93, No. 1, Jul. 1996, pp. 123-135.

Singh et al., Rice Phospholipase A Superfamily: Organization, Phylogenetic and Expression Analysis During Abiotic Stresses and Development, PLoS One, vol. 7, No. 2, Feb. 2012, pp. 1-15.

Wan et al., Efficient Production of Doubled Haploid Plants Through Colchicine Treatment of Anther-Derived Maize Callus, Theoretical and Applied Genetics, vol. 77, No. 6, Jun. 1989, pp. 889-892.

Wedzony et al., Production of Doubled Haploids in Triticale (×Triticosecale Wittm.) by Means of Crosses with Maize (Zea mays L.) Using Picloram and Dicamba, Plant Breeding, vol. 117, No. 3, Jul. 1998, pp. 211-215.

Wedzony, Protocol for Doubled Haploid Production in Hexaploidy Triticale (x Triticosecale Wittm.) by Crosses with Maize, Doubled Haploid Production in Crop Plants, 2003, pp. 135-140.

Zhang et al., The CRISPR/Cas9 System Produces Specific and Homozygous Targeted Gene Editing in Rice in One Generation, Plant Biotechnology Journal, vol. 12, No. 6, Aug. 2014, pp. 797-807.

* cited by examiner 23396
15722 bp prSoUbi4 (1797 bp)
RB (25 bp)
oCOLE1 (807 bp)
oVS1 (405 bp)
cRepA (1074 bp)
cSpecR (789 bp)
LB (25 bp)
tNOS (253 bp)
cPMI (1179 bp)
prZmUbi1 (1992 bp)
rsgRNAZmVLHP-01 (105 bp)
xZmVLHP-01 (20 bp)
prOsU3 (375 bp)
tNOS (253 bp)
cCas9 (4170 bp)

SEQUENCE LISTING

<160> NUMBER OF SEQ ID NOS: 119

<210> SEQ ID NO 1
<211> LENGTH: 15722
<212> TYPE: DNA
<213> ORGANISM: Artificial Sequence
<220> FEATURE:
<223> OTHER INFORMATION: vector 23396

```
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
<223> OTHER INFORMATION: xZmVLHP
<220> FEATURE:
<221> NAME/KEY: misc_feature
<222> LOCATION: (6927)..(7032)
<223> OTHER INFORMATION: rsgRNAZmVLHP-01
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01

<400> SEQUENCE: 1
attcctgtgg ttggcatgca catacaaatg gacgaacgga taaacctttt cacgcccttt        60
taaatatccg attattctaa taaacgctct tttctcttag gtttacccgc caatatatcc       120
tgtcaaacac tgatagttta aactgaaggc gggaaacgac aatctgatca tgagcggaga       180
attaagggag tcacgttatg accccggccg atgacgcggg acaagccgtt ttacgtttgg       240
aactgacaga accgcaacgc tgcaggaatt ggccgcagcg gccatttaaa caaagcttgg       300
taccattatg tggtctaggt aggttctata tataagaaaa cttgaaatgt tctaaaaaaa       360
```

-continued

```
aattcaagcc catgcatgat tgaagcaaac ggtatagcaa cggtgttaac ctgatctagt   420
gatctcttgc aatccttaac ggccacctac cgcaggtagc aaacggcgtc cccctcctcg   480
atatctccgc ggcgacctct ggctttttcc gcggaattgc gcggtgggga cggattccac   540
gagaccgcga cgcaaccgcc tctcgccgct gggccccaca ccgctcggtg ccgtagcctc   600
acgggactct ttctccctcc tccccgtta taaattggct tcatcccctc cttgcctcat   660
ccatccaaat cccagtcccc aatcccatcc cttcgtagga gaaattcatc gaagctaagc   720
gaatcctcgc gatcctctca aggtactgcg agttttcgat cccctctcg acccctcgta   780 tgtttgtgtt tgtcgtagcg tttgattagg tatgctttcc ctgtttgtgt cgtcgtagc   840 gtttgattag gtatgctttc cctgttcgtg ttcatcgtag tgtttgatta ggtcgtgtga   900
ggcgatggcc tgctcgcgtc cttcgatctg tagtcgattt gcgggtcgtg gtgtagatct   960
gcgggctgtg atgaagttat ttggtgtgat ctgctcgcct gattctgcgg gttggctcga  1020
gtagatatga tggttggacc ggttggttcg tttaccgcgc tagggttggg ctgggatgat  1080
gttgcatgcg ccgttgcgcg tgatcccgca gcaggacttg cgtttgattg ccagatctcg  1140
ttacgattat gtgatttggt ttggactttt tagatctgta gcttctgctt atgtgccaga  1200
tgcgcctact gctcatatgc ctgatgataa tcataaatgg ctgtggaact aactagttga  1260
ttgcggagtc atgtatcagc tacaggtgta gggactagct acaggtgtag ggacttgcgt  1320
ctaattgttt ggtcctttac tcatgttgca attatgcaat ttagtttaga ttgtttgttc  1380
cactcatcta ggctgtaaaa gggacactgc ttagattgct gtttaatctt tttagtagat  1440
tatattatat tggtaactta ttacccctat tacatgccat acgtgacttc tgctcatgcc  1500
tgatgataat catagatcac tgtggaatta attagttgat tgttgaatca tgtttcatgt  1560
acataccacg gcacaattgc ttagttcctt aacaaatgca aattttactg atccatgtat  1620
gatttgcgtg gttctctaat gtgaaatact atagctactt gttagtaaga atcaggttcg  1680
tatgcttaat gctgtatgtg ccttctgctc atgcctgatg ataatcatat atcactggaa  1740
ttaattagtt gatcgtttaa tcatatatca agtacatacc atgccacaat ttttagtcac  1800
ttaacccatg cagattgaac tggtccctgc atgttttgct aaattgttct attctgatta  1860
gaccatatat catgtatttt tttttggtaa tggttctctt attttaaatg ctatatagtt  1920
ctggtacttg ttagaaagat ctgcttcata gtttagttgc ctatccctcg aattaggatg  1980
ctgagcagct gatcctatag ctttgtttca tgtatcaatt cttttgtgtt caacagtcag  2040
tttttgttag attcattgta acttatggtc gcttactctt ctggtcctca atgcttgcag  2100
gatcgcggcc gctcatatgg acaagaagta cagcatcggc ctggacatcg gcaccaacag  2160
cgtgggctgg gccgtgatca ccgacgagta caaggtgccg agcaagaagt tcaaggtgct  2220
gggcaacacc gacaggcaca gcatcaagaa gaacctgatc ggcgccctgc tgttcgacag  2280
cggcgagacc gccgaggcca ccaggctgaa gaggaccgcc aggaggaggt acaccaggag  2340
gaagaacagg atctgctacc tgcaggagat cttcagcaac gagatggcca aggtggacga  2400
cagcttcttc cacaggctgg aggagagctt cctggtggag gaggacaaga agcacgagag  2460
gcacccgatc ttcggcaaca tcgtggacga ggtggcctac cacgagaagt acccgaccat  2520
ctaccacctg aggaagaagc tggtggacag caccgacaag gccgacctga ggctgatcta  2580
cctggccctg gcccacatga tcaagttcag gggccacttc ctgatcgagg cgacctgaa  2640 cccggacaac agcgacgtgg acaagctgtt catccagctg gtgcagacct acaaccagct  2700
gttcgaggag aacccgatca cgccagcgg cgtggacgcc aaggccatcc tgagcgccag  2760
```

-continued

```
gctgagcaag agcaggaggc tggagaacct gatcgcccag ctgccgggcg agaagaagaa      2820
cggcctgttc ggcaacctga tcgccctgag cctgggcctg accccgaact tcaagagcaa      2880
cttcgacctg gccgaggacg ccaagctgca gctgagcaag gacacctacg acgacgacct      2940
ggacaacctg ctggcccaga tcggcgacca gtacgccgac ctgttcctgg ccgccaagaa      3000
cctgagcgac gccatcctgc tgagcgacat cctgagggtg aacaccgaga tcaccaaggc      3060
cccgctgagc gccagcatga tcaagaggta cgacgagcac caccaggacc tgaccctgct      3120
gaaggccctg gtgaggcagc agctgccgga gaagtacaag gagatcttct cgaccagag       3180 caagaacggc tacgccggct acatcgacgg cggcgccagc caggaggagt ctacaagtt        3240 catcaagccg atcctggaga agatggacgg caccgaggag ctgctggtga agctgaacag      3300
ggaggacctg ctgaggaagc agaggacctt cgacaacggc agcatcccgc accagatcca      3360
cctgggcgag ctgcacgcca tcctgaggag gcaggaggac ttctacccgt tcctgaagga      3420
caacagggag aagatcgaga agatcctgac cttccgcatc ccgtactacg tgggcccgct      3480
ggccaggggc aacagcaggt tcgcctggat gaccaggaag agcgaggaga ccatcacccc      3540
gtggaacttc gaggaggtgg tggacaaggg cgccagcgcc cagagcttca tcgagaggat      3600
gaccaacttc gacaagaacc tgccgaacga gaaggtgctg ccgaagcaca gcctgctgta      3660
cgagtacttc accgtgtaca acgagctgac caaggtgaag tacgtgaccg agggcatgag      3720
gaagccggcc ttcctgagcg gcgagcagaa gaaggccatc gtggacctgc tgttcaagac      3780
caacaggaag gtgaccgtga agcagctgaa ggaggactac ttcaagaaga tcgagtgctt      3840
cgacagcgtg gagatcagcg gcgtggagga caggttcaac gccagcctgg gcacctacca      3900
cgacctgctg aagatcatca aggacaagga cttcctggac aacgaggaga cgaggacat       3960 cctggaggac atcgtgctga ccctgaccct gttcgaggac agggagatga tcgaggagag      4020
gctgaagacc tacgcccacc tgttcgacga caaggtgatg aagcagctga gaggaggag       4080 gtacaccggc tggggcaggc tgagcaggaa gctgatcaac ggcatcaggg acaagcagag      4140
cggcaagacc atcctggact tcctgaagag cgacggcttc gccaacagga acttcatgca      4200
gctgatccac gacgacagcc tgaccttcaa ggaggacatc cagaaggccc aggtgagcgg      4260
ccagggcgac agcctgcacg agcacatcgc caacctggcc ggcagcccgg ccatcaagaa      4320
gggcatcctg cagaccgtga aggtggtgga cgagctggtg aaggtgatgg gcaggcacaa      4380
gccggagaac atcgtgatcg agatggccag ggagaaccag accacccaga agggccagaa      4440
gaacagcagg gagaggatga agaggatcga ggagggcatc aaggagctgg gcagccagat      4500
cctgaaggag caccccggtgg agaacaccca gctgcagaac gagaagctgt acctgtacta      4560
cctgcagaac ggcagggaca tgtacgtgga ccaggagctg gacatcaaca ggctgagcga      4620
ctacgacgtg gaccacatcg tgccgcagag cttcctgaag gacgacagca tcgacaacaa      4680
ggtgctgacc aggagcgaca gaacagggg caagagcgac aacgtgccga gcgaggaggt      4740
ggtgaagaag atgaaaaact actggaggca gctgctgaac gccaagctga tcacccagag      4800
gaagttcgac aacctgacca aggccgagag gggcggcctg agcgagctgg acaaggccgg      4860
cttcattaaa aggcagctgg tggagaccag gcagatcacc aagcacgtgg cccagatcct      4920
ggacagcagg atgaacacca gtacgacga gaacgacaag ctgatcaggg aggtgaaggt       4980 gatcacccctg aagagcaagc tggtgagcga cttcaggaag gacttccagt tctacaaggt      5040
gagggagatc aataaattacc accacgccca cgacgcctac ctgaacgccg tggtgggcac      5100
```

-continued

```
cgccctgatt aaaaagtacc cgaagctgga gagcgagttc gtgtacggcg actacaaggt    5160
gtacgacgtg aggaagatga tcgccaagag cgagcaggag atcggcaagg ccaccgccaa    5220
gtacttcttc tacagcaaca tcatgaactt cttcaagacc gagatcaccc tggccaacgg    5280
cgagatcagg aagaggccgc tgatcgagac caacggcgag accggcgaga tcgtgtggga    5340
caagggcagg gacttcgcca ccgtgaggaa ggtgctgtcc atgccgcagg tgaacatcgt    5400
gaagaagacc gaggtgcaga ccggcggctt cagcaaggag agcatcctgc cgaagaggaa    5460
cagcgacaag ctgatcgcca ggaagaagga ctgggacccg aagaagtacg cgcggcttcga   5520 cagcccgacc gtggcctaca gcgtgctggt ggtggccaag gtggagaagg caagagcaa    5580 gaagctgaag agcgtgaagg agctggtggg catcaccatc atggagagga gcagcttcga    5640
gaagaaccca gtggacttcc tggaggccaa gggctacaag gaggtgaaga aggacctgat    5700
cattaaactg ccgaagtaca gcctgttcga gctggagaac ggcaggaaga ggatgctggc    5760
cagcgccggc gagctgcaga agggcaacga gctggccctg ccgagcaagt acgtgaactt    5820
cctgtacctg gccagccact acgagaagct gaagggcagc ccggaggaca acgagcagaa    5880
gcagctgttc gtggagcagc acaagcacta cctggacgag atcatcgagc agatcagcga    5940
gttcagcaag agggtgatcc tggccgacgc caacctggac aaggtgctga gcgcctacaa    6000
caagcacagg gacaagccga tcagggagca ggccgagaac atcatccacc tgttcaccct    6060
gaccaacctg ggcgccccgg ccgccttcaa gtacttcgac accaccatcg acaggaagag    6120
gtacaccagc accaaggagg tgctggacgc caccctgatc caccagagca tcaccggcct    6180
gtacgagacc aggatcgacc tgagccagct gggcggcgac agcagcccgc cgaagaagaa    6240
gaggaaggtg agctggaagg acgccagcgg ctggagcagg atgtgaagct tgatcgttca    6300
aacatttggc aataaagttt cttaagattg aatcctgttg ccggtcttgc gatgattatc    6360
atataatttc tgttgaatta cgttaagcat gtaataatta acatgtaatg catgacgtta    6420
tttatgagat gggttttttat gattagagtc ccgcaattat acatttaata cgcgatagaa    6480
aacaaaatat agcgcgcaaa ctaggataaa ttatcgcgcg cggtgtcatc tatgttacta    6540
gatcttcgaa gggatcttta aacatacgaa cagatcactt aaagttcttc tgaagcaact    6600
taaagttatc aggcatgcat ggatcttgga ggaatcagat gtgcagtcag ggaccatagc    6660
acaggacagg cgtcttctac tggtgctacc agcaaatgct ggaagccggg aacactgggt    6720
acgttggaaa ccacgtgatg tggagtaaga taaactgtag gagaaaagca tttcgtagtg    6780
ggccatgaag cctttcagga catgtattgc agtatgggcc ggcccattac gcaattggac    6840
gacaacaaag actagtatta gtaccacctc ggctatccac atagatcaaa gctggtttaa    6900
aagagttgtg cagatgatcc gtggcagcag gaggcgtcga gcagcggttt tagagctaga    6960
aatagcaagt taaaataagg ctagtccgtt atcaacttga aaaagtggca ccgagtcggt    7020
gctttttttt tcggaccgcg cctgcagtgc agcgtgaccc ggtcgtgccc ctctctagag    7080
ataatgagca ttgcatgtct aagttataaa aaattaccac atattttttt tgtcacactt    7140
gtttgaagtg cagtttatct atctttatac atatatttaa actttactct acgaataata    7200
taatctatag tactacaata atatcagtgt tttagagaat catataaatg aacagttaga    7260
catggtctaa aggacaattg agtattttga caacaggact ctacagtttt atctttttag    7320
tgtgcatgtg ttctcctttt tttttgcaaa tagcttcacc tatataatac ttcatccatt    7380
ttattagtac atccatttag ggtttagggt taatggtttt tatagactaa ttttttttagt    7440 acatctattt tattctattt tagcctctaa attaagaaaa ctaaaactct attttagttt    7500
```

-continued

```
ttttatttaa taatttagat ataaaataga ataaaataaa gtgactaaaa attaaacaaa    7560 tacccttttaa gaaattaaaa aaactaagga aacatttttc ttgtttcgag tagataatgc    7620
cagcctgtta aacgccgtcg acgagtctaa cggacaccaa ccagcgaacc agcagcgtcg    7680
cgtcgggcca agcgaagcag acggcacggc atctctgtcg ctgcctctgg acccctctcg    7740
agagttccgc tccaccgttg gacttgctcc gctgtcggca tccagaaatt gcgtggcgga    7800
gcggcagacg tgagccggca cggcaggcgg cctcctcctc ctctcacggc accggcagct    7860
acgggggatt cctttcccac cgctccttcg ctttcccttc ctcgcccgcc gtaataaata    7920
gacaccccct ccacaccctc tttccccaac ctcgtgttgt tcggagcgca cacacacaca    7980
accagatctc ccccaaatcc acccgtcggc acctccgctt caaggtacgc cgctcgtcct    8040
cccccccccc cctctctacc ttctctagat cggcgttccg gtccatggtt agggcccggt    8100
agttctactt ctgttcatgt ttgtgttaga tccgtgtttg tgttagatcc gtgctgctag    8160
cgttcgtaca cggatgcgac ctgtacgtca gacacgttct gattgctaac ttgccagtgt    8220
ttctctttgg ggaatcctgg gatggctcta gccgttccgc agacgggatc gatttcatga    8280
ttttttttgt ttcgttgcat agggtttggt ttgcccttt t cctttatttc aatatatgcc    8340
gtgcacttgt ttgtcgggtc atctttcat  gcttttttt t gtcttggttg tgatgatgtg    8400
gtctggttgg gcggtcgttc tagatcggag tagaattctg tttcaaacta cctggtggat    8460
ttattaattt tggatctgta tgtgtgtgcc atacatattc atagttacga attgaagatg    8520
atggatggaa atatcgatct aggataggta tacatgttga tgcgggtttt actgatgcat    8580
atacagagat gcttttttgtt cgcttggttg tgatgatgtg gtgtggttgg gcggtcgttc    8640
attcgttcta gatcggagta gaatactgtt tcaaactacc tggtgtattt attaattttg    8700
gaactgtatg tgtgtgtcat acatcttcat agttacgagt ttaagatgga tggaaatatc    8760
gatctaggat aggtatacat gttgatgtgg gttttactga tgcatataca tgatggcata    8820
tgcagcatct attcatatgc tctaaccttg agtacctatc tattataata aacaagtatg    8880
ttttataatt attttgatct tgatatactt ggatgatggc atatgcagca gctatatgtg    8940
gattttttta gccctgcctt catacgctat ttatttgctt ggtactgttt cttttgtcga    9000
tgctcaccct gttgtttggt gttacttctg cagggatccg gcagcagcca tgcagaagct    9060
gatcaacagc gtgcagaact acgcctgggg cagcaagacc gccctgaccg agctgtacgg    9120
catggagaac cccagcagcc agcccatggc cgagctgtgg atgggcgccc accccaagag    9180
cagcagccgc gtgcagaacg ccgccggcga catcgtgagc ctgcgcgacg tgatcgagag    9240
cgacaagagc accctgctgg gcgaggccgt ggccaagcgc ttcggcgagc tgcccttcct    9300
gttcaaggtg ctgtgcgccg cccagcccct gagcatccag gtgcacccca caagcacaa     9360 cagcgagatc ggcttcgcca aggagaacgc cgccggcatc cccatggacg ccgccgagcg    9420
caactacaag gaccccaacc acaagcccga gctggtgttc gccctgaccc ccttcctggc    9480
catgaacgcc ttccgcgagt tcagcgagat cgtgagcctg ctgcagcccg tggccggcgc    9540 ccacccgcc atcgcccact tcctgcagca gcccgacgcc gagcgcctga gcgagctgtt     9600
cgccagcctg ctgaacatgc agggcgagga aaagagccgc gccctggcca tcctgaagag    9660
cgccctggac agccagcagg gcgagccctg gcagaccatc gcctgatca  gcgagttcta     9720 ccccgaggac agcggcctgt tcagccccct gctgctgaac gtggtgaagc tgaacccgg      9780 cgaggccatg ttcctgttcg ccgagacccc ccacgcctac ctgcagggcg tggccctgga    9840
```

-continued

```
ggtgatggcc aacagcgaca acgtgctgcg cgccggcctg acccccaagt acatcgacat      9900
ccccgagctg gtggccaacg tgaagttcga ggccaagccc gccaaccagc tgctgaccca      9960
gcccgtgaag cagggcgccg agctggactt ccccatcccc gtggacgact tcgccttcag     10020
cctgcacgac ctgagcgaca aggagaccac catcagccag cagagcgccg ccatcctgtt     10080
ctgcgtggag ggcgacgcca ccctgtggaa gggcagccag cagctgcagc tgaagcccgg     10140
cgagagcgcc ttcatcgccg ccaacgagag ccccgtgacc gtgaagggcc acggccgcct     10200
ggcccgcgtg tacaacaagc tgtgatagga gctcgatccg tcgacctgca gatcgttcaa     10260
acatttggca ataaagtttc ttaagattga atcctgttgc cggtcttgcg atgattatca     10320
tataatttct gttgaattac gttaagcatg taataattaa catgtaatgc atgacgttat     10380
ttatgagatg ggtttttatg attagagtcc cgcaattata catttaatac gcgatagaaa     10440
acaaaatata gcgcgcaaac taggataaat tatcgcgcgc ggtgtcatct atgttactag     10500
atcggcgcgc cgcaattgaa gtttgggcgg ccagcatggc cgtatccgca atgtgttatt     10560
aagttgtcta agcgtcaatt tgtttacacc acaatatatc ctgccaccag ccagccaaca     10620
gctccccgac cggcagctcg gcacaaaatc accactcgat acaggcagcc catcagaatt     10680
aattctcatg tttgacagct tatcatcgac tgcacggtgc accaatgctt ctggcgtcag     10740
gcagccatcg gaagctgtgg tatggctgtg caggtcgtaa atcactgcat aattcgtgtc     10800
gctcaaggcg cactcccgtt ctggataatg ttttttgcgc cgacatcata acggttctgg     10860
caaatattct gaaatgagct gttgacaatt aatcatccgg ctcgtataat gtgtggaatt     10920
gtgagcggat aacaatttca cacaggaaac agaccatgag ggaagcgttg atcgccgaag     10980
tatcgactca actatcagag gtagttggcg tcatcgagcg ccatctcgaa ccgacgttgc     11040
tggccgtaca tttgtacggc tccgcagtgg atggcggcct gaagccacac agtgatattg     11100
atttgctggt tacggtgacc gtaaggcttg atgaaacaac gcggcgagct ttgatcaacg     11160
accttttgga aacttcggct tcccctggag agagcgagat tctccgcgct gtagaagtca     11220
ccattgttgt gcacgacgac atcattccgt ggcgttatcc agctaagcgc gaactgcaat     11280
ttggagaatg gcagcgcaat gacattcttg caggtatctt cgagccagcc acgatcgaca     11340
ttgatctggc tatcttgctg acaaaagcaa gagaacatag cgttgccttg gtaggtccag     11400
cggcggagga actctttgat ccggttcctg aacaggatct atttgaggcg ctaaatgaaa     11460
ccttaacgct atggaactcg ccgcccgact gggctggcga tgagcgaaat gtagtgctta     11520
cgttgtcccg catttggtac agcgcagtaa ccggcaaaat cgcgccgaag gatgtcgctg     11580
ccgactgggc aatggagcgc ctgccggccc agtatcagcc cgtcatactt gaagctaggc     11640
aggcttatct tggacaagaa gatcgcttgg cctcgcgcgc agatcagttg gaagaatttg     11700
ttcactacgt gaaaggcgag atcaccaaag tagtcggcaa ataaagctct agtggatctc     11760
cgtacccggg gatctggctc gcggcggacg cacgacgccg gggcgagacc ataggcgatc     11820
tcctaaatca atagtagctg taacctcgaa gcgtttcact tgtaacaacg attgagaatt     11880
tttgtcataa aattgaaata cttggttcgc attttttgtca tccgcggtca gccgcaattc     11940
tgacgaactg cccatttagc tggagatgat tgtacatcct tcacgtgaaa atttctcaag     12000
cgctgtgaac aagggttcag attttagatt gaaaggtgag ccgttgaaac acgttcttct     12060
tgtcgatgac gacgtcgcta tgcggcatct tattattgaa taccttacga tccacgcctt     12120
caaagtgacc gcggtagccg acagcaccca gttcacaaga gtactctctt ccgcgacggt     12180
cgatgtcgtg gttgttgatc tagatttagg tcgtgaagat gggctcgagc taggagcaag     12240
```

```
tgattttatc gctaagccgt tcagtatcag agagtttcta gcacgcattc gggttgcctt   12300
gcgcgtgcgc cccaacgttg tccgctccaa agaccgacgg tctttttgtt ttactgactg   12360
gacacttaat ctcaggcaac gtcgcttgat gtccgaagct ggcggtgagg tgaaacttac   12420
ggcaggtgag ttcaatcttc tcctcgcgtt tttagagaaa ccccgcgacg ttctatcgcg   12480
cgagcaactt ctcattgcca gtcgagtacg cgacgaggag gtttatgaca ggagtataga   12540
tgttctcatt ttgaggctgc gccgcaaact tgaggcagat ccgtcaagcc ctcaactgat   12600
aaaaacagca agaggtgccg gttatttctt tgacgcggac gtgcaggttt cgcacggggg   12660
gacgatggca gcctgagcca attcccagat ccccgaggaa tcggcgtgag cggtcgcaaa   12720
ccatccggcc cggtacaaat cggcgcggcg ctgggtgatg acctggtgga gaagttgaag   12780
gccgcgcagg ccgcccagcg gcaacgcatc gaggcagaag cacgccccgg tgaatcgtgg   12840
caagcggccg ctgatcgaat ccgcaaagaa tcccggcaac cgccggcagc cggtgcgccg   12900
tcgattagga agccgcccaa gggcgacgag caaccagatt ttttcgttcc gatgctctat   12960
gacgtgggca cccgcgatag tcgcagcatc atggacgtgg ccgtttteccg tctgtcgaag   13020 cgtgaccgac gagctggcga ggtgatccgc tacgagcttc cagacgggca cgtagaggtt   13080
tccgcagggc cggccggcat ggccagtgtg tgggattacg acctggtact gatggcggtt   13140
tcccatctaa ccgaatccat gaaccgatac cgggaaggga agggagacaa gcccggccgc   13200
gtgttccgtc cacacgttgc ggacgtactc aagttctgcc ggcgagccga tggcggaaag   13260
cagaaagacg acctggtaga aacctgcatt cggttaaaca ccacgcacgt tgccatgcag   13320
cgtacgaaga aggccaagaa cggccgcctg gtgacggtat ccgagggtga agccttgatt   13380
agccgctaca agatcgtaaa gagcgaaacc gggcggccgg agtacatcga gatcgagcta   13440
gctgattgga tgtaccgcga gatcacagaa ggcaagaacc cggacgtgct gacggttcac   13500
cccgattact ttttgatcga tcccggcatc ggccgttttc tctaccgcct ggcacgccgc   13560
gccgcaggca aggcagaagc cagatggttg ttcaagacga tctacgaacg cagtggcagc   13620
gccggagagt tcaagaagtt ctgtttcacc gtgcgcaagc tgatcgggtc aaatgacctg   13680
ccggagtacg atttgaagga ggaggcgggg caggctggcc cgatcctagt catgcgctac   13740
cgcaacctga tcgagggcga agcatccgcc ggttcctaat gtacggagca gatgctaggg   13800
caaattgccc tagcagggga aaaaggtcga aaaggtctct ttcctgtgga tagcacgtac   13860
attgggaacc caaagccgta cattgggaac cggaacccgt acattgggaa cccaaagccg   13920
tacattggga accggtcaca catgtaagtg actgatataa aagagaaaaa aggcgatttt   13980
tccgcctaaa actctttaaa acttattaaa actcttaaaa cccgcctggc ctgtgcataa   14040
ctgtctggca agcgcacagc cgaagagctg caaaaagcgc ctacccttcg gtcgctgcgc   14100
tccctacgcc ccgccgcttc gcgtcggcct atcgcggccg ctggccgctc aaaaatggct   14160
ggcctacggc caggcaatct accagggcgc ggacaagccg cgccgtcgcc actcgaccgc   14220
cggcgctgag gtctgcctcg tgaagaaggt gttgctgact cataccaggc ctgaatcgcc   14280
ccatcatcca gccagaaagt gagggagcca cggttgatga gagctttgtt gtaggtggac   14340
cagttggtga ttttgaactt ttgctttgcc acggaacggt ctgcgttgtc gggaagatgc   14400
gtgatctgat ccttcaactc agcaaaagtt cgatttattc aacaaagccg ccgtcccgtc   14460
aagtcagcgt aatgctctgc cagtgttaca accaattaac caattctgat tagaaaaact   14520
catcgagcat caaatgaaac tgcaatttat tcatatcagg attatcaata ccatattttt   14580
```

-continued

```
gaaaaagccg tttctgtaat gaaggagaaa actcaccgag gcagttccat aggatggcaa   14640
gatcctggta tcggtctgcg attccgactc gtccaacatc aatacaacct attaatttcc   14700
cctcgtcaaa aataaggtta tcaagtgaga atcaccatg agtgacgact gaatccggtg    14760
agaatggcaa aagctctgca ttaatgaatc ggccaacgcg cggggagagg cggtttgcgt   14820
attgggcgct cttccgcttc ctcgctcact gactcgctgc gctcggtcgt tcggctgcgg   14880
cgagcggtat cagctcactc aaaggcggta atacggttat ccacagaatc aggggataac   14940
gcaggaaaga acatgtgagc aaaaggccag caaaaggcca ggaaccgtaa aaaggccgcg   15000
ttgctggcgt ttttccatag gctccgcccc cctgacgagc atcacaaaaa tcgacgctca   15060
agtcagaggt ggcgaaaccc gacaggacta taaagatacc aggcgtttcc ccctggaagc   15120
tccctcgtgc gctctcctgt tccgaccctg ccgcttaccg gatacctgtc cgcctttctc   15180
ccttcgggaa gcgtggcgct ttctcatagc tcacgctgta ggtatctcag ttcggtgtag   15240
gtcgttcgct ccaagctggg ctgtgtgcac gaaccccccg ttcagcccga ccgctgcgcc   15300
ttatccggta actatcgtct tgagtccaac ccggtaagac acgacttatc gccactggca   15360
gcagccactg gtaacaggat tagcagagcg aggtatgtag gcggtgctac agagttcttg   15420
aagtggtggc ctaactacgg ctacactaga agaacagtat ttggtatctg cgctctgctg   15480
aagccagtta ccttcggaaa aagagttggt agctcttgat ccggcaaaca aaccaccgct   15540
ggtagcggtg gtttttttgt ttgcaagcag cagattacgc gcagaaaaaa aggatctcaa   15600
gaagatcctt tgatctttc tacggggtct gacgctcagt ggaacgaaaa ctcacgttaa   15660
gggattttgg tcatgagatt atcaaaaagg atcttcacct agatcctttt gatccggaat   15720
ta                                                                  15722
```

```
<210> SEQ ID NO 2
<211> LENGTH: 20
<212> TYPE: DNA
<213> ORGANISM: Artificial Sequence
<220> FEATURE:
<223> OTHER INFORMATION: gRNA sequence for editing VLHP1

<400> SEQUENCE: 2
gcaggaggcg tcgagcagcg                                                       20

<210> SEQ ID NO 3
<211> LENGTH: 15722
<212> TYPE: DNA
<213> ORGANISM: Artificial Sequence
<220> FEATURE:
<223> OTHER INFORMATION: vector 23399
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
```

-continued

```
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
<223> OTHER INFORMATION: xZmGW2
<220> FEATURE:
<221> NAME/KEY: misc_feature
<222> LOCATION: (6927)..(7031)
<223> OTHER INFORMATION: rsgRNAZmGW2-02
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01
<220> FEATURE:
<221> NAME/KEY: misc_feature
<222> LOCATION: (13822)..(14226)
<223> OTHER INFORMATION: oVS1-02
<220> FEATURE:
<221> NAME/KEY: misc_feature
<222> LOCATION: (14904)..(15710)
<223> OTHER INFORMATION: oCOLE-06

<400> SEQUENCE: 3
attcctgtgg ttggcatgca catacaaatg gacgaacgga taaacctttt cacgcccttt      60
taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg acccccgccg atgacgcggg acaagccgtt ttacgtttgg     240
aactgacaga accgcaacgc tgcaggaatt ggccgcagcg gccatttaaa caaagcttgg     300
taccattatg tggtctaggt aggttctata tataagaaaa cttgaaatgt tctaaaaaaa     360
aattcaagcc catgcatgat tgaagcaaac ggtatagcaa cggtgttaac ctgatctagt     420
gatctcttgc aatccttaac ggccacctac cgcaggtagc aaacggcgtc ccctcctcg      480 atatctccgc ggcgacctct ggcttttttcc gcggaattgc gcggtgggga cggattccac     540
gagaccgcga cgcaaccgcc tctcgccgct gggccccaca ccgctcggtg ccgtagcctc     600
acgggactct ttctccctcc tccccgtta taaattggct tcatccctc cttgcctcat      660 ccatccaaat cccagtcccc aatcccatcc cttcgtagga gaaattcatc gaagctaagc     720
```

-continued

```
gaatcctcgc gatcctctca aggtactgcg agttttcgat cccctctcg acccctcgta      780 tgtttgtgtt tgtcgtagcg tttgattagg tatgctttcc ctgtttgtgt tcgtcgtagc      840
gtttgattag gtatgctttc cctgttcgtg ttcatcgtag tgtttgatta ggtcgtgtga      900
ggcgatggcc tgctcgcgtc cttcgatctg tagtcgattt gcgggtcgtg gtgtagatct      960
gcgggctgtg atgaagttat ttggtgtgat ctgctcgcct gattctgcgg gttggctcga     1020
gtagatatga tggttggacc ggttggttcg tttaccgcgc tagggttggg ctgggatgat     1080
gttgcatgcg ccgttgcgcg tgatcccgca gcaggacttg cgtttgattg ccagatctcg     1140
ttacgattat gtgatttggt ttggactttt tagatctgta gcttctgctt atgtgccaga     1200
tgcgcctact gctcatatgc ctgatgataa tcataaatgg ctgtggaact aactagttga     1260
ttgcggagtc atgtatcagc tacaggtgta gggactagct acaggtgtag ggacttgcgt     1320
ctaattgttt ggtcctttac tcatgttgca attatgcaat ttagtttaga ttgtttgttc     1380
cactcatcta ggctgtaaaa gggacactgc ttagattgct gtttaatctt tttagtagat     1440
tatattatat tggtaactta ttacccctat tacatgccat acgtgacttc tgctcatgcc     1500
tgatgataat catagatcac gtgtggaatta attagttgat tgttgaatca tgtttcatgt     1560
acataccacg gcacaattgc ttagttcctt aacaaatgca aattttactg atccatgtat     1620
gatttgcgtg gttctctaat gtgaaatact atagctactt gttagtaaga atcaggttcg     1680
tatgcttaat gctgtatgtg ccttctgctc atgcctgatg ataatcatat atcactggaa     1740
ttaattagtt gatcgtttaa tcatatatca agtacatacc atgccacaat ttttagtcac     1800
ttaacccatg cagattgaac tggtccctgc atgtttgct aaattgttct attctgatta     1860
gaccatatat catgtatttt tttttggtaa tggttctctt attttaaatg ctatatagtt     1920
ctggtacttg ttagaaagat ctgcttcata gtttagttgc ctatccctcg aattaggatg     1980
ctgagcagct gatcctatag ctttgtttca tgtatcaatt cttttgtgtt caacagtcag     2040
tttttgttag attcattgta acttatggtc gcttactctt ctggtcctca atgcttgcag     2100
gatcgcggcc gctcatatgg acaagaagta cagcatcggc ctggacatcg gcaccaacag     2160
cgtgggctgg gccgtgatca ccgacgagta caaggtgccg agcaagaagt tcaaggtgct     2220
gggcaacacc gacaggcaca gcatcaagaa gaacctgatc ggcgccctgc tgttcgacag     2280
cggcgagacc gccgaggcca ccaggctgaa gaggaccgcc aggaggaggt acaccaggag     2340
gaagaacagg atctgctacc tgcaggagat cttcagcaac gagatggcca aggtggacga     2400
cagcttcttc cacaggctgg aggagagctt cctggtggag gaggacaaga agcacgagag     2460
gcacccgatc ttcggcaaca tcgtggacga ggtggcctac cacgagaagt acccgaccat     2520
ctaccacctg aggaagaagc tggtggacag caccgacaag gccgacctga ggctgatcta     2580
cctggccctg gcccacatga tcaagttcag gggccacttc ctgatcgagg cgacctgaa     2640 cccgacaac agcgacgtgg acaagctgtt catccagctg gtgcagacct acaaccagct     2700
gttcgaggag aacccgatca cgccagcgg cgtggacgcc aaggccatcc tgagcgccag     2760
gctgagcaag agcaggaggc tggagaacct gatcgcccag ctgccgggcg agaagaagaa     2820
cggcctgttc ggcaacctga tcgccctgag cctgggcctg acccgaact tcaagagcaa     2880 cttcgacctg gccgaggacg ccaagctgca gctgagcaag gacacctacg acgacgacct     2940
ggacaacctg ctggcccaga tcggcgacca gtacgcgac ctgttcctgg ccgccaagaa     3000
cctgagcgac gccatcctgc tgagcgacat cctgagggt aacaccgaga tcaccaaggc     3060
cccgctgagc gccagcatga tcaagaggta cgacgagcac caccaggacc tgaccctgct     3120
```

-continued

```
gaaggccctg gtgaggcagc agctgccgga gaagtacaag gagatcttct tcgaccagag    3180
caagaacggc tacgccggct acatcgacgg cggcgccagc caggaggagt tctacaagtt    3240
catcaagccg atcctggaga agatggacgg caccgaggag ctgctggtga agctgaacag    3300
ggaggacctg ctgaggaagc agaggacctt cgacaacggc agcatcccgc accagatcca    3360
cctgggcgag ctgcacgcca tcctgaggag gcaggaggac ttctacccgt tcctgaagga    3420
caacagggag aagatcgaga agatcctgac cttccgcatc ccgtactacg tgggcccgct    3480 ggccagggggc aacagcaggt tcgcctggat gaccaggaag agcgaggaga ccatcacccc    3540
gtggaacttc gaggaggtgg tggacaaggg cgccagcgcc cagagcttca tcgagaggat    3600
gaccaacttc gacaagaacc tgccgaacga gaaggtgctg ccgaagcaca gcctgctgta    3660
cgagtacttc accgtgtaca acagctgac caaggtgaag tacgtgaccg agggcatgag    3720
gaagccggcc ttcctgagcg gcgagcagaa gaaggccatc gtggacctgc tgttcaagac    3780
caacaggaag gtgaccgtga agcagctgaa ggaggactac ttcaagaaga tcgagtgctt    3840
cgacagcgtg gagatcagcg gcgtggagga caggttcaac gccagcctgg gcacctacca    3900
cgacctgctg aagatcatca aggacaagga cttcctggac aacgaggaga acgaggacat    3960
cctggaggac atcgtgctga ccctgacct gttcgaggac agggagatga tcgaggagag    4020
gctgaagacc tacgcccacc tgttcgacga caaggtgatg aagcagctga agaggaggag    4080
gtacaccggc tggggcaggc tgagcaggaa gctgatcaac ggcatcaggg acaagcagag    4140
cggcaagacc atcctggact tcctgaagag cgacggcttc gccaacagga acttcatgca    4200
gctgatccac gacgacagcc tgaccttcaa ggaggacatc cagaaggccc aggtgagcgg    4260
ccagggcgac agcctgcacg agcacatcgc caacctggcc ggcagcccgg ccatcaagaa    4320
gggcatcctg cagaccgtga aggtggtgga cgagctggtg aaggtgatgg gcaggcacaa    4380
gccggagaac atcgtgatcg agatggccag ggagaaccag accacccaga agggccagaa    4440
gaacagcagg gagaggatga agaggatcga ggagggcatc aaggagctgg gcagccagat    4500
cctgaaggag caccccggtg agaacacccca gctgcagaac gagaagctgt acctgtacta    4560
cctgcagaac ggcaggggaca tgtacgtgga ccaggagctg gacatcaaca ggctgagcga    4620
ctacgacgtg gaccacatcg tgccgcagag cttcctgaag gacgacagca tcgacaacaa    4680
ggtgctgacc aggagcgaca agaacagggg caagagcgac aacgtgccga gcgaggaggt    4740
ggtgaagaag atgaaaaact actggaggca gctgctgaac gccaagctga tcacccagag    4800
gaagttcgac aacctgacca aggccgagag gggcggcctg agcgagctgg acaaggccgg    4860
cttcattaaa aggcagctgg tggagaccag gcagatcacc aagcacgtgg cccagatcct    4920
ggacagcagg atgaacacca agtacgacga gaacgacaag ctgatcaggg aggtgaaggt    4980 gatcacccctg aagagcaagc tggtgagcga cttcaggaag gacttccagt tctacaaggt    5040
gagggagatc aataattacc accacgccca cgacgcctac ctgaacgccg tggtgggcac    5100
cgccctgatt aaaaagtacc cgaagctgga gagcgagttc gtgtacggcg actacaaggt    5160
gtacgacgtg aggaagatga tcgccaagag cgagcaggag atcggcaagg ccaccgccaa    5220
gtacttcttc tacagcaaca tcatgaactt cttcaagacc gagatcaccc tggccaacgg    5280
cgagatcagg aagaggccgc tgatcgagac caacggcgag accggcgaga tcgtgtggga    5340
caagggcagg gacttcgcca ccgtgaggaa ggtgctgtcc atgccgcagg tgaacatcgt    5400
gaagaagacc gaggtgcaga ccggcggctt cagcaaggag agcatcctgc cgaagaggaa    5460
```

```
cagcgacaag ctgatcgcca ggaagaagga ctgggacccg aagaagtacg gcggcttcga   5520
cagcccgacc gtggcctaca gcgtgctggt ggtggccaag gtggagaagg caagagcaa    5580 gaagctgaag agcgtgaagg agctggtggg catcaccatc atggagagga gcagcttcga   5640
gaagaaccca gtggacttcc tggaggccaa gggctacaag gaggtgaaga aggacctgat   5700
cattaaactg ccgaagtaca gcctgttcga gctggagaac ggcaggaaga ggatgctggc   5760
cagcgccggc gagctgcaga agggcaacga gctggccctg ccgagcaagt acgtgaactt   5820
cctgtacctg gccagccact acgagaagct gaagggcagc ccggaggaca acgagcagaa   5880
gcagctgttc gtggagcagc acaagcacta cctggacgag atcatcgagc agatcagcga   5940
gttcagcaag agggtgatcc tggccgacgc caacctggac aaggtgctga gcgcctacaa   6000
caagcacagg gacaagccga tcagggagca ggccgagaac atcatccacc tgttcaccct   6060
gaccaacctg ggcgccccgg ccgccttcaa gtacttcgac accaccatcg acaggaagag   6120
gtacaccagc accaaggagg tgctggacgc caccctgatc caccagagca tcaccggcct   6180
gtacgagacc aggatcgacc tgagccagct gggcggcgac agcagcccgc cgaagaagaa   6240
gaggaaggtg agctggaagg acgccagcgg ctggagcagg atgtgaagct tgatcgttca   6300
aacatttggc aataaagttt cttaagattg aatcctgttg ccggtcttgc gatgattatc   6360
atataatttc tgttgaatta cgttaagcat gtaataatta acatgtaatg catgacgtta   6420
tttatgagat gggtttttat gattagagtc ccgcaattat acatttaata cgcgatagaa   6480
aacaaaatat agcgcgcaaa ctaggataaa ttatcgcgcg cggtgtcatc tatgttacta   6540
gatcttcgaa gggatcttta aacatacgaa cagatcactt aaagttcttc tgaagcaact   6600
taaagttatc aggcatgcat ggatcttgga ggaatcagat gtgcagtcag ggaccatagc   6660
acaggacagg cgtcttctac tggtgctacc agcaaatgct ggaagccggg aacactgggt   6720
acgttggaaa ccacgtgatg tggagtaaga taaactgtag gagaaaagca tttcgtagtg   6780
ggccatgaag cctttcagga catgtattgc agtatgggcc ggcccattac gcaattggac   6840
gacaacaaag actagtatta gtaccacctc ggctatccac atagatcaaa gctggtttaa   6900
aagagttgtg cagatgatcc gtggcaaagc tcgcgccctg ctaccgtttt tagagctaga   6960
aatagcaagt taaaataagg ctagtccgtt atcaacttga aaaagtggca ccgagtcggt   7020 gcttttttt tcggaccgcg cctgcagtgc agcgtgaccc ggtcgtgccc ctctctagag   7080
ataatgagca ttgcatgtct aagttataaa aaattaccac atatttttt tgtcacactt   7140 gtttgaagtg cagtttatct atctttatac atatatttaa actttactct acgaataata   7200
taatctatag tactacaata atatcagtgt tttagagaat catataaatg aacagttaga   7260
catggtctaa aggacaattg agtattttga caacaggact ctacagtttt atcttttag    7320 tgtgcatgtg ttctcctttt tttttgcaaa tagcttcacc tatataatac ttcatccatt   7380
ttattagtac atccatttag ggtttagggt taatggtttt tatagactaa ttttttagt    7440 acatctattt tattctattt tagcctctaa attaagaaaa ctaaaactct attttagttt   7500
ttttatttaa taatttagat ataaaataga ataaaataaa gtgactaaaa attaaacaaa   7560 tacccttaa gaaattaaaa aaactaagga aacatttttc ttgtttcgag tagataatgc    7620
cagcctgtta aacgccgtcg acgagtctaa cggacaccaa ccagcgaacc agcagcgtcg   7680
cgtcgggcca agcgaagcag acggcacggc atctctgtcg ctgcctctgg accctctcg    7740 agagttccgc tccaccgttg gacttgctcc gctgtcggca tccagaaatt gcgtggcgga   7800
gcggcagacg tgagccggca cggcaggcgg cctcctcctc ctctcacggc accggcagct   7860
```

-continued

```
acgggggatt cctttcccac cgctccttcg ctttcccttc ctcgcccgcc gtaataaata      7920
gacaccccct ccacaccctc tttccccaac ctcgtgttgt tcggagcgca cacacacaca      7980
accagatctc ccccaaatcc acccgtcggc acctccgctt caaggtacgc cgctcgtcct      8040 ccccccccc cctctctacc ttctctagat cggcgttccg gtccatggtt agggcccggt      8100
agttctactt ctgttcatgt ttgtgttaga tccgtgtttg tgttagatcc gtgctgctag      8160
cgttcgtaca cggatgcgac ctgtacgtca gacacgttct gattgctaac ttgccagtgt      8220
ttctctttgg ggaatcctgg gatggctcta gccgttccgc agacgggatc gatttcatga      8280 tttttttgt ttcgttgcat agggtttggt ttgccctttt cctttatttc aatatatgcc      8340
gtgcacttgt ttgtcgggtc atctttcat gcttttttttt gtcttggttg tgatgatgtg      8400
gtctggttgg gcggtcgttc tagatcggag tagaattctg tttcaaacta cctggtggat      8460
ttattaattt tggatctgta tgtgtgtgcc atacatattc atagttacga attgaagatg      8520
atggatggaa atatcgatct aggataggta tacatgttga tgcgggtttt actgatgcat      8580
atacagagat gctttttgtt cgcttggttg tgatgatgtg gtgtggttgg gcggtcgttc      8640
attcgttcta gatcggagta gaatactgtt tcaaactacc tggtgtattt attaatttttg     8700 gaactgtatg tgtgtgtcat acatcttcat agttacgagt ttaagatgga tggaaatatc      8760
gatctaggat aggtatacat gttgatgtgg gttttactga tgcatataca tgatggcata      8820
tgcagcatct attcatatgc tctaaccttg agtacctatc tattataata aacaagtatg      8880
ttttataatt attttgatct tgatatactt ggatgatggc atatgcagca gctatatgtg      8940 gatttttttta gccctgcctt catacgctat ttatttgctt ggtactgttt cttttgtcga      9000
tgctcaccct gttgtttggt gttacttctg cagggatccg gcagcagcca tgcagaagct      9060
gatcaacagc gtgcagaact acgcctgggg cagcaagacc gccctgaccg agctgtacgg      9120
catggagaac cccagcagcc agcccatggc cgagctgtgg atgggcgccc accccaagag      9180
cagcagccgc gtgcagaacg ccgccggcga catcgtgagc ctgcgcgacg tgatcgagag      9240
cgacaagagc accctgctgg gcgaggccgt ggccaagcgc ttcggcgagc tgcccttcct      9300
gttcaaggtg ctgtgcgccg cccagcccct gagcatccag gtgcacccca acaagcacaa      9360
cagcgagatc ggcttcgcca aggagaacgc cgccggcatc cccatggacg ccgccgagcg      9420
caactacaag gaccccaacc acaagcccga gctggtgttc gccctgaccc ccttcctggc      9480
catgaacgcc ttccgcgagt tcagcgagat cgtgagcctg ctgcagcccg tggccggcgc      9540
ccacccccgc atcgcccact tcctgcagca gcccgacgcc gagcgcctga gcgagctgtt      9600
cgccagcctg ctgaacatgc agggcgagga gaagagccgc gccctggcca tcctgaagag      9660
cgccctggac agccagcagg gcgagccctg gcagaccatc cgcctgatca gcgagttcta      9720
ccccgaggac agcggcctgt tcagccccct gctgctgaac gtggtgaagc tgaaccccgg      9780
cgaggccatg ttcctgttcg ccgagacccc ccacgcctac ctgcagggcg tggccctgga      9840
ggtgatggcc aacagcgaca acgtgctgcg cgccggcctg accccccaagt acatcgacat      9900 ccccgagctg gtggccaacg tgaagttcga ggccaagccc gccaaccagc tgctgacccca      9960 gcccgtgaag cagggcgccg agctggactt ccccatcccc gtggacgact cgccttcag      10020 cctgcacgac ctgagcgaca aggagaccac catcagccag cagagcgccg ccatcctgtt      10080
ctgcgtggag ggcgacgcca ccctgtggaa gggcagccag cagctgcagc tgaagcccgg      10140
cgagagcgcc ttcatcgccg ccaacgagag ccccgtgacc gtgaagggcc acggccgcct      10200
```

-continued

```
ggcccgcgtg tacaacaagc tgtgatagga gctcgatccg tcgacctgca gatcgttcaa    10260
acatttggca ataaagtttc ttaagattga atcctgttgc cggtcttgcg atgattatca    10320
tataatttct gttgaattac gttaagcatg taataattaa catgtaatgc atgacgttat    10380
ttatgagatg ggttttttatg attagagtcc cgcaattata catttaatac gcgatagaaa    10440
acaaaatata gcgcgcaaac taggataaat tatcgcgcgc ggtgtcatct atgttactag    10500
atcggcgcgc cgcaattgaa gtttgggcgg ccagcatggc cgtatccgca atgtgttatt    10560
aagttgtcta agcgtcaatt tgtttacacc acaatatatc ctgccaccag ccagccaaca    10620 gctcccgac cggcagctcg gcacaaaatc accactcgat acaggcagcc catcagaatt    10680
aattctcatg tttgacagct tatcatcgac tgcacggtgc accaatgctt ctggcgtcag    10740
gcagccatcg gaagctgtgg tatggctgtg caggtcgtaa atcactgcat aattcgtgtc    10800
gctcaaggcg cactcccgtt ctggataatg tttttttgcgc cgacatcata acggttctgg    10860
caaatattct gaaatgagct gttgacaatt aatcatccgg ctcgtataat gtgtggaatt    10920
gtgagcggat aacaatttca cacaggaaac agaccatgag ggaagcgttg atcgccgaag    10980
tatcgactca actatcagag gtagttggcg tcatcgagcg ccatctcgaa ccgacgttgc    11040
tggccgtaca tttgtacggc tccgcagtgg atggcggcct gaagccacac agtgatattg    11100
atttgctggt tacggtgacc gtaaggcttg atgaaacaac gcggcgagct ttgatcaacg    11160
accttttgga aacttcggct tcccctggag agagcgagat tctccgcgct gtagaagtca    11220
ccattgttgt gcacgacgac atcattccgt ggcgttatcc agctaagcgc gaactgcaat    11280
ttggagaatg gcagcgcaat gacattcttg caggtatctt cgagccagcc acgatcgaca    11340
ttgatctggc tatcttgctg acaaaagcaa gagaacatag cgttgccttg gtaggtccag    11400
cggcggagga actctttgat ccggttcctg aacaggatct atttgaggcg ctaaatgaaa    11460
ccttaacgct atggaactcg ccgcccgact gggctggcga tgagcgaaat gtagtgctta    11520
cgttgtcccg catttggtac agcgcagtaa ccggcaaaat cgcgccgaag gatgtcgctg    11580
ccgactgggc aatggagcgc ctgccggccc agtatcagcc cgtcatactt gaagctaggc    11640
aggcttatct tggacaagaa gatcgcttgg cctcgcgcgc agatcagttg gaagaatttg    11700
ttcactacgt gaaaggcgag atcaccaaag tagtcggcaa ataaagctct agtggatctc    11760
cgtacccggg gatctggctc gcggcggacg cacgacgccg gggcgagacc ataggcgatc    11820
tcctaaatca atagtagctg taacctcgaa gcgtttcact tgtaacaacg attgagaatt    11880
tttgtcataa aattgaaata cttggttcgc atttttgtca tccgcggtca gccgcaattc    11940
tgacgaactg cccatttagc tggagatgat tgtacatcct tcacgtgaaa atttctcaag    12000
cgctgtgaac aagggttcag attttagatt gaaaggtgag ccgttgaaac acgttcttct    12060
tgtcgatgac gacgtcgcta tgcggcatct tattattgaa taccttacga tccacgcctt    12120
caaagtgacc gcggtagccg acagcaccca gttcacaaga gtactctctt ccgcgacggt    12180
cgatgtcgtg gttgttgatc tagatttagg tcgtgaagat gggctcgagc taggagcaag    12240
tgattttatc gctaagccgt tcagtatcag agagtttcta gcacgcattc gggttgcctt    12300
gcgcgtgcgc cccaacgttg tccgctccaa agaccgacgg tcttttttgtt ttactgactg    12360 gacacttaat ctcaggcaac gtcgcttgat gtccgaagct ggcggtgagg tgaaacttac    12420
ggcaggtgag ttcaatcttc tcctcgcgtt tttagagaaa ccccgcgacg ttctatcgcg    12480
cgagcaactt ctcattgcca gtcgagtacg cgacgaggag gtttatgaca ggagtataga    12540
tgttctcatt ttgaggctgc gccgcaaact tgaggcagat ccgtcaagcc ctcaactgat    12600
```

-continued

```
aaaaacagca agaggtgccg gttatttctt tgacgcggac gtgcaggttt cgcacggggg    12660
gacgatggca gcctgagcca attcccagat ccccgaggaa tcggcgtgag cggtcgcaaa    12720
ccatccggcc cggtacaaat cggcgcggcg ctgggtgatg acctggtgga gaagttgaag    12780
gccgcgcagg ccgcccagcg gcaacgcatc gaggcagaag cacgccccgg tgaatcgtgg    12840
caagcggccg ctgatcgaat ccgcaaagaa tcccggcaac cgccggcagc cggtgcgccg    12900
tcgattagga agccgcccaa gggcgacgag caaccagatt ttttcgttcc gatgctctat    12960
gacgtgggca cccgcgatag tcgcagcatc atggacgtgg ccgtttccg tctgtcgaag      13020 cgtgaccgac gagctggcga ggtgatccgc tacgagcttc cagacgggca cgtagaggtt    13080
tccgcagggc cggccggcat ggccagtgtg tgggattacg acctggtact gatggcggtt    13140
tcccatctaa ccgaatccat gaaccgatac cgggaaggga agggagacaa gcccggccgc    13200
gtgttccgtc cacacgttgc ggacgtactc aagttctgcc ggcgagccga tggcggaaag    13260
cagaaagacg acctggtaga aacctgcatt cggttaaaca ccacgcacgt tgccatgcag    13320
cgtacgaaga aggccaagaa cggccgcctg gtgacggtat ccgagggtga agccttgatt    13380
agccgctaca agatcgtaaa gagcgaaacc gggcggccgg agtacatcga gatcgagcta    13440
gctgattgga tgtaccgcga gatcacagaa ggcaagaacc cggacgtgct gacggttcac    13500
cccgattact ttttgatcga tcccggcatc ggccgttttc tctaccgcct ggcacgccgc    13560
gccgcaggca aggcagaagc cagatggttg ttcaagacga tctacgaacg cagtggcagc    13620
gccggagagt tcaagaagtt ctgtttcacc gtgcgcaagc tgatcgggtc aaatgacctg    13680
ccggagtacg atttgaagga ggaggcgggg caggctggcc cgatcctagt catgcgctac    13740
cgcaacctga tcgagggcga agcatccgcc ggttcctaat gtacggagca gatgctaggg    13800
caaattgccc tagcagggga aaaaggtcga aaaggtctct ttcctgtgga tagcacgtac    13860
attgggaacc caaagccgta cattgggaac cggaacccgt acattgggaa cccaaagccg    13920
tacattggga accggtcaca catgtaagtg actgatataa aagagaaaaa aggcgatttt    13980
tccgcctaaa actctttaaa acttattaaa actcttaaaa cccgcctggc ctgtgcataa    14040
ctgtctggcc agcgcacagc cgaagagctg caaaaagcgc ctacccttcg gtcgctgcgc    14100
tccctacgcc ccgccgcttc gcgtcggcct atcgcggccg ctggccgctc aaaaatggct    14160
ggcctacggc caggcaatct accagggcgc ggacaagccg cgccgtcgcc actcgaccgc    14220
cggcgctgag gtctgcctcg tgaagaaggt gttgctgact cataccaggc ctgaatcgcc    14280
ccatcatcca gccagaaagt gagggagcca cggttgatga gagctttgtt gtaggtggac    14340
cagttggtga ttttgaactt ttgctttgcc acggaacggt ctgcgttgtc gggaagatgc    14400
gtgatctgat ccttcaactc agcaaaagtt cgatttattc aacaaagccg ccgtcccgtc    14460
aagtcagcgt aatgctctgc cagtgttaca accaattaac caattctgat tagaaaaact    14520
catcgagcat caaatgaaac tgcaatttat tcatatcagg attatcaata ccatattttt    14580
gaaaaagccg tttctgtaat gaaggagaaa actcaccgag gcagttccat aggatggcaa    14640
gatcctggta tcggtctgcg attccgactc gtccaacatc aatacaacct attaatttcc    14700
cctcgtcaaa aataaggtta tcaagtgaga atcaccatg agtgacgact gaatccggtg    14760
agaatggcaa aagctctgca ttaatgaatc ggccaacgcg cggggagagg cggtttgcgt    14820
attgggcgct cttccgcttc ctcgctcact gactcgctgc gctcggtcgt tcggctgcgg    14880
cgagcggtat cagctcactc aaaggcggta atacggttat ccacagaatc aggggataac    14940
```

-continued

```
gcaggaaaga acatgtgagc aaaaggccag caaaaggcca ggaaccgtaa aaaggccgcg    15000
ttgctggcgt ttttccatag gctccgcccc cctgacgagc atcacaaaaa tcgacgctca    15060
agtcagaggt ggcgaaaccc gacaggacta taaagatacc aggcgtttcc ccctggaagc    15120
tccctcgtgc gctctcctgt tccgaccctg ccgcttaccg gatacctgtc cgcctttctc    15180
ccttcgggaa gcgtggcgct ttctcatagc tcacgctgta ggtatctcag ttcggtgtag    15240
gtcgttcgct ccaagctggg ctgtgtgcac gaacccccccg ttcagcccga ccgctgcgcc    15300
ttatccggta actatcgtct tgagtccaac ccggtaagac acgacttatc gccactggca    15360
gcagccactg gtaacaggat tagcagagcg aggtatgtag gcggtgctac agagttcttg    15420
aagtggtggc ctaactacgg ctacactaga agaacagtat ttggtatctg cgctctgctg    15480
aagccagtta ccttcggaaa aagagttggt agctcttgat ccggcaaaca aaccaccgct    15540
ggtagcggtg gtttttttgt ttgcaagcag cagattacgc gcagaaaaaa aggatctcaa    15600
gaagatcctt tgatctttc tacggggtct gacgctcagt ggaacgaaaa ctcacgttaa    15660
gggattttgg tcatgagatt atcaaaaagg atcttcacct agatccttt gatccggaat    15720 ta                                                                   15722

<210> SEQ ID NO 4
<211> LENGTH: 20
<212> TYPE: DNA
<213> ORGANISM: Artificial Sequence
<220> FEATURE:
<223> OTHER INFORMATION: for editing GW2-2

<400> SEQUENCE: 4
aagctcgcgc cctgctaccc                                                20

<210> SEQ ID NO 5
<211> LENGTH: 19617
<212> TYPE: DNA
<213> ORGANISM: Artificial Sequence
<220> FEATURE:
<223> OTHER INFORMATION: vector 22808
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2119)..(5193)
<223> OTHER INFORMATION: cTNPLAIIAFw-01
<220> FEATURE:
<221> NAME/KEY: terminator
<222> LOCATION: (5200)..(5452)
<223> OTHER INFORMATION: tNOS-05-01
<220> FEATURE:
<221> NAME/KEY: promoter
<222> LOCATION: (5486)..(7478)
<223> OTHER INFORMATION: prUbi1-10
<220> FEATURE:
<221> NAME/KEY: gene
<222> LOCATION: (7492)..(10566)
<223> OTHER INFORMATION: cTNPLAIIARv-01
<220> FEATURE:
<221> NAME/KEY: terminator
<222> LOCATION: (10573)..(10825)
<223> OTHER INFORMATION: tNOS-05-01
<220> FEATURE:
<221> NAME/KEY: promoter
<222> LOCATION: (10844)..(12835)
<223> OTHER INFORMATION: prUbi1-04
```

-continued

```
<220> FEATURE:
<221> NAME/KEY: gene
<222> LOCATION: (12852)..(14030)
<223> OTHER INFORMATION: cPMI-09
<220> FEATURE:
<221> NAME/KEY: terminator
<222> LOCATION: (14053)..(14305)
<223> OTHER INFORMATION: tNOS-05-01
<220> FEATURE:
<221> NAME/KEY: misc_feature
<222> LOCATION: (14349)..(14478)
<223> OTHER INFORMATION: bNLB-03
<220> FEATURE:
<221> NAME/KEY: gene
<222> LOCATION: (14758)..(15546)
<223> OTHER INFORMATION: cSpec-03
<220> FEATURE:
<221> NAME/KEY: promoter
<222> LOCATION: (15641)..(15771)
<223> OTHER INFORMATION: prVirG-01
<220> FEATURE:
<221> NAME/KEY: gene
<222> LOCATION: (15846)..(16571)
<223> OTHER INFORMATION: cVirG-01
<220> FEATURE:
<221> NAME/KEY: gene
<222> LOCATION: (16601)..(17674)
<223> OTHER INFORMATION: cRepA-01
<220> FEATURE:
<221> NAME/KEY: misc_feature
<222> LOCATION: (17717)..(18121)
<223> OTHER INFORMATION: oVS1-02
<220> FEATURE:
<221> NAME/KEY: misc_feature
<222> LOCATION: (18799)..(19605)
<223> OTHER INFORMATION: oCOLE-06

<400> SEQUENCE: 5
attcctgtgg ttggcatgca catacaaatg gacgaacgga taaacctttt cacgcccttt        60
taaatatccg attattctaa taaacgctct tttctcttag gtttacccgc caatatatcc       120
tgtcaaacac tgatagttta aactgaaggc gggaaacgac aatctgatca tgagcggaga       180
attaagggag tcacgttatg accccgccg atgacgcggg acaagccgtt ttacgtttgg       240
aactgacaga accgcaacgc tgcaggaatt ggccgcagcg gccatttaaa caaagcttgg       300
taccattatg tggtctaggt aggttctata tataagaaaa cttgaaatgt tctaaaaaaa       360
aattcaagcc catgcatgat tgaagcaaac ggtatagcaa cggtgttaac ctgatctagt       420
gatctcttgc aatccttaac ggccacctac cgcaggtagc aaacggcgtc ccctcctcg       480 atatctccgc ggcgacctct ggctttttcc gcggaattgc gcggtgggga cggattccac       540
gagaccgcga cgcaaccgcc tctcgccgct gggccccaca ccgctcggtg ccgtagcctc       600
acgggactct ttctccctcc tccccgtta taaattggct tcatccctc cttgcctcat       660 ccatccaaat cccagtcccc aatcccatcc cttcgtagga gaaattcatc gaagctaagc       720
gaatcctcgc gatcctctca aggtactgcg agttttcgat cccctctcg acccctcgta       780 tgtttgtgtt tgtcgtagcg tttgattagg tatgctttcc ctgtttgtgt tcgtcgtagc       840
gtttgattag gtatgctttc cctgttcgtg ttcatcgtag tgtttgatta ggtcgtgtga       900
ggcgatggcc tgctcgcgtc cttcgatctg tagtcgattt gcgggtcgtg gtgtagatct       960
gcgggctgtg atgaagttat ttggtgtgat ctgctcgcct gattctgcgg gttggctcga      1020
gtagatatga tggttggacc ggttggttcg tttaccgcgc tagggttggg ctgggatgat      1080
gttgcatgcg ccgttgcgcg tgatcccgca gcaggacttg cgtttgattg ccagatctcg      1140
ttacgattat gtgatttggt ttggactttt tagatctgta gcttctgctt atgtgccaga      1200
```

-continued

```
tgcgcctact gctcatatgc ctgatgataa tcataaatgg ctgtggaact aactagttga   1260
ttgcggagtc atgtatcagc tacaggtgta gggactagct acaggtgtag ggacttgcgt   1320
ctaattgttt ggtcctttac tcatgttgca attatgcaat ttagtttaga ttgtttgttc   1380
cactcatcta ggctgtaaaa gggacactgc ttagattgct gtttaatctt tttagtagat   1440
tatattatat tggtaactta ttacccctat tacatgccat acgtgacttc tgctcatgcc   1500
tgatgataat catagatcac tgtggaatta attagttgat tgttgaatca tgtttcatgt   1560
acataccacg gcacaattgc ttagttcctt aacaaatgca aattttactg atccatgtat   1620
gatttgcgtg gttctctaat gtgaaatact atagctactt gttagtaaga atcaggttcg   1680
tatgcttaat gctgtatgtg ccttctgctc atgcctgatg ataatcatat atcactggaa   1740
ttaattagtt gatcgtttaa tcatatatca agtacatacc atgccacaat ttttagtcac   1800
ttaacccatg cagattgaac tggtccctgc atgtttttgct aaattgttct attctgatta   1860
gaccatatat catgtatttt tttttggtaa tggttctctt attttaaatg ctatatagtt   1920
ctggtacttg ttagaaagat ctgcttcata gtttagttgc ctatccctcg aattaggatg   1980
ctgagcagct gatcctatag ctttgtttca tgtatcaatt cttttgtgtt caacagtcag   2040
tttttgttag attcattgta acttatggtc gcttactctt ctggtcctca atgcttgcag   2100
gatcgcggcc gcgccaccat gggaaaacct attcctaatc ctctgctggg cctggattct   2160
accggaggca tggcccctaa gaaaaagcgg aaggtggacg gcgagtgga cctgagaaca    2220 ctgggatatt ctcagcagca gcaggagaag atcaagccca aggtgagatc tacagtggcc   2280
cagcaccacg aagccctggt gggacacgga tttacacacg cccacattgt ggccctgtct   2340
cagcaccctg ccgccctggg aacagtggcc gtgaaatatc aggatatgat gccgccctg    2400 cctgaggcca cacgaagc cattgtggga gtgggaaaac agtggtctgg agccagagcc    2460
ctggaagccc tgctgacagt ggccggagaa ctgagaggac ctcctctgca gctggataca   2520
ggacagctgc tgaagattgc caaaaggggc ggagtgaccg cggtggaagc cgtgcacgcc   2580
tggagaaatg ccctgacagg agccctctg aacctgaccc ccgaacaggt ggtggccatt    2640
gccagccacg acggcggcaa gcaggccctg gaaaccgtgc agagactgct gcccgtgctg   2700
tgccaggccc atggcctgac acctgaacag gtggtggcta tcgcctctca cgacggagga   2760
aaacaggctc tggaaacagt gcagcggctg ctgcctgtgc tgtgtcaggc tcacggcttg   2820
actccagaac aggtggtggc tattgcttcc aatattgggg ggaaacaggc cctggaaact   2880
gtgcagcgcc tgctgccagt gctgtgccag gctcacggac tgacccccga acaggtggtg   2940
gccattgcca gcaacaacgg cggcaagcag gccctggaaa ccgtgcagag actgctgccc   3000
gtgctgtgcc aggcccatgg cctgacacct gaacaggtgg tggctatcgc ctctaacaac   3060
ggaggaaaac aggctctgga aacagtgcag cggctgctgc ctgtgctgtg tcaggctcac   3120
ggcttgactc cagaacaggt ggtggctatt gcttccaaca cggggggaa acaggccctg    3180 gaaactgtgc agcgcctgct gccagtgctg tgccaggctc acgggctgac ccccgaacag   3240
gtggtggcca ttgccagcaa cggcggcggc aagcaggccc tggaaaccgt gcagagactg   3300
ctgcccgtgc tgtgccaggc ccatggcctg acacctgaac aggtggtggc tatcgcctct   3360
cacgacggag gaaaacaggc tctggaaaca gtgcagcggc tgctgcctgt gctgtgtcag   3420
gctcacggct tgactccaga acaggtggtg gctattgctt ccaatattgg ggggaaacag   3480
gccctggaaa ctgtgcagcg cctgctgcca gtgctgtgcc aggctcacgg cctcactccc   3540
gaacaggtgg tggccattgc cagcaacatc ggcggcaagc aggccctgga aaccgtgcag   3600
```

-continued

```
agactgctgc ccgtgctgtg ccaggcccat ggcctgacac ctgaacaggt ggtggctatc    3660
gcctctcacg acggaggaaa acaggctctg gaaacagtgc agcggctgct gcctgtgctg    3720
tgtcaggctc acggcttgac tccagaacag gtggtggcta ttgcttccaa caacgggggg    3780
aaacaggccc tggaaactgt gcagcgcctg ctgccagtgc tgtgccaggc tcacggactg    3840
acccccgaac aggtggtggc cattgccagc aacggcggcg gcaagcaggc cctggaaacc    3900
gtgcagagac tgctgcccgt gctgtgccag gcccatggcc tgacacctga acaggtggtg    3960
gctatcgcct ctaacaacgg aggaaaacaa gcactcgaga cagtgcagcg gctgctgcct    4020
gtgctgtgtc aggctcacgg cttgactcca gaacaggtgg tggctattgc ttccaacaac    4080 gggggaaac aggccctgga aactgtgcag cgcctgctgc cagtgctgtg ccaggctcac    4140
gggctgaccc ccgaacaggt ggtggccatt gccagcaaca tcggcggcaa gcaggccctg    4200
gaaaccgtgc agagactgct gcccgtgctg tgccaggccc atggcctgac acctgaacag    4260
gtggtggcta tcgcctctaa caacggagga aaacaggctc tggaaacagt gcagcggctg    4320
ctgcctgtgc tgtgtcaggc tcacggcttg actccacagc aggtcgtggc aattgctagc    4380
aatatcggcg gacggcccgc cctggagagc attgtggccc agctgtctag acctgatcct    4440
gccctggccg ccctgacaaa tgatcacctg gtggccctgg cctgtctggg aggcagacct    4500
gccctggatg ccgtgaaaaa aggactgcct cacgcccctg ccctgattaa aagaacaaat    4560
agaagaatcc ccgagcggac ctctcacaga gtggccggat cccagctggt gaaatctgag    4620
ctggaggaga agaagtctga gctgagacac aagctgaagt acgtgcctca cgagtacatc    4680
gagctgatcg agatcgccag aaatagcacc caggatagaa tcctggagat gaaggtgatg    4740
gagttcttca tgaaagtgta cggctacaga ggaaagcatc tgggaggaag cagaaaacct    4800
gacggagcca tttatacagt gggcagccct atcgattatg gcgtgatcgt ggatacaaag    4860
gcctacagcg gaggctacaa tctgcctatt ggacaggccg atgagatgca gagatacgtg    4920
gaggagaacc aaaccaggaa caagcatatc aaccctaacg agtggtggaa ggtgtaccct    4980
tctagcgtga ccgagttcaa gttcctgttt gtgagcggcc acttcaaggg caattataag    5040
gcccagctga ccaggctgaa ccacatcaca aattgtaatg cgccgtgct gtctgtggag    5100 gaactgctga ttggaggaga gatgattaag gccggaacac tgacactgga ggaggtgaga    5160
agaaagttca caacggcga gatcaacttc tgaaagcttg atcgttcaaa catttggcaa    5220
taaagtttct taagattgaa tcctgttgcc ggtcttgcga tgattatcat ataatttctg    5280
ttgaattacg ttaagcatgt aataattaac atgtaatgca tgacgttatt tatgagatgg    5340
gtttttatga ttagagtccc gcaattatac atttaatacg cgatagaaaa caaaatatag    5400
cgcgcaaact aggataaatt atcgcgcgcg gtgtcatcta tgttactaga tcttcgaacc    5460
ctagtcgaag acaaccggtg catgcctgca gtgcagcgtg acccggtcgt gcccctctct    5520
agagataatg agcattgcat gtctaagtta taaaaaatta ccacatattt tttttgtcac    5580
acttgtttga agtgcagttt atctatcttt atacatatat ttaaacttta ctctacgaat    5640
aatataatct atagtactac aataatatca gtgtttaga gaatcatata aatgaacagt    5700
tagacatggt ctaaaggaca attgagtatt ttgacaacag gactctacag ttttatcttt    5760
ttagtgtgca tgtgttctcc tttttttttg caaatagctt cacctatata atacttcatc    5820 catttttta gtacatccat ttagggttta gggttaatgg ttttttataga ctaattttt    5880 tagtacatct attttattct attttagcct ctaaattaag aaaactaaaa ctctatttta    5940
```

-continued

```
gttttttttat ttaataatttt agatataaaa tagaataaaa taaagtgact aaaaattaaa    6000 caaatacccct ttaagaaatt aaaaaaacta aggaaacatt tttcttgttt cgagtagata    6060
atgccagcct gttaaacgcc gtcgacgagt ctaacggaca ccaaccagcg aaccagcagc    6120
gtcgcgtcgg gccaagcgaa gcagacggca cggcatctct gtcgctgcct ctggacccct    6180
ctcgagagtt ccgctccacc gttggacttg ctccgctgtc ggcatccaga aattgcgtgg    6240
cggagcggca gacgtgagcc ggcacggcag gcggcctcct cctcctctca cggcaccggc    6300
agctacgggg gattcctttc ccaccgctcc ttcgctttcc cttcctcgcc cgccgtaata    6360
aatagacacc ccctccacac cctctttccc caacctcgtg ttgttcggag cgcacacaca    6420
cacaaccaga tctcccccaa atccacccgt cggcacctcc gcttcaaggt acgccgctcg    6480
tcctcccccc cccccctct ctaccttctc tagatcggcg ttccggtcca tggttagggc    6540
ccggtagttc tacttctgtt catgtttgtg ttagatccgt gtttgtgtta gatccgtgct    6600
gctagcgttc gtacacggat gcgacctgta cgtcagacac gttctgattg ctaacttgcc    6660
agtgtttctc tttggggaat cctgggatgg ctctagccgt tccgcagacg ggatcgattt    6720
catgattttt tttgtttcgt tgcatagggt ttggtttgcc ctttttcctt atttcaatat    6780
atgccgtgca cttgtttgtc gggtcatctt ttcatgcttt tttttgtctt ggttgtgatg    6840
atgtggtctg gttgggcggt cgttctagat cggagtagaa ttctgtttca aactacctgg    6900
tggatttatt aattttggat ctgtatgtgt gtgccataca tattcatagt tacgaattga    6960
agatgatgga tggaaatatc gatctaggat aggtatacat gttgatgcgg gttttactga    7020
tgcatataca gagatgcttt ttgttcgctt ggttgtgatg atgtggtgtg gttgggcggt    7080
cgttcattcg ttctagatcg gagtagaata ctgtttcaaa ctacctggtg tatttattaa    7140
ttttggaact gtatgtgtgt gtcatacatc ttcatagtta cgagtttaag atggatggaa    7200
atatcgatct aggataggta tacatgttga tgtgggtttt actgatgcat atacatgatg    7260
gcatatgcag catctattca tatgctctaa ccttgagtac ctatctatta taataaacaa    7320
gtatgtttta taattatttt gatcttgata tacttggatg atggcatatg cagcagctat    7380
atgtggattt ttttagccct gccttcatac gctatttatt tgcttggtac tgtttctttt    7440
gtcgatgctc accctgttgt ttggtgttac ttctgcagcg gccgcgccac catgggaaaa    7500
cctattccta atcctctgct gggcctggat tctaccggag gcatggcccc taagaaaaag    7560
cggaaggtgg acggcggagt ggacctgaga acactgggat attctcagca gcagcaggag    7620
aagatcaagc ccaaggtgag atctacagtg gcccagcacc acgaagccct ggtgggacac    7680
ggatttacac acgcccacat tgtggccctg tctcagcacc ctgccgccct gggaacagtg    7740
gccgtgaaat atcaggatat gattgccgcc ctgcctgagg ccacacacga agccattgtg    7800
ggagtgggaa aacagtggtc tggagccaga gccctggaag ccctgctgac agtggccgga    7860
gaactgagag acctcctct gcagctggat acaggacagc tgctgaagat gccaaaagg    7920 ggcggagtga ccgcggtgga agccgtgcac gcctggagaa atgccctgac aggagcccct    7980
ctgaacctga cccccgaaca ggtggtggcc attgccagca acaacggcgg caagcaggcc    8040
ctggaaaccg tgcagagact gctgcccgtg ctgtgccagg cccatggcct gacacctgaa    8100
caggtggtgg ctatcgcctc tcacgacgga ggaaaacagg ctctggaaac agtgcagcgg    8160
ctgctgcctg tgctgtgtca ggctcacggc ttgactccag aacaggtggt ggctattgct    8220
tccaacggcg ggggaaaca ggccctggaa actgtgcagc gctgctgcc agtgctgtgc    8280 caggctcacg gactgacccc cgaacaggtg gtggccattg ccagcaacgg cggcggcaag    8340
```

-continued

```
caggccctgg aaaccgtgca gagactgctg cccgtgctgt gccaggccca tggcctgaca    8400
cctgaacagg tggtggctat cgcctctcac gacggaggaa aacaggctct ggaaacagtg    8460
cagcggctgc tgcctgtgct gtgtcaggct cacggcttga ctccagaaca ggtggtggct    8520
attgcttccc acgacggggg gaaacaggcc ctggaaactg tgcagcgcct gctgccagtg    8580
ctgtgccagg ctcacgggct gaccccgaa caggtggtgg ccattgccag caacggcggc    8640
ggcaagcagg ccctggaaac cgtgcagaga ctgctgcccg tgctgtgcca ggcccatggc    8700
ctgacacctg aacaggtggt ggctatcgcc tctaacggcg gaggaaaaca ggctctggaa    8760
acagtgcagc ggctgctgcc tgtgctgtgt caggctcacg gcttgactcc agaacaggtg    8820
gtggctattg cttcccacga cgggggggaaa caggccctgg aaactgtgca gcgcctgctg    8880
ccagtgctgt gccaggctca cggcctcact cccgaacagg tggtggccat tgccagcaac    8940
aacggcggca gcaggccct ggaaaccgtg cagagactgc tgcccgtgct gtgccaggcc    9000 catgcctga cacctgaaca ggtggtggct atcgcctctc acgacggagg aaaacaggct    9060
ctggaaacag tgcagcggct gctgcctgtg ctgtgtcagg ctcacggctt gactccagaa    9120
caggtggtgg ctattgcttc ccacgacggg gggaaacagg ccctggaaac tgtgcagcgc    9180
ctgctgccag tgctgtgcca ggctcacgga ctgaccccg aacaggtggt ggccattgcc    9240
agcaacatcg gcggcaagca ggccctggaa accgtgcaga gactgctgcc cgtgctgtgc    9300
caggcccatg gcctgacacc tgaacaggtg gtggctatcg cctctaacaa cggaggaaaa    9360
caagcactcg agacagtgca gcggctgctg cctgtgctgt gtcaggctca cggcttgact    9420
ccagaacagg tggtggctat tgcttccaac ggcggggggga aacaggccct ggaaactgtg    9480
cagcgcctgc tgccagtgct gtgccaggct cacgggctga cccccgaaca ggtggtggcc    9540
attgccagcc acgacggcgg caagcaggcc ctggaaaccg tgcagagact gctgcccgtg    9600
ctgtgccagg cccatggcct gacacctgaa caggtggtgg ctatcgcctc taatatcgga    9660
ggaaaacagg ctctggaaac agtgcagcgg ctgctgcctg tgctgtgtca ggctcacggc    9720
ttgactccac agcaggtcgt ggcaattgct agccacgacg gcggacggcc cgccctggag    9780
agcattgtgg cccagctgtc tagacctgat cctgccctgg ccgccctgac aaatgatcac    9840
ctggtggccc tggcctgtct gggaggcaga cctgccctgg atgccgtgaa aaaaggactg    9900
cctcacgccc ctgccctgat aaaagaaca aatagaagaa tccccgagcg gacctctcac    9960
agagtggccg gatcccagct ggtgaaatct gagctggagg agaagaagtc tgagctgaga   10020
cacaagctga gtacgtgcc tcacgagtac atcgagctga tcgagatcgc cagaaatagc   10080
acccaggata gaatcctgga gatgaaggtg atggagttct tcatgaaagt gtacggctac   10140
agaggaaagc atctgggagg aagcagaaaa cctgacggag ccatttatac agtgggcagc   10200
cctatcgatt atggcgtgat cgtggataca aaggcctaca gcggaggcta caatctgcct   10260
attggacagc ccgatgagat gcagagatac gtggaggaga ccaaaccag gaacaagcat   10320 atcaacccta cgagtggtg gaaggtgtac ccttctagcg tgaccgagtt caagttcctg   10380
tttgtgagcg ccacttcaa gggcaattat aaggcccagc tgaccaggct gaaccacatc   10440
acaaattgta atgcgccgt gctgtctgtg gaggaactgc tgattggagg agagatgatt   10500
aaggccggaa cactgacact ggaggaggtg agaagaaagt caacaacgg cgagatcaac   10560 ttctgaaagc ttgatcgttc aaacatttgg caataaagtt tcttaagatt gaatcctgtt   10620
gccggtcttg cgatgattat catataattt ctgttgaatt acgttaagca tgtaataatt   10680
```

-continued

```
aacatgtaat gcatgacgtt atttatgaga tgggttttta tgattagagt cccgcaatta   10740
tacatttaat acgcgataga aaacaaaata tagcgcgcaa actaggataa attatcgcgc   10800
gcggtgtcat ctatgttact agatcttcga agacggaccg cgcctgcagt gcagcgtgac   10860
ccggtcgtgc ccctctctag agataatgag cattgcatgt ctaagttata aaaaattacc   10920
acatattttt tttgtcacac ttgtttgaag tgcagtttat ctatctttat acatatattt   10980
aaactttact ctacgaataa tataatctat agtactacaa taatatcagt gttttagaga   11040
atcatataaa tgaacagtta gacatggtct aaaggacaat tgagtatttt gacaacagga   11100
ctctacagtt ttatcttttt agtgtgcatg tgttctcctt ttttttttgca aatagcttca   11160 cctatataat acttcatcca ttttattagt acatccattt agggtttagg gttaatggtt   11220
tttatagact aatttttttta gtacatctat tttattctat tttagcctct aaattaagaa   11280
aactaaaact ctattttagt tttttatttt aataatttag atataaaata gaataaaata   11340
aagtgactaa aaattaaaca aatacccttt aagaaattaa aaaaactaag gaaacatttt   11400
tcttgtttcg agtagataat gccagcctgt taaacgccgt cgacgagtct aacggacacc   11460
aaccagcgaa ccagcagcgt cgcgtcgggc caagcgaagc agacggcacg gcatctctgt   11520
cgctgcctct ggacccctct cgagagttcc gctccaccgt tggacttgct ccgctgtcgg   11580
catccagaaa ttgcgtggcg gagcggcaga cgtgagccgg cacggcaggc ggcctcctcc   11640
tcctctcacg gcaccggcag ctacggggga ttcctttccc accgctcctt cgctttccct   11700
tcctcgcccg ccgtaataaa tagacacccc ctccacaccc tctttcccca acctcgtgtt   11760
gttcggagcg cacacacaca caaccagatc tcccccaaat ccacccgtcg gcacctccgc   11820
ttcaaggtac gccgctcgtc ctccccccccc ccctctctc ccttctctag atcggcgttc   11880
cggtccatgg ttagggcccg gtagttctac ttctgttcat gtttgtgtta gatccgtgtt   11940
tgtgttagat ccgtgctgct agcgttcgta cacggatgcg acctgtacgt cagacacgtt   12000
ctgattgcta acttgccagt gtttctcttt ggggaatcct gggatggctc tagccgttcc   12060
gcagacggga tcgatttcat gatttttttt gtttcgttgc atagggtttg gtttgccctt   12120
ttcctttatt tcaatatatg ccgtgcactt gtttgtcggg tcatcttttc atgctttttt   12180
ttgtcttggt tgtgatgatg tggtctggtt gggcggtcgt tctagatcgg agtagaattc   12240
tgtttcaaac tacctggtgg atttattaat tttggatctg tatgtgtgtg ccatacatat   12300
tcatagttac gaattgaaga tgatggatgg aaatatcgat ctaggatagg tatacatgtt   12360
gatgcgggct ttactgatgc atatacagag atgcttttttg ttcgcttggt tgtgatgatg   12420
tggtgtggtt gggcggtcgt tcattcgttc tagatcggag tagaatactg tttcaaacta   12480
cctggtgtat ttattaattt tggaactgta tgtgtgtgtc atacatcttc atagttacga   12540
gtttaagatg gatggaaata tcgatctagg ataggtatac atgttgatgt gggtttttact   12600 gatgcatata catgatggca tatgcagcat ctattcatat gctctaacct tgagtaccta   12660
tctattataa taaacaagta tgttttataa ttatttttgat cttgatatac ttggatgatg   12720
gcatatgcag cagctatatg tggattttttt tagccctgcc ttcatacgct atttatttgc   12780
ttggtactgt ttcttttttgtc gatgctcacc ctgttgtttg gtgttacttc tgcagggatc   12840
cggcagcagc catgcagaag ctgatcaaca gcgtgcagaa ctacgcctgg ggcagcaaga   12900
ccgccctgac cgagctgtac ggcatggaga accccagcag ccagcccatg gccgagctgt   12960
ggatgggcgc ccaccccaag agcagcagcc gcgtgcagaa cgccgccggc gacatcgtga   13020
gcctgcgcga cgtgatcgag agcgacaaga gcaccctgct gggcgaggcc gtggccaagc   13080
```

-continued

```
gcttcggcga gctgcccttc ctgttcaagg tgctgtgcgc cgcccagccc ctgagcatcc   13140
aggtgcaccc caacaagcac aacagcgaga tcggcttcgc caaggagaac gccgccggca   13200
tccccatgga cgccgccgag cgcaactaca aggaccccaa ccacaagccc gagctggtgt   13260
tcgccctgac ccccttcctg gccatgaacg ccttccgcga gttcagcgag atcgtgagcc   13320
tgctgcagcc cgtggccggc gcccaccccg ccatcgccca cttcctgcag cagcccgacg   13380
ccgagcgcct gagcgagctg ttcgccagcc tgctgaacat gcagggcgag gagaagagcc   13440
gcgccctggc catcctgaag agcgccctgg acagccagca gggcgagccc tggcagacca   13500
tccgcctgat cagcgagttc taccccgagg acagcggcct gttcagcccc ctgctgctga   13560
acgtggtgaa gctgaacccc ggcgaggcca tgttcctgtt cgccgagacc ccccacgcct   13620
acctgcaggg cgtggccctg gaggtgatgg ccaacagcga caacgtgctg cgcgccggcc   13680
tgacccccaa gtacatcgac atccccgagc tggtggccaa cgtgaagttc gaggccaagc   13740
ccgccaacca gctgctgacc cagcccgtga agcaggcgc cgagctggac ttccccatcc   13800
ccgtggacga cttcgccttc agcctgcacg acctgagcga caaggagacc accatcagcc   13860
agcagagcgc cgccatcctg ttctgcgtgg agggcgacgc caccctgtgg aagggcagcc   13920
agcagctgca gctgaagccc ggcgagagcg ccttcatcgc cgccaacgag agccccgtga   13980
ccgtgaaggg ccacggccgc ctggcccgcg tgtacaacaa gctgtgatag gagctcgatc   14040
cgtcgacctg cagatcgttc aaacatttgg caataaagtt tcttaagatt gaatcctgtt   14100
gccggtcttg cgatgattat catataattt ctgttgaatt acgttaagca tgtaataatt   14160
aacatgtaat gcatgacgtt atttatgaga tgggttttta tgattagagt cccgcaatta   14220
tacatttaat acgcgataga aaacaaaata tagcgcgcaa actaggataa attatcgcgc   14280
gcggtgtcat ctatgttact agatcggcgc gccgcaattg aagtttgggc ggccagcatg   14340
gccgtatccg caatgtgtta ttaagttgtc taagcgtcaa tttgtttaca ccacaatata   14400
tcctgccacc agccagccaa cagctccccg accggcagct cggcacaaaa tcaccactcg   14460
atacaggcag cccatcagaa ttaattctca tgtttgacag cttatcatcg actgcacggt   14520
gcaccaatgc ttctggcgtc aggcagccat cggaagctgt ggtatggctg tgcaggtcgt   14580
aaatcactgc ataattcgtg tcgctcaagg cgcactcccg ttctggataa tgttttttgc   14640
gccgacatca taacggttct ggcaaatatt ctgaaatgag ctgttgacaa ttaatcatcc   14700
ggctcgtata atgtgtggaa ttgtgagcgg ataacaattt cacacaggaa acagaccatg   14760
agggaagcgt tgatcgccga agtatcgact caactatcag aggtagttgg cgtcatcgag   14820
cgccatctcg aaccgacgtt gctggccgta catttgtacg gctccgcagt ggatggcggc   14880
ctgaagccac acagtgatat tgatttgctg gttacggtga ccgtaaggct tgatgaaaca   14940
acgcggcgag ctttgatcaa cgaccttttg gaaacttcgg cttcccctgg agagagcgag   15000
attctccgcg ctgtagaagt caccattgtt gtgcacgacg acatcattcc gtggcgttat   15060
ccagctaagc gcgaactgca atttggagaa tggcagcgca atgacattct gcaggtatc   15120 ttcgagccag ccacgatcga cattgatctg gctatcttgc tgacaaaagc aagagaacat   15180
agcgttgcct tggtaggtcc agcggcggag gaactctttg atccggttcc tgaacaggat   15240
ctatttgagg cgctaaatga aaccttaacg ctatggaact cgccgcccga ctgggctggc   15300
gatgagcgaa atgtagtgct tacgttgtcc cgcatttggt acagcgcagt aaccggcaaa   15360
atcgcgccga aggatgtcgc tgccgactgg gcaatggagc gcctgccggc ccagtatcag   15420
```

-continued

```
cccgtcatac ttgaagctag gcaggcttat cttggacaag aagatcgctt ggcctcgcgc    15480
gcagatcagt tggaagaatt tgttcactac gtgaaaggcg agatcaccaa agtagtcggc    15540
aaataaagct ctagtggatc tccgtacccg gggatctggc tcgcggcgga cgcacgacgc    15600
cggggcgaga ccataggcga tctcctaaat caatagtagc tgtaacctcg aagcgtttca    15660
cttgtaacaa cgattgagaa tttttgtcat aaaattgaaa tacttggttc gcatttttgt    15720
catccgcggt cagccgcaat tctgacgaac tgcccattta gctggagatg attgtacatc    15780
cttcacgtga aaatttctca agcgctgtga acaagggttc agattttaga ttgaaaggtg    15840
agccgttgaa acacgttctt cttgtcgatg acgacgtcgc tatgcggcat cttattattg    15900
aataccttac gatccacgcc ttcaaagtga ccgcggtagc cgacagcacc cagttcacaa    15960
gagtactctc ttccgcgacg gtcgatgtcg tggttgttga tctagattta ggtcgtgaag    16020
atgggctcga gatcgttcgt aatctggcgg caaagtctga tattccaatc ataattatca    16080
gtggcgaccg ccttgaggag acggataaag ttgttgcact cgagctagga gcaagtgatt    16140
ttatcgctaa gccgttcagt atcagagagt ttctagcacg cattcgggtt gccttgcgcg    16200
tgcgccccaa cgttgtccgc tccaaagacc gacggtcttt ttgtttttact gactggacac    16260 ttaatctcag gcaacgtcgc ttgatgtccg aagctggcgg tgaggtgaaa cttacggcag    16320
gtgagttcaa tcttctcctc gcgttttttag agaaaccccg cgacgttcta tcgcgcgagc    16380
aacttctcat tgccagtcga gtacgcgacg aggaggttta tgacaggagt atagatgttc    16440
tcattttgag gctgcgccgc aaacttgagg cagatccgtc aagccctcaa ctgataaaaa    16500
cagcaagagg tgccggttat ttctttgacg cggacgtgca ggtttcgcac ggggggacga    16560
tggcagcctg agccaattcc cagatccccg aggaatcggc gtgagcggtc gcaaaccatc    16620
cggcccggta caaatcggcg cggcgctggg tgatgacctg gtggagaagt tgaaggccgc    16680
gcaggccgcc cagcggcaac gcatcgaggc agaagcacgc cccggtgaat cgtggcaagc    16740
ggccgctgat cgaatccgca aagaatcccg gcaaccgccg gcagccggtg cgccgtcgat    16800
taggaagccg cccaagggcg acgagcaacc agatttttc gttccgatgc tctatgacgt    16860
gggcacccgc gatagtcgca gcatcatgga cgtggccgtt ttccgtctgt cgaagcgtga    16920
ccgacgagct ggcgaggtga tccgctacga gcttccagac gggcacgtag aggtttccgc    16980
agggccggcc ggcatggcca gtgtgtggga ttacgacctg gtactgatgg cggtttccca    17040
tctaaccgaa tccatgaacc gataccggga agggaaggga gacaagcccg gccgcgtgtt    17100
ccgtccacac gttgcggacg tactcaagtt ctgccggcga gccgatggcg gaaagcagaa    17160
agacgacctg gtagaaacct gcattcggtt aaacaccacg cacgttgcca tgcagcgtac    17220
gaagaaggcc aagaacggcc gcctggtgac ggtatccgag ggtgaagcct tgattagccg    17280
ctacaagatc gtaaagagcg aaaccgggcg gccggagtac atcgagatcg agctagctga    17340
ttggatgtac cgcgagatca cagaaggcaa gaacccggac gtgctgacgg ttcaccccga    17400 ttacttttg atcgatcccg gcatcggccg ttttctctac cgcctggcac gccgcgccgc    17460
aggcaaggca gaagccagat ggttgttcaa gacgatctac gaacgcagtg gcagcgccgg    17520
agagttcaag aagttctgtt tcaccgtgcg caagctgatc gggtcaaatg acctgccgga    17580
gtacgatttg aaggaggagg cggggcaggc tggcccgatc ctagtcatgc gctaccgcaa    17640
cctgatcgag ggcgaagcat ccgccggttc ctaatgtacg gagcagatgc tagggcaaat    17700
tgccctagca ggggaaaaag gtcgaaaagg tctctttcct gtggatagca cgtacattgg    17760
gaacccaaag ccgtacattg ggaaccggaa cccgtacatt gggaacccaa agccgtacat    17820
```

-continued

```
tgggaaccgg tcacacatgt aagtgactga tataaaagag aaaaaaggcg atttttccgc   17880
ctaaaactct ttaaaactta ttaaaactct taaaacccgc ctggcctgtg cataactgtc   17940
tggccagcgc acagccgaag agctgcaaaa agcgcctacc cttcggtcgc tgcgctccct   18000
acgccccgcc gcttcgcgtc ggcctatcgc ggccgctggc cgctcaaaaa tggctggcct   18060
acggccaggc aatctaccag ggcgcggaca agccgcgccg tcgccactcg accgccggcg   18120
ctgaggtctg cctcgtgaag aaggtgttgc tgactcatac caggcctgaa tcgccccatc   18180
atccagccag aaagtgaggg agccacggtt gatgagagct ttgttgtagg tggaccagtt   18240
ggtgattttg aacttttgct ttgccacgga acggtctgcg ttgtcgggaa gatgcgtgat   18300
ctgatccttc aactcagcaa aagttcgatt tattcaacaa agccgccgtc ccgtcaagtc   18360
agcgtaatgc tctgccagtg ttacaaccaa ttaaccaatt ctgattagaa aaactcatcg   18420
agcatcaaat gaaactgcaa tttattcata tcaggattat caataccata tttttgaaaa   18480
agccgtttct gtaatgaagg agaaaactca ccgaggcagt tccataggat ggcaagatcc   18540
tggtatcggt ctgcgattcc gactcgtcca acatcaatac aacctattaa tttcccctcg   18600
tcaaaaataa ggttatcaag tgagaaatca ccatgagtga cgactgaatc cggtgagaat   18660
ggcaaaagct ctgcattaat gaatcggcca acgcgcgggg agaggcggtt tgcgtattgg   18720
gcgctcttcc gcttcctcgc tcactgactc gctgcgctcg gtcgttcggc tgcggcgagc   18780
ggtatcagct cactcaaagg cggtaatacg gttatccaca gaatcagggg ataacgcagg   18840
aaagaacatg tgagcaaaag gccagcaaaa ggccaggaac cgtaaaaagg ccgcgttgct   18900
ggcgtttttc cataggctcc gcccccctga cgagcatcac aaaaatcgac gctcaagtca   18960
gaggtggcga aacccgacag gactataaag ataccaggcg tttccccctg gaagctccct   19020
cgtgcgctct cctgttccga ccctgccgct taccggatac ctgtccgcct ttctcccttc   19080
gggaagcgtg gcgctttctc atagctcacg ctgtaggtat ctcagttcgg tgtaggtcgt   19140
tcgctccaag ctgggctgtg tgcacgaacc ccccgttcag cccgaccgct gcgccttatc   19200
cggtaactat cgtcttgagt ccaacccggt aagacacgac ttatcgccac tggcagcagc   19260
cactggtaac aggattagca gagcgaggta tgtaggcggt gctacagagt tcttgaagtg   19320
gtggcctaac tacggctaca ctagaagaac agtatttggt atctgcgctc tgctgaagcc   19380
agttaccttc ggaaaaagag ttggtagctc ttgatccggc aaacaaacca ccgctggtag   19440
cggtggtttt tttgtttgca agcagcagat tacgcgcaga aaaaaaggat ctcaagaaga   19500
tcctttgatc ttttctacgg ggtctgacgc tcagtggaac gaaaactcac gttaagggat   19560
tttggtcatg agattatcaa aaaggatctt cacctagatc cttttgatcc ggaatta     19617
```

```
<210> SEQ ID NO 6
<211> LENGTH: 55
<212> TYPE: DNA
<213> ORGANISM: Artificial Sequence
<220> FEATURE:
<223> OTHER INFORMATION: target sequence for the TALEN of 22808

<400> SEQUENCE: 6
tccagggtca acgtggagac agggaggtac gaaccggtga ctggcgaagg aagca       55

<210> SEQ ID NO 7
<211> LENGTH: 15722
<212> TYPE: DNA
<213> ORGANISM: Artificial Sequence
<220> FEATURE:
```

```
<223> OTHER INFORMATION: vector 23123
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
<223> OTHER INFORMATION: xZmPLAIIA
<220> FEATURE:
<221> NAME/KEY: misc_feature
<222> LOCATION: (6927)..(7031)
<223> OTHER INFORMATION: rsgRNAZmPLAIIA02
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01
<220> FEATURE:
<221> NAME/KEY: misc_feature
<222> LOCATION: (13822)..(14226)
<223> OTHER INFORMATION: oVS1-02
<220> FEATURE:
<221> NAME/KEY: misc_feature
<222> LOCATION: (14904)..(15710)
<223> OTHER INFORMATION: oCOLE-06

<400> SEQUENCE: 7
attcctgtgg ttggcatgca catacaaatg gacgaacgga taaacctttt cacgcccttt        60
taaatatccg attattctaa taaacgctct tttctcttag gtttacccgc caatatatcc       120
```

-continued

```
tgtcaaacac tgatagttta aactgaaggc gggaaacgac aatctgatca tgagcggaga      180
attaagggag tcacgttatg accccgccg atgacgcggg acaagccgtt ttacgtttgg      240
aactgacaga accgcaacgc tgcaggaatt ggccgcagcg gccatttaaa caaagcttgg      300
taccattatg tggtctaggt aggttctata tataagaaaa cttgaaatgt tctaaaaaaa      360
aattcaagcc catgcatgat tgaagcaaac ggtatagcaa cggtgttaac ctgatctagt      420
gatctcttgc aatccttaac ggccacctac cgcaggtagc aaacggcgtc cccctcctcg      480
atatctccgc ggcgacctct ggcttttttcc gcggaattgc gcggtgggga cggattccac      540
gagaccgcga cgcaaccgcc tctcgccgct gggccccaca ccgctcggtg ccgtagcctc      600
acgggactct ttctccctcc tccccgtta taaattggct tcatcccctc cttgcctcat      660
ccatccaaat cccagtcccc aatcccatcc cttcgtagga gaaattcatc gaagctaagc      720
gaatcctcgc gatcctctca aggtactgcg agttttcgat cccctctcg accctcgta      780 tgtttgtgtt tgtcgtagcg tttgattagg tatgctttcc ctgtttgtgt tcgtcgtagc      840
gtttgattag gtatgctttc cctgttcgtg ttcatcgtag tgtttgatta ggtcgtgtga      900
ggcgatggcc tgctcgcgtc cttcgatctg tagtcgattt gcgggtcgtg gtgtagatct      960
gcgggctgtg atgaagttat ttggtgtgat ctgctcgcct gattctgcgg gttggctcga     1020
gtagatatga tggttggacc ggttggttcg tttaccgcgc tagggttggg ctgggatgat     1080
gttgcatgcg ccgttgcgcg tgatcccgca gcaggacttg cgtttgattg ccagatctcg     1140
ttacgattat gtgatttggt ttggactttt tagatctgta gcttctgctt atgtgccaga     1200
tgcgcctact gctcatatgc ctgatgataa tcataaatgg ctgtggaact aactagttga     1260
ttgcggagtc atgtatcagc tacaggtgta gggactagct acaggtgtag ggacttgcgt     1320
ctaattgttt ggtcctttac tcatgttgca attatgcaat ttagtttaga ttgtttgttc     1380
cactcatcta ggctgtaaaa gggacactgc ttagattgct gtttaatctt tttagtagat     1440
tatattatat tggtaactta ttaccctat tacatgccat acgtgacttc tgctcatgcc     1500
tgatgataat catagatcac tgtggaatta attagttgat tgttgaatca tgtttcatgt     1560
acataccacg gcacaattgc ttagttcctt aacaaatgca aattttactg atccatgtat     1620
gatttgcgtg gttctctaat gtgaaatact atagctactt gttagtaaga atcaggttcg     1680
tatgcttaat gctgtatgtg ccttctgctc atgcctgatg ataatcatat atcactggaa     1740
ttaattagtt gatcgtttaa tcatatatca agtacatacc atgccacaat ttttagtcac     1800
ttaacccatg cagattgaac tggtccctgc atgtttttgct aaattgttct attctgatta    1860
gaccatatat catgtatttt ttttttggtaa tggttctctt attttaaatg ctatatagtt    1920
ctggtacttg ttagaaagat ctgcttcata gtttagttgc ctatccctcg aattaggatg     1980
ctgagcagct gatcctatag ctttgtttca tgtatcaatt cttttgtgtt caacagtcag     2040 ttttttgttag attcattgta acttatggtc gcttactctt ctggtcctca atgcttgcag    2100
gatcgcggcc gctcatatgg acaagaagta cagcatcggc ctggacatcg gcaccaacag     2160
cgtgggctgg gccgtgatca ccgacgagta caaggtgccg agcaagaagt tcaaggtgct     2220
gggcaacacc gacaggcaca gcatcaagaa gaacctgatc ggcgccctgc tgttcgacag     2280
cggcgagacc gccgaggcca ccaggctgaa gaggaccgcc aggaggaggt acaccaggag     2340
gaagaacagg atctgctacc tgcaggagat cttcagcaac gagatggcca aggtggacga     2400
cagcttcttc cacaggctgg aggagagctt cctggtggag gaggacaaga gcacgagag     2460
```

-continued

```
gcacccgatc ttcggcaaca tcgtggacga ggtggcctac cacgagaagt acccgaccat   2520
ctaccacctg aggaagaagc tggtggacag caccgacaag gccgacctga ggctgatcta   2580
cctggccctg gcccacatga tcaagttcag gggccacttc ctgatcgagg gcgacctgaa   2640
cccggacaac agcgacgtgg acaagctgtt catccagctg gtgcagacct acaaccagct   2700
gttcgaggag aacccgatca cgccagcgg cgtggacgcc aaggccatcc tgagcgccag   2760
gctgagcaag agcaggaggc tggagaacct gatcgcccag ctgccgggcg agaagaagaa   2820
cggcctgttc ggcaacctga tcgccctgag cctgggcctg accccgaact tcaagagcaa   2880
cttcgacctg gccgaggacg ccaagctgca gctgagcaag gacacctacg acgacgacct   2940
ggacaacctg ctggcccaga tcggcgacca gtacgccgac ctgttcctgg ccgccaagaa   3000
cctgagcgac gccatcctgc tgagcgacat cctgagggtg aacaccgaga tcaccaaggc   3060
cccgctgagc gccagcatga tcaagaggta cgacgagcac caccaggacc tgaccctgct   3120
gaaggccctg gtgaggcagc agctgccgga gaagtacaag gagatcttct tcgaccagag   3180
caagaacggc tacgccggct acatcgacgg cggcgccagc caggaggagt tctacaagtt   3240
catcaagccg atcctggaga agatggacgg caccgaggag ctgctggtga agctgaacag   3300
ggaggacctg ctgaggaagc agaggacctt cgacaacggc agcatcccgc accagatcca   3360
cctgggcgag ctgcacgcca tcctgaggag gcaggaggac ttctacccgt tcctgaagga   3420
caacagggag aagatcgaga agatcctgac cttccgcatc ccgtactacg tgggcccgct   3480
ggccaggggc aacagcaggt tcgcctggat gaccaggaag agcgaggaga ccatcacccc   3540
gtggaacttc gaggaggtgg tggacaaggg cgccagcgcc cagagcttca tcgagaggat   3600
gaccaacttc gacaagaacc tgccgaacga gaaggtgctg ccgaagcaca gcctgctgta   3660
cgagtacttc accgtgtaca acgagctgac caaggtgaag tacgtgaccg agggcatgag   3720
gaagccggcc ttcctgagcg gcgagcagaa gaaggccatc gtggacctgc tgttcaagac   3780
caacaggaag gtgaccgtga agcagctgaa ggaggactac ttcaagaaga tcgagtgctt   3840
cgacagcgtg gagatcagcg gcgtggagga caggttcaac gccagcctgg gcacctacca   3900
cgacctgctg aagatcatca ggacaaggga cttcctggac aacgaggaga cgaggacat   3960 cctggaggac atcgtgctga ccctgaccct gttcgaggac agggagatga tcgaggagag   4020
gctgaagacc tacgcccacc tgttcgacga caaggtgatg aagcagctga agaggaggag   4080
gtacaccggc tggggcaggc tgagcaggaa gctgatcaac ggcatcaggg acaagcagag   4140
cggcaagacc atcctggact tcctgaagag cgacggcttc gccaacagga acttcatgca   4200
gctgatccac gacgacagcc tgaccttcaa ggaggacatc cagaaggccc aggtgagcgg   4260
ccagggcgac agcctgcacg agcacatcgc caacctggcc ggcagcccgg ccatcaagaa   4320
gggcatcctg cagaccgtga aggtggtgga cgagctggtg aaggtgatgg caggcacaa   4380 gccgagaac atcgtgatcg agatggccag ggagaaccag accacccaga agggccagaa   4440
gaacagcagg gagaggatga gaggatcga ggagggcatc aaggagctgg gcagccagat   4500
cctgaaggag caccggtgg agaacaccca gctgcagaac gagaagctgt acctgtacta   4560
cctgcagaac ggcagggaca tgtacgtgga ccaggagctg gacatcaaca ggctgagcga   4620
ctacgacgtg gaccacatcg tgccgcagag cttcctgaag gacgacagca tcgacaacaa   4680
ggtgctgacc aggagcgaca gaacagggg caagagcgac aacgtgccga gcgaggaggt   4740
ggtgaagaag atgaaaaact actgagagca gctgctgaac gccaagctga tcacccagag   4800
gaagttcgac aacctgacca aggccgagag gggcggcctg agcgagctgg acaaggccgg   4860
```

```
cttcattaaa aggcagctgg tggagaccag gcagatcacc aagcacgtgg cccagatcct    4920
ggacagcagg atgaacacca agtacgacga gaacgacaag ctgatcaggg aggtgaaggt    4980
gatcaccctg aagagcaagc tggtgagcga cttcaggaag gacttccagt tctacaaggt    5040
gagggagatc aataattacc accacgccca cgacgcctac ctgaacgccg tggtgggcac    5100
cgccctgatt aaaaagtacc cgaagctgga gagcgagttc gtgtacggcg actacaaggt    5160
gtacgacgtg aggaagatga tcgccaagag cgagcaggat atcggcaagg ccaccgccaa    5220
gtacttcttc tacagcaaca tcatgaactt cttcaagacc gagatcaccc tggccaacgg    5280
cgagatcagg aagaggccgc tgatcgagac caacggcgag accggcgaga tcgtgtggga    5340
caagggcagg gacttcgcca ccgtgaggaa ggtgctgtcc atgccgcagg tgaacatcgt    5400
gaagaagacc gaggtgcaga ccggcggctt cagcaaggag agcatcctgc cgaagaggaa    5460
cagcgacaag ctgatcgcca ggaagaagga ctgggacccg aagaagtacg gcggcttcga    5520
cagcccgacc gtggcctaca gcgtgctggt ggtggccaag gtggagaagg gcaagagcaa    5580
gaagctgaag agcgtgaagg agctggtggg catcaccatc atggagagga gcagcttcga    5640
gaagaaccca gtggacttcc tggaggccaa gggctacaag gaggtgaaga aggacctgat    5700
cattaaactg ccgaagtaca gcctgttcga gctggagaac ggcaggaaga ggatgctggc    5760
cagcgccggc gagctgcaga agggcaacga gctggccctg ccgagcaagt acgtgaactt    5820
cctgtacctg gccagccact acgagaagct gaagggcagc ccggaggaca cgagcagaa    5880 gcagctgttc gtggagcagc acaagcacta cctggacgag atcatcgagc agatcagcga    5940
gttcagcaag agggtgatcc tggccgacgc caacctggac aaggtgctga gcgcctacaa    6000
caagcacagg gacaagccga tcagggagca ggccgagaac atcatccacc tgttcacccct    6060 gaccaacctg ggcgccccgg ccgccttcaa gtacttcgac accaccatcg acaggaagag    6120
gtacaccagc accaaggagg tgctggacgc caccctgatc caccagagca tcaccggcct    6180
gtacgagacc aggatcgacc tgagccagct gggcggcgac agcagcccgc cgaagaagaa    6240
gaggaaggtg agctggaagg acgccagcgg ctggagcagg atgtgaagct tgatcgttca    6300
aacatttggc aataaagttt cttaagattg aatcctgttg ccggtcttgc gatgattatc    6360
atataatttc tgttgaatta cgttaagcat gtaataatta acatgtaatg catgacgtta    6420
tttatgagat gggtttttat gattagagtc ccgcaattat acatttaata cgcgatagaa    6480
aacaaaatat agcgcgcaaa ctaggataaa ttatcgcgcg cggtgtcatc tatgttacta    6540
gatcttcgaa gggatcttta aacatacgaa cagatcactt aaagttcttc tgaagcaact    6600
taaagttatc aggcatgcat ggatcttgga ggaatcagat gtgcagtcag ggaccatagc    6660
acaggacagg cgtcttctac tggtgctacc agcaaatgct ggaagccggg aacactgggt    6720
acgttggaaa ccacgtgatg tggagtaaga taaactgtag gagaaaagca tttcgtagtg    6780
ggccatgaag cctttcagga catgtattgc agtatgggcc ggcccattac gcaattggac    6840
gacaacaaag actagtatta gtaccacctc ggctatccac atagatcaaa gctggtttaa    6900
aagagttgtg cagatgatcc gtggcagggt caacgtggag acaggggttt tagagctaga    6960
aatagcaagt taaaataagg ctagtccgtt atcaacttga aaaagtggca ccgagtcggt    7020
gctttttttt tcggaccgcg cctgcagtgc agcgtgaccc ggtcgtgccc ctctctagag    7080
ataatgagca ttgcatgtct aagttataaa aaattaccac atattttttt tgtcacactt    7140
gtttgaagtg cagtttatct atctttatac atatatttaa actttactct acgaataata    7200
```

-continued

```
taatctatag tactacaata atatcagtgt tttagagaat catataaatg aacagttaga    7260
catggtctaa aggacaattg agtattttga caacaggact ctacagtttt atctttttag    7320
tgtgcatgtg ttctcctttt tttttgcaaa tagcttcacc tatataatac ttcatccatt    7380
ttattagtac atccatttag ggtttagggt taatggtttt tatagactaa tttttttagt    7440
acatctattt tattctattt tagcctctaa attaagaaaa ctaaaactct attttagttt    7500
ttttatttaa taatttagat ataaaataga ataaaataaa gtgactaaaa attaaacaaa    7560
taccctttaa gaaattaaaa aaactaagga aacatttttc ttgtttcgag tagataatgc    7620
cagcctgtta aacgccgtcg acgagtctaa cggacaccaa ccagcgaacc agcagcgtcg    7680
cgtcgggcca agcgaagcag acggcacggc atctctgtcg ctgcctctgg acccctctcg    7740
agagttccgc tccaccgttg gacttgctcc gctgtcggca tccagaaatt gcgtggcgga    7800
gcggcagacg tgagccggca cggcaggcgg cctcctcctc ctctcacggc accggcagct    7860
acgggggatt cctttcccac cgctccttcg cttttccttc ctcgcccgcc gtaataaata    7920 gacacccct ccacaccctc tttccccaac ctcgtgttgt tcggacgca cacacacaca     7980 accagatctc ccccaaatcc acccgtcggc acctccgctt caaggtacgc cgctcgtcct    8040
cccccccccc cctctctacc ttctctagat cggcgttccg gtccatggtt agggcccggt    8100
agttctactt ctgttcatgt ttgtgttaga tccgtgtttg tgttagatcc gtgctgctag    8160
cgttcgtaca cggatgcgac ctgtacgtca gacacgttct gattgctaac ttgccagtgt    8220
ttctctttgg ggaatcctgg gatggctcta gccgttccgc agacgggatc gatttcatga    8280 tttttttgt ttcgttgcat agggtttggt ttgccctttt cctttatttc aatatatgcc     8340
gtgcacttgt ttgtcgggtc atcttttcat gctttttttt gtcttggttg tgatgatgtg    8400
gtctggttgg gcggtcgttc tagatcggag tagaattctg tttcaaacta cctggtggat    8460
ttattaattt tggatctgta tgtgtgtgcc atacatattc atagttacga attgaagatg    8520
atggatggaa atatcgatct aggataggta tacatgttga tgcgggtttt actgatgcat    8580
atacagagat gcttttttgtt cgcttggttg tgatgatgtg gtgtggttgg gcggtcgttc   8640
attcgttcta gatcggagta gaatactgtt tcaaactacc tggtgtattt attaatttttg   8700 gaactgtatg tgtgtgtcat acatcttcat agttacgagt ttaagatgga tggaaatatc    8760
gatctaggat aggtatacat gttgatgtgg gttttactga tgcatataca tgatggcata    8820
tgcagcatct attcatatgc tctaaccttg agtacctatc tattataata aacaagtatg    8880
ttttataatt attttgatct tgatatactt ggatgatggc atatgcagca gctatatgtg    8940 gatttttta gccctgcctt catacgctat ttatttgctt ggtactgttt cttttgtcga     9000
tgctcaccct gttgtttggt gttacttctg cagggatccg gcagcagcca tgcagaagct    9060
gatcaacagc gtgcagaact acgcctgggg cagcaagacc gccctgaccg agctgtacgg    9120
catggagaac cccagcagcc agcccatggc cgagctgtgg atgggcgccc accccaagag    9180
cagcagccgc gtgcagaacg ccgccggcga catcgtgagc ctgcgcgacg tgatcgagag    9240
cgacaagagc accctgctgg gcgaggccgt ggccaagcgc ttcggcgagc tgcccttcct    9300
gttcaaggtg ctgtgcgccg cccagcccct gagcatccag gtgcacccca caagcacaa     9360 cagcgagatc ggcttcgcca aggagaacgc cgccggcatc cccatggacg ccgccgagcg    9420
caactacaag gaccccaacc acaagcccga gctggtgttc gccctgaccc ccttcctggc    9480
catgaacgcc ttccgcgagt tcagcgagat cgtgagcctg ctgcagcccg tggccggcgc    9540
ccaccccgcc atcgcccact tcctgcagca gcccgacgcc gagcgcctga gcgagctgtt    9600
```

-continued

```
cgccagcctg ctgaacatgc agggcgagga gaagagccgc gccctggcca tcctgaagag   9660
cgccctggac agccagcagg gcgagccctg gcagaccatc cgcctgatca gcgagttcta   9720
ccccgaggac agcggcctgt tcagcccccct gctgctgaac gtggtgaagc tgaaccccgg   9780
cgaggccatg ttcctgttcg ccgagacccc ccacgcctac ctgcagggcg tggccctgga   9840
ggtgatggcc aacagcgaca acgtgctgcg cgccggcctg accccccaagt acatcgacat   9900 ccccgagctg gtggccaacg tgaagttcga ggccaagccc gccaaccagc tgctgaccca   9960
gcccgtgaag cagggcgccg agctggactt ccccatcccc gtggacgact tcgccttcag  10020
cctgcacgac ctgagcgaca aggagaccac catcagccag cagagcgccg ccatcctgtt  10080
ctgcgtggag ggcgacgcca ccctgtggaa gggcagccag cagctgcagc tgaagcccgg  10140
cgagagcgcc ttcatcgccg ccaacgagag ccccgtgacc gtgaagggcc acggccgcct  10200
ggcccgcgtg tacaacaagc tgtgatagga gctcgatccg tcgacctgca gatcgttcaa  10260
acatttggca ataaagtttc ttaagattga atcctgttgc cggtcttgcg atgattatca  10320
tataatttct gttgaattac gttaagcatg taataattaa catgtaatgc atgacgttat  10380
ttatgagatg ggtttttatg attagagtcc cgcaattata catttaatac gcgatagaaa  10440
acaaaatata gcgcgcaaac taggataaat tatcgcgcgc ggtgtcatct atgttactag  10500
atcggcgcgc cgcaattgaa gtttgggcgg ccagcatggc cgtatccgca atgtgttatt  10560
aagttgtcta agcgtcaatt tgtttacacc acaatatatc ctgccaccag ccagccaaca  10620
gctccccgac cggcagctcg gcacaaaatc accactcgat acaggcagcc catcagaatt  10680
aattctcatg tttgacagct tatcatcgac tgcacggtgc accaatgctt ctggcgtcag  10740
gcagccatcg gaagctgtgg tatggctgtg caggtcgtaa atcactgcat aattcgtgtc  10800
gctcaaggcg cactcccgtt ctggataatg ttttttgcgc cgacatcata acggttctgg  10860
caaatattct gaaatgagct gttgacaatt aatcatccgg ctcgtataat gtgtggaatt  10920
gtgagcggat aacaatttca cacaggaaac agaccatgag ggaagcgttg atcgccgaag  10980
tatcgactca actatcagag gtagttggcg tcatcgagcg ccatctcgaa ccgacgttgc  11040
tggccgtaca tttgtacggc tccgcagtgg atggcggcct gaagccacac agtgatattg  11100
atttgctggt tacggtgacc gtaaggcttg atgaaacaac gcggcgagct ttgatcaacg  11160 acctttgga aacttcggct tcccctggag agagcgagat tctccgcgct gtagaagtca  11220
ccattgttgt gcacgacgac atcattccgt ggcgttatcc agctaagcgc gaactgcaat  11280
ttggagaatg gcagcgcaat gacattcttg caggtatctt cgagccagcc acgatcgaca  11340
ttgatctggc tatcttgctg acaaaagcaa gagaacatag cgttgccttg gtaggtccag  11400
cggcggagga actctttgat ccggttcctg aacaggatct atttgaggcg ctaaatgaaa  11460
ccttaacgct atggaactcg ccgcccgact gggctggcga tgagcgaaat gtagtgctta  11520
cgttgtcccg catttggtac agcgcagtaa ccggcaaaat cgcgccgaag gatgtcgctg  11580
ccgactgggc aatggagcgc ctgccggccc agtatcagcc cgtcatactt gaagctaggc  11640
aggcttatct tggacaagaa gatcgcttgg cctcgcgcgc agatcagttg gaagaatttg  11700
ttcactacgt gaaaggcgag atcaccaaag tagtcggcaa ataaagctct agtggatctc  11760
cgtacccggg gatctggctc gcggcggacg cacgacgccg gggcgagacc ataggcgatc  11820
tcctaaatca atagtagctg taacctcgaa gcgtttcact tgtaacaacg attgagaatt  11880
tttgtcataa aattgaaata cttggttcgc atttttgtca tccgcggtca gccgcaattc  11940
```

-continued

```
tgacgaactg cccatttagc tggagatgat tgtacatcct tcacgtgaaa atttctcaag    12000
cgctgtgaac aagggttcag attttagatt gaaaggtgag ccgttgaaac acgttcttct    12060
tgtcgatgac gacgtcgcta tgcggcatct tattattgaa taccttacga tccacgcctt    12120
caaagtgacc gcggtagccg acagcaccca gttcacaaga gtactctctt ccgcgacggt    12180
cgatgtcgtg gttgttgatc tagatttagg tcgtgaagat gggctcgagc taggagcaag    12240
tgattttatc gctaagccgt tcagtatcag agagtttcta gcacgcattc gggttgcctt    12300
gcgcgtgcgc cccaacgttg tccgctccaa agaccgacgg tcttttttgtt ttactgactg    12360 gacacttaat ctcaggcaac gtcgcttgat gtccgaagct ggcggtgagg tgaaacttac    12420
ggcaggtgag ttcaatcttc tcctcgcgtt tttagagaaa ccccgcgacg ttctatcgcg    12480
cgagcaactt ctcattgcca gtcgagtacg cgacgaggag gtttatgaca ggagtataga    12540
tgttctcatt ttgaggctgc gccgcaaact tgaggcagat ccgtcaagcc ctcaactgat    12600
aaaaacagca agaggtgccg gttatttctt tgacgcggac gtgcaggttt cgcacggggg    12660
gacgatggca gcctgagcca attcccagat ccccgaggaa tcggcgtgag cggtcgcaaa    12720
ccatccggcc cggtacaaat cggcgcggcg ctgggtgatg acctggtgga gaagttgaag    12780
gccgcgcagg ccgcccagcg gcaacgcatc gaggcagaag cacgccccgg tgaatcgtgg    12840
caagcggccg ctgatcgaat ccgcaaagaa tcccggcaac cgccggcagc cggtgcgccg    12900
tcgattagga agccgcccaa gggcgacgag caaccagatt ttttcgttcc gatgctctat    12960
gacgtgggca cccgcgatag tcgcagcatc atggacgtgg ccgtttttccg tctgtcgaag    13020 cgtgaccgac gagctggcga ggtgatccgc tacgagcttc cagacgggca cgtagaggtt    13080
tccgcagggc cggccggcat ggccagtgtg tgggattacg acctggtact gatggcggtt    13140
tcccatctaa ccgaatccat gaaccgatac cgggaaggga agggagacaa gcccggccgc    13200
gtgttccgtc cacacgttgc ggacgtactc aagttctgcc ggcgagccga tggcggaaag    13260
cagaaagacg acctggtaga aacctgcatt cggttaaaca ccacgcacgt tgccatgcag    13320
cgtacgaaga aggccaagaa cggccgcctg gtgacggtat ccgagggtga agccttgatt    13380
agccgctaca agatcgtaaa gagcgaaacc gggcggccgg agtacatcga gatcgagcta    13440
gctgattgga tgtaccgcga gatcacagaa ggcaagaacc cggacgtgct gacggttcac    13500
cccgattact ttttgatcga tcccggcatc ggccgttttc tctaccgcct ggcacgccgc    13560
gccgcaggca aggcagaagc cagatggttg ttcaagacga tctacgaacg cagtggcagc    13620
gccggagagt tcaagaagtt ctgtttcacc gtgcgcaagc tgatcgggtc aaatgacctg    13680
ccggagtacg atttgaagga ggaggcgggg caggctggcc cgatcctagt catgcgctac    13740
cgcaacctga tcgagggcga agcatccgcc ggttcctaat gtacggagca gatgctaggg    13800
caaattgccc tagcagggga aaaaggtcga aaaggtctct ttcctgtgga tagcacgtac    13860
attgggaacc caaagccgta cattgggaac cggaacccgt acattgggaa cccaaagccg    13920
tacattggga accggtcaca catgtaagtg actgatataa aagagaaaaa aggcgatttt    13980
tccgcctaaa actctttaaa acttattaaa actcttaaaa cccgcctggc ctgtgcataa    14040
ctgtctggcc agcgcacagc cgaagagctg caaaaagcgc ctacccttcg gtcgctgcgc    14100
tccctacgcc ccgccgcttc gcgtcggcct atcgcggccg ctggccgctc aaaaatggct    14160
ggcctacggc caggcaatct accagggcgc ggacaagccg cgccgtcgcc actcgaccgc    14220
cggcgctgag gtctgcctcg tgaagaaggt gttgctgact cataccaggc ctgaatcgcc    14280
ccatcatcca gccagaaagt gagggagcca cggttgatga gagctttgtt gtaggtggac    14340
```

```
cagttggtga ttttgaactt ttgctttgcc acggaacggt ctgcgttgtc gggaagatgc    14400
gtgatctgat ccttcaactc agcaaaagtt cgatttattc aacaaagccg ccgtcccgtc    14460
aagtcagcgt aatgctctgc cagtgttaca accaattaac caattctgat tagaaaaact    14520
catcgagcat caaatgaaac tgcaatttat tcatatcagg attatcaata ccatattttt    14580
gaaaaagccg tttctgtaat gaaggagaaa actcaccgag gcagttccat aggatggcaa    14640
gatcctggta tcggtctgcg attccgactc gtccaacatc aatacaacct attaatttcc    14700
cctcgtcaaa aataaggtta tcaagtgaga aatcaccatg agtgacgact gaatccggtg    14760
agaatggcaa aagctctgca ttaatgaatc ggccaacgcg cggggagagg cggtttgcgt    14820
attgggcgct cttccgcttc ctcgctcact gactcgctgc gctcggtcgt tcggctgcgg    14880
cgagcggtat cagctcactc aaaggcggta atacggttat ccacagaatc aggggataac    14940
gcaggaaaga acatgtgagc aaaaggccag caaaaggcca ggaaccgtaa aaaggccgcg    15000
ttgctggcgt ttttccatag gctccgcccc cctgacgagc atcacaaaaa tcgacgctca    15060
agtcagaggt ggcgaaaccc gacaggacta taaagatacc aggcgtttcc ccctggaagc    15120
tccctcgtgc gctctcctgt tccgaccctg ccgcttaccg gatacctgtc cgcctttctc    15180
ccttcgggaa gcgtggcgct ttctcatagc tcacgctgta ggtatctcag ttcggtgtag    15240
gtcgttcgct ccaagctggg ctgtgtgcac gaacccccg ttcagcccga ccgctgcgcc    15300
ttatccggta actatcgtct tgagtccaac ccggtaagac acgacttatc gccactggca    15360
gcagccactg gtaacaggat tagcagagcg aggtatgtag gcggtgctac agagttcttg    15420
aagtggtggc ctaactacgg ctacactaga agaacagtat ttggtatctg cgctctgctg    15480
aagccagtta ccttcggaaa aagagttggt agctcttgat ccggcaaaca aaccaccgct    15540
ggtagcggtg gtttttttgt ttgcaagcag cagattacgc gcagaaaaaa aggatctcaa    15600
gaagatcctt tgatcttttc tacggggtct gacgctcagt ggaacgaaaa ctcacgttaa    15660
gggattttgg tcatgagatt atcaaaaagg atcttcacct agatcctttt gatccggaat    15720
ta                                                                   15722
```

<210> SEQ ID NO 8
<211> LENGTH: 20
<212> TYPE: DNA
<213> ORGANISM: Artificial Sequence
<220> FEATURE:
<223> OTHER INFORMATION: for editing MTL

<400> SEQUENCE: 8

```
gggtcaacgt ggagacaggg                                                       20
```

<210> SEQ ID NO 9
<211> LENGTH: 41
<212> TYPE: DNA
<213> ORGANISM: Zea mays

<400> SEQUENCE: 9

```
agggtcaacg tggagacagg gaggtacgaa ccggtgactg g                                41
```

<210> SEQ ID NO 10
<211> LENGTH: 45
<212> TYPE: DNA
<213> ORGANISM: Zea mays

<400> SEQUENCE: 10

-continued agggtcaacg tggagacagg cgaggaggta cgaaccggtg actgg                              45

<210> SEQ ID NO 11
<211> LENGTH: 42
<212> TYPE: DNA
<213> ORGANISM: Artificial Sequence
<220> FEATURE:
<223> OTHER INFORMATION: mutated MTL

<400> SEQUENCE: 11
agggtcaacg tggagacaag ggaggtacga accggtgact gg                                 42

<210> SEQ ID NO 12
<211> LENGTH: 28
<212> TYPE: DNA
<213> ORGANISM: Artificial Sequence
<220> FEATURE:
<223> OTHER INFORMATION: mutated MTL portion

<400> SEQUENCE: 12
agggtcaacg tggagaaccg gtgactgg                                                 28

<210> SEQ ID NO 13
<211> LENGTH: 40
<212> TYPE: DNA
<213> ORGANISM: Artificial Sequence
<220> FEATURE:
<223> OTHER INFORMATION: mutated MTL portion

<400> SEQUENCE: 13
agggtcaacg tggagacggg aggtacgaac cggtgactgg                                    40

<210> SEQ ID NO 14
<211> LENGTH: 28
<212> TYPE: DNA
<213> ORGANISM: Artificial Sequence
<220> FEATURE:
<223> OTHER INFORMATION: mutated MTL portion

<400> SEQUENCE: 14
agggtcaacg tggagaaccg gtgactgg                                                 28

<210> SEQ ID NO 15
<211> LENGTH: 42
<212> TYPE: DNA
<213> ORGANISM: Artificial Sequence
<220> FEATURE:
<223> OTHER INFORMATION: mutated MTL portion

<400> SEQUENCE: 15
agggtcaacg tggagacaag ggaggtacga accggtgact gg                                 42

<210> SEQ ID NO 16
<211> LENGTH: 40
<212> TYPE: DNA
<213> ORGANISM: Artificial Sequence
<220> FEATURE:
<223> OTHER INFORMATION: mutated MTL portion

<400> SEQUENCE: 16
agggtcaacg tggagacggg aggtacgaac cggtgactgg                                    40

<210> SEQ ID NO 17
<211> LENGTH: 41
<212> TYPE: DNA
<213> ORGANISM: Artificial Sequence -continued

```
<220> FEATURE:
<223> OTHER INFORMATION: unmutated MTL portion

<400> SEQUENCE: 17
agggtcaacg tggagacagg gaggtacgaa ccggtgactg g                      41

<210> SEQ ID NO 18
<211> LENGTH: 28
<212> TYPE: DNA
<213> ORGANISM: Artificial Sequence
<220> FEATURE:
<223> OTHER INFORMATION: mutated MTL portion

<400> SEQUENCE: 18
agggtcaacg tggagaaccg gtgactgg                                     28

<210> SEQ ID NO 19
<211> LENGTH: 1371
<212> TYPE: DNA
<213> ORGANISM: Zea mays

<400> SEQUENCE: 19
agttcatcac taatcacact tattgttccc tcgacgagta tctagctagc tcattaatcg    60
atcaatcggg gtgtgcggtc gaaggcggca atggcgagct actcgtcgcg gcgtccatgc   120
aatacctgta gcacgaaggc gatggccggg agcgtggtcg gcgagcccgt cgtgctgggg   180
cagagggtga cggtgctgac ggtggacggc ggcggcgtcc ggggtctcat cccgggaacc   240
atcctcgcct tcctcgaggc caggctgcag gagctggacg gaccggaggc gaggctggcg   300
gactacttcg actacatcgc cggaaccagc accggcggtc tcatcaccgc catgctcacc   360
gcgcccggca aggacaagcg gcctctctac gctgccaagg acatcaacca cttttacatg   420
gagaactgcc cgcgcatctt ccctcagaag agcaggcttg cggccgccat gtccgcgctg   480
aggaagccaa agtacaacgg caagtgcatg cgcagcctga ttaggagcat cctcggcgag   540
acgagggcca agagcacgcc tctgaagaac gctctgctct cggacgtgtg cattggcacg   600
tccgccgcgc cgacctacct cccggcgcac tacttccaga ctgaagacgc caacggcaag   660
gagcgcgaat acaacctcat cgacggcggt gtggcggcca caaacccgac gatggttgcg   720
atgacgcaga tcaccaaaaa gatgcttgcc agcaaggaca aggccgagga gctgtaccca   780
gtgaagccgt cgaactgccg caggttcctg gtgctgtcca tcgggacggg gtcgacgtcc   840
gagcagggcc tctacacggc gcggcagtgc tcccggtggg gtatctgccg gtggctccgc   900
aacaacggca tggcccccat catcgacatc ttcatggcgg ccagctcgga cctggtggac   960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acagggaggt acgaaccggt gactggcgaa ggaagcaatg ccgatgccct cggtgggctc  1200
gctaggcagc tctccgagga gaggagaaca aggctcgcgc gccgcgtgtc tgccatcaac  1260
ccaagaggct ctagatgtgc gtcgtacgat atctaagaca agtggcttta ctgtcagtca  1320
catgcttgta aataagtaga ctttatttta ataaaacata aaaatatata t           1371

<210> SEQ ID NO 20
<211> LENGTH: 15722
<212> TYPE: DNA
<213> ORGANISM: Artificial Sequence
<220> FEATURE:
```

<223> OTHER INFORMATION: vector 23397
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
<223> OTHER INFORMATION: xZmVLHP
<220> FEATURE:
<221> NAME/KEY: misc_feature
<222> LOCATION: (6927)..(7031)
<223> OTHER INFORMATION: rsgRNAZmVLHP-02
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01
<220> FEATURE:
<221> NAME/KEY: misc_feature
<222> LOCATION: (13822)..(14226)
<223> OTHER INFORMATION: oVS1-02
<220> FEATURE:
<221> NAME/KEY: misc_feature
<222> LOCATION: (14904)..(15710)
<223> OTHER INFORMATION: oCOLE-06

<400> SEQUENCE: 20
attcctgtgg ttggcatgca catacaaatg gacgaacgga taaacctttt cacgcccttt        60
taaatatccg attattctaa taaacgctct tttctcttag gtttacccgc caatatatcc       120

-continued

```
tgtcaaacac tgatagttta aactgaaggc gggaaacgac aatctgatca tgagcggaga       180
attaagggag tcacgttatg acccccgccg atgacgcggg acaagccgtt ttacgtttgg       240
aactgacaga accgcaacgc tgcaggaatt ggccgcagcg gccatttaaa caaagcttgg       300
taccattatg tggtctaggt aggttctata tataagaaaa cttgaaatgt tctaaaaaaa       360
aattcaagcc catgcatgat tgaagcaaac ggtatagcaa cggtgttaac ctgatctagt       420
gatctcttgc aatccttaac ggccacctac cgcaggtagc aaacggcgtc cccctcctcg       480
atatctccgc ggcgacctct ggcttttttcc gcggaattgc gcggtgggga cggattccac       540
gagaccgcga cgcaaccgcc tctcgccgct gggccccaca ccgctcggtg ccgtagcctc       600
acgggactct ttctccctcc tccccgtta taaattggct tcatcccctc cttgcctcat       660
ccatccaaat cccagtcccc aatcccatcc cttcgtagga gaaattcatc gaagctaagc       720
gaatcctcgc gatcctctca aggtactgcg agttttcgat cccctctcg accctcgta        780 tgtttgtgtt tgtcgtagcg tttgattagg tatgctttcc ctgtttgtgt tcgtcgtagc       840
gtttgattag gtatgctttc cctgttcgtg ttcatcgtag tgtttgatta ggtcgtgtga       900
ggcgatggcc tgctcgcgtc cttcgatctg tagtcgattt gcgggtcgtg gtgtagatct       960
gcgggctgtg atgaagttat ttggtgtgat ctgctcgcct gattctgcgg gttggctcga      1020
gtagatatga tggttggacc ggttggttcg tttaccgcgc tagggttggg ctgggatgat      1080
gttgcatgcg ccgttgcgcg tgatcccgca gcaggacttg cgtttgattg ccagatctcg      1140
ttacgattat gtgatttggt ttggactttt tagatctgta gcttctgctt atgtgccaga      1200
tgcgcctact gctcatatgc ctgatgataa tcataaatgg ctgtggaact aactagttga      1260
ttgcggagtc atgtatcagc tacaggtgta gggactagct acaggtgtag ggacttgcgt      1320
ctaattgttt ggtcctttac tcatgttgca attatgcaat ttagtttaga ttgtttgttc      1380
cactcatcta ggctgtaaaa gggacactgc ttagattgct gtttaatctt tttagtagat      1440
tatattatat tggtaactta ttacccctat tacatgccat acgtgacttc tgctcatgcc      1500
tgatgataat catagatcac tgtggaatta attagttgat tgttgaatca tgtttcatgt      1560
acataccacg gcacaattgc ttagttcctt aacaaatgca aattttactg atccatgtat      1620
gatttgcgtg gttctctaat gtgaaatact atagctactt gttagtaaga atcaggttcg      1680
tatgcttaat gctgtatgtg ccttctgctc atgcctgatg ataatcatat atcactggaa      1740
ttaattagtt gatcgtttaa tcatatatca agtacatacc atgccacaat ttttagtcac      1800
ttaacccatg cagattgaac tggtccctgc atgttttgct aaattgttct attctgatta      1860
gaccatatat catgtatttt tttttggtaa tggttctctt attttaaatg ctatatagtt      1920
ctggtacttg ttagaaagat ctgcttcata gtttagttgc ctatccctcg aattaggatg      1980
ctgagcagct gatcctatag ctttgtttca tgtatcaatt cttttgtgtt caacagtcag      2040
tttttgttag attcattgta acttatggtc gcttactctt ctggtcctca atgcttgcag      2100
gatcgcggcc gctcatatgg acaagaagta cagcatcggc ctggacatcg gcaccaacag      2160
cgtgggctgg gccgtgatca ccgacgagta caaggtgccg agcaagaagt tcaaggtgct      2220
gggcaacacc gacaggcaca gcatcaagaa gaacctgatc ggcgccctgc tgttcgacag      2280
cggcgagacc gccgaggcca ccaggctgaa gaggaccgcc aggaggaggt acaccaggag      2340
gaagaacagg atctgctacc tgcaggagat cttcagcaac gagatggcca aggtggacga      2400
cagcttcttc cacaggctgg aggagagctt cctggtggag gaggacaaga agcacgagag      2460
```

-continued

```
gcacccgatc ttcggcaaca tcgtggacga ggtggcctac cacgagaagt acccgaccat    2520
ctaccacctg aggaagaagc tggtggacag caccgacaag gccgacctga ggctgatcta    2580
cctggccctg gcccacatga tcaagttcag gggccacttc ctgatcgagg gcgacctgaa    2640
cccggacaac agcgacgtgg acaagctgtt catccagctg gtgcagacct acaaccagct    2700
gttcgaggag aacccgatca cgccagcgg cgtggacgcc aaggccatcc tgagcgccag    2760
gctgagcaag agcaggaggc tggagaacct gatcgcccag ctgccgggcg agaagaagaa    2820
cggcctgttc ggcaacctga tcgccctgag cctgggcctg accccgaact tcaagagcaa    2880
cttcgacctg gccgaggacg ccaagctgca gctgagcaag gacacctacg acgacgacct    2940
ggacaacctg ctggcccaga tcggcgacca gtacgccgac ctgttcctgg ccgccaagaa    3000
cctgagcgac gccatcctgc tgagcgacat cctgagggtg aacaccgaga tcaccaaggc    3060
cccgctgagc gccagcatga tcaagaggta cgacgagcac caccaggacc tgaccctgct    3120
gaaggccctg gtgaggcagc agctgccgga gaagtacaag gagatcttct tcgaccagag    3180
caagaacggc tacgccggct acatcgacgg cggcgccagc caggaggagt tctacaagtt    3240
catcaagccg atcctggaga agatggacgg caccgaggag ctgctggtga agctgaacag    3300
ggaggacctg ctgaggaagc agaggacctt cgacaacggc agcatcccgc accagatcca    3360
cctgggcgag ctgcacgcca tcctgaggag gcaggaggac ttctacccgt tcctgaagga    3420
caacagggag aagatcgaga agatcctgac cttccgcatc ccgtactacg tgggcccgct    3480
ggccaggggc aacagcaggt tcgcctggat gaccaggaag agcgaggaga ccatcacccc    3540
gtggaacttc gaggaggtgg tggacaaggg cgccagcgcc cagagcttca tcgagaggat    3600
gaccaacttc gacaagaacc tgccgaacga gaaggtgctg ccgaagcaca gcctgctgta    3660
cgagtacttc accgtgtaca acgagctgac caaggtgaag tacgtgaccg agggcatgag    3720
gaagccggcc ttcctgagcg gcgagcagaa gaaggccatc gtggacctgc tgttcaagac    3780
caacaggaag gtgaccgtga agcagctgaa ggaggactac ttcaagaaga tcgagtgctt    3840
cgacagcgtg gagatcagcg gcgtggagga caggttcaac gccagcctgg gcacctacca    3900
cgacctgctg aagatcatca aggacaagga cttcctggac aacgaggaga cgaggacat    3960 cctggaggac atcgtgctga ccctgaccct gttcgaggac agggagatga tcgaggagag    4020
gctgaagacc tacgcccacc tgttcgacga caaggtgatg aagcagctga agaggaggag    4080
gtacaccggc tggggcaggc tgagcaggaa gctgatcaac ggcatcaggg acaagcagag    4140
cggcaagacc atcctggact tcctgaagag cgacggcttc gccaacagga acttcatgca    4200
gctgatccac gacgacagcc tgaccttcaa ggaggacatc cagaaggccc aggtgagcgg    4260
ccagggcgac agcctgcacg agcacatcgc caacctggcc ggcagcccgg ccatcaagaa    4320
gggcatcctg cagaccgtga aggtggtgga cgagctggtg aaggtgatgg gcaggcacaa    4380 gccgagaac atcgtgatcg agatggccag ggagaaccag accacccaga ggggccagaa    4440
gaacagcagg gagaggatga gagaggatcga ggagggcatc aaggagctgg gcagccagat    4500
cctgaaggag caccggtgg agaacaccca gctgcagaac gagaagctgt acctgtacta    4560
cctgcagaac ggcagggaca tgtacgtgga ccaggagctg gacatcaaca ggctgagcga    4620
ctacgacgtg gaccacatcg tgccgcagag cttcctgaag gacgacagca tcgacaacaa    4680
ggtgctgacc aggagcgaca gaacagggg caagagcgac aacgtgccga gcgaggaggt    4740
ggtgaagaag atgaaaaact actgagggca gctgctgaac gccaagctga tcacccagag    4800
gaagttcgac aacctgacca aggccgagag gggcggcctg agcgagctgg acaaggccgg    4860
```

```
cttcattaaa aggcagctgg tggagaccag gcagatcacc aagcacgtgg cccagatcct   4920
ggacagcagg atgaacacca agtacgacga gaacgacaag ctgatcaggg aggtgaaggt   4980
gatcaccctg aagagcaagc tggtgagcga cttcaggaag gacttccagt tctacaaggt   5040
gagggagatc aataattacc accacgccca cgacgcctac ctgaacgccg tggtgggcac   5100
cgccctgatt aaaaagtacc cgaagctgga gagcgagttc gtgtacggcg actacaaggt   5160
gtacgacgtg aggaagatga tcgccaagag cgagcaggag atcggcaagg ccaccgccaa   5220
gtacttcttc tacagcaaca tcatgaactt cttcaagacc gagatcaccc tggccaacgg   5280
cgagatcagg aagaggccgc tgatcgagac caacggcgag accggcgaga tcgtgtggga   5340
caagggcagg gacttcgcca ccgtgaggaa ggtgctgtcc atgccgcagg tgaacatcgt   5400
gaagaagacc gaggtgcaga ccggcggctt cagcaaggag agcatcctgc cgaagaggaa   5460
cagcgacaag ctgatcgcca ggaagaagga ctgggacccg aagaagtacg cggcttcga   5520 cagcccgacc gtggcctaca gcgtgctggt ggtggccaag gtggagaagg caagagcaa   5580 gaagctgaag agcgtgaagg agctggtggg catcaccatc atggagagga gcagcttcga   5640
gaagaaccca gtggacttcc tggaggccaa gggctacaag gaggtgaaga aggacctgat   5700
cattaaactg ccgaagtaca gcctgttcga gctggagaac ggcaggaaga ggatgctggc   5760
cagcgccggc gagctgcaga agggcaacga gctggccctg ccgagcaagt acgtgaactt   5820
cctgtacctg gccagccact acgagaagct gaagggcagc ccggaggaca acgagcagaa   5880
gcagctgttc gtggagcagc acaagcacta cctggacgag atcatcgagc agatcagcga   5940
gttcagcaag agggtgatcc tggccgacgc caacctggac aaggtgctga gcgcctacaa   6000
caagcacagg gacaagccga tcagggagca ggccgagaac atcatccacc tgttcacoct   6060 gaccaacctg ggcgcccegg ccgccttcaa gtacttcgac accaccatcg acaggaagag   6120
gtacaccagc accaaggagg tgctggacgc caccctgatc caccagagca tcaccggcct   6180
gtacgagacc aggatcgacc tgagccagct gggcggcgac agcagcccgc cgaagaagaa   6240
gaggaaggtg agctggaagg acgccagcgg ctggagcagg atgtgaagct tgatcgttca   6300
aacatttggc aataaagttt cttaagattg aatcctgttg ccggtcttgc gatgattatc   6360
atataatttc tgttgaatta cgttaagcat gtaataatta acatgtaatg catgacgtta   6420
tttatgagat gggtttttat gattagagtc ccgcaattat acatttaata cgcgatagaa   6480
aacaaaatat agcgcgcaaa ctaggataaa ttatcgcgcg cggtgtcatc tatgttacta   6540
gatcttcgaa gggatcttta aacatacgaa cagatcactt aaagttcttc tgaagcaact   6600
taaagttatc aggcatgcat ggatcttgga ggaatcagat gtgcagtcag ggaccatagc   6660
acaggacagg cgtcttctac tggtgctacc agcaaatgct ggaagccggg aacactgggt   6720
acgttggaaa ccacgtgatg tggagtaaga taaactgtag gagaaaagca tttcgtagtg   6780
ggccatgaag cctttcagga catgtattgc agtatgggcc ggcccattac gcaattggac   6840
gacaacaaag actagtatta gtaccacctc ggctatccac atagatcaaa gctggtttaa   6900
aagagttgtg cagatgatcc gtggcagctg gagctgagct tccggggttt tagagctaga   6960
aatagcaagt taaaataagg ctagtccgtt atcaacttga aaaagtggca ccgagtcggt   7020
gctttttttt tcggaccgcg cctgcagtgc agcgtgaccc ggtcgtgccc ctctctagag   7080
ataatgagca ttgcatgtct aagttataaa aaattaccac atattttttt tgtcacactt   7140
gtttgaagtg cagtttatct atctttatac atatatttaa actttactct acgaataata   7200
```

-continued

```
taatctatag tactacaata atatcagtgt tttagagaat catataaatg aacagttaga   7260
catggtctaa aggacaattg agtattttga caacaggact ctacagtttt atctttttag   7320
tgtgcatgtg ttctcctttt tttttgcaaa tagcttcacc tatataatac ttcatccatt   7380
ttattagtac atccatttag ggtttagggt taatggtttt tatagactaa ttttttttagt   7440 acatctattt tattctattt tagcctctaa attaagaaaa ctaaaactct attttagttt   7500
ttttatttaa taatttagat ataaaataga ataaaataaa gtgactaaaa attaaacaaa   7560 tacccttttaa gaaattaaaa aaactaagga aacatttttc ttgtttcgag tagataatgc   7620
cagcctgtta aacgccgtcg acgagtctaa cggacaccaa ccagcgaacc agcagcgtcg   7680
cgtcgggcca agcgaagcag acggcacggc atctctgtcg ctgcctctgg acccctctcg   7740
agagttccgc tccaccgttg gacttgctcc gctgtcggca tccagaaatt gcgtggcgga   7800
gcggcagacg tgagccggca cggcaggcgg cctcctcctc ctctcacggc accggcagct   7860
acgggggatt cctttcccac cgctccttcg ctttcccttc ctcgcccgcc gtaataaata   7920 gacacccct ccacaccctc tttccccaac ctcgtgttgt tcggacgcac cacacacaca   7980
accagatctc ccccaaatcc acccgtcggc acctccgctt caaggtacgc cgctcgtcct   8040 ccccccccccc cctctctacc ttctctagat cggcgttccg gtccatggtt agggcccggt   8100
agttctactt ctgttcatgt ttgtgttaga tccgtgtttg tgttagatcc gtgctgctag   8160
cgttcgtaca cggatgcgac ctgtacgtca gacacgttct gattgctaac ttgccagtgt   8220
ttctctttgg ggaatcctgg gatggctcta gccgttccgc agacgggatc gatttcatga   8280
ttttttttgt ttcgttgcat agggtttggt ttgcccttt cctttatttc aatatatgcc   8340
gtgcacttgt ttgtcgggtc atcttttcat gctttttttt gtcttggttg tgatgatgtg   8400
gtctggttgg gcggtcgttc tagatcggag tagaattctg tttcaaacta cctggtggat   8460
ttattaattt tggatctgta tgtgtgtgcc atacatattc atagttacga attgaagatg   8520
atggatggaa atatcgatct aggataggta tacatgttga tgcgggtttt actgatgcat   8580
atacagagat gctttttgtt cgcttggttg tgatgatgtg gtgtggttgg gcggtcgttc   8640
attcgttcta gatcggagta gaatactgtt tcaaactacc tggtgtattt attaattttg   8700
gaactgtatg tgtgtgtcat acatcttcat agttacgagt ttaagatgga tggaaatatc   8760
gatctaggat aggtatacat gttgatgtgg gttttactga tgcatataca tgatggcata   8820
tgcagcatct attcatatgc tctaaccttg agtacctatc tattataata aacaagtatg   8880
ttttataatt attttgatct tgatatactt ggatgatggc atatgcagca gctatatgtg   8940
gattttttta gccctgcctt catacgctat ttatttgctt ggtactgttt cttttgtcga   9000
tgctcaccct gttgtttggt gttacttctg cagggatccg gcagcagcca tgcagaagct   9060
gatcaacagc gtgcagaact acgcctgggg cagcaagacc gccctgaccg agctgtacgg   9120
catggagaac cccagcagcc agcccatggc cgagctgtgg atgggcgccc accccaagag   9180
cagcagccgc gtgcagaacg ccgccggcga catcgtgagc ctgcgcgacg tgatcgagag   9240
cgacaagagc accctgctgg gcgaggccgt ggccaagcgc ttcggcgagc tgcccttcct   9300
gttcaaggtg ctgtgcgccg cccagcccct gagcatccag gtgcacccca acaagcacaa   9360
cagcgagatc ggcttcgcca aggagaacgc cgccggcatc cccatggacg ccgccgagcg   9420
caactacaag gaccccaacc acaagcccga gctggtgttc gccctgaccc ccttcctggc   9480
catgaacgcc ttccgcgagt tcagcgagat cgtgagcctg ctgcagcccg tggccggcgc   9540
ccaccccgcc atcgcccact tcctgcagca gcccgacgcc gagcgcctga gcgagctgtt   9600
```

-continued

```
cgccagcctg ctgaacatgc agggcgagga gaagagccgc gccctggcca tcctgaagag    9660
cgccctggac agccagcagg gcgagccctg gcagaccatc cgcctgatca gcgagttcta    9720
ccccgaggac agcgggcctgt tcagcccct gctgctgaac gtggtgaagc tgaaccccgg    9780
cgaggccatg ttcctgttcg ccgagacccc ccacgcctac ctgcagggcg tggccctgga    9840
ggtgatggcc aacagcgaca acgtgctgcg cgccggcctg acccccaagt acatcgacat    9900
ccccgagctg gtggccaacg tgaagttcga ggccaagccc gccaaccagc tgctgaccca    9960
gcccgtgaag cagggcgccg agctggactt ccccatcccc gtggacgact tcgccttcag    10020
cctgcacgac ctgagcgaca aggagaccac catcagccag cagagcgccg ccatcctgtt    10080
ctgcgtggag ggcgacgcca ccctgtggaa gggcagccag cagctgcagc tgaagcccgg    10140
cgagagcgcc ttcatcgccg ccaacgagag ccccgtgacc gtgaagggcc acggccgcct    10200
ggcccgcgtg tacaacaagc tgtgatagga gctcgatccg tcgacctgca gatcgttcaa    10260
acatttggca ataaagtttc ttaagattga atcctgttgc cggtcttgcg atgattatca    10320
tataatttct gttgaattac gttaagcatg taataattaa catgtaatgc atgacgttat    10380
ttatgagatg ggtttttatg attagagtcc cgcaattata catttaatac gcgatagaaa    10440
acaaaatata gcgcgcaaac taggataaat tatcgcgcgc ggtgtcatct atgttactag    10500
atcggcgcgc cgcaattgaa gtttgggcgg ccagcatggc cgtatccgca atgtgttatt    10560
aagttgtcta agcgtcaatt tgtttacacc acaatatatc ctgccaccag ccagccaaca    10620
gctccccgac cggcagctcg gcacaaaatc accactcgat acaggcagcc catcagaatt    10680
aattctcatg tttgacagct tatcatcgac tgcacggtgc accaatgctt ctggcgtcag    10740
gcagccatcg gaagctgtgg tatggctgtg caggtcgtaa atcactgcat aattcgtgtc    10800
gctcaaggcg cactcccgtt ctggataatg ttttttgcgc cgacatcata acggttctgg    10860
caaatattct gaaatgagct gttgacaatt aatcatccgg ctcgtataat gtgtggaatt    10920
gtgagcggat aacaatttca cacaggaaac agaccatgag ggaagcgttg atcgccgaag    10980
tatcgactca actatcagag gtagttggcg tcatcgagcg ccatctcgaa ccgacgttgc    11040
tggccgtaca tttgtacggc tccgcagtgg atggcggcct gaagccacac agtgatattg    11100
atttgctggt tacggtgacc gtaaggcttg atgaaacaac gcggcgagct ttgatcaacg    11160
accttttgga aacttcggct tcccctggag agagcgagat tctccgcgct gtagaagtca    11220
ccattgttgt gcacgacgac atcattccgt ggcgttatcc agctaagcgc gaactgcaat    11280
ttggagaatg gcagcgcaat gacattcttg caggtatctt cgagccagcc acgatcgaca    11340
ttgatctggc tatcttgctg acaaaagcaa gagaacatag cgttgccttg gtaggtccag    11400
cggcggagga actctttgat ccggttcctg aacaggatct atttgaggcg ctaaatgaaa    11460
ccttaacgct atggaactcg ccgcccgact gggctggcga tgagcgaaat gtagtgctta    11520
cgttgtcccg catttggtac agcgcagtaa ccggcaaaat cgcgccgaag gatgtcgctg    11580
ccgactgggc aatggagcgc ctgccggccc agtatcagcc cgtcatactt gaagctaggc    11640
aggcttatct tggacaagaa gatcgcttgg cctcgcgcgc agatcagttg gaagaatttg    11700
ttcactacgt gaaaggcgag atcaccaaag tagtcggcaa ataaagctct agtggatctc    11760
cgtacccggg gatctggctc gcggcggacg cacgacgccg gggcgagacc ataggcgatc    11820
tcctaaatca atagtagctg taacctcgaa gcgtttcact tgtaacaacg attgagaatt    11880
tttgtcataa aattgaaata cttggttcgc attttttgtca tccgcggtca gccgcaattc    11940
```

-continued

```
tgacgaactg cccatttagc tggagatgat tgtacatcct tcacgtgaaa atttctcaag    12000
cgctgtgaac aagggttcag attttagatt gaaaggtgag ccgttgaaac acgttcttct    12060
tgtcgatgac gacgtcgcta tgcggcatct tattattgaa taccttacga tccacgcctt    12120
caaagtgacc gcggtagccg acagcaccca gttcacaaga gtactctctt ccgcgacggt    12180
cgatgtcgtg gttgttgatc tagatttagg tcgtgaagat gggctcgagc taggagcaag    12240
tgattttatc gctaagccgt tcagtatcag agagtttcta gcacgcattc gggttgcctt    12300
gcgcgtgcgc cccaacgttg tccgctccaa agaccgacgg tctttttgtt ttactgactg    12360
gacacttaat ctcaggcaac gtcgcttgat gtccgaagct ggcggtgagg tgaaacttac    12420
ggcaggtgag ttcaatcttc tcctcgcgtt tttagagaaa ccccgcgacg ttctatcgcg    12480
cgagcaactt ctcattgcca gtcgagtacg cgacgaggag gtttatgaca ggagtataga    12540
tgttctcatt ttgaggctgc gccgcaaact tgaggcagat ccgtcaagcc ctcaactgat    12600
aaaaacagca agaggtgccg gttatttctt tgacgcggac gtgcaggttt cgcacggggg    12660
gacgatggca gcctgagcca attcccagat ccccgaggaa tcggcgtgag cggtcgcaaa    12720
ccatccggcc cggtacaaat cggcgcggcg ctgggtgatg acctggtgga gaagttgaag    12780
gccgcgcagg ccgcccagcg gcaacgcatc gaggcagaag cacgccccgg tgaatcgtgg    12840
caagcggccg ctgatcgaat ccgcaaagaa tcccggcaac cgccggcagc cggtgcgccg    12900
tcgattagga agccgcccaa gggcgacgag caaccagatt ttttcgttcc gatgctctat    12960
gacgtgggca cccgcgatag tcgcagcatc atggacgtgg ccgttttccg tctgtcgaag    13020
cgtgaccgac gagctggcga ggtgatccgc tacgagcttc cagacgggca cgtagaggtt    13080
tccgcagggc cggccggcat ggccagtgtg tgggattacg acctggtact gatggcggtt    13140
tcccatctaa ccgaatccat gaaccgatac cgggaaggga agggagacaa gcccggccgc    13200
gtgttccgtc cacacgttgc ggacgtactc aagttctgcc ggcgagccga tggcggaaag    13260
cagaaagacg acctggtaga aacctgcatt cggttaaaca ccacgcacgt tgccatgcag    13320
cgtacgaaga aggccaagaa cggccgcctg gtgacggtat ccgagggtga agccttgatt    13380
agccgctaca agatcgtaaa gagcgaaacc gggcggccgg agtacatcga gatcgagcta    13440
gctgattgga tgtaccgcga gatcacagaa ggcaagaacc cggacgtgct gacggttcac    13500
cccgattact tttttgatcga tcccggcatc ggccgttttc tctaccgcct ggcacgccgc    13560
gccgcaggca aggcagaagc cagatggttg ttcaagacga tctacgaacg cagtggcagc    13620
gccggagagt tcaagaagtt ctgtttcacc gtgcgcaagc tgatcgggtc aaatgacctg    13680
ccggagtacg atttgaagga ggaggcgggg caggctggcc cgatcctagt catgcgctac    13740
cgcaacctga tcgagggcga agcatccgcc ggttcctaat gtacggagca gatgctaggg    13800
caaattgccc tagcagggga aaaaggtcga aaaggtctct ttcctgtgga tagcacgtac    13860
attgggaacc caaagccgta cattgggaac cggaacccgt acattgggaa cccaaagccg    13920
tacattggga accggtcaca catgtaagtg actgatataa aagagaaaaa aggcgatttt    13980
tccgcctaaa actctttaaa acttattaaa actcttaaaa cccgcctggc ctgtgcataa    14040
ctgtctggcc agcgcacagc cgaagagctg caaaaagcgc ctacccttcg gtcgctgcgc    14100
tccctacgcc ccgccgcttc gcgtcggcct atcgcggccg ctggccgctc aaaaatggct    14160
ggcctacggc caggcaatct accagggcgc ggacaagccg cgccgtcgcc actcgaccgc    14220
cggcgctgag gtctgcctcg tgaagaaggt gttgctgact cataccaggc ctgaatcgcc    14280
ccatcatcca gccagaaagt gagggagcca cggttgatga gagctttgtt gtaggtggac    14340
```

```
cagttggtga ttttgaactt ttgctttgcc acggaacggt ctgcgttgtc gggaagatgc    14400
gtgatctgat ccttcaactc agcaaaagtt cgatttattc aacaaagccg ccgtcccgtc    14460
aagtcagcgt aatgctctgc cagtgttaca accaattaac caattctgat tagaaaaact    14520
catcgagcat caaatgaaac tgcaatttat tcatatcagg attatcaata ccatattttt    14580
gaaaaagccg tttctgtaat gaaggagaaa actcaccgag gcagttccat aggatggcaa    14640
gatcctggta tcggtctgcg attccgactc gtccaacatc aatacaacct attaatttcc    14700
cctcgtcaaa aataaggtta tcaagtgaga atcaccatg agtgacgact gaatccggtg     14760
agaatggcaa aagctctgca ttaatgaatc ggccaacgcg cggggagagg cggtttgcgt    14820
attgggcgct cttccgcttc ctcgctcact gactcgctgc gctcggtcgt tcggctgcgg    14880
cgagcggtat cagctcactc aaaggcggta atacggttat ccacagaatc aggggataac    14940
gcaggaaaga acatgtgagc aaaaggccag caaaaggcca ggaaccgtaa aaaggccgcg    15000
ttgctggcgt ttttccatag gctccgcccc cctgacgagc atcacaaaaa tcgacgctca    15060
agtcagaggt ggcgaaaccc gacaggacta taaagatacc aggcgtttcc ccctggaagc    15120
tccctcgtgc gctctcctgt tccgaccctg ccgcttaccg gatacctgtc cgcctttctc    15180
ccttcgggaa gcgtggcgct ttctcatagc tcacgctgta ggtatctcag ttcggtgtag    15240
gtcgttcgct ccaagctggg ctgtgtgcac gaacccccg ttcagcccga ccgctgcgcc     15300
ttatccggta actatcgtct tgagtccaac ccggtaagac acgacttatc gccactggca    15360
gcagccactg gtaacaggat tagcagagcg aggtatgtag gcggtgctac agagttcttg    15420
aagtggtggc ctaactacgg ctacactaga agaacagtat ttggtatctg cgctctgctg    15480
aagccagtta ccttcggaaa aagagttggt agctcttgat ccggcaaaca aaccaccgct    15540
ggtagcggtg gtttttttgt ttgcaagcag cagattacgc gcagaaaaaa aggatctcaa    15600
gaagatcctt tgatctttc tacggggtct gacgctcagt ggaacgaaaa ctcacgttaa     15660
gggattttgg tcatgagatt atcaaaaagg atcttcacct agatcctttt gatccggaat    15720
ta                                                                   15722
```

<210> SEQ ID NO 21
<211> LENGTH: 20
<212> TYPE: DNA
<213> ORGANISM: Artificial Sequence
<220> FEATURE:
<223> OTHER INFORMATION: for editing VLHP2

<400> SEQUENCE: 21
gctggagctg agcttccggg                                                         20

<210> SEQ ID NO 22
<211> LENGTH: 15722
<212> TYPE: DNA
<213> ORGANISM: Artificial Sequence
<220> FEATURE:
<223> OTHER INFORMATION: vector 23398
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)

-continued

```
<223> OTHER INFORMATION: cCas9-01
<220> FEATURE:
<221> NAME/KEY: misc_feature
<222> LOCATION: (5606)..(5608)
<223> OTHER INFORMATION: L to V mutation
<220> FEATURE:
<221> NAME/KEY: misc_feature
<222> LOCATION: (5651)..(5653)
<223> OTHER INFORMATION: I to V mutation
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
<223> OTHER INFORMATION: xZmGW2
<220> FEATURE:
<221> NAME/KEY: misc_feature
<222> LOCATION: (6927)..(7031)
<223> OTHER INFORMATION: rsgRNAZmGW2-01
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01
<220> FEATURE:
<221> NAME/KEY: misc_feature
<222> LOCATION: (13822)..(14226)
<223> OTHER INFORMATION: oVS1-02
<220> FEATURE:
<221> NAME/KEY: misc_feature
<222> LOCATION: (14904)..(15710)
<223> OTHER INFORMATION: oCOLE-06

<400> SEQUENCE: 22
attcctgtgg ttggcatgca catacaaatg gacgaacgga taaacctttt cacgcccttt        60
taaatatccg attattctaa taaacgctct tttctcttag gtttacccgc caatatatcc       120
tgtcaaacac tgatagttta aactgaaggc gggaaacgac aatctgatca tgagcggaga       180
attaagggag tcacgttatg acccccgccg atgacgcggg acaagccgtt ttacgtttgg       240
aactgacaga accgcaacgc tgcaggaatt ggccgcagcg gccatttaaa caaagcttgg       300
taccattatg tggtctaggt aggttctata tataagaaaa cttgaaatgt tctaaaaaaa       360
aattcaagcc catgcatgat tgaagcaaac ggtatagcaa cggtgttaac ctgatctagt       420
gatctcttgc aatccttaac ggccacctac cgcaggtagc aaacggcgtc cccctcctcg       480
```

```
atatctccgc ggcgacctct ggcttttttcc gcggaattgc gcggtgggga cggattccac    540
gagaccgcga cgcaaccgcc tctcgccgct gggccccaca ccgctcggtg ccgtagcctc    600
acgggactct ttctccctcc tccccgtta taaattggct tcatccctc cttgcctcat      660 ccatccaaat cccagtcccc aatcccatcc cttcgtagga gaaattcatc gaagctaagc    720
gaatcctcgc gatcctctca aggtactgcg agttttcgat cccctctcg accctcgta      780 tgtttgtgtt tgtcgtagcg tttgattagg tatgctttcc ctgtttgtgt tcgtcgtagc    840
gtttgattag gtatgctttc cctgttcgtg ttcatcgtag tgtttgatta ggtcgtgtga    900
ggcgatggcc tgctcgcgtc cttcgatctg tagtcgattt gcgggtcgtg gtgtagatct    960
gcgggctgtg atgaagttat ttggtgtgat ctgctcgcct gattctgcgg gttggctcga   1020
gtagatatga tggttggacc ggttggttcg tttaccgcgc tagggttggg ctgggatgat   1080
gttgcatgcg ccgttgcgcg tgatcccgca gcaggacttg cgtttgattg ccagatctcg   1140
ttacgattat gtgatttggt ttggactttt tagatctgta gcttctgctt atgtgccaga   1200
tgcgcctact gctcatatgc ctgatgataa tcataaatgg ctgtggaact aactagttga   1260
ttgcggagtc atgtatcagc tacaggtgta gggactagct acaggtgtag ggacttgcgt   1320
ctaattgttt ggtcctttac tcatgttgca attatgcaat ttagtttaga ttgtttgttc   1380
cactcatcta ggctgtaaaa gggacactgc ttagattgct gtttaatctt tttagtagat   1440
tatattatat tggtaactta ttacccctat tacatgccat acgtgacttc tgctcatgcc   1500
tgatgataat catagatcac tgtggaatta attagttgat tgttgaatca tgtttcatgt   1560
acataccacg gcacaattgc ttagttcctt aacaaatgca aattttactg atccatgtat   1620
gatttgcgtg gttctctaat gtgaaatact atagctactt gttagtaaga atcaggttcg   1680
tatgcttaat gctgtatgtg ccttctgctc atgcctgatg ataatcatat atcactggaa   1740
ttaattagtt gatcgtttaa tcatatatca agtacatacc atgccacaat ttttagtcac   1800
ttaacccatg cagattgaac tggtccctgc atgtttttgct aaattgttct attctgatta  1860
gaccatatat catgtatttt tttttggtaa tggttctctt attttaaatg ctatatagtt   1920
ctggtacttg ttagaaagat ctgcttcata gtttagttgc ctatccctcg aattaggatg   1980
ctgagcagct gatcctatag ctttgtttca tgtatcaatt cttttgtgtt caacagtcag   2040
tttttgttag attcattgta acttatggtc gcttactctt ctggtcctca atgcttgcag   2100
gatcgcggcc gctcatatgg acaagaagta cagcatcggc ctggacatcg gcaccaacag   2160
cgtgggctgg gccgtgatca ccgacgagta caaggtgccg agcaagaagt tcaaggtgct   2220
gggcaacacc gacaggcaca gcatcaagaa gaacctgatc ggcgccctgc tgttcgacag   2280
cggcgagacc gccgaggcca ccaggctgaa gaggaccgcc aggaggaggt acaccaggag   2340
gaagaacagg atctgctacc tgcaggagat cttcagcaac gagatggcca aggtggacga   2400
cagcttcttc cacaggctgg aggagagctt cctggtggag gaggacaaga agcacgagag   2460
gcacccgatc ttcggcaaca tcgtggacga ggtggcctac cacgagaagt acccgaccat   2520
ctaccacctg aggaagaagc tggtggacag caccgacaag gccgacctga ggctgatcta   2580
cctggccctg gcccacatga tcaagttcag gggccacttc ctgatcgagg cgacctgaa    2640 cccggacaac agcgacgtgg acaagctgtt catccagctg gtgcagacct acaaccagct   2700
gttcgaggag aacccgatca cgccagcggc cgtggacgcc aaggccatcc tgagcgccag   2760
gctgagcaag agcaggaggc tggagaacct gatcgcccag ctgccgggcg agaagaagaa   2820
```

-continued

```
cggcctgttc ggcaacctga tcgccctgag cctgggcctg accccgaact tcaagagcaa      2880
cttcgacctg gccgaggacg ccaagctgca gctgagcaag gacacctacg acgacgacct      2940
ggacaacctg ctggcccaga tcggcgacca gtacgccgac ctgttcctgg ccgccaagaa      3000
cctgagcgac gccatcctgc tgagcgacat cctgagggtg aacaccgaga tcaccaaggc      3060
cccgctgagc gccagcatga tcaagaggta cgacgagcac caccaggacc tgaccctgct      3120
gaaggccctg gtgaggcagc agctgccgga gaagtacaag gagatcttct tcgaccagag      3180
caagaacggc tacgccggct acatcgacgg cggcgccagc caggaggagt tctacaagtt      3240
catcaagccg atcctggaga agatggacgg caccgaggag ctgctggtga agctgaacag      3300
ggaggacctg ctgaggaagc agaggacctt cgacaacggc agcatcccgc accagatcca      3360
cctgggcgag ctgcacgcca tcctgaggag gcaggaggac ttctacccgt tcctgaagga      3420
caacagggag aagatcgaga agatcctgac cttccgcatc ccgtactacg tgggcccgct      3480 ggccagggggc aacagcaggt tcgcctggat gaccaggaag agcgaggaga ccatcacccc      3540
gtggaacttc gaggaggtgg tggacaaggg cgccagcgcc cagagcttca tcgagaggat      3600
gaccaacttc gacaagaacc tgccgaacga gaaggtgctg ccgaagcaca gcctgctgta      3660
cgagtacttc accgtgtaca acgagctgac caaggtgaag tacgtgaccg agggcatgag      3720
gaagccggcc ttcctgagcg gcgagcagaa gaaggccatc gtggacctgc tgttcaagac      3780
caacaggaag gtgaccgtga agcagctgaa ggaggactac ttcaagaaga tcgagtgctt      3840
cgacagcgtg gagatcagcg gcgtggagga caggttcaac gccagcctgg gcacctacca      3900
cgacctgctg aagatcatca ggacaaggga cttcctggac aacgaggaga cgaggacat      3960 cctggaggac atcgtgctga ccctgaccct gttcgaggac agggagatga tcgaggagag      4020
gctgaagacc tacgcccacc tgttcgacga caaggtgatg aagcagctga agaggaggag      4080
gtacaccggc tggggcaggc tgagcaggaa gctgatcaac ggcatcaggg acaagcagag      4140
cggcaagacc atcctggact tcctgaagag cgacggcttc gccaacagga acttcatgca      4200
gctgatccac gacgacagcc tgaccttcaa ggaggacatc cagaaggccc aggtgagcgg      4260
ccagggcgac agcctgcacg agcacatcgc caacctggcc ggcagcccgg ccatcaagaa      4320
gggcatcctg cagaccgtga aggtggtgga cgagctggtg aaggtgatgg gcaggcacaa      4380
gccggagaac atcgtgatcg agatggccag ggagaaccag accacccaga agggccagaa      4440
gaacagcagg gagaggatga agaggatcga ggagggcatc aaggagctgg gcagccagat      4500
cctgaaggag caccccggtgg agaacaccca gctgcagaac gagaagctgt acctgtacta      4560
cctgcagaac ggcagggaca tgtacgtgga ccaggagctg gacatcaaca ggctgagcga      4620
ctacgacgtg gaccacatcg tgccgcagag cttcctgaag gacgacagca tcgacaacaa      4680
ggtgctgacc aggagcgaca gaacaggggg caagagcgac aacgtgccga gcgaggaggt      4740
ggtgaagaag atgaaaaaact actggaggca gctgctgaac gccaagctga tcacccagag      4800
gaagttcgac aacctgacca aggccgagag gggcggcctg agcgagctgg acaaggccgg      4860
cttcattaaa aggcagctgg tggagaccag gcagatcacc aagcacgtgg cccagatcct      4920
ggacagcagg atgaacacca gtacgacga gaacgacaag ctgatcaggg aggtgaaggt      4980
gatcaccctg aagagcaagc tggtgagcga cttcaggaag gacttccagt tctacaaggt      5040
gagggagatc aataattacc accacgccca cgacgcctac ctgaacgccg tggtgggcac      5100
cgccctgatt aaaaagtacc cgaagctgga gagcgagttc gtgtacgcg actacaaggt      5160 gtacgacgtg aggaagatga tcgccaagag cgagcaggag atcggcaagg ccaccgccaa      5220
```

-continued

```
gtacttcttc tacagcaaca tcatgaactt cttcaagacc gagatcaccc tggccaacgg    5280
cgagatcagg aagaggccgc tgatcgagac caacggcgag accggcgaga tcgtgtggga    5340
caagggcagg gacttcgcca ccgtgaggaa ggtgctgtcc atgccgcagg tgaacatcgt    5400
gaagaagacc gaggtgcaga ccggcggctt cagcaaggag agcatcctgc cgaagaggaa    5460
cagcgacaag ctgatcgcca ggaagaagga ctgggacccg aagaagtacg gcggcttcga    5520
cagcccgacc gtggcctaca gcgtgctggt ggtggccaag gtgggagaag gcaagagcaa    5580
gaagctgaag agcgtgaagg agctggtggg catcaccatc atggagagga gcagcttcga    5640
gaagaaccca gtggacttcc tggaggccaa gggctacaag gaggtgaaga aggacctgat    5700
cattaaactg ccgaagtaca gcctgttcga gctggagaac ggcaggaaga ggatgctggc    5760
cagcgccggc gagctgcaga agggcaacga gctggccctg ccgagcaagt acgtgaactt    5820
cctgtacctg gccagccact acgagaagct gaagggcagc ccggaggaca acgagcagaa    5880
gcagctgttc gtggagcagc acaagcacta cctggacgag atcatcgagc agatcagcga    5940
gttcagcaag agggtgatcc tggccgacgc caacctggac aaggtgctga gcgcctacaa    6000
caagcacagg gacaagccga tcagggagca ggccgagaac atcatccacc tgttcaccct    6060
gaccaacctg ggcgcccggg ccgccttcaa gtacttcgac accaccatcg acaggaagag    6120
gtacaccagc accaaggagg tgctggacgc caccctgatc caccagagca tcaccggcct    6180
gtacgagacc aggatcgacc tgagccagct gggcggcgac agcagcccgc cgaagaagaa    6240
gaggaaggtg agctggaagg acgccagcgg ctggagcagg atgtgaagct tgatcgttca    6300
aacatttggc aataaagttt cttaagattg aatcctgttg ccggtcttgc gatgattatc    6360
atataatttc tgttgaatta cgttaagcat gtaataatta acatgtaatg catgacgtta    6420
tttatgagat gggtttttat gattagagtc ccgcaattat acatttaata cgcgatagaa    6480
aacaaaatat agcgcgcaaa ctaggataaa ttatcgcgcg cggtgtcatc tatgttacta    6540
gatcttcgaa gggatcttta aacatacgaa cagatcactt aaagttcttc tgaagcaact    6600
taaagttatc aggcatgcat ggatcttgga ggaatcagat gtgcagtcag gaccatagc     6660 acaggacagg cgtcttctac tggtgctacc agcaaatgct ggaagccggg aacactgggt    6720
acgttggaaa ccacgtgatg tggagtaaga taaactgtag gagaaaagca tttcgtagtg    6780
ggccatgaag cctttcagga catgtattgc agtatgggcc ggcccattac gcaattggac    6840
gacaacaaag actagtatta gtaccacctc ggctatccac atagatcaaa gctggtttaa    6900
aagagttgtg cagatgatcc gtggcagagc ggttcacgcg ccgcagttt tagagctaga     6960 aatagcaagt aaaataagg ctagtccgtt atcaacttga aaaagtggca ccgagtcggt     7020
gctttttttt tcggaccgcg cctgcagtgc agcgtgaccc ggtcgtgccc ctctctagag    7080
ataatgagca ttgcatgtct aagttataaa aaattaccac atattttttt tgtcacactt    7140
gtttgaagtg cagtttatct atctttatac atatatttaa actttactct acgaataata    7200
taatctatag tactacaata atatcagtgt tttagagaat catataaatg aacagttaga    7260
catggtctaa aggacaattg agtattttga caacaggact ctacagtttt atcttttttag   7320 tgtgcatgtg ttctcctttt tttttgcaaa tagcttcacc tatataatac ttcatccatt    7380
ttattagtac atccatttag ggtttagggt taatggtttt tatagactaa tttttttagt    7440
acatctattt tattctattt tagcctctaa attaagaaaa ctaaaactct attttagttt    7500
ttttatttaa taatttagat ataaaataga ataaaataaa gtgactaaaa attaaacaaa    7560
```

-continued

```
taccctttaa gaaattaaaa aaactaagga aacatttttc ttgtttcgag tagataatgc    7620
cagcctgtta aacgccgtcg acgagtctaa cggacaccaa ccagcgaacc agcagcgtcg    7680
cgtcgggcca agcgaagcag acggcacggc atctctgtcg ctgcctctgg acccctctcg    7740
agagttccgc tccaccgttg gacttgctcc gctgtcggca tccagaaatt gcgtggcgga    7800
gcggcagacg tgagccggca cggcaggcgg cctcctcctc ctctcacggc accggcagct    7860
acgggggatt cctttcccac cgctccttcg ctttcccttc ctcgcccgcc gtaataaata    7920 gacacccct ccacaccctc tttccccaac ctcgtgttgt tcggagcgca cacacacaca    7980
accagatctc ccccaaatcc acccgtcggc acctccgctt caaggtacgc cgctcgtcct    8040
cccccccccc cctctctacc ttctctagat cggcgttccg gtccatggtt agggcccggt    8100
agttctactt ctgttcatgt ttgtgttaga tccgtgtttg tgttagatcc gtgctgctag    8160
cgttcgtaca cggatgcgac ctgtacgtca gacacgttct gattgctaac ttgccagtgt    8220
ttctctttgg ggaatcctgg gatggctcta gccgttccgc agacgggatc gatttcatga    8280 tttttttgt ttcgttgcat agggtttggt ttgccctttt cctttatttc aatatatgcc    8340
gtgcacttgt ttgtcgggtc atcttttcat gcttttttt gtcttggttg tgatgatgtg    8400
gtctggttgg gcggtcgttc tagatcggag tagaattctg tttcaaacta cctggtggat    8460
ttattaattt tggatctgta tgtgtgtgcc atacatattc atagttacga attgaagatg    8520
atggatggaa atatcgatct aggataggta tacatgttga tgcgggtttt actgatgcat    8580
atacagagat gcttttttgtt cgcttggttg tgatgatgtg gtgtggttgg gcggtcgttc    8640
attcgttcta gatcggagta gaatactgtt tcaaactacc tggtgtattt attaattttg    8700
gaactgtatg tgtgtgtcat acatcttcat agttacgagt ttaagatgga tggaaatatc    8760
gatctaggat aggtatacat gttgatgtgg gttttactga tgcatataca tgatggcata    8820
tgcagcatct attcatatgc tctaaccttg agtacctatc tattataata aacaagtatg    8880
ttttataatt attttgatct tgatatactt ggatgatggc atatgcagca gctatatgtg    8940 gatttttta gccctgcctt catacgctat ttatttgctt ggtactgttt cttttgtcga    9000
tgctcaccct gttgtttggt gttacttctg cagggatccg gcagcagcca tgcagaagct    9060
gatcaacagc gtgcagaact acgcctgggg cagcaagacc gccctgaccg agctgtacgg    9120
catggagaac cccagcagcc agcccatggc cgagctgtgg atgggcgccc accccaagag    9180
cagcagccgc gtgcagaacg ccgccggcga catcgtgagc ctgcgcgacg tgatcgagag    9240
cgacaagagc accctgctgg gcgaggccgt ggccaagcgc ttcggcgagc tgcccttcct    9300
gttcaaggtg ctgtgcgccg cccagcccct gagcatccag gtgcacccca acaagcacaa    9360
cagcgagatc ggcttcgcca aggagaacgc cgccggcatc cccatggacg ccgccgagcg    9420
caactacaag gaccccaacc acaagcccga gctggtgttc gccctgaccc ccttcctggc    9480
catgaacgcc ttccgcgagt tcagcgagat cgtgagcctg ctgcagcccg tggcggcgc    9540 ccaccccgcc atcgcccact tcctgcagca gcccgacgcc gagcgcctga gcgagctgtt    9600
cgccagcctg ctgaacatgc agggcgagga gaagagccgc gccctggcca tcctgaagag    9660
cgccctggac agccagcagg gcgagccctg gcagaccatc cgcctgatca gcgagttcta    9720
ccccgaggac agcggcctgt tcagcccct gctgctgaac gtggtgaagc tgaacccegg    9780 cgaggccatg ttcctgttcg ccgagacccc ccacgcctac ctgcagggcg tggccctgga    9840
ggtgatggca aacagcgaca acgtgctgcg cgccggcctg acccccaagt acatcgacat    9900 cccccgagctg gtggccaacg tgaagttcga ggccaagccc gccaaccagc tgctgacccca    9960
```

-continued

```
gcccgtgaag cagggcgccg agctggactt ccccatcccc gtggacgact tcgccttcag  10020
cctgcacgac ctgagcgaca aggagaccac catcagccag cagagcgccg ccatcctgtt  10080
ctgcgtggag ggcgacgcca ccctgtggaa gggcagccag cagctgcagc tgaagcccgg  10140
cgagagcgcc ttcatcgccg ccaacgagag ccccgtgacc gtgaagggcc acggccgcct  10200
ggcccgcgtg tacaacaagc tgtgtatagga gctcgatccg tcgacctgca gatcgttcaa  10260
acatttggca ataaagtttc ttaagattga atcctgttgc cggtcttgcg atgattatca  10320
tataatttct gttgaattac gttaagcatg taataattaa catgtaatgc atgacgttat  10380
ttatgagatg ggtttttatg attagagtcc cgcaattata catttaatac gcgatagaaa  10440
acaaaatata gcgcgcaaac taggataaat tatcgcgcgc ggtgtcatct atgttactag  10500
atcggcgcgc cgcaattgaa gtttgggcgg ccagcatggc cgtatccgca atgtgttatt  10560
aagttgtcta agcgtcaatt tgtttacacc acaatatatc ctgccaccag ccagccaaca  10620
gctccccgac cggcagctcg gcacaaaatc accactcgat acaggcagcc catcagaatt  10680
aattctcatg tttgacagct tatcatcgac tgcacggtgc accaatgctt ctggcgtcag  10740
gcagccatcg gaagctgtgg tatggctgtg caggtcgtaa atcactgcat aattcgtgtc  10800
gctcaaggcg cactcccgtt ctggataatg ttttttgcgc cgacatcata acggttctgg  10860
caaatattct gaaatgagct gttgacaatt aatcatccgg ctcgtataat gtgtggaatt  10920
gtgagcggat aacaatttca cacaggaaac agaccatgag ggaagcgttg atcgccgaag  10980
tatcgactca actatcagag gtagttggcg tcatcgagcg ccatctcgaa ccgacgttgc  11040
tggccgtaca tttgtacggc tccgcagtgg atggcggcct gaagccacac agtgatattg  11100
atttgctggt tacggtgacc gtaaggcttg atgaaacaac gcggcgagct ttgatcaacg  11160
acctttggga aacttcggct tcccctggag agagcgagat tctccgcgct gtagaagtca  11220
ccattgttgt gcacgacgac atcattccgt ggcgttatcc agctaagcgc gaactgcaat  11280
ttggagaatg gcagcgcaat gacattcttg caggtatctt cgagccagcc acgatcgaca  11340
ttgatctggc tatcttgctg acaaaagcaa gagaacatag cgttgccttg gtaggtccag  11400
cggcggagga actctttgat ccggttcctg aacaggatct atttgaggcg ctaaatgaaa  11460
ccttaacgct atggaactcg ccgcccgact gggctggcga tgagcgaaat gtagtgctta  11520
cgttgtcccg catttggtac agcgcagtaa ccggcaaaat cgcgccgaag gatgtcgctg  11580
ccgactgggc aatggagcgc ctgccggccc agtatcagcc cgtcatactt gaagctaggc  11640
aggcttatct tggacaagaa gatcgcttgg cctcgcgcgc agatcagttg gaagaatttg  11700
ttcactacgt gaaaggcgag atcaccaaag tagtcggcaa ataaagctct agtggatctc  11760
cgtacccggg gatctggctc gcggcggacg cacgacgccg gggcgagacc ataggcgatc  11820
tcctaaatca atagtagctg taacctcgaa gcgtttcact tgtaacaacg attgagaatt  11880
tttgtcataa aattgaaata cttggttcgc atttttgtca tccgcggtca gccgcaattc  11940
tgacgaactg cccatttagc tggagatgat tgtacatcct tcacgtgaaa atttctcaag  12000
cgctgtgaac aagggttcag attttagatt gaaaggtgag ccgttgaaac acgttcttct  12060
tgtcgatgac gacgtcgcta tgcggcatct tattattgaa taccttacga tccacgcctt  12120
caaagtgacc gcggtagccg acagcaccca gttcacaaga gtactctctt ccgcgacggt  12180
cgatgtcgtg gttgttgatc tagatttagg tcgtgaagat gggctcgagc taggagcaag  12240
tgattttatc gctaagccgt tcagtatcag agagtttcta gcacgcattc gggttgcctt  12300
```

-continued

```
gcgcgtgcgc cccaacgttg tccgctccaa agaccgacgg tcttttttgtt ttactgactg   12360 gacacttaat ctcaggcaac gtcgcttgat gtccgaagct ggcggtgagg tgaaacttac   12420
ggcaggtgag ttcaatcttc tcctcgcgtt tttagagaaa ccccgcgacg ttctatcgcg   12480
cgagcaactt ctcattgcca gtcgagtacg cgacgaggag gtttatgaca ggagtataga   12540
tgttctcatt ttgaggctgc gccgcaaact tgaggcagat ccgtcaagcc ctcaactgat   12600
aaaaacagca agaggtgccg gttatttctt tgacgcggac gtgcaggttt cgcacggggg   12660
gacgatggca gcctgagcca attcccagat ccccgaggaa tcggcgtgag cggtcgcaaa   12720
ccatccggcc cggtacaaat cggcgcggcg ctgggtgatg acctggtgga gaagttgaag   12780
gccgcgcagg ccgcccagcg gcaacgcatc gaggcagaag cacgccccgg tgaatcgtgg   12840
caagcggccg ctgatcgaat ccgcaaagaa tcccggcaac cgccggcagc cggtgcgccg   12900
tcgattagga agccgcccaa gggcgacgag caaccagatt ttttcgttcc gatgctctat   12960
gacgtgggca cccgcgatag tcgcagcatc atggacgtgg ccgtttttccg tctgtcgaag   13020 cgtgaccgac gagctggcga ggtgatccgc tacgagcttc cagacgggca cgtagaggtt   13080
tccgcagggc cggccggcat ggccagtgtg tgggattacg acctggtact gatggcggtt   13140
tcccatctaa ccgaatccat gaaccgatac cgggaaggga agggagacaa gcccggccgc   13200
gtgttccgtc cacacgttgc ggacgtactc aagttctgcc ggcgagccga tggcggaaag   13260
cagaaagacg acctggtaga aacctgcatt cggttaaaca ccacgcacgt tgccatgcag   13320
cgtacgaaga aggccaagaa cggccgcctg gtgacggtat ccgagggtga agccttgatt   13380
agccgctaca agatcgtaaa gagcgaaacc gggcggccgg agtacatcga gatcgagcta   13440
gctgattgga tgtaccgcga gatcacagaa ggcaagaacc cggacgtgct gacggttcac   13500
cccgattact ttttgatcga tcccggcatc ggccgttttc tctaccgcct ggcacgccgc   13560
gccgcaggca aggcagaagc cagatggttg ttcaagacga tctacgaacg cagtggcagc   13620
gccggagagt tcaagaagtt ctgtttcacc gtgcgcaagc tgatcgggtc aaatgacctg   13680
ccggagtacg atttgaagga ggaggcgggg caggctggcc cgatcctagt catgcgctac   13740
cgcaacctga tcgagggcga agcatccgcc ggttcctaat gtacggagca gatgctaggg   13800
caaattgccc tagcaggggga aaaaggtcga aaaggtctct ttcctgtgga tagcacgtac   13860
attgggaacc caaagccgta cattgggaac cggaacccgt acattgggaa cccaaagccg   13920
tacattggga accggtcaca catgtaagtg actgatataa aagagaaaaa aggcgatttt   13980
tccgcctaaa actctttaaa acttattaaa actcttaaaa cccgcctggc ctgtgcataa   14040
ctgtctggcc agcgcacagc cgaagagctg caaaaagcgc ctacccttcg gtcgctgcgc   14100
tccctacgcc ccgccgcttc gcgtcggcct atcgcggccg ctggccgctc aaaaatggct   14160
ggcctacggc caggcaatct accagggcgc ggacaagccg cgccgtcgcc actcgaccgc   14220
cggcgctgag gtctgcctcg tgaagaaggt gttgctgact cataccaggc ctgaatcgcc   14280
ccatcatcca gccagaaagt gagggagcca cggttgatga gagctttgtt gtaggtggac   14340
cagttggtga ttttgaactt ttgctttgcc acggaacggt ctgcgttgtc gggaagatgc   14400
gtgatctgat ccttcaactc agcaaaagtt cgatttattc aacaaagccg ccgtcccgtc   14460
aagtcagcgt aatgctctgc cagtgttaca accaattaac caattctgat tagaaaaact   14520
catcgagcat caaatgaaac tgcaatttat tcatatcagg attatcaata ccatattttt   14580
gaaaaagccg tttctgtaat gaaggagaaa actcaccgag gcagttccat aggatggcaa   14640
gatcctggta tcggtctgcg attccgactc gtccaacatc aatacaacct attaatttcc   14700
```

-continued

```
cctcgtcaaa aataaggtta tcaagtgaga aatcaccatg agtgacgact gaatccggtg    14760
agaatggcaa aagctctgca ttaatgaatc ggccaacgcg cggggagagg cggtttgcgt    14820
attgggcgct cttccgcttc ctcgctcact gactcgctgc gctcggtcgt tcggctgcgg    14880
cgagcggtat cagctcactc aaaggcggta atacggttat ccacagaatc aggggataac    14940
gcaggaaaga acatgtgagc aaaaggccag caaaaggcca ggaaccgtaa aaaggccgcg    15000
ttgctggcgt ttttccatag gctccgcccc cctgacgagc atcacaaaaa tcgacgctca    15060
agtcagaggt ggcgaaaccc gacaggacta taaagatacc aggcgtttcc ccctggaagc    15120
tccctcgtgc gctctcctgt tccgaccctg ccgcttaccg gatacctgtc cgcctttctc    15180
ccttcgggaa gcgtggcgct ttctcatagc tcacgctgta ggtatctcag ttcggtgtag    15240
gtcgttcgct ccaagctggg ctgtgtgcac gaaccccccg ttcagcccga ccgctgcgcc    15300
ttatccggta actatcgtct tgagtccaac ccggtaagac acgacttatc gccactggca    15360
gcagccactg gtaacaggat tagcagagcg aggtatgtag gcggtgctac agagttcttg    15420
aagtggtggc ctaactacgg ctacactaga agaacagtat ttggtatctg cgctctgctg    15480
aagccagtta ccttcggaaa aagagttggt agctcttgat ccggcaaaca aaccaccgct    15540
ggtagcggtg gtttttttgt ttgcaagcag cagattacgc gcagaaaaaa aggatctcaa    15600
gaagatcctt tgatcttttc tacggggtct gacgctcagt ggaacgaaaa ctcacgttaa    15660
gggattttgg tcatgagatt atcaaaaagg atcttcacct agatcctttt gatccggaat    15720
ta                                                                   15722
```

```
<210> SEQ ID NO 23
<211> LENGTH: 20
<212> TYPE: DNA
<213> ORGANISM: Artificial Sequence
<220> FEATURE:
<223> OTHER INFORMATION: for editing GW2-1

<400> SEQUENCE: 23
gagcggttca cgcggccgca                                                       20

<210> SEQ ID NO 24
<211> LENGTH: 15721
<212> TYPE: DNA
<213> ORGANISM: Artificial Sequence
<220> FEATURE:
<223> OTHER INFORMATION: vector 23763
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: misc_feature
<222> LOCATION: (6221)..(6283)
```

```
<223> OTHER INFORMATION: xSV40NLS-03
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6945)
<223> OTHER INFORMATION: xTaVLHP1
<220> FEATURE:
<221> NAME/KEY: misc_feature
<222> LOCATION: (6927)..(7030)
<223> OTHER INFORMATION: rsgRNA TaVLHP1-01
<220> FEATURE:
<221> NAME/KEY: promoter
<222> LOCATION: (7041)..(9032)
<223> OTHER INFORMATION: prUbi1-04
<220> FEATURE:
<221> NAME/KEY: gene
<222> LOCATION: (9049)..(10227)
<223> OTHER INFORMATION: cPMI-09
<220> FEATURE:
<221> NAME/KEY: terminator
<222> LOCATION: (10250)..(10502)
<223> OTHER INFORMATION: tNOS-05-01
<220> FEATURE:
<221> NAME/KEY: misc_feature
<222> LOCATION: (10546)..(10675)
<223> OTHER INFORMATION: bNLB-03
<220> FEATURE:
<221> NAME/KEY: gene
<222> LOCATION: (10955)..(11743)
<223> OTHER INFORMATION: cSpec-03
<220> FEATURE:
<221> NAME/KEY: promoter
<222> LOCATION: (11838)..(11968)
<223> OTHER INFORMATION: prVirG-01
<220> FEATURE:
<221> NAME/KEY: gene
<222> LOCATION: (12705)..(13778)
<223> OTHER INFORMATION: cRepA-01
<220> FEATURE:
<221> NAME/KEY: misc_feature
<222> LOCATION: (13821)..(14225)
<223> OTHER INFORMATION: oVS1-02
<220> FEATURE:
<221> NAME/KEY: misc_feature
<222> LOCATION: (14903)..(15709)
<223> OTHER INFORMATION: oCOLE-06

<400> SEQUENCE: 24
attcctgtgg ttggcatgca catacaaatg gacgaacgga taaacctttt cacgcccttt        60
taaatatccg attattctaa taaacgctct tttctcttag gtttacccgc caatatatcc       120
tgtcaaacac tgatagttta aactgaaggc gggaaacgac aatctgatca tgagcggaga       180
attaagggag tcacgttatg accccgccg atgacgcggg acaagccgtt ttacgtttgg        240
aactgacaga accgcaacgc tgcaggaatt ggccgcagcg gccatttaaa caaagcttgg       300
taccattatg tggtctaggt aggttctata tataagaaaa cttgaaatgt tctaaaaaaa       360
aattcaagcc catgcatgat tgaagcaaac ggtatagcaa cggtgttaac ctgatctagt       420
gatctcttgc aatccttaac ggccacctac cgcaggtagc aaacggcgtc ccctcctcg        480 atatctccgc ggcgacctct ggcttttttcc gcggaattgc gcggtgggga cggattccac     540
gagaccgcga cgcaaccgcc tctcgccgct gggccccaca ccgctcggtg ccgtagcctc       600
acgggactct ttctccctcc tccccgtta taaattggct tcatccctc cttgcctcat         660 ccatccaaat cccagtcccc aatcccatcc cttcgtagga gaaattcatc gaagctaagc       720
```

-continued

```
gaatcctcgc gatcctctca aggtactgcg agttttcgat cccctctcg accctcgta    780 tgtttgtgtt tgtcgtagcg tttgattagg tatgctttcc ctgtttgtgt tcgtcgtagc    840
gtttgattag gtatgctttc cctgttcgtg ttcatcgtag tgtttgatta ggtcgtgtga    900
ggcgatggcc tgctcgcgtc cttcgatctg tagtcgattt gcgggtcgtg gtgtagatct    960
gcgggctgtg atgaagttat ttggtgtgat ctgctcgcct gattctgcgg gttggctcga    1020
gtagatatga tggttggacc ggttggttcg tttaccgcgc tagggttggg ctgggatgat    1080
gttgcatgcg ccgttgcgcg tgatcccgca gcaggacttg cgtttgattg ccagatctcg    1140
ttacgattat gtgatttggt ttggactttt tagatctgta gcttctgctt atgtgccaga    1200
tgcgcctact gctcatatgc ctgatgataa tcataaatgg ctgtggaact aactagttga    1260
ttgcggagtc atgtatcagc tacaggtgta gggactagct acaggtgtag ggacttgcgt    1320
ctaattgttt ggtcctttac tcatgttgca attatgcaat ttagtttaga ttgtttgttc    1380
cactcatcta ggctgtaaaa gggacactgc ttagattgct gtttaatctt tttagtagat    1440
tatattatat tggtaactta ttaccctat tacatgccat acgtgacttc tgctcatgcc    1500
tgatgataat catagatcac tgtggaatta attagttgat tgttgaatca tgtttcatgt    1560
acataccacg gcacaattgc ttagttcctt aacaaatgca aattttactg atccatgtat    1620
gatttgcgtg gttctctaat gtgaaatact atagctactt gttagtaaga atcaggttcg    1680
tatgcttaat gctgtatgtg ccttctgctc atgcctgatg ataatcatat atcactggaa    1740
ttaattagtt gatcgtttaa tcatatatca agtacatacc atgccacaat ttttagtcac    1800
ttaacccatg cagattgaac tggtccctgc atgtttgct aaattgttct attctgatta    1860
gaccatatat catgtatttt ttttggtaa tggttctctt attttaaatg ctatatagtt    1920
ctggtacttg ttagaaagat ctgcttcata gtttagttgc ctatccctcg aattaggatg    1980
ctgagcagct gatcctatag ctttgtttca tgtatcaatt cttttgtgtt caacagtcag    2040
tttttgttag attcattgta acttatggtc gcttactctt ctggtcctca atgcttgcag    2100
gatcgcggcc gctcatatgg acaagaagta cagcatcggc ctggacatcg gcaccaacag    2160
cgtgggctgg gccgtgatca ccgacgagta caaggtgccg agcaagaagt tcaaggtgct    2220
gggcaacacc gacaggcaca gcatcaagaa gaacctgatc ggcgccctgc tgttcgacag    2280
cggcgagacc gccgaggcca ccaggctgaa gaggaccgcc aggaggaggt acaccaggag    2340
gaagaacagg atctgctacc tgcaggagat cttcagcaac gagatggcca aggtggacga    2400
cagcttcttc cacaggctgg aggagagctt cctggtggag gaggacaaga agcacgagag    2460
gcacccgatc ttcggcaaca tcgtggacga ggtggcctac cacgagaagt acccgaccat    2520
ctaccacctg aggaagaagc tggtggacag caccgacaag gccgacctga ggctgatcta    2580
cctggccctg gcccacatga tcaagttcag gggccacttc ctgatcgagg gcgacctgaa    2640
cccggacaac agcgacgtgg acaagctgtt catccagctg gtgcagacct acaaccagct    2700
gttcgaggag aacccgatca cgccagcgg cgtggacgcc aaggccatcc tgagcgccag    2760
gctgagcaag agcaggaggc tggagaacct gatcgcccag ctgccgggcg agaagaagaa    2820
cggcctgttc ggcaacctga tcgccctgag cctgggcctg accccgaact tcaagagcaa    2880
cttcgacctg gccgaggacg ccaagctgca gctgagcaag gacacctacg acgacgacct    2940
ggacaacctg ctggcccaga tcggcgacca gtacgcgac ctgttcctgg ccgccaagaa    3000
cctgagcgac gccatcctgc tgagcgacat cctgagggtg aacaccgaga tcaccaaggc    3060
```

-continued

```
cccgctgagc gccagcatga tcaagaggta cgacgagcac caccaggacc tgaccctgct   3120
gaaggccctg gtgaggcagc agctgccgga gaagtacaag gagatcttct tcgaccagag   3180
caagaacggc tacgccggct acatcgacgg cggcgccagc caggaggagt tctacaagtt   3240
catcaagccg atcctggaga agatggacgg caccgaggag ctgctggtga agctgaacag   3300
ggaggacctg ctgaggaagc agaggacctt cgacaacggc agcatcccgc accagatcca   3360
cctgggcgag ctgcacgcca tcctgaggag gcaggaggac ttctacccgt tcctgaagga   3420
caacagggag aagatcgaga agatcctgac cttccgcatc ccgtactacg tgggcccgct   3480 ggccagggggc aacagcaggt tcgcctggat gaccaggaag agcgaggaga ccatcaccccc   3540 gtggaacttc gaggaggtgg tggacaaggg cgccagcgcc cagagcttca tcgagaggat   3600
gaccaacttc gacaagaacc tgccgaacga gaaggtgctg ccgaagcaca gcctgctgta   3660
cgagtacttc accgtgtaca acgagctgac caaggtgaag tacgtgaccg agggcatgag   3720
gaagccggcc ttcctgagcg gcgagcagaa gaaggccatc gtggacctgc tgttcaagac   3780
caacaggaag gtgaccgtga agcagctgaa ggaggactac ttcaagaaga tcgagtgctt   3840
cgacagcgtg gagatcagcg gcgtggagga caggttcaac gccagcctgg gcacctacca   3900
cgacctgctg aagatcatca aggacaagga cttcctggac aacgaggaga cgaggacat   3960 cctggaggac atcgtgctga ccctgaccct gttcgaggac agggagatga tcgaggagag   4020
gctgaagacc tacgcccacc tgttcgacga caaggtgatg aagcagctga gaggaggag   4080 gtacaccggc tggggcaggc tgagcaggaa gctgatcaac ggcatcaggg acaagcagag   4140
cggcaagacc atcctggact tcctgaagag cgacggcttc gccaacagga acttcatgca   4200
gctgatccac gacgacagcc tgaccttcaa ggaggacatc cagaaggccc aggtgagcgg   4260
ccagggcgac agcctgcacg agcacatcgc caacctggcc ggcagcccgg ccatcaagaa   4320
gggcatcctg cagaccgtga aggtggtgga cgagctggtg aaggtgatgg gcaggcacaa   4380
gccggagaac atcgtgatcg agatggccag ggagaaccag accacccaga agggccagaa   4440
gaacagcagg gagaggatga gagaggatcga ggagggcatc aaggagctgg gcagccagat   4500
cctgaaggag cacccggtgg agaacaccca gctgcagaac gagaagctgt acctgtacta   4560
cctgcagaac ggcagggaca tgtacgtgga ccaggagctg gacatcaaca ggctgagcga   4620
ctacgacgtg gaccacatcg tgccgcagag cttcctgaag gacgacagca tcgacaacaa   4680
ggtgctgacc aggagcgaca gaacagggg caagagcgac aacgtgccga gcgaggaggt   4740
ggtgaagaag atgaaaaact actggaggca gctgctgaac gccaagctga tcacccagag   4800
gaagttcgac aacctgacca ggccgagag gggcggcctg agcgagctgg acaaggccgg   4860
cttcattaaa aggcagctgg tggagaccag gcagatcacc aagcacgtgg cccagatcct   4920
ggacagcagg atgaacacca gtacgacga gaacgacaag ctgatcaggg aggtgaaggt   4980
gatcaccctg aagagcaagc tggtgagcga cttcaggaag gacttccagt tctacaaggt   5040
gagggagatc aataattacc accacgccca cgacgcctac ctgaacgccg tggtgggcac   5100
cgccctgatt aaaaagtacc cgaagctgga gagcgagttc gtgtacggcg actacaaggt   5160
gtacgacgtg aggaagatga tcgccaagag cgagcaggag atcggcaagg ccaccgccaa   5220
gtacttcttc tacagcaaca tcatgaactt cttcaagacc gagatcaccc tggccaacgg   5280
cgagatcagg aagaggccgc tgatcgagac caacggcgag accggcgaga tcgtgtggga   5340
caagggcagg gacttcgcca ccgtgaggaa ggtgctgtcc atgccgcagg tgaacatcgt   5400
gaagaagacc gaggtgcaga ccggcggctt cagcaaggag agcatcctgc cgaagaggaa   5460
```

```
cagcgacaag ctgatcgcca ggaagaagga ctgggacccg aagaagtacg gcggcttcga   5520
cagcccgacc gtggcctaca gcgtgctggt ggtggccaag gtggagaagg gcaagagcaa   5580
gaagctgaag agcgtgaagg agctggtggg catcaccatc atggagagga gcagcttcga   5640
gaagaaccca gtggacttcc tggaggccaa gggctacaag gaggtgaaga aggacctgat   5700
cattaaactg ccgaagtaca gcctgttcga gctggagaac ggcaggaaga ggatgctggc   5760
cagcgccggc gagctgcaga agggcaacga gctggccctg ccgagcaagt acgtgaactt   5820
cctgtacctg gccagccact acgagaagct gaagggcagc ccggaggaca acgagcagaa   5880
gcagctgttc gtggagcagc acaagcacta cctggacgag atcatcgagc agatcagcga   5940
gttcagcaag agggtgatcc tggccgacgc caacctggac aaggtgctga gcgcctacaa   6000
caagcacagg gacaagccga tcagggagca ggccgagaac atcatccacc tgttcaccct   6060
gaccaacctg ggcgccccgg ccgccttcaa gtacttcgac accaccatcg acaggaagag   6120
gtacaccagc accaaggagg tgctggacgc caccctgatc caccagagca tcaccggcct   6180
gtacgagacc aggatcgacc tgagccagct gggcggcgac agcagcccgc cgaagaagaa   6240
gaggaaggtg agctggaagg acgccagcgg ctggagcagg atgtgaagct tgatcgttca   6300
aacatttggc aataaagttt cttaagattg aatcctgttg ccggtcttgc gatgattatc   6360
atataatttc tgttgaatta cgttaagcat gtaataatta acatgtaatg catgacgtta   6420
tttatgagat gggtttttat gattagagtc ccgcaattat acatttaata cgcgatagaa   6480
aacaaaatat agcgcgcaaa ctaggataaa ttatcgcgcg cggtgtcatc tatgttacta   6540
gatcttcgaa gggatcttta aacatacgaa cagatcactt aaagttcttc tgaagcaact   6600
taaagttatc aggcatgcat ggatcttgga ggaatcagat gtgcagtcag ggaccatagc   6660
acaggacagg cgtcttctac tggtgctacc agcaaatgct ggaagccggg aacactgggt   6720
acgttggaaa ccacgtgatg tggagtaaga taaactgtag gagaaaagca tttcgtagtg   6780
ggccatgaag cctttcagga catgtattgc agtatgggcc ggcccattac gcaattggac   6840
gacaacaaag actagtatta gtaccacctc ggctatccac atagatcaaa gctggtttaa   6900
aagagttgtg cagatgatcc gtggcagacg agcaggcgca gttccgtttt agagctagaa   6960
atagcaagtt aaaataaggc tagtccgtta tcaacttgaa aaagtggcac cgagtcggtg   7020
cttttttttt cggaccgcgc ctgcagtgca gcgtgacccg gtcgtgcccc tctctagaga   7080
taatgagcat tgcatgtcta agttataaaa aattaccaca tatttttttt gtcacacttg   7140
tttgaagtgc agtttatcta tctttataca tatatttaaa cttttactcta cgaataatat   7200 aatctatagt actacaataa tatcagtgtt ttagagaatc atataaatga acagttagac   7260
atggtctaaa ggacaattga gtattttgac aacaggactc tacagtttta tcttttttagt   7320 gtgcatgtgt tctccttttt ttttgcaaat agcttcacct atataatact tcatccattt   7380
tattagtaca tccatttagg gtttagggtt aatggttttt atagactaat ttttttagta   7440
catctatttt attctatttt agcctctaaa ttaagaaaac taaaactcta ttttagtttt   7500
tttatttaat aatttagata taaaatagaa taaaataaag tgactaaaaa ttaaacaaat   7560 acccttaag aaattaaaaa aactaaggaa acatttttct tgtttcgagt agataatgcc   7620
agcctgttaa acgccgtcga cgagtctaac ggacaccaac cagcgaacca gcagcgtcgc   7680
gtcgggccaa gcgaagcaga cggcacggca tctctgtcgc tgcctctgga cccctctcga   7740
gagttccgct ccaccgttgg acttgctccg ctgtcggcat ccagaaattg cgtggcggag   7800
```

```
cggcagacgt gagccggcac ggcaggcggc ctcctcctcc tctcacggca ccggcagcta    7860
cgggggattc ctttcccacc gctccttcgc tttcccttcc tcgcccgccg taataaatag    7920
acaccccctc cacaccctct ttccccaacc tcgtgttgtt cggagcgcac acacacacaa    7980
ccagatctcc cccaaatcca cccgtcggca cctccgcttc aaggtacgcc gctcgtcctc    8040
cccccccccc ctctctacct tctctagatc ggcgttccgg tccatggtta gggcccggta    8100
gttctacttc tgttcatgtt tgtgttagat ccgtgtttgt gttagatccg tgctgctagc    8160
gttcgtacac ggatgcgacc tgtacgtcag acacgttctg attgctaact tgccagtgtt    8220
tctctttggg gaatcctggg atggctctag ccgttccgca gacgggatcg atttcatgat    8280
tttttttgtt tcgttgcata gggtttggtt tgccctttc ctttatttca atatatgccg    8340
tgcacttgtt tgtcgggtca tcttttcatg ctttttttg tcttggttgt gatgatgtgg    8400
tctggttggg cggtcgttct agatcggagt agaattctgt ttcaaactac ctggtggatt    8460
tattaatttt ggatctgtat gtgtgtgcca tacatattca tagttacgaa ttgaagatga    8520
tggatggaaa tatcgatcta ggataggtat acatgttgat gcgggtttta ctgatgcata    8580
tacagagatg cttttttgttc gcttggttgt gatgatgtgg tgtggttggg cggtcgttca    8640
ttcgttctag atcggagtag aatactgttt caaactacct ggtgtattta ttaatttggg    8700
aactgtatgt gtgtgtcata catcttcata gttacgagtt taagatggat ggaaatatcg    8760
atctaggata ggtatacatg ttgatgtggg ttttactgat gcatatacat gatggcatat    8820
gcagcatcta ttcatatgct ctaaccttga gtacctatct attataataa acaagtatgt    8880
tttataatta ttttgatctt gatatacttg gatgatggca tatgcagcag ctatatgtgg    8940 attttttttag ccctgccttc atacgctatt tatttgcttg gtactgtttc ttttgtcgat    9000
gctcaccctg ttgtttggtg ttacttctgc agggatccgg cagcagccat gcagaagctg    9060
atcaacagcg tgcagaacta cgcctggggc agcaagaccg ccctgaccga gctgtacggc    9120
atggagaacc ccagcagcca gcccatggcc gagctgtgga tgggcgccca ccccaagagc    9180
agcagccgcg tgcagaacgc cgccggcgac atcgtgagcc tgcgcgacgt gatcgagagc    9240
gacaagagca ccctgctggg cgaggccgtg gccaagcgct cggcgagct gcccttcctg    9300 ttcaaggtgc tgtgcgccgc ccagcccctg agcatccagg tgcaccccaa caagcacaac    9360
agcgagatcg gcttcgccaa ggagaacgcc gccggcatcc ccatggacgc cgccgagcgc    9420
aactacaagg accccaacca caagcccgag ctggtgttcg ccctgaccc cttcctggcc    9480 atgaacgcct ccgcgagtt cagcgagatc gtgagcctgc tgcagcccgt ggccggcgcc    9540
caccccgcca tcgcccactt cctgcagcag cccgacgccg agcgcctgag cgagctgttc    9600
gccagcctgc tgaacatgca gggcgaggag aagagccgcg ccctggccat cctgaagagc    9660
gccctggaca gccagcaggg cgagccctgg cagaccatcc gcctgatcag cgagttctac    9720
cccgaggaca gcggcctgtt cagcccctg ctgctgaacg tggtgaagct gaacccggc    9780 gaggccatgt tcctgttcgc cgagacccc cacgcctacc tgcagggcgt ggccctggag    9840
gtgatggcca acagcgacaa cgtgctgcgc gccggcctga cccccaagta catcgacatc    9900
cccgagctgg tggccaacgt gaagttcgag gccaagcccg ccaaccagct gctgaccag    9960 cccgtgaagc agggcgccga gctggacttc cccatccccg tggacgactt cgccttcagc   10020
ctgcacgacc tgagcgacaa ggagaccacc atcagccagc agagcgccgc catcctgttc   10080
tgcgtggagg cgacgccac cctgtggaag ggcagccagc agctgcagct gaagcccggc   10140
gagagcgcct tcatcgccgc caacgagagc cccgtgaccg tgaagggcca cggccgcctg   10200
```

-continued

```
gcccgcgtgt acaacaagct gtgataggag ctcgatccgt cgacctgcag atcgttcaaa    10260
catttggcaa taaagtttct taagattgaa tcctgttgcc ggtcttgcga tgattatcat    10320
ataatttctg ttgaattacg ttaagcatgt aataattaac atgtaatgca tgacgttatt    10380
tatgagatgg gtttttatga ttagagtccc gcaattatac atttaatacg cgatagaaaa    10440
caaaatatag cgcgcaaact aggataaatt atcgcgcgcg gtgtcatcta tgttactaga    10500
tcggcgcgcc gcaattgaag tttgggcggc cagcatggcc gtatccgcaa tgtgttatta    10560
agttgtctaa gcgtcaattt gtttacacca caatatatcc tgccaccagc cagccaacag    10620
ctccccgacc ggcagctcgg cacaaaatca ccactcgata caggcagccc atcagaatta    10680
attctcatgt ttgacagctt atcatcgact gcacggtgca ccaatgcttc tggcgtcagg    10740
cagccatcgg aagctgtggt atggctgtgc aggtcgtaaa tcactgcata attcgtgtcg    10800
ctcaaggcgc actcccgttc tggataatgt tttttgcgcc gacatcataa cggttctggc    10860
aaatattctg aaatgagctg ttgacaatta atcatccggc tcgtataatg tgtggaattg    10920
tgagcggata acaatttcac acaggaaaca gaccatgagg gaagcgttga tcgccgaagt    10980
atcgactcaa ctatcagagg tagttggcgt catcgagcgc catctcgaac cgacgttgct    11040
ggccgtacat ttgtacggct ccgcagtgga tggcggcctg aagccacaca gtgatattga    11100
tttgctggtt acggtgaccg taaggcttga tgaaacaacg cggcgagctt tgatcaacga    11160
ccttttggaa acttcggctt ccctggaga gagcgagatt ctccgcgctg tagaagtcac    11220
cattgttgtg cacgacgaca tcattccgtg gcgttatcca gctaagcgcg aactgcaatt    11280
tggagaatgg cagcgcaatg acattcttgc aggtatcttc gagccagcca cgatcgacat    11340
tgatctggct atcttgctga caaaagcaag agaacatagc gttgccttgg taggtccagc    11400
ggcggaggaa ctctttgatc cggttcctga acaggatcta tttgaggcgc taaatgaaac    11460
cttaacgcta tggaactcgc cgcccgactg ggctggcgat gagcgaaatg tagtgcttac    11520
gttgtcccgc atttggtaca gcgcagtaac cggcaaaatc gcgccgaagg atgtcgctgc    11580
cgactgggca atggagcgcc tgccggccca gtatcagccc gtcatacttg aagctaggca    11640
ggcttatctt ggacaagaag atcgcttggc ctcgcgcgca gatcagttgg aagaatttgt    11700
tcactacgtg aaaggcgaga tcaccaaagt agtcggcaaa taaagctcta gtggatctcc    11760
gtacccgggg atctggctcg cggcggacgc acgacgccgg ggcgagacca taggcgatct    11820
cctaaatcaa tagtagctgt aacctcgaag cgtttcactt gtaacaacga ttgagaattt    11880
ttgtcataaa attgaaatac ttggttcgca tttttgtcat ccgcggtcag ccgcaattct    11940
gacgaactgc ccatttagct ggagatgatt gtacatcctt cacgtgaaaa tttctcaagc    12000
gctgtgaaca agggttcaga ttttagattg aaaggtgagc cgttgaaaca cgttcttctt    12060
gtcgatgacg acgtcgctat gcggcatctt attattgaat accttacgat ccacgccttc    12120
aaagtgaccg cggtagccga cagcacccag ttcacaagag tactctcttc cgcgacggtc    12180
gatgtcgtgg ttgttgatct agatttaggt cgtgaagatg ggctcgagct aggagcaagt    12240
gattttatcg ctaagccgtt cagtatcaga gagtttctag cacgcattcg ggttgccttg    12300
cgcgtgcgcc ccaacgttgt ccgctccaaa gaccgacggt ctttttgttt tactgactgg    12360
acacttaatc tcaggcaacg tcgcttgatg tccgaagctg gcggtgaggt gaaacttacg    12420
gcaggtgagt tcaatcttct cctcgcgttt ttagagaaac cccgcgacgt tctatcgcgc    12480
gagcaacttc tcattgccag tcgagtacgc gacgaggagg tttatgacag gagtatagat    12540
```

-continued

```
gttctcattt tgaggctgcg ccgcaaactt gaggcagatc cgtcaagccc tcaactgata    12600
aaaacagcaa gaggtgccgg ttatttcttt gacgcggacg tgcaggtttc gcacggggggg   12660 acgatggcag cctgagccaa ttcccagatc cccgaggaat cggcgtgagc ggtcgcaaac    12720
catccggccc ggtacaaatc ggcgcggcgc tgggtgatga cctggtggag aagttgaagg    12780
ccgcgcaggc cgcccagcgg caacgcatcg aggcagaagc acgccccggt gaatcgtggc    12840
aagcggccgc tgatcgaatc cgcaaagaat cccggcaacc gccggcagcc ggtgcgccgt    12900
cgattaggaa gccgcccaag ggcgacgagc aaccagattt tttcgttccg atgctctatg    12960
acgtgggcac ccgcgatagt cgcagcatca tggacgtggc cgttttccgt ctgtcgaagc    13020
gtgaccgacg agctggcgag gtgatccgct acgagcttcc agacgggcac gtagaggttt    13080
ccgcagggcc ggccggcatg gccagtgtgt gggattacga cctggtactg atggcggttt    13140
cccatctaac cgaatccatg aaccgatacc gggaagggaa gggagacaag cccggccgcg    13200
tgttccgtcc acacgttgcg gacgtactca agttctgccg gcgagccgat ggcggaaagc    13260
agaaagacga cctggtagaa acctgcattc ggttaaacac cacgcacgtt gccatgcagc    13320
gtacgaagaa ggccaagaac ggccgcctgg tgacggtatc cgagggtgaa gccttgatta    13380
gccgctacaa gatcgtaaag agcgaaaccg ggcggccgga gtacatcgag atcgagctag    13440
ctgattggat gtaccgcgag atcacagaag gcaagaaccc ggacgtgctg acggttcacc    13500
ccgattactt tttgatcgat cccggcatcg gccgtttttct ctaccgcctg gcacgccgcg   13560
ccgcaggcaa ggcagaagcc agatggttgt tcaagacgat ctacgaacgc agtggcagcg    13620
ccggagagtt caagaagttc tgtttcaccg tgcgcaagct gatcgggtca aatgacctgc    13680
cggagtacga tttgaaggag gaggcggggc aggctggccc gatcctagtc atgcgctacc    13740
gcaacctgat cgagggcgaa gcatccgccg gttcctaatg tacggagcag atgctagggc    13800
aaattgccct agcaggggaa aaaggtcgaa aaggtctctt tcctgtggat agcacgtaca    13860
ttgggaaccc aaagccgtac attgggaacc ggaacccgta cattgggaac ccaaagccgt    13920
acattgggaa ccggtcacac atgtaagtga ctgatataaa agagaaaaaa ggcgattttt    13980
ccgcctaaaa ctctttaaaa cttattaaaa ctcttaaaac ccgcctggcc tgtgcataac    14040
tgtctggcca gcgcacagcc gaagagctgc aaaaagcgcc tacccttcgg tcgctgcgct    14100
ccctacgccc cgccgcttcg cgtcggccta tcgcggccgc tggccgctca aaaatggctg    14160
gcctacggcc aggcaatcta ccagggcgcg gacaagccgc gccgtcgcca ctcgaccgcc    14220
ggcgctgagg tctgcctcgt gaagaaggtg ttgctgactc ataccaggcc tgaatcgccc    14280
catcatccag ccagaaagtg agggagccac ggttgatgag agctttgttg taggtggacc    14340
agttggtgat tttgaacttt tgctttgcca cggaacggtc tgcgttgtcg ggaagatgcg    14400
tgatctgatc cttcaactca gcaaaagttc gatttattca acaaagccgc cgtcccgtca    14460
agtcagcgta atgctctgcc agtgttacaa ccaattaacc aattctgatt agaaaaactc    14520
atcgagcatc aaatgaaact gcaatttatt catatcagga ttatcaatac catattttg     14580 aaaaagccgt ttctgtaatg aaggagaaaa ctcaccgagg cagttccata ggatggcaag    14640
atcctggtat cggtctgcga ttccgactcg tccaacatca atacaaccta ttaatttccc    14700
ctcgtcaaaa ataaggttat caagtgagaa atcaccatga gtgacgactg aatccggtga    14760
gaatggcaaa agctctgcat taatgaatcg gccaacgcgc ggggagaggc ggtttgcgta    14820
ttgggcgctc ttccgcttcc tcgctcactg actcgctgcg ctcggtcgtt cggctgcggc    14880
gagcggtatc agctcactca aaggcggtaa tacggttatc cacagaatca ggggataacg    14940
```

-continued

```
caggaaagaa catgtgagca aaaggccagc aaaaggccag gaaccgtaaa aaggccgcgt   15000
tgctggcgtt tttccatagg ctccgccccc ctgacgagca tcacaaaaat cgacgctcaa   15060
gtcagaggtg gcgaaacccg acaggactat aaagatacca ggcgtttccc cctggaagct   15120
ccctcgtgcg ctctcctgtt ccgaccctgc cgcttaccgg atacctgtcc gcctttctcc   15180
cttcgggaag cgtggcgctt tctcatagct cacgctgtag gtatctcagt tcggtgtagg   15240
tcgttcgctc caagctgggc tgtgtgcacg aaccccccgt tcagcccgac cgctgcgcct   15300
tatccggtaa ctatcgtctt gagtccaacc cggtaagaca cgacttatcg ccactggcag   15360
cagccactgg taacaggatt agcagagcga ggtatgtagg cggtgctaca gagttcttga   15420
agtggtggcc taactacggc tacactagaa gaacagtatt tggtatctgc gctctgctga   15480
agccagttac cttcggaaaa agagttggta gctcttgatc cggcaaacaa accaccgctg   15540
gtagcggtgg tttttttgtt tgcaagcagc agattacgcg cagaaaaaaa ggatctcaag   15600
aagatccttt gatcttttct acggggtctg acgctcagtg gaacgaaaac tcacgttaag   15660
ggattttggt catgagatta tcaaaaagga tcttcaccta gatccttttg atccggaatt   15720
a                                                                   15721
```

```
<210> SEQ ID NO 25
<211> LENGTH: 19
<212> TYPE: DNA
<213> ORGANISM: Artificial Sequence
<220> FEATURE:
<223> OTHER INFORMATION: for editing VLHP1 in wheat

<400> SEQUENCE: 25
gacgagcagg cgcagttcc                                                       19
```

```
<210> SEQ ID NO 26
<211> LENGTH: 20
<212> TYPE: DNA
<213> ORGANISM: Triticum aestivum

<400> SEQUENCE: 26
gctggagctg agcttccggg                                                      20
```

```
<210> SEQ ID NO 27
<211> LENGTH: 20
<212> TYPE: DNA
<213> ORGANISM: Triticum aestivum

<400> SEQUENCE: 27
tctggagctg agcttccggg                                                      20
```

```
<210> SEQ ID NO 28
<211> LENGTH: 20
<212> TYPE: DNA
<213> ORGANISM: Zea mays

<400> SEQUENCE: 28
aggcgtcgag cagcgaggtg                                                      20
```

```
<210> SEQ ID NO 29
<211> LENGTH: 20
<212> TYPE: DNA
<213> ORGANISM: Artificial Sequence
<220> FEATURE:
<223> OTHER INFORMATION: edited ZmVLHP-03 portion
```

-continued

<400> SEQUENCE: 29
aggcgttgag cagcgaggtg                                                    20

<210> SEQ ID NO 30
<211> LENGTH: 75
<212> TYPE: DNA
<213> ORGANISM: Artificial Sequence
<220> FEATURE:
<223> OTHER INFORMATION: repair donor template for creating E149L
      mutation in ZmPYL-D

<400> SEQUENCE: 30
ccttggtgtt gccgtcgggg acgtcgacga cgaatgacag gatgacgagc gtccctggcc        60
ggccgtcgat gacct                                                         75

<210> SEQ ID NO 31
<211> LENGTH: 15722
<212> TYPE: DNA
<213> ORGANISM: Artificial Sequence
<220> FEATURE:
<223> OTHER INFORMATION: vector 23136
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
<223> OTHER INFORMATION: xZmPYL-D
<220> FEATURE:
<221> NAME/KEY: misc_feature
<222> LOCATION: (6927)..(7031)
<223> OTHER INFORMATION: rsgRBAZmPYLd-02
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:

```
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01
<220> FEATURE:
<221> NAME/KEY: misc_feature
<222> LOCATION: (13822)..(14226)
<223> OTHER INFORMATION: oVS1-02
<220> FEATURE:
<221> NAME/KEY: misc_feature
<222> LOCATION: (14904)..(15710)
<223> OTHER INFORMATION: oCOLE-06

<400> SEQUENCE: 31
attcctgtgg ttggcatgca catacaaatg gacgaacgga taaacctttt cacgcccttt      60
taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg accccgccg atgacgcggg acaagccgtt ttacgtttgg      240
aactgacaga accgcaacgc tgcaggaatt ggccgcagcg gccatttaaa caaagcttgg     300
taccattatg tggtctaggt aggttctata tataagaaaa cttgaaatgt tctaaaaaaa     360
aattcaagcc catgcatgat tgaagcaaac ggtatagcaa cggtgttaac ctgatctagt     420
gatctcttgc aatccttaac ggccacctac cgcaggtagc aaacggcgtc ccctcctcg      480 atatctccgc ggcgacctct ggctttttcc gcggaattgc gcggtgggga cggattccac     540
gagaccgcga cgcaaccgcc tctcgccgct gggccccaca ccgctcggtg ccgtagcctc     600
acgggactct ttctccctcc tcccccgtta taaattggct tcatcccctc cttgcctcat     660
ccatccaaat cccagtcccc aatcccatcc cttcgtagga gaaattcatc gaagctaagc     720
gaatcctcgc gatcctctca aggtactgcg agttttcgat cccctctcg accctcgta      780 tgtttgtgtt tgtcgtagcg tttgattagg tatgctttcc ctgtttgtgt tcgtcgtagc     840
gtttgattag gtatgctttc cctgttcgtg ttcatcgtag tgtttgatta ggtcgtgtga     900
ggcgatggcc tgctcgcgtc cttcgatctg tagtcgattt gcgggtcgtg gtgtagatct     960
gcgggctgtg atgaagttat ttggtgtgat ctgctcgcct gattctgcgg gttggctcga    1020
gtagatatga tggttggacc ggttggttcg tttaccgcgc tagggttggg ctgggatgat    1080
gttgcatgcg ccgttgcgcg tgatcccgca gcaggacttg cgtttgattg ccagatctcg    1140
ttacgattat gtgatttggt ttggactttt tagatctgta gcttctgctt atgtgccaga    1200
tgcgcctact gctcatatgc ctgatgataa tcataaatgg ctgtggaact aactagttga    1260
ttgcggagtc atgtatcagc tacaggtgta gggactagct acaggtgtag ggacttgcgt    1320
ctaattgttt ggtcctttac tcatgttgca attatgcaat ttagtttaga ttgtttgttc    1380
cactcatcta ggctgtaaaa gggacactgc ttagattgct gtttaatctt tttagtagat    1440
tatattatat tggtaactta ttacccctat tacatgccat acgtgacttc tgctcatgcc    1500
tgatgataat catagatcac tgtggaatta attagttgat tgttgaatca tgtttcatgt    1560
acataccacg gcacaattgc ttagttcctt aacaaatgca aattttactg atccatgtat    1620
gatttgcgtg gttctctaat gtgaaatact atagctactt gttagtaaga atcaggttcg    1680
tatgcttaat gctgtatgtg ccttctgctc atgcctgatg ataatcatat atcactggaa    1740
```

-continued

```
ttaattagtt gatcgtttaa tcatatatca agtacatacc atgccacaat ttttagtcac    1800
ttaacccatg cagattgaac tggtccctgc atgtttttgct aaattgttct attctgatta    1860
gaccatatat catgtatttt tttttggtaa tggttctctt attttaaatg ctatatagtt    1920
ctggtacttg ttagaaagat ctgcttcata gtttagttgc ctatccctcg aattaggatg    1980
ctgagcagct gatcctatag ctttgtttca tgtatcaatt cttttgtgtt caacagtcag    2040
tttttgttag attcattgta acttatggtc gcttactctt ctggtcctca atgcttgcag    2100
gatcgcggcc gctcatatgg acaagaagta cagcatcggc ctggacatcg gcaccaacag    2160
cgtgggctgg gccgtgatca ccgacgagta caaggtgccg agcaagaagt tcaaggtgct    2220
gggcaacacc gacaggcaca gcatcaagaa gaacctgatc ggcgccctgc tgttcgacag    2280
cggcgagacc gccgaggcca ccaggctgaa gaggaccgcc aggaggaggt acaccaggag    2340
gaagaacagg atctgctacc tgcaggagat cttcagcaac gagatggcca aggtggacga    2400
cagcttcttc cacaggctgg aggagagctt cctggtggag gaggacaaga agcacgagag    2460
gcacccgatc ttcggcaaca tcgtggacga ggtggcctac cacgagaagt acccgaccat    2520
ctaccacctg aggaagaagc tggtggacag caccgacaag gccgacctga ggctgatcta    2580
cctggccctg gcccacatga tcaagttcag gggccacttc ctgatcgagg gcgacctgaa    2640
cccggacaac agcgacgtgg acaagctgtt catccagctg gtgcagacct acaaccagct    2700
gttcgaggag aacccgatca cgccagcggc cgtggacgcc aaggccatcc tgagcgccag    2760
gctgagcaag agcaggaggc tggagaacct gatcgcccag ctgccgggcg agaagaagaa    2820
cggcctgttc ggcaacctga tcgccctgag cctgggcctg accccgaact tcaagagcaa    2880
cttcgacctg gccgaggacg ccaagctgca gctgagcaag gacacctacg acgacgacct    2940
ggacaacctg ctggcccaga tcggcgacca gtacgccgac ctgttcctgg ccgccaagaa    3000
cctgagcgac gccatcctgc tgagcgacat cctgagggtg aacaccgaga tcaccaaggc    3060
cccgctgagc gccagcatga tcaagaggta cgacgagcac caccaggacc tgaccctgct    3120
gaaggccctg gtgaggcagc agctgccgga gaagtacaag gagatcttct cgaccagag    3180 caagaacggc tacgccggct acatcgacgg cggcgccagc caggaggagt tctacaagtt    3240
catcaagccg atcctggaga gatggacgg caccgaggag ctgctggtga agctgaacag    3300
ggaggacctg ctgaggaagc agaggaccct cgacaacggc agcatcccgc accagatcca    3360
cctgggcgag ctgcacgcca tcctgaggag gcaggaggac ttctacccgt tcctgaagga    3420
caacagggag aagatcgaga agatcctgac cttccgcatc ccgtactacg tgggccgct    3480 ggccagggc aacagcaggt tcgcctggat gaccaggaag agcgaggaga ccatcacccc    3540
gtggaacttc gaggaggtgg tggacaaggg cgccagcgcc cagagcttca tcgagaggat    3600
gaccaacttc gacaagaacc tgccgaacga aaggtgctg ccgaagcaca gcctgctgta    3660
cgagtacttc accgtgtaca acgagctgac caaggtgaag tacgtgaccg agggcatgag    3720
gaagccggcc ttcctgagcg gcgagcagaa aaaggccatc gtggacctgc tgttcaagac    3780
caacaggaag gtgaccgtga agcagctgaa ggaggactac ttcaagaaga tcgagtgctt    3840
cgacagcgtg gagatcagcg gcgtggagga caggttcaac gccagcctgg gcacctacca    3900
cgacctgctg aagatcatca aggacaagga cttcctggac aacgaggaga cgaggacat    3960 cctggaggac atcgtgctga ccctgaccct gttcgaggac agggagatga tcgaggagag    4020
gctgaagacc tacgcccacc tgttcgacga caaggtgatg aagcagctga agaggaggag    4080
```

-continued

```
gtacaccggc tggggcaggc tgagcaggaa gctgatcaac ggcatcaggg acaagcagag   4140
cggcaagacc atcctggact tcctgaagag cgacggcttc gccaacagga acttcatgca   4200
gctgatccac gacgacagcc tgaccttcaa ggaggacatc cagaaggccc aggtgagcgg   4260
ccagggcgac agcctgcacg agcacatcgc caacctggcc ggcagcccgg ccatcaagaa   4320
gggcatcctg cagaccgtga aggtggtgga cgagctggtg aaggtgatgg gcaggcacaa   4380
gccggagaac atcgtgatcg agatggccag ggagaaccag accacccaga agggccagaa   4440
gaacagcagg gagaggatga agaggatcga ggagggcatc aaggagctgg gcagccagat   4500
cctgaaggag cacccggtgg agaacaccca gctgcagaac gagaagctgt acctgtacta   4560
cctgcagaac ggcagggaca tgtacgtgga ccaggagctg gacatcaaca ggctgagcga   4620
ctacgacgtg gaccacatcg tgccgcagag cttcctgaag gacgcacagca tcgacaacaa   4680 ggtgctgacc aggagcgaca agaacagggg caagagcgac aacgtgccga gcgaggaggt   4740
ggtgaagaag atgaaaaact actggaggca gctgctgaac gccaagctga tcacccagag   4800
gaagttcgac aacctgacca aggccgagag gggcggcctg agcgagctgg acaaggccgg   4860
cttcattaaa aggcagctgg tggagaccag gcagatcacc aagcacgtgg cccagatcct   4920
ggacagcagg atgaacacca gtacgacga gaacgacaag ctgatcaggg aggtgaaggt   4980
gatcaccctg aagagcaagc tggtgagcga cttcaggaag gacttccagt tctacaaggt   5040
gagggagatc aataattacc accacgccca cgacgcctac ctgaacgccg tggtgggcac   5100
cgccctgatt aaaaagtacc cgaagctgga gagcgagttc gtgtacggcg actacaaggt   5160
gtacgacgtg aggaagatga tcgccaagag cgagcaggag atcggcaagg ccaccgccaa   5220
gtacttcttc tacagcaaca tcatgaactt cttcaagacc gagatcaccc tggccaacgg   5280
cgagatcagg aagaggccgc tgatcgagac caacggcgag accggcgaga tcgtgtggga   5340
caagggcagg gacttcgcca ccgtgaggaa ggtgctgtcc atgccgcagg tgaacatcgt   5400
gaagaagacc gaggtgcaga ccggcggctt cagcaaggag agcatcctgc cgaagaggaa   5460
cagcgacaag ctgatcgcca ggaagaagga ctgggacccg aagaagtacg gcggcttcga   5520
cagcccgacc gtggcctaca gcgtgctggt ggtggccaag gtggagaagg caagagcaa   5580 gaagctgaag agcgtgaagg agctggtggg catcaccatc atggagagga gcagcttcga   5640
gaagaaccca gtggacttcc tggaggccaa gggctacaag gaggtgaaga aggacctgat   5700
cattaaactg ccgaagtaca gcctgttcga gctggagaac ggcaggaaga ggatgctggc   5760
cagcgccggc gagctgcaga agggcaacga gctggccctg ccgagcaagt acgtgaactt   5820
cctgtacctg gccagccact acgagaagct gaagggcagc ccggaggaca cgagcagaa   5880 gcagctgttc gtggagcagc acaagcacta cctggacgag atcatcgagc agatcagcga   5940
gttcagcaag agggtgatcc tggccgacgc caacctggac aaggtgctga gcgcctacaa   6000
caagcacagg gacaagccga tcagggagca ggccgagaac atcatccacc tgttcaccct   6060
gaccaacctg ggcgccccgg ccgccttcaa gtacttcgac accaccatcg acaggaagag   6120
gtacaccagc accaaggagg tgctggacgc caccctgatc caccagagca tcaccggcct   6180
gtacgagacc aggatcgacc tgagccagct gggcggcgac agcagcccgc cgaagaagaa   6240
gaggaaggtg agctggaagg acgccagcgg ctggagcagg atgtgaagct tgatcgttca   6300
aacatttggc aataaagttt cttaagattg aatcctgttg ccggtcttgc gatgattatc   6360
atataatttc tgttgaatta cgttaagcat gtaataatta acatgtaatg catgacgtta   6420
tttatgagat gggtttttat gattagagtc ccgcaattat acatttaata cgcgatagaa   6480
```

-continued

```
aacaaaatat agcgcgcaaa ctaggataaa ttatcgcgcg cggtgtcatc tatgttacta   6540
gatcttcgaa gggatcttta aacatacgaa cagatcactt aaagttcttc tgaagcaact   6600
taaagttatc aggcatgcat ggatcttgga ggaatcagat gtgcagtcag ggaccatagc   6660
acaggacagg cgtcttctac tggtgctacc agcaaatgct ggaagccggg aacactgggt   6720
acgttggaaa ccacgtgatg tggagtaaga taaactgtag gagaaaagca tttcgtagtg   6780
ggccatgaag cctttcagga catgtattgc agtatgggcc ggcccattac gcaattggac   6840
gacaacaaag actagtatta gtaccacctc ggctatccac atagatcaaa gctggtttaa   6900
aagagttgtg cagatgatcc gtggcagtcg gggacgtcga cgacgagttt tagagctaga   6960
aatagcaagt taaaataagg ctagtccgtt atcaacttga aaaagtggca ccgagtcggt   7020
gctttttttt tcggaccgcg cctgcagtgc agcgtgaccc ggtcgtgccc ctctctagag   7080
ataatgagca ttgcatgtct aagttataaa aaattaccac atattttttt tgtcacactt   7140
gtttgaagtg cagtttatct atctttatac atatatttaa actttactct acgaataata   7200
taatctatag tactacaata atatcagtgt tttagagaat catataaatg aacagttaga   7260
catggtctaa aggacaattg agtattttga caacaggact ctacagtttt atcttttttag   7320 tgtgcatgtg ttctcctttt tttttgcaaa tagcttcacc tatataatac ttcatccatt   7380
ttattagtac atccatttag ggtttagggt taatggtttt tatagactaa ttttttttagt   7440 acatctattt tattctattt tagcctctaa attaagaaaa ctaaaactct attttagttt   7500
ttttatttaa taatttagat ataaaataga ataaaataaa gtgactaaaa attaaacaaa   7560 tacccttaa gaaattaaaa aaactaagga aacattttc ttgtttcgag tagataatgc   7620
cagcctgtta aacgccgtcg acgagtctaa cggacaccaa ccagcgaacc agcagcgtcg   7680
cgtcgggcca agcgaagcag acggcacggc atctctgtcg ctgcctctgg accctctcg   7740 agagttccgc tccaccgttg gacttgctcc gctgtcggca tccagaaatt gcgtggcgga   7800
gcggcagacg tgagccggca cggcaggcgg cctcctcctc ctctcacggc accggcagct   7860
acgggggatt cctttcccac cgctccttcg ctttcccttc ctcgcccgcc gtaataaata   7920 gacacccct ccacaccctc tttccccaac ctcgtgttgt tcggagcgca cacacacaca   7980
accagatctc ccccaaatcc acccgtcggc acctccgctt caaggtacgc cgctcgtcct   8040 ccccccccc cctctctacc ttctctagat cggcgttccg gtccatggtt agggcccggt   8100
agttctactt ctgttcatgt ttgtgttaga tccgtgtttg tgttagatcc gtgctgctag   8160
cgttcgtaca cggatgcgac ctgtacgtca gacacgttct gattgctaac ttgccagtgt   8220
ttctctttgg ggaatcctgg gatggctcta gccgttccgc agacgggatc gatttcatga   8280
ttttttttgt ttcgttgcat agggtttggt ttgccctttt cctttatttc aatatatgcc   8340
gtgcacttgt ttgtcgggtc atcttttcat gctttttttt gtcttggttg tgatgatgtg   8400
gtctggttgg gcggtcgttc tagatcggag tagaattctg tttcaaacta cctggtggat   8460
ttattaattt tggatctgta tgtgtgtgcc atacatattc atagttacga attgaagatg   8520
atggatggaa atatcgatct aggataggta tacatgttga tgcgggtttt actgatgcat   8580
atacagagat gctttttgtt cgcttggttg tgatgatgtg gtgtggttgg gcggtcgttc   8640
attcgttcta gatcggagta gaatactgtt tcaaactacc tggtgtattt attaattttg   8700
gaactgtatg tgtgtgtcat acatcttcat agttacgagt ttaagatgga tggaaatatc   8760
gatctaggat aggtatacat gttgatgtgg gttttactga tgcatataca tgatggcata   8820
```

```
tgcagcatct attcatatgc tctaaccttg agtacctatc tattataata aacaagtatg   8880
ttttataatt attttgatct tgatatactt ggatgatggc atatgcagca gctatatgtg   8940 gatttttta gccctgcctt catacgctat ttatttgctt ggtactgttt cttttgtcga   9000
tgctcaccct gttgtttggt gttacttctg cagggatccg gcagcagcca tgcagaagct   9060
gatcaacagc gtgcagaact acgcctgggg cagcaagacc gccctgaccg agctgtacgg   9120
catggagaac cccagcagcc agcccatggc cgagctgtgg atgggcgccc accccaagag   9180
cagcagccgc gtgcagaacg ccgccggcga catcgtgagc ctgcgcgacg tgatcgagag   9240
cgacaagagc accctgctgg gcgaggccgt ggccaagcgc ttcggcgagc tgcccttcct   9300
gttcaaggtg ctgtgcgccg cccagcccct gagcatccag gtgcacccca acaagcacaa   9360
cagcgagatc ggcttcgcca aggagaacgc cgccggcatc cccatggacg ccgccgagcg   9420
caactacaag gaccccaacc acaagcccga gctggtgttc gccctgaccc ccttcctggc   9480
catgaacgcc ttccgcgagt tcagcgagat cgtgagcctg ctgcagcccg tggccggcgc   9540
ccaccccgcc atcgcccact tcctgcagca gcccgacgcc gagcgcctga gcgagctgtt   9600
cgccagcctg ctgaacatgc agggcgagga aagagccgc gccctggcca tcctgaagag   9660
cgccctggac agccagcagg gcgagccctg gcagaccatc cgcctgatca gcgagttcta   9720
ccccgaggac agcggcctgt tcagcccccct gctgctgaac gtggtgaagc tgaaccccgg   9780
cgaggccatg ttcctgttcg ccgagacccc ccacgcctac ctgcagggcg tggccctgga   9840
ggtgatggcc aacagcgaca acgtgctgcg cgccggcctg accccaagt acatcgacat   9900 ccccgagctg gtggccaacg tgaagttcga ggccaagccc gccaaccagc tgctgaccca   9960
gcccgtgaag cagggcgccg agctggactt ccccatcccc gtggacgact tcgccttcag  10020
cctgcacgac ctgagcgaca aggagaccac catcagccag cagagcgccg ccatcctgtt  10080
ctgcgtggag ggcgacgcca ccctgtggaa gggcagccag cagctgcagc tgaagcccgg  10140
cgagagcgcc ttcatcgccg ccaacgagag ccccgtgacc gtgaagggcc acggccgcct  10200
ggcccgcgtg tacaacaagc tgtgatagga gctcgatccg tcgacctgca gatcgttcaa  10260
acatttggca ataaagtttc ttaagattga atcctgttgc cggtcttgcg atgattatca  10320
tataatttct gttgaattac gttaagcatg taataattaa catgtaatgc atgacgttat  10380
ttatgagatg ggtttttatg attagagtcc cgcaattata catttaatac gcgatagaaa  10440
acaaaatata gcgcgcaaac taggataaat tatcgcgcgc ggtgtcatct atgttactag  10500
atcggcgcgc cgcaattgaa gtttgggcgg ccagcatggc cgtatccgca atgtgttatt  10560
aagttgtcta agcgtcaatt tgtttacacc acaatatatc ctgccaccag ccagccaaca  10620
gctccccgac cggcagctcg gcacaaaatc accactcgat acaggcagcc catcagaatt  10680
aattctcatg tttgacagct tatcatcgac tgcacggtgc accaatgctt ctggcgtcag  10740
gcagccatcg gaagctgtgg tatggctgtg caggtcgtaa atcactgcat aattcgtgtc  10800
gctcaaggcg cactcccgtt ctggataatg ttttttgcgc cgacatcata acggttctgg  10860
caaatattct gaaatgagct gttgacaatt aatcatccgg ctcgtataat gtgtggaatt  10920
gtgagcggat aacaatttca cacaggaaac agaccatgag ggaagcgttg atcgccgaag  10980
tatcgactca actatcagag gtagttggcg tcatcgagcg ccatctcgaa ccgacgttgc  11040
tggccgtaca tttgtacggc tccgcagtgg atggcggcct gaagccacac agtgatattg  11100
atttgctggt tacggtgacc gtaaggcttg atgaaacaac gcggcgagct ttgatcaacg  11160
accttttgga aacttcggct tcccctggag agagcgagat tctccgcgct gtagaagtca  11220
```

-continued

```
ccattgttgt gcacgacgac atcattccgt ggcgttatcc agctaagcgc gaactgcaat    11280
ttggagaatg gcagcgcaat gacattcttg caggtatctt cgagccagcc acgatcgaca    11340
ttgatctggc tatcttgctg acaaaagcaa gagaacatag cgttgccttg gtaggtccag    11400
cggcggagga actctttgat ccggttcctg aacaggatct atttgaggcg ctaaatgaaa    11460
ccttaacgct atggaactcg ccgcccgact gggctggcga tgagcgaaat gtagtgctta    11520
cgttgtcccg catttggtac agcgcagtaa ccggcaaaat cgcgccgaag gatgtcgctg    11580
ccgactgggc aatggagcgc ctgccggccc agtatcagcc cgtcatactt gaagctaggc    11640
aggcttatct tggacaagaa gatcgcttgg cctcgcgcgc agatcagttg gaagaatttg    11700
ttcactacgt gaaaggcgag atcaccaaag tagtcggcaa ataaagctct agtggatctc    11760
cgtacccggg gatctggctc gcggcggacg cacgacgccg gggcgagacc ataggcgatc    11820
tcctaaatca atagtagctg taacctcgaa gcgtttcact tgtaacaacg attgagaatt    11880
tttgtcataa aattgaaata cttggttcgc atttttgtca tccgcggtca gccgcaattc    11940
tgacgaactg cccatttagc tggagatgat tgtacatcct tcacgtgaaa atttctcaag    12000
cgctgtgaac aagggttcag attttagatt gaaaggtgag ccgttgaaac acgttcttct    12060
tgtcgatgac gacgtcgcta tgcggcatct tattattgaa taccttacga tccacgcctt    12120
caaagtgacc gcggtagccg acagcaccca gttcacaaga gtactctctt ccgcgacggt    12180
cgatgtcgtg gttgttgatc tagatttagg tcgtgaagat gggctcgagc taggagcaag    12240
tgattttatc gctaagccgt tcagtatcag agagtttcta gcacgcattc gggttgcctt    12300
gcgcgtgcgc cccaacgttg tccgctccaa agaccgacgg tcttttttgtt ttactgactg    12360 gacacttaat ctcaggcaac gtcgcttgat gtccgaagct ggcggtgagg tgaaacttac    12420
ggcaggtgag ttcaatcttc tcctcgcgtt tttagagaaa ccccgcgacg ttctatcgcg    12480
cgagcaactt ctcattgcca gtcgagtacg cgacgaggag gtttatgaca ggagtataga    12540
tgttctcatt ttgaggctgc gccgcaaact tgaggcagat ccgtcaagcc ctcaactgat    12600
aaaaacagca agaggtgccg gttatttctt tgacgcggac gtgcaggttt cgcacggggg    12660
gacgatggca gcctgagcca attcccagat ccccgaggaa tcggcgtgag cggtcgcaaa    12720
ccatccggcc cggtacaaat cggcgcggcg ctgggtgatg acctggtgga gaagttgaag    12780
gccgcgcagg ccgcccagcg gcaacgcatc gaggcagaag cacgccccgg tgaatcgtgg    12840
caagcggccg ctgatcgaat ccgcaaagaa tcccggcaac cgccggcagc cggtgcgccg    12900
tcgattagga agccgcccaa gggcgacgag caaccagatt ttttcgttcc gatgctctat    12960
gacgtgggca cccgcgatag tcgcagcatc atggacgtgg ccgttttccg tctgtcgaag    13020
cgtgaccgac gagctggcga ggtgatccgc tacgagcttc cagacgggca cgtagaggtt    13080
tccgcagggc cggccggcat ggccagtgtg tgggattacg acctggtact gatggcggtt    13140
tcccatctaa ccgaatccat gaaccgatac cgggaaggga aggagacaa gcccggccgc    13200 gtgttccgtc cacacgttgc ggacgtactc aagttctgcc ggcgagccga tggcggaaag    13260
cagaaagacg acctggtaga aacctgcatt cggttaaaca ccacgcacgt tgccatgcag    13320
cgtacgaaga aggccaagaa cggccgcctg gtgacggtat ccgagggtga agccttgatt    13380
agccgctaca agatcgtaaa gagcgaaacc gggcggccgg agtacatcga gatcgagcta    13440
gctgattgga tgtaccgcga gatcacagaa ggcaagaacc cggacgtgct gacggttcac    13500
cccgattact ttttgatcga tcccggcatc ggccgttttc tctaccgcct ggcacgccgc    13560
```

-continued

```
gccgcaggca aggcagaagc cagatggttg ttcaagacga tctacgaacg cagtggcagc   13620
gccggagagt tcaagaagtt ctgtttcacc gtgcgcaagc tgatcgggtc aaatgacctg   13680
ccggagtacg atttgaagga ggaggcgggg caggctggcc cgatcctagt catgcgctac   13740
cgcaacctga tcgagggcga agcatccgcc ggttcctaat gtacggagca gatgctaggg   13800
caaattgccc tagcaggggga aaaaggtcga aaaggtctct ttcctgtgga tagcacgtac   13860
attgggaacc caaagccgta cattgggaac cggaacccgt acattgggaa cccaaagccg   13920
tacattggga accggtcaca catgtaagtg actgatataa aagagaaaaa aggcgatttt   13980
tccgcctaaa actctttaaa acttattaaa actcttaaaa cccgcctggc ctgtgcataa   14040
ctgtctggcc agcgcacagc cgaagagctg caaaaagcgc ctaccttcg gtcgctgcgc   14100 tccctacgcc ccgccgcttc gcgtcggcct atcgcggccg ctggccgctc aaaaatggct   14160
ggcctacggc caggcaatct accagggcgc ggacaagccg cgccgtcgcc actcgaccgc   14220
cggcgctgag gtctgcctcg tgaagaaggt gttgctgact cataccaggc ctgaatcgcc   14280
ccatcatcca gccagaaagt gagggagcca cggttgatga gagctttgtt gtaggtggac   14340
cagttggtga ttttgaactt ttgctttgcc acggaacggt ctgcgttgtc gggaagatgc   14400
gtgatctgat ccttcaactc agcaaaagtt cgatttattc aacaaagccg ccgtcccgtc   14460
aagtcagcgt aatgctctgc cagtgttaca accaattaac caattctgat tagaaaaact   14520
catcgagcat caaatgaaac tgcaatttat tcatatcagg attatcaata ccatattttt   14580
gaaaaagccg tttctgtaat gaaggagaaa actcaccgag gcagttccat aggatggcaa   14640
gatcctggta tcggtctgcg attccgactc gtccaacatc aatacaacct attaatttcc   14700
cctcgtcaaa aataaggtta tcaagtgaga aatcaccatg agtgacgact gaatccggtg   14760
agaatggcaa aagctctgca ttaatgaatc ggccaacgcg cggggagagg cggtttgcgt   14820
attgggcgct cttccgcttc ctcgctcact gactcgctgc gctcggtcgt tcggctgcgg   14880
cgagcggtat cagctcactc aaaggcggta atacggttat ccacagaatc aggggataac   14940
gcaggaaaga acatgtgagc aaaaggccag caaaaggcca ggaaccgtaa aaaggccgcg   15000
ttgctggcgt ttttccatag gctccgcccc cctgacgagc atcacaaaaa tcgacgctca   15060
agtcagaggt ggcgaaaccc gacaggacta taaagatacc aggcgtttcc ccctggaagc   15120
tccctcgtgc gctctcctgt ccgaccctg ccgcttaccg gatacctgtc cgcctttctc    15180
ccttcgggaa gcgtggcgct ttctcatagc tcacgctgta ggtatctcag ttcggtgtag   15240
gtcgttcgct ccaagctggg ctgtgtgcac gaacccccg ttcagcccga ccgctgcgcc    15300
ttatccggta actatcgtct tgagtccaac ccggtaagac acgacttatc gccactggca   15360
gcagccactg gtaacaggat tagcagagcg aggtatgtag gcggtgctac agagttcttg   15420
aagtggtggc ctaactacgg ctacactaga agaacagtat ttggtatctg cgctctgctg   15480
aagccagtta ccttcggaaa aagagttggt agctcttgat ccggcaaaca aaccaccgct   15540
ggtagcggtg gtttttttgt ttgcaagcag cagattacgc gcagaaaaaa aggatctcaa   15600
gaagatcctt tgatcttttc tacggggtct gacgctcagt ggaacgaaaa ctcacgttaa   15660
gggattttgg tcatgagatt atcaaaaagg atcttcacct agatcctttt gatccggaat   15720
ta                                                                   15722
```

<210> SEQ ID NO 32
<211> LENGTH: 20
<212> TYPE: DNA
<213> ORGANISM: Artificial Sequence -continued

```
<220> FEATURE:
<223> OTHER INFORMATION: encoding gRNA for vector 23136

<400> SEQUENCE: 32 gtcgggacg tcgacgacga                                                      20

<210> SEQ ID NO 33
<211> LENGTH: 1823
<212> TYPE: DNA
<213> ORGANISM: Oryza sativa

<400> SEQUENCE: 33
acagtgacta gtgacaaacg atcgatcgat ccctccatcc acaaaccctc ctcgatctca      60
tcttccttcg tctcgtcaat ggcggcgagc tactcgtgcc ggcggacatg cgaggcgtgc     120
agcacgaggg cgatggccgg gtgcgtggtg ggcgagccgg cgtcggcgcc ggggcagcgg     180
gtgacgttgc tggcgatcga cggcggcggc atcaggggcc tcatcccggg caccatcctc     240
gccttcctcg aggccaggct gcaggagctg gatggccccg acgcgcgcct cgccgattac     300
ttcgactgca tcgccgggac cagcaccggc ggcctcatca ccgccatgct cgccgcgccc     360
ggcgaccacg gccgcccgct cttcgccgcc agcgacatca accgcttcta cctcgacaac     420
ggcccactca tcttcccaca aaagtaactg atcacctcga attcgatctc ctctcttcga     480
tctctgcatt atttgatttg attggggatt gtgggcggcg tggcgtggcg tccaggaggt     540
gcggcatggc ggcggccatg gcggcgctga cgaggccgag gtacaacggc aagtacctgc     600
aggggaagat caggaagatg ctgggcgaga cgagggtgcg cgacacgctg acgaacgtcg     660
tcatccccac gttcgacgtc aggctgctcc agccaaccat cttctccaca tacgacgtgc     720
gtgcgttgat tccatccgca ttggcgttgg aatcagctga ttgtttgatt gatcgaacaa     780
ttgatcggtt aaaattttgc aggcgaagag catgccgctc aagaacgcgc tcctctccga     840
catctgcatc agcacatccg cggcgccgac ctacctcccc gcgcactgct tccagaccac     900
cgacgacgcc accggcaagg tccgcgagtt cgacctcatc gacggcggcg tcgccgccaa     960
caacccggta actaatcaat caagcaatcc atcaaacgaa gatccacatg tgcattcctg    1020
tggtacaaat gctgatcgat cgatggatgg atcgattttc gcgagaacgt acagacgatg    1080
gtggccatga cgcagatcac caagaagata atggtgaagg acaaggagga gctgtacccg    1140
gtaaagccgt cggactgcgg taagttcctg gtgctgtccg tgggcaccgg gtcgacgtcg    1200
gaccagggga tgtacacggc gaggcagtgc tcgcggtggg ggatcgtccg gtggctgcgc    1260
aacaagggga tggcgcccat catcgacatc ttcatggcgg ccagctccga cctcgtcgac    1320
atccacgccg ccgtcatgtt ccagtcgctg cacagcgacg gcgactacct ccgcatccag    1380
gacaacacgc tccacggcga cgccgccacg gtggacgccg ccaccaggga caacatgcgg    1440
gcgctcgtcg ggatcggcga gcggatgctg gcgcagcggg tgtcgagggt caacgtcgag    1500
accggcaggt acgtcgaggt gcccggcgcc ggcagcaacg ccgacgcgct gaggggcttc    1560
gccaggcagc tctccgagga gaggagggcg aggctaggtc ggcgaaacgc ctgcggcggc    1620
ggcggcgaag gagagcccag cggcgtggcg tgcaagcgtt agtaactgta cacgcatcat    1680
gctgacgcga tctttttat ttttctttt ttttttttac ctttctagcg gacatgggga    1740
ataacaagac gtgacagtag tgcaatcggt ttgtaacgtg cgtataccaa cattgatcca    1800
tttcttcatc acagtttcag ttc                                             1823

<210> SEQ ID NO 34
```

```
<211> LENGTH: 15921
<212> TYPE: DNA
<213> ORGANISM: Artificial Sequence
<220> FEATURE:
<223> OTHER INFORMATION: Vector 24038
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (313)..(1149)
<223> OTHER INFORMATION: prZmGRMZM5G876285-01
<220> FEATURE:
<221> NAME/KEY: gene
<222> LOCATION: (1152)..(5412)
<223> OTHER INFORMATION: cCas9-12
<220> FEATURE:
<221> NAME/KEY: terminator
<222> LOCATION: (5419)..(6736)
<223> OTHER INFORMATION: tZmGRMZM5G876285-01
<220> FEATURE:
<221> NAME/KEY: promoter
<222> LOCATION: (6750)..(7124)
<223> OTHER INFORMATION: prOsU3-01
<220> FEATURE:
<221> NAME/KEY: misc_feature
<222> LOCATION: (7126)..(7145)
<223> OTHER INFORMATION: xZmVLHP2
<220> FEATURE:
<221> NAME/KEY: misc_feature
<222> LOCATION: (7126)..(7230)
<223> OTHER INFORMATION: rsgRNAZmVLHP-02
<220> FEATURE:
<221> NAME/KEY: misc_feature
<222> LOCATION: (7146)..(7157)
<223> OTHER INFORMATION: rCrRNA-01
<220> FEATURE:
<221> NAME/KEY: misc_feature
<222> LOCATION: (7146)..(7230)
<223> OTHER INFORMATION: rsgRNAbase-01
<220> FEATURE:
<221> NAME/KEY: misc_feature
<222> LOCATION: (7162)..(7230)
<223> OTHER INFORMATION: rTracrRNA-01
<220> FEATURE:
<221> NAME/KEY: promoter
<222> LOCATION: (7241)..(9232)
<223> OTHER INFORMATION: prUbi-04
<220> FEATURE:
<221> NAME/KEY: gene
<222> LOCATION: (9249)..(10427)
<223> OTHER INFORMATION: cPMI-09
<220> FEATURE:
<221> NAME/KEY: terminator
<222> LOCATION: (10450)..(10702)
<223> OTHER INFORMATION: tNOS-05-01
<220> FEATURE:
<221> NAME/KEY: misc_feature
<222> LOCATION: (10746)..(10875)
<223> OTHER INFORMATION: bNLB-03
<220> FEATURE:
<221> NAME/KEY: gene
<222> LOCATION: (11155)..(11943)
<223> OTHER INFORMATION: cSpec-03
<220> FEATURE:
<221> NAME/KEY: promoter
<222> LOCATION: (12038)..(12168)
<223> OTHER INFORMATION: prVirG-01
<220> FEATURE:
<221> NAME/KEY: gene
<222> LOCATION: (12243)..(12875)
<223> OTHER INFORMATION: cVirG-09
<220> FEATURE:
<221> NAME/KEY: gene
<222> LOCATION: (12905)..(13978)
<223> OTHER INFORMATION: cRepA-01
<220> FEATURE:
<221> NAME/KEY: misc_feature
```

```
<222> LOCATION: (14021)..(14425)
<223> OTHER INFORMATION: oVA1-02
<220> FEATURE:
<221> NAME/KEY: misc_feature
<222> LOCATION: (15103)..(15909)
<223> OTHER INFORMATION: oCOLE-06

<400> SEQUENCE: 34
attcctgtgg ttggcatgca catacaaatg gacgaacgga taaacctttt cacgcccttt      60
taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg accccgccg atgacgcggg acaagccgtt ttacgtttgg      240
aactgacaga accgcaacgc tgcaggaatt ggccgcagcg gccatttaaa caaagcttgg     300
taccgggacc ctaagtaatc ttgtgctaca aatttatttt tcagacagaa aaatctattt     360
agctaactaa ttaatacaaa ttaataccaa gcaacgatag atgaacatct agttgtctaa     420
ttagctaact aattaataca aattaagtag aatccttacc gtggggagat ggggcgcgac     480
gaagtgctcg agcttggggc gcggcgaccg gcgacgtgaa gcttgggggc gcggggggccg     540 gacggcgctg cgggcggcat ggcgggcggc tgcgggcggc ggcgcgggcg caggaaacaa     600
acgacgggag tgggaggaag gagaaagcgg cgcgccggtt tagtcctagc tcggcgccaa     660
gatctgtggc gccgagctag gtgccacgat ggccgccgcg tcagcaaagc tcggcgccaa     720
ggcatgttgc gccgagccgt gttagctcgg cgtcatagct catggtgccg agttttgggt     780
ctaaaattgc gtttaagtat tctagggatc taaacgcaaa tatttttcga aaatagggcc     840
gaaaaacaaa aaaaatcgg tcgtttcgtc gagcacatcg tccagcctat cttgcatgtc     900
catcctctct atggttcgcg agccgcgcgc atggcgctcc aaaggagggg cgaggttgaa     960
tatagacaga tggaatgggt ggttctctat ttatagcgca tgcagtcgtc ccctggcaca    1020
cctatttata tgtgagcgtt cctggcacta gagagatcga tcgatcgagc ttaattgcgc    1080
cactgctcgt tatcctcctc ttgcattgca ttgcaggtcg tagttgagca gcagcaacca    1140
ctgcacaggc catggacaag aagtacagca tcggcctgga catcggcacc aacagcgtgg    1200
gctgggccgt gatcaccgac gagtacaagg tgataccaat ttgcatgatc cttgttcgtt    1260
ctagctcttg catgccgatc agttgaatca cgcggtttcc ttctgcgcat ttgcatccag    1320
gtgccgagca agaagttcaa ggtgctgggc aacaccgaca ggcacagcat caagaagaac    1380
ctgatcggcg ccctgctgtt cgacagcggc gagaccgccg aggccaccag gctgaagagg    1440
accgccagga ggaggtacac caggaggaag aacaggatct gctacctgca ggagatcttc    1500
agcaacgaga tggccaaggt ggacgacagc ttcttccaca ggctggagga gagcttcctg    1560
gtggaggagg acaagaagca cgagaggcac ccgatcttcg gcaacatcgt ggacgaggtg    1620
gcctaccacg agaagtaccc gaccatctac cacctgagga gaagctggt ggacagcacc    1680 gacaaggccg acctgaggct gatctacctg gccctggccc acatgatcaa gttcagggc    1740 cacttcctga tcgagggcga cctgaacccg gacaacagcg acgtggacaa gctgttcatc    1800
cagctggtgc agacctacaa ccagctgttc gaggagaacc cgatcaacgc cagcggcgtg    1860
gacgccaagg ccatcctgag cgccaggctg agcaagagca ggaggctgga gaacctgatc    1920
gcccagctgc cgggcgagaa gaagaacggc ctgttcggca acctgatcgc cctgagcctg    1980
ggcctgaccc cgaacttcaa gagcaacttc gacctggccg aggacgccaa gctgcagctg    2040
agcaaggaca cctacgacga cgacctggac aacctgctgg cccagatcgg cgaccagtac    2100
```

| | | | | |
|---|---|---|---|---|
| gccgacctgt | tcctggccgc | caagaacctg | agcgacgcca | tcctgctgag | cgacatcctg | 2160 |
| agggtgaaca | ccgagatcac | caaggccccg | ctgagcgcca | gcatgatcaa | gaggtacgac | 2220 |
| gagcaccacc | aggacctgac | cctgctgaag | gccctggtga | ggcagcagct | gccggagaag | 2280 |
| tacaaggaga | tcttcttcga | ccagagcaag | aacggctacg | ccggctacat | cgacggcggc | 2340 |
| gccagccagg | aggagttcta | caagttcatc | aagccgatcc | tggagaagat | ggacggcacc | 2400 |
| gaggagctgc | tggtgaagct | gaacagggag | gacctgctga | ggaagcagag | gaccttcgac | 2460 |
| aacggcagca | tcccgcacca | gatccacctg | ggcgagctgc | acgccatcct | gaggaggcag | 2520 |
| gaggacttct | acccgttcct | gaaggacaac | agggagaaga | tcgagaagat | cctgaccttc | 2580 |
| cgcatcccgt | actacgtggg | cccgctggcc | aggggcaaca | gcaggttcgc | ctggatgacc | 2640 |
| aggaagagcg | aggagaccat | caccccgtgg | aacttcgagg | aggtggtgga | caagggcgcc | 2700 |
| agcgcccaga | gcttcatcga | gaggatgacc | aacttcgaca | agaacctgcc | gaacgagaag | 2760 |
| gtgctgccga | agcacagcct | gctgtacgag | tacttcaccg | tgtacaacga | gctgaccaag | 2820 |
| gtgaagtacg | tgaccgaggg | catgaggaag | ccggccttcc | tgagcggcga | gcagaagaag | 2880 |
| gccatcgtgg | acctgctgtt | caagaccaac | aggaaggtga | ccgtgaagca | gctgaaggag | 2940 |
| gactacttca | agaagatcga | gtgcttcgac | agcgtggaga | tcagcggcgt | ggaggacagg | 3000 |
| ttcaacgcca | gcctgggcac | ctaccacgac | ctgctgaaga | tcatcaagga | caaggacttc | 3060 |
| ctggacaacg | aggagaacga | ggacatcctg | gaggacatcg | tgctgaccct | gaccctgttc | 3120 |
| gaggacaggg | agatgatcga | ggagaggctg | aagacctacg | cccacctgtt | cgacgacaag | 3180 |
| gtgatgaagc | agctgaagag | gaggaggtac | accggctggg | gcaggctgag | caggaagctg | 3240 |
| atcaacggca | tcagggacaa | gcagagcggc | aagaccatcc | tggacttcct | gaagagcgac | 3300 |
| ggcttcgcca | acaggaactt | catgcagctg | atccacgacg | acagcctgac | cttcaaggag | 3360 |
| gacatccaga | aggcccaggt | gagcggccag | ggcgacagcc | tgcacgagca | catcgccaac | 3420 |
| ctggccggca | gcccggccat | caagaagggc | atcctgcaga | ccgtgaaggt | ggtggacgag | 3480 |
| ctggtgaagg | tgatgggcag | gcacaagccg | gagaacatcg | tgatcgagat | ggccagggag | 3540 |
| aaccagacca | cccagaaggg | ccagaagaac | agcagggaga | ggatgaagag | gatcgaggag | 3600 |
| ggcatcaagg | agctgggcag | ccagatcctg | aaggagcacc | cggtggagaa | cacccagctg | 3660 |
| cagaacgaga | agctgtacct | gtactacctg | cagaacggca | gggacatgta | cgtggaccag | 3720 |
| gagctggaca | tcaacaggct | gagcgactac | gacgtggacc | acatcgtgcc | gcagagcttc | 3780 |
| ctgaaggacg | acagcatcga | caacaaggtg | ctgaccagga | gcgacaagaa | caggggcaag | 3840 |
| agcgacaacg | tgccgagcga | ggaggtggtg | aagaagatga | aaaactactg | gaggcagctg | 3900 |
| ctgaacgcca | agctgatcac | ccagaggaag | ttcgacaacc | tgaccaaggc | cgagagrgggc | 3960 |
| ggcctgagcg | agctggacaa | ggccggcttc | attaaaaggc | agctggtgga | gaccaggcag | 4020 |
| atcaccaagc | acgtggccca | gatcctggac | agcaggatga | acaccaagta | cgacgagaac | 4080 |
| gacaagctga | tcagggaggt | gaaggtgatc | accctgaaga | gcaagctggt | gagcgacttc | 4140 |
| aggaaggact | ccagttcta | caaggtgagg | gagatcaata | attaccacca | cgcccacgac | 4200 |
| gcctacctga | acgccgtggt | gggcaccgcc | ctgattaaaa | agtacccgaa | gctggagagc | 4260 |
| gagttcgtgt | acggcgacta | caaggtgtac | gacgtgagga | agatgatcgc | caagagcgag | 4320 |
| caggagatcg | gcaaggccac | cgccaagtac | ttcttctaca | gcaacatcat | gaacttcttc | 4380 |
| aagaccgaga | tcacctggc | caacggcgag | atcaggaaga | ggccgctgat | cgagaccaac | 4440 |
| ggcgagaccg | gcgagatcgt | gtgggacaag | ggcagggact | cgccaccgt | gaggaaggtg | 4500 |

-continued

```
ctgtccatgc cgcaggtgaa catcgtgaag aagaccgagg tgcagaccgg cggcttcagc      4560
aaggagagca tcctgccgaa gaggaacagc gacaagctga tcgccaggaa gaaggactgg      4620
gacccgaaga agtacggcgg cttcgacagc ccgaccgtgg cctacagcgt gctggtggtg      4680
gccaaggtgg agaagggcaa gagcaagaag ctgaagagcg tgaaggagct ggtgggcatc      4740
accatcatgg agaggagcag cttcgagaag aacccagtgg acttcctgga ggccaagggc      4800
tacaaggagg tgaagaagga cctgatcatt aaactgccga agtacagcct gttcgagctg      4860
gagaacggca ggaagaggat gctggccagc gccggcgagc tgcagaaggg caacgagctg      4920
gccctgccga gcaagtacgt gaacttcctg tacctggcca gccactacga gaagctgaag      4980
ggcagcccgg aggacaacga gcagaagcag ctgttcgtgg agcagcacaa gcactacctg      5040
gacgagatca tcgagcagat cagcgagttc agcaagaggg tgatcctggc cgacgccaac      5100
ctggacaagg tgctgagcgc ctacaacaag cacagggaca agccgatcag ggagcaggcc      5160
gagaacatca tccacctgtt caccctgacc aacctgggcg ccccggccgc cttcaagtac      5220
ttcgacacca ccatcgacag gaagaggtac accagcacca aggaggtgct ggacgccacc      5280
ctgatccacc agagcatcac cggcctgtac gagaccagga tcgacctgag ccagctgggc      5340
ggcgacagca gcccgccgaa gaagaagagg aaggtgagct ggaaggacgc cagcggctgg      5400
agcaggatgt gagctctaat gcatccaaac aacgacacca acgccaacat taattaatta      5460
gtagtctcca tgccctggga ttgtgcgtgg ccgctccgtt gaacaccacc catccttcgt      5520
tcggcatttt ttcccccctt gtttatataa ttttattgta tcgttttggc aaataatttt      5580
gtgattcgac cccaaagcaa gtttggttgt cttacgattt gtaaacctgg aacaatatat      5640
aatgtgattg aactgctttg tctattcttt ttgtagtacg ataatatgta tatgtattcc      5700
atgcgatctc ttctagggcg acgactaatg tgcaagtgtg tgtttgcatg cgctgagcac      5760
ggagtttgta ttcaggggtc aatatctttc gattcctttia tctaaaaagg tgttgcatat      5820
atctaaaaaa aagaaaaaaa aggcttacaa ctgttgaaaa aataagcatt tttagtttta      5880
atttaattca gaaaatcata gtgatatatg tgacgatatg catgtgcata tgtatcacta      5940
ctcacataaa cagtaaacaa cagtaaaata tgtataaata caaaaataac aaagtgtacc      6000
ctgcggaggg accgatgttc aaggcatctg tggctccatt cacacgagac atctcgtgtg      6060
tatgttcgat gtagtcatac gcagtcgagg cagtcagatg tacgcagtgc agtccctcga      6120
tcggcgccgg cgacgaggaa cttgatcagt gctggtcgag cggacgaagc gagcagtcgc      6180
gagtacgctc ccgaaaaaca tgatcgctcg cacacccatg caagtgtcgc tctgcggacg      6240
acgatttcgg aagcctacgc gtatgagaat gtttgtatgt gtgttctctc gtaaccagaa      6300
gcctcatctc ctccgtatat atacacgcgc agagggaggc caacagatag taacggtgga      6360
aggaatactc ggaccaaggt ccgatctacc atggccacgg cccggcctgg ccagcggcgc      6420
gtgcgtgtgg cagtccttca tccttttatc agcttatcaa tagatgcacc aaaagatccac      6480 ctatttaagt tgattgaatt gtctcttgta cttccggtat gttactaaag taataataca      6540
ccgtagcatt aaattgggcc tttagcattg gctattattg aatattaatt tgagccagac      6600
ccaccaccag atgctaagtc acaccaaaat gctctcatca tctcaaacat ttcatatact      6660
ggtgtttcga tggagactat taagttgaac atccacctag aatctagatt acacttgacc      6720
acaactacat aatggacgga ccgttcgaag ggatctttaa acatacgaac agatcactta      6780
aagttcttct gaagcaactt aaagttatca ggcatgcatg gatcttggag gaatcagatg      6840
```

-continued

```
tgcagtcagg gaccatagca caggacaggc gtcttctact ggtgctacca gcaaatgctg    6900
gaagccggga acactgggta cgttggaaac cacgtgatgt ggagtaagat aaactgtagg    6960
agaaaagcat ttcgtagtgg gccatgaagc ctttcaggac atgtattgca gtatgggccg    7020
gcccattacg caattggacg acaacaaaga ctagtattag taccacctcg gctatccaca    7080
tagatcaaag ctggtttaaa agagttgtgc agatgatccg tggcagctgg agctgagctt    7140
ccggggtttt agagctagaa atagcaagtt aaaataaggc tagtccgtta tcaacttgaa    7200
aaagtggcac cgagtcggtg cttttttttt cggaccgcgc ctgcagtgca gcgtgacccg    7260
gtcgtgcccc tctctagaga taatgagcat tgcatgtcta agttataaaa aattaccaca    7320 tattttttt gtcacacttg tttgaagtgc agtttatcta tctttataca tatatttaaa    7380
ctttactcta cgaataatat aatctatagt actacaataa tatcagtgtt ttagagaatc    7440
atataaatga acagttagac atggtctaaa ggacaattga gtattttgac aacaggactc    7500
tacagtttta tcttttttagt gtgcatgtgt tctccttttt ttttgcaaat agcttcacct    7560
atataatact tcatccattt tattagtaca tccatttagg gtttagggtt aatggttttt    7620
atagactaat ttttttagta catctatttt attctatttt agcctctaaa ttaagaaaac    7680
taaaactcta ttttagtttt tttatttaat aatttagata taaaatagaa taaaataaag    7740
tgactaaaaa ttaaacaaat acccctttaag aaattaaaaa aactaaggaa acatttttct    7800
tgtttcgagt agataatgcc agcctgttaa acgccgtcga cgagtctaac ggacaccaac    7860
cagcgaacca gcagcgtcgc gtcgggccaa gcgaagcaga cggcacggca tctctgtcgc    7920
tgcctctgga cccctctcga gagttccgct ccaccgttgg acttgctccg ctgtcggcat    7980
ccagaaattg cgtggcggag cggcagacgt gagccggcac ggcaggcggc ctcctcctcc    8040
tctcacggca ccggcagcta cggggggattc ctttcccacc gctccttcgc tttcccttcc    8100
tcgcccgccg taataaatag acaccccctc cacaccctct ttccccaacc tcgtgttgtt    8160
cggagcgcac acacacacaa ccagatctcc cccaaatcca cccgtcggca cctccgcttc    8220
aaggtacgcc gctcgtcctc cccccccccc ctctctacct tctctagatc ggcgttccgg    8280
tccatggtta gggcccggta gttctacttc tgttcatgtt tgtgttagat ccgtgtttgt    8340
gttagatccg tgctgctagc gttcgtacac ggatgcgacc tgtacgtcag acacgttctg    8400
attgctaact tgccagtgtt tctctttggg gaatcctggg atggctctag ccgttccgca    8460
gacgggatcg atttcatgat ttttttttgtt tcgttgcata gggtttggtt tgccctttttc    8520 ctttatttca atatatgccg tgcacttgtt tgtcgggtca tcttttcatg ctttttttttg    8580 tcttggttgt gatgatgtgg tctggttggg cggtcgttct agatcggagt agaattctgt    8640
ttcaaactac ctggtggatt tattaattttt ggatctgtat gtgtgtgcca tacatattca    8700
tagttacgaa ttgaagatga tggatggaaa tatcgatcta ggataggtat acatgttgat    8760
gcgggtttta ctgatgcata tacagagatg ctttttgttc gcttggttgt gatgatgtgg    8820
tgtggttggg cggtcgttca ttcgttctag atcggagtag aatactgttt caaactacct    8880
ggtgtattta ttaattttgg aactgtatgt gtgtgtcata catcttcata gttacgagtt    8940
taagatggat ggaaatatcg atctaggata ggtatacatg ttgatgtggg ttttactgat    9000
gcatatacat gatggcatat gcagcatcta ttcatatgct ctaaccttga gtacctatct    9060
attataataa acaagtatgt tttataatta ttttgatctt gatatacttg gatgatggca    9120
tatgcagcag ctatatgtgg attttttttag ccctgccttc atacgctatt tatttgcttg    9180
gtactgtttc ttttgtcgat gctcaccctg ttgtttggtg ttacttctgc agggatccgg    9240
```

-continued

```
cagcagccat gcagaagctg atcaacagcg tgcagaacta cgcctggggc agcaagaccg   9300
ccctgaccga gctgtacggc atggagaacc ccagcagcca gcccatggcc gagctgtgga   9360
tgggcgccca ccccaagagc agcagccgcg tgcagaacgc cgccggcgac atcgtgagcc   9420
tgcgcgacgt gatcgagagc gacaagagca ccctgctggg cgaggccgtg gccaagcgct   9480
tcggcgagct gcccttcctg ttcaaggtgc tgtgcgccgc ccagcccctg agcatccagg   9540
tgcaccccaa caagcacaac agcgagatcg gcttcgccaa ggagaacgcc gccggcatcc   9600
ccatggacgc cgccgagcgc aactacaagg accccaacca caagcccgag ctggtgttcg   9660
ccctgacccc cttcctggcc atgaacgcct tccgcgagtt cagcgagatc gtgagcctgc   9720
tgcagcccgt ggccggcgcc caccccgcca tcgcccactt cctgcagcag cccgacgccg   9780
agcgcctgag cgagctgttc gccagcctgc tgaacatgca gggcgaggag aagagccgcg   9840
ccctggccat cctgaagagc gccctggaca gccagcaggg cgagccctgg cagaccatcc   9900
gcctgatcag cgagttctac cccgaggaca gcggcctgtt cagccccctg ctgctgaacg   9960
tggtgaagct gaaccccggc gaggccatgt cctgttcgc cgagacccccc cacgcctacc   10020 tgcagggcgt ggccctggag gtgatggcca acagcgacaa cgtgctgcgc gccggcctga   10080
cccccaagta catcgacatc cccgagctgg tggccaacgt gaagttcgag gccaagcccg   10140
ccaaccagct gctgacccag cccgtgaagc agggcgccga gctggacttc cccatccccg   10200
tggacgactt cgccttcagc ctgcacgacc tgagcgcaca ggagaccacc atcagccagc   10260
agagcgccgc catcctgttc tgcgtggagg gcgacgccac cctgtggaag ggcagccagc   10320
agctgcagct gaagcccggc gagagcgcct tcatcgccgc caacgagagc cccgtgaccg   10380
tgaagggcca cggccgcctg gcccgcgtgt acaacaagct gtgataggag ctcgatccgt   10440
cgacctgcag atcgttcaaa catttggcaa taaagtttct taagattgaa tcctgttgcc   10500
ggtcttgcga tgattatcat ataatttctg ttgaattacg ttaagcatgt aataattaac   10560
atgtaatgca tgacgttatt tatgagatgg gtttttatga ttagagtccc gcaattatac   10620
atttaatacg cgatagaaaa caaaatatag cgcgcaaact aggataaatt atcgcgcgcg   10680
gtgtcatcta tgttactaga tcggcgcgcc gcaattgaag tttgggcggc cagcatggcc   10740
gtatccgcaa tgtgttatta agttgtctaa gcgtcaattt gtttacacca caatatatcc   10800
tgccaccagc cagccaacag ctccccgacc ggcagctcgg cacaaaatca ccactcgata   10860
caggcagccc atcagaatta attctcatgt ttgacagctt atcatcgact gcacggtgca   10920
ccaatgcttc tggcgtcagg cagccatcgg aagctgtggt atggctgtgc aggtcgtaaa   10980
tcactgcata attcgtgtcg ctcaaggcgc actcccgttc tggataatgt tttttgcgcc   11040
gacatcataa cggttctggc aaatattctg aaatgagctg ttgacaatta atcatccggc   11100
tcgtataatg tgtggaattg tgagcggata acaatttcac acaggaaaca gaccatgagg   11160
gaagcgttga tcgccgaagt atcgactcaa ctatcagagg tagttggcgt catcgagcgc   11220
catctcgaac cgacgttgct ggccgtacat ttgtacggct ccgcagtgga tggcggcctg   11280
aagccacaca gtgatattga tttgctggtt acggtgaccg taaggcttga tgaaacaacg   11340
cggcgagctt tgatcaacga ccttttggaa acttcggctt cccctggaga gagcgagatt   11400
ctccgcgctg tagaagtcac cattgttgtg cacgacgaca tcattccgtg cgttatcca   11460 gctaagcgcg aactgcaatt tggagaatgg cagcgcaatg acattcttgc aggtatcttc   11520
gagccagcca cgatcgacat tgatctggct atcttgctga caaaagcaag agaacatagc   11580
```

-continued

```
gttgccttgg taggtccagc ggcggaggaa ctctttgatc cggttcctga acaggatcta  11640
tttgaggcgc taaatgaaac cttaacgcta tggaactcgc cgcccgactg ggctggcgat  11700
gagcgaaatg tagtgcttac gttgtcccgc atttggtaca gcgcagtaac cggcaaaatc  11760
gcgccgaagg atgtcgctgc cgactgggca atggagcgcc tgccggccca gtatcagccc  11820
gtcatacttg aagctaggca ggcttatctt ggacaagaag atcgcttggc ctcgcgcgca  11880
gatcagttgg aagaatttgt tcactacgtg aaaggcgaga tcaccaaagt agtcggcaaa  11940
taaagctcta gtggatctcc gtacccgggg atctggctcg cggcggacgc acgacgccgg  12000
ggcgagacca taggcgatct cctaaatcaa tagtagctgt aacctcgaag cgtttcactt  12060
gtaacaacga ttgagaattt ttgtcataaa attgaaatac ttggttcgca tttttgtcat  12120
ccgcggtcag ccgcaattct gacgaactgc ccatttagct ggagatgatt gtacatcctt  12180
cacgtgaaaa tttctcaagc gctgtgaaca agggttcaga ttttagattg aaaggtgagc  12240
cgttgaaaca cgttcttctt gtcgatgacg acgtcgctat gcggcatctt attattgaat  12300
accttacgat ccacgccttc aaagtgaccg cggtagccga cagcacccag ttcacaagag  12360
tactctcttc cgcgacggtc gatgtcgtgg ttgttgatct agatttaggt cgtgaagatg  12420
ggctcgagct aggagcaagt gattttatcg ctaagccgtt cagtatcaga gagtttctag  12480
cacgcattcg ggttgccttg cgcgtgcgcc ccaacgttgt ccgctccaaa gaccgacggt  12540 cttttttgttt tactgactgg acacttaatc tcaggcaacg tcgcttgatg tccgaagctg  12600
gcggtgaggt gaaacttacg gcaggtgagt tcaatcttct cctcgcgttt ttagagaaac  12660
cccgcgacgt tctatcgcgc gagcaacttc tcattgccag tcgagtacgc gacgaggagg  12720
tttatgacag gagtatagat gttctcattt tgaggctgcg ccgcaaactt gaggcagatc  12780
cgtcaagccc tcaactgata aaaacagcaa gaggtgccgg ttatttcttt gacgcggacg  12840
tgcaggtttc gcacgggggg acgatggcag cctgagccaa ttcccagatc cccgaggaat  12900
cggcgtgagc ggtcgcaaac catccggccc ggtacaaatc ggcgcggcgc tgggtgatga  12960
cctggtggag aagttgaagg ccgcgcaggc cgcccagcgg caacgcatcg aggcagaagc  13020 acgcccggt gaatcgtggc aagcggccgc tgatcgaatc cgcaaagaat cccggcaacc  13080
gccggcagcc ggtgcgccgt cgattaggaa gccgcccaag ggcgacgagc aaccagattt  13140
tttcgttccg atgctctatg acgtgggcac ccgcgatagt cgcagcatca tggacgtggc  13200
cgttttccgt ctgtcgaagc gtgaccgacg agctggcgag gtgatccgct acgagcttcc  13260
agacgggcac gtagaggttt ccgcagggcc ggccggcatg gccagtgtgt gggattacga  13320
cctggtactg atggcggttt cccatctaac cgaatccatg aaccgatacc gggaagggaa  13380
gggagacaag cccggccgcg tgttccgtcc acacgttgcg gacgtactca agttctgccg  13440
gcgagccgat ggcggaaagc agaaagacga cctggtagaa acctgcattc ggttaaacac  13500
cacgcacgtt gccatgcagc gtacgaagaa ggccaagaac ggccgcctgg tgacggtatc  13560
cgagggtgaa gccttgatta gccgctacaa gatcgtaaag agcgaaaccg ggcggccgga  13620
gtacatcgag atcgagctag ctgattggat gtaccgcgag atcacagaag gcaagaaccc  13680
ggacgtgctg acggttcacc ccgattactt tttgatcgat cccggcatcg gccgttttct  13740
ctaccgcctg gcacgccgcg ccgcaggcaa ggcagaagcc agatggttgt tcaagacgat  13800
ctacgaacgc agtggcagcg ccggagagtt caagaagttc tgtttcaccg tgcgcaagct  13860
gatcgggtca aatgacctgc cggagtacga tttgaaggag gaggcggggc aggctggccc  13920
gatcctagtc atgcgctacc gcaacctgat cgagggcgaa gcatccgccg gttcctaatg  13980
```

```
tacggagcag atgctagggc aaattgccct agcaggggaa aaaggtcgaa aaggtctctt   14040
tcctgtggat agcacgtaca ttgggaaccc aaagccgtac attgggaacc ggaacccgta   14100
cattgggaac ccaaagccgt acattgggaa ccggtcacac atgtaagtga ctgatataaa   14160
agagaaaaaa ggcgattttt ccgcctaaaa ctctttaaaa cttattaaaa ctcttaaaac   14220
ccgcctggcc tgtgcataac tgtctggcca gcgcacagcc gaagagctgc aaaaagcgcc   14280
tacccttcgg tcgctgcgct ccctacgccc cgccgcttcg cgtcggccta tcgcggccgc   14340
tggccgctca aaaatggctg gcctacggcc aggcaatcta ccagggcgcg gacaagccgc   14400
gccgtcgcca ctcgaccgcc ggcgctgagg tctgcctcgt gaagaaggtg ttgctgactc   14460
ataccaggcc tgaatcgccc catcatccag ccagaaagtg agggagccac ggttgatgag   14520
agctttgttg taggtggacc agttggtgat tttgaacttt tgctttgcca cggaacggtc   14580
tgcgttgtcg ggaagatgcg tgatctgatc cttcaactca gcaaaagttc gatttattca   14640
acaaagccgc cgtcccgtca agtcagcgta atgctctgcc agtgttacaa ccaattaacc   14700
aattctgatt agaaaaactc atcgagcatc aaatgaaact gcaatttatt catatcagga   14760
ttatcaatac catatttttg aaaaagccgt ttctgtaatg aaggagaaaa ctcaccgagg   14820
cagttccata ggatggcaag atcctggtat cggtctgcga ttccgactcg tccaacatca   14880
atacaaccta ttaatttccc ctcgtcaaaa ataaggttat caagtgagaa atcaccatga   14940
gtgacgactg aatccggtga gaatggcaaa agctctgcat taatgaatcg gccaacgcgc   15000
ggggagaggc ggtttgcgta ttgggcgctc ttccgcttcc tcgctcactg actcgctgcg   15060
ctcggtcgtt cggctgcggc gagcggtatc agctcactca aaggcggtaa tacggttatc   15120
cacagaatca ggggataacg caggaaagaa catgtgagca aaaggccagc aaaaggccag   15180
gaaccgtaaa aaggccgcgt tgctggcgtt tttccatagg ctccgccccc ctgacgagca   15240
tcacaaaaat cgacgctcaa gtcagaggtg gcgaaacccg acaggactat aaagatacca   15300
ggcgtttccc cctggaagct ccctcgtgcg ctctcctgtt ccgaccctgc cgcttaccgg   15360
atacctgtcc gcctttctcc cttcgggaag cgtggcgctt tctcatagct cacgctgtag   15420
gtatctcagt tcggtgtagg tcgttcgctc caagctgggc tgtgtgcacg aaccccccgt   15480
tcagcccgac cgctgcgcct tatccggtaa ctatcgtctt gagtccaacc cggtaagaca   15540
cgacttatcg ccactggcag cagccactgg taacaggatt agcagagcga ggtatgtagg   15600
cggtgctaca gagttcttga agtggtggcc taactacggc tacactagaa gaacagtatt   15660
tggtatctgc gctctgctga gccagttacc ttcggaaaa agagttggta gctcttgatc   15720
cggcaaacaa accaccgctg gtagcggtgg ttttttgtt tgcaagcagc agattacgcg   15780
cagaaaaaaa ggatctcaag aagatccttt gatctttct acggggtctg acgctcagtg   15840
gaacgaaaac tcacgttaag ggattttggt catgagatta tcaaaaagga tcttcaccta   15900
gatccttttg atccggaatt a                                             15921
```

<210> SEQ ID NO 35
<211> LENGTH: 17954
<212> TYPE: DNA
<213> ORGANISM: artificial sequence
<220> FEATURE:
<223> OTHER INFORMATION: vector 24039
<220> FEATURE:
<221> NAME/KEY: misc_feature
<222> LOCATION: (4)..(259)
<223> OTHER INFORMATION: bNRB-05
<220> FEATURE:

-continued

```
<221> NAME/KEY: promoter
<222> LOCATION: (315)..(1729)
<223> OTHER INFORMATION: prZmGRMZM2G020852-01
<220> FEATURE:
<221> NAME/KEY: gene
<222> LOCATION: (1731)..(5979)
<223> OTHER INFORMATION: cCas9-13
<220> FEATURE:
<221> NAME/KEY: terminator
<222> LOCATION: (5989)..(8769)
<223> OTHER INFORMATION: tZmGRMZM2G020852-01
<220> FEATURE:
<221> NAME/KEY: promoter
<222> LOCATION: (8783)..(9157)
<223> OTHER INFORMATION: prOsU3-01
<220> FEATURE:
<221> NAME/KEY: misc_feature
<222> LOCATION: (9159)..(9178)
<223> OTHER INFORMATION: xZmVLHP2
<220> FEATURE:
<221> NAME/KEY: misc_feature
<222> LOCATION: (9159)..(9263)
<223> OTHER INFORMATION: rsgRNAZmVLHP-02
<220> FEATURE:
<221> NAME/KEY: misc_feature
<222> LOCATION: (9179)..(9190)
<223> OTHER INFORMATION: rCrRNA-01
<220> FEATURE:
<221> NAME/KEY: misc_feature
<222> LOCATION: (9195)..(9263)
<223> OTHER INFORMATION: rTracrRNA-01
<220> FEATURE:
<221> NAME/KEY: promoter
<222> LOCATION: (9274)..(11265)
<223> OTHER INFORMATION: prUbi1-04
<220> FEATURE:
<221> NAME/KEY: gene
<222> LOCATION: (11282)..(12460)
<223> OTHER INFORMATION: cPMI-09
<220> FEATURE:
<221> NAME/KEY: terminator
<222> LOCATION: (12483)..(12735)
<223> OTHER INFORMATION: tNOS-05-01
<220> FEATURE:
<221> NAME/KEY: misc_feature
<222> LOCATION: (12779)..(12908)
<223> OTHER INFORMATION: bNLB-03
<220> FEATURE:
<221> NAME/KEY: gene
<222> LOCATION: (13188)..(13976)
<223> OTHER INFORMATION: cSpec-03
<220> FEATURE:
<221> NAME/KEY: promoter
<222> LOCATION: (14071)..(14201)
<223> OTHER INFORMATION: prVirG-01
<220> FEATURE:
<221> NAME/KEY: gene
<222> LOCATION: (14276)..(14908)
<223> OTHER INFORMATION: cVirG-09
<220> FEATURE:
<221> NAME/KEY: gene
<222> LOCATION: (14938)..(16011)
<223> OTHER INFORMATION: cRepA-01
<220> FEATURE:
<221> NAME/KEY: misc_feature
<222> LOCATION: (16054)..(16458)
<223> OTHER INFORMATION: oVS1-02
<220> FEATURE:
<221> NAME/KEY: misc_feature
<222> LOCATION: (17136)..(17942)
<223> OTHER INFORMATION: oCOLE-o6

<400> SEQUENCE: 35
attcctgtgg ttggcatgca catacaaatg gacgaacgga taaacctttt cacgcccttt        60
taaatatccg attattctaa taaacgctct tttctcttag gtttacccgc caatatatcc       120
tgtcaaacac tgatagttta aactgaaggc gggaaacgac aatctgatca tgagcggaga       180
```

-continued

```
attaagggag tcacgttatg accccgccg atgacgcggg acaagccgtt ttacgtttgg      240
aactgacaga accgcaacgc tgcaggaatt ggccgcagcg gccatttaaa caaagcttgg      300
taccggaccg ttataacagt gaatacaaaa atgacattcg tgttatttag cacaagttac      360
gatctatttc aggaacatgc cggaattttc gaacaccatt ctcacaaaac atgaccttga      420
acttgcgatc cagttgtttt aaaattatat aaaacaaaaa caaagtcaga aaatcatgaa      480
acttgtcgac atgtcatgat atcatatgta gagactctaa taaaaagttg agattgtttc      540
atgaaagttg tcacacacta tgtgtagaaa cttagcccgt ctacattgaa gttctatgat      600
ttcatgtgaa ggacacctag gcatcgatgt ttatgataat atcttatgtt tgtttggaca      660
aaatattaaa aacaaataaa aggggtccct gatcactttg acgagcattg cattcagcaa      720
agggtgcctt tgttgagtgc aatggtcata gaactcggta gaaaagacat acataaacat      780
cgggaaactt gctttaccgc acgctatggc caagacactc ggcaaactag gctcctttgt      840
tgagtgccat ctcaagcact cgacattgga actacgacta ggcctcacgg aagctttctt      900
tgccgagtgc cactaagcga ggaactcgga cactcagcaa cagctctgtc atcgtcacga      960
tgtcttttct ttgtcgtgta ccagttggca ctcggttaag actttactga gtgcccgata    1020
gaaagtactc ggcaaagaga ccgttgccga cgtttggttc actgagggct ctttgctgcc    1080
ttttggactt gacaaagaag tcatctccag tactgtctcc taggacgcag gatttatgtt    1140
ttttcccgga gctcgatctg tgggacatca cagatggtcc aatctggtga tctaaaatgg    1200
acggtttgcc aagcccacag agaagtcttt aagatcttcc acgatgcacg catgctttaa    1260
ggttagatag tgtttggtcc aaaaaagcgt caacaatcag gaaattagaa ctaaaattat    1320
taaaggacag atcaaaaggc atgcatgttc ttcttctata gtgtgtgttg agcctgagtt    1380 ttgatttttag gctttattag gggactcgca gtctagctaa ggagttgtat tgatgttctg    1440
acaaatatta tgttcgatcg tcacagtggt cttgtgcgga tcgattaggc ccgatcatgg    1500
tgaaataaac taaccaccgg taagcccggg cagccctaga gcatgcagcg gcctacgtga    1560
agcccgcgtg tcgcatcgtc gtccgtcaga cgctaacggc aggccgctgc atgcgttgcc    1620
ggcgaactct ctcctgagcc actcgtcatc catataagta gacatcccat cactgtcgtc    1680
tatcaacaac acacagagcg acatttcgaa taacacagtt gagcgcgacc atggacaaga    1740
agtacagcat cggcctggac atcggcacca acagcgtggg ctgggccgtg atcaccgacg    1800
agtacaaggt acgagcggga tacatgttta tactcctcct gtaggtcgct ccttcatgta    1860
atgtgttgcg attaaaacgg tgcgcaggtg ccgagcaaga agttcaaggt gctgggcaac    1920
accgacaggc acagcatcaa gaagaacctg atcggcgccc tgctgttcga cagcggcgag    1980
accgccgagg ccaccaggct gaagaggacc gccaggagga ggtacaccag gaggaagaac    2040
aggatctgct acctgcagga gatcttcagc aacgagatgg ccaaggtgga cgacagcttc    2100
ttccacaggc tggaggagag cttcctggtg gaggaggaca gaagcacga gaggcacccg    2160 atcttcggca acatcgtgga cgaggtggcc taccacgaga gtacccgac catctaccac    2220 ctgaggaaga gctggtggga cagcaccgac aaggccgacc tgaggctgat ctacctggcc    2280
ctggcccaca tgatcaagtt cagggggccac ttcctgatcg agggcgacct gaacccggac    2340
aacagcgacg tggacaagct gttcatccag ctggtgcaga cctacaacca gctgttcgag    2400
gagaacccga tcaacgccag cggcgtggac gccaaggcca tcctgagcgc caggctgagc    2460
aagagcagga ggctggagaa cctgatcgcc cagctgccgg cgagaagaa gaacggcctg    2520
```

-continued

```
ttcggcaacc tgatcgccct gagcctgggc ctgaccccga acttcaagag caacttcgac   2580
ctggccgagg acgccaagct gcagctgagc aaggacacct acgacgacga cctggacaac   2640
ctgctggccc agatcggcga ccagtacgcc gacctgttcc tggccgccaa gaacctgagc   2700
gacgccatcc tgctgagcga catcctgagg gtgaacaccg agatcaccaa ggccccgctg   2760
agcgccagca tgatcaagag gtacgacgag caccaccagg acctgaccct gctgaaggcc   2820
ctggtgaggc agcagctgcc ggagaagtac aaggagatct tcttcgacca gagcaagaac   2880
ggctacgccg gctacatcga cggcggcgcc agccaggagg agttctacaa gttcatcaag   2940
ccgatcctgg agaagatgga cggcaccgag gagctgctgg tgaagctgaa cagggaggac   3000
ctgctgagga agcagaggac cttcgacaac ggcagcatcc cgcaccagat ccacctgggc   3060
gagctgcacg ccatcctgag gaggcaggag gacttctacc cgttcctgaa ggacaacagg   3120
gagaagatcg agaagatcct gaccttccgc atcccgtact acgtgggccc gctggccagg   3180
ggcaacagca ggttcgcctg gatgaccagg aagagcgagg agaccatcac cccgtggaac   3240
ttcgaggagg tggtggacaa gggcgccagc gcccagagct catcgagag gatgaccaac   3300 ttcgacaaga acctgccgaa cgagaaggtg ctgccgaagc acagcctgct gtacgagtac   3360
ttcaccgtgt acaacgagct gaccaaggtg aagtacgtga ccgagggcat gaggaagccg   3420
gccttcctga gcggcgagca gaagaaggcc atcgtggacc tgctgttcaa gaccaacagg   3480
aaggtgaccg tgaagcagct gaaggaggac tacttcaaga gatcgagtg cttcgacagc   3540 gtggagatca gcggcgtgga ggacaggttc aacgccagcc tgggcaccta ccacgacctg   3600
ctgaagatca tcaaggacaa ggacttcctg gacaacgagg agaacgagga catcctggag   3660
gacatcgtgc tgaccctgac cctgttcgag gacagggaga tgatcgagga gaggctgaag   3720
acctacgccc acctgttcga cgacaaggtg atgaagcagc tgaagaggag gaggtacacc   3780
ggctggggca ggctgagcag gaagctgatc aacggcatca gggacaagca gagcggcaag   3840
accatcctgg acttcctgaa gagcgacggc ttcgccaaca ggaacttcat gcagctgatc   3900
cacgacgaca gcctgacctt caaggaggac atccagaagg cccaggtgag cggccagggc   3960
gacagcctgc acgagcacat cgccaacctg gccggcagcc cggccatcaa gaagggcatc   4020
ctgcagaccg tgaaggtggt ggacgagctg gtgaaggtga tgggcaggca caagccggag   4080
aacatcgtga tcgagatggc cagggagaac cagaccaccc agaagggcca gaagaacagc   4140
agggagagga tgaagaggat cgaggagggc atcaaggagc tgggcagcca gatcctgaag   4200
gagcacccgg tggagaacac ccagctgcag aacgagaagc tgtacctgta ctacctgcag   4260
aacggcaggg acatgtacgt ggaccaggag ctggacatca caggctgagc cgactacgac   4320
gtggaccaca tcgtgccgca gagcttcctg aaggacgaca gcatcgacaa caaggtgctg   4380
accaggagcg acaagaacag gggcaagagc gacaacgtgc cgagcgagga ggtggtgaag   4440
aagatgaaaa actactggag gcagctgctg aacgccaagc tgatcaccca gaggaagttc   4500
gacaacctga ccaaggccga gaggggcggc ctgagcgagc tggacaaggc cggcttcatt   4560
aaaaggcagc tggtggagac caggcagatc accaagcacg tggcccagat cctggacagc   4620
aggatgaaca ccaagtacga cgagaacgac aagctgatca gggaggtgaa ggtgatcacc   4680
ctgaagagca gctggtgag cgacttcagg aaggacttcc agttctacaa ggtgagggag   4740
atcaataatt accaccacgc ccacgacgcc tacctgaacg ccgtggtggg caccgccctg   4800
attaaaaagt acccgaagct ggagagcgag ttcgtgtacg gcgactacaa ggtgtacgac   4860
gtgaggaaga tgatcgccaa gagcgagcag gagatcggca aggccaccgc caagtacttc   4920
```

-continued

```
ttctacagca acatcatgaa cttcttcaag accgagatca ccctggccaa cggcgagatc    4980
aggaagaggc cgctgatcga gaccaacggc gagaccggcg agatcgtgtg ggacaagggc    5040
agggacttcg ccaccgtgag gaaggtgctg tccatgccgc aggtgaacat cgtgaagaag    5100
accgaggtgc agaccggcgg cttcagcaag gagagcatcc tgccgaagag gaacagcgac    5160
aagctgatcg ccaggaagaa ggactgggac ccgaagaagt acggcggctt cgacagcccg    5220
accgtggcct acagcgtgct ggtggtggcc aaggtggaga agggcaagag caagaagctg    5280
aagagcgtga aggagctggt gggcatcacc atcatggaga ggagcagctt cgagaagaac    5340
ccagtggact tcctggaggc caagggctac aaggaggtga agaaggacct gatcattaaa    5400
ctgccgaagt acagcctgtt cgagctggag aacggcagga agaggatgct ggccagcgcc    5460
ggcgagctgc agaagggcaa cgagctggcc ctgccgagca agtacgtgaa cttcctgtac    5520
ctggccagcc actacgagaa gctgaagggc agcccggagg acaacgagca gaagcagctg    5580
ttcgtggagc agcacaagca ctacctggac gagatcatcg agcagatcag cgagttcagc    5640
aagagggtga tcctggccga cgccaacctg gacaaggtgc tgagcgccta caacaagcac    5700
agggacaagc cgatcaggga gcaggccgag aacatcatcc acctgttcac cctgaccaac    5760
ctgggcgccc cggccgcctt caagtacttc gacaccacca tcgacaggaa gaggtacacc    5820
agcaccaagg aggtgctgga cgccaccctg atccaccaga gcatcaccgg cctgtacgag    5880
accaggatcg acctgagcca gctgggcggc gacagcagcc cgccgaagaa gaagaggaag    5940
gtgagctgga aggacgccag cggctggagc aggatgtgag ctcaattaac tttgaattcc    6000
cttcgattca tccggcgcgg tgggctatgg acctgcagca gcaagctaat taagtttata    6060
tatattgcat gagagagcat gcaccgctaa ccatatatac tactgagact tctgaattct    6120
agtatatgta atccttttgt ttgggtttag gaggcaattc taatcatgta tgccgaattc    6180
caaagagtgg aaaacaagca aaatgttaaa tatacatgcc attttcggag gcaatttttt    6240
tcatgagggc atgttgctat aattccgggg accttggact tcttggagca ccttcctgtg    6300
acttaggcat acatgattag attataatcc aattagttaa gtcatagaaa attacctcat    6360
tctcatctcc atctccattt ctctatttct tctcaatcaa ggaccaaaat agcacttttg    6420
ctaaaaaaca agttagattg caaaccaaag tgcacaatac atagtaaaag gtatatgcaa    6480
catatttgaa tactcaaacc tctcatactt acattttcca tcattttgtt ccatttagcc    6540
tgtttgagct cggggttgga ctccaaaacc tcatgtcaac ataacttgat cctttttagca    6600 aactatgagc tctaacacca tacaatggtc aacaagaact attccaaaca taggaatgac    6660
ccaaactaca agtcaaagta tacttagctc tttgggcact tacaggttct aactttgata    6720
attctgtact tcttgtgacc atgactctgc tcgagctagg atcttgagcc ttatgactta    6780
aacaattaaa ccacaaacat tacctcaatg gttgtaagcc acgtccatat atcacagact    6840
tcaatgcatt cagactattc acagcttgac caaccttgac ctcttgcaag aacctcttct    6900
tctttgtgac cttaggtact ttagtcttct tgaccttctc ccttgctctt cataccttga    6960
agtccttctt gccttcacct tagttcaatc agctatctcc aagtcatgca cattgagttc    7020
cacttagtca atgtccatcc ttcaacttga cttgtgatgt ccacaattca tagtcatctc    7080
agtctatggg tccatcatgc ttgactccat gtgatgaacc ttgtaaggtt ttcactaagt    7140
acatgctcag acctttaatt gtgttgccat ccaaaaaaac caaaacctag attggaccat    7200
tcattatatt catcaatcat tgtacttgca agagtgatca aggtcatatt atttctctca    7260
```

```
actactccat tttgttgagg ggtgtcagtt gtggagactt cttgtttgat cccaacctca    7320
tcacaatact catgaatata gttgttgtca aattcatttc cattgtcact tcttattttt    7380
cttgattttg caatcaaact cattttgtac tttcatggta aatttattca atgttgatgc    7440
aacttttgac ttttcttgaa gaaagaacac tcaattacat ctagagaaat catcaacaac    7500
gaccaaacaa tacaggtttc ccccaacact agcatattat gtaggaccaa ataaatccat    7560
gtgaagtaac tctagtggtc ttggtgttga cataaaagcg tttgtaggat gtgtattggc    7620
aacttgtttt ccagcttgac atgcactata aaagatttc cttttttcaaa cacaacatct    7680 ttcaaatctc taaccatttc tttctttgga agcttcttgt tggggaaatg atccccggac    7740
cctaggaccc accggtcaga gagcgcgagg aagagccccc ggtcgctggg acccgttggt    7800
ccgctggaaa atgtggttac gtcaaccctg aaagaacccg cccctggttg agccccgtgg    7860
caccgagcct agggtcgagc gcggtggaat ctgacaggag gggccagaca tgttggaggg    7920
gaaccactca agtggatccc gcgcctggcc ccagaatgac ccgtcattaa tacccaacca    7980
cattaaccat gcctggcacc gagccatagc acggacgtcg gtccacttcc cactcatgac    8040
ctacgaacca gttgggctgc atagcactca tgaccgatag gttgaaggct tggcttcgca    8100
gagtgaaagg cgctgcatac atgtgaaggc tcgacttctt tttcttttcc tttctttcct    8160
tttctatttt taggtttcca atttaaattc caattttttt gtggagttca tatttggatc    8220
aaatagacaa attcacctat cagtatgaat agatgcattt attttgttta tatctatttt    8280
cttcatattt atatagtatt tcccttattc tttatatcat tttcaatttg taattggtaa    8340
gtttggtctt aaattcccca tttgggcact aatatatttt tattaatatt attattatta    8400
ttattattat tatttataga tgcacaaaca cataaactcc gacatgatgc atagattatt    8460
ttagatgtca ctagttaatg gttcacttta aatatggtta ttcccatgtt ctaatgagta    8520
gagggcaaag catatattga ggtcaactct ttccttatta tttacaaatt ggggaaattc    8580
tattcataac tcttcttctc tctcccaagt agcttaatct tcaccatggt gatttcattg    8640
cactttgcac attttgatca ctttattcct tgtaacccga gtcaaagtgt caatgatctt    8700
gataggatac tccgtgcagg ttagatcacc ttgcacactg agttcttcca ttggtaactg    8760
ttcctctggc ggaccgttcg aagggatctt taaacatacg aacagatcac ttaaagttct    8820
tctgaagcaa cttaaagtta tcaggcatgc atggatcttg gaggaatcag atgtgcagtc    8880
agggaccata gcacaggaca ggcgtcttct actggtgcta ccagcaaatg ctggaagccg    8940
ggaacactgg gtacgttgga aaccacgtga tgtggagtaa gataaactgt aggagaaaag    9000
catttcgtag tgggccatga agcctttcag gacatgtatt gcagtatggg ccggcccatt    9060
acgcaattgg acgacaacaa agactagtat tagtaccacc tcggctatcc acatagatca    9120
aagctggttt aaaagagttg tgcagatgat ccgtggcagc tggagctgag cttccggggt    9180
tttagagcta gaaatagcaa gttaaaataa ggctagtccg ttatcaactt gaaaaagtgg    9240
caccgagtcg gtgctttttt tttcggaccg cgcctgcagt gcagcgtgac ccggtcgtgc    9300
ccctctctag agataatgag cattgcatgt ctaagttata aaaaattacc acatattttt    9360
tttgtcacac ttgtttgaag tgcagtttat ctatctttat acatatattt aaactttact    9420
ctacgaataa tataatctat agtactacaa taatatcagt gttttagaga atcatataaa    9480
tgaacagtta gacatggtct aaaggacaat tgagtatttt gacaacagga ctctacagtt    9540
ttatcttttt agtgtgcatg tgttctcctt ttttttttgca aatagcttca cctatataat    9600
acttcatcca ttttattagt acatccattt agggtttagg gttaatggtt tttatagact    9660
```

-continued

```
aattttttta gtacatctat tttattctat tttagcctct aaattaagaa aactaaaact    9720
ctattttagt ttttttattt aataatttag atataaaata gaataaaata aagtgactaa    9780
aaattaaaca aatacccttt aagaaattaa aaaaactaag gaaacatttt tcttgtttcg    9840
agtagataat gccagcctgt taaacgccgt cgacgagtct aacggacacc aaccagcgaa    9900
ccagcagcgt cgcgtcgggc caagcgaagc agacggcacg gcatctctgt cgctgcctct    9960
ggacccctct cgagagttcc gctccaccgt tggacttgct ccgctgtcgg catccagaaa   10020
ttgcgtggcg gagcggcaga cgtgagccgg cacggcaggc ggcctcctcc tcctctcacg   10080
gcaccggcag ctacggggga ttcctttccc accgctcctt cgctttccct tcctcgcccg   10140
ccgtaataaa tagacacccc ctccacaccc tctttcccca acctcgtgtt gttcggagcg   10200
cacacacaca caaccagatc tcccccaaat ccacccgtcg gcacctccgc ttcaaggtac   10260
gccgctcgtc ctcccccccc ccctctcta ccttctctag atcggcgttc cggtccatgg   10320
ttagggcccg gtagttctac ttctgttcat gtttgtgtta gatccgtgtt tgtgttagat   10380
ccgtgctgct agcgttcgta cacggatgcg acctgtacgt cagacacgtt ctgattgcta   10440
acttgccagt gtttctcttt ggggaatcct gggatggctc tagccgttcc gcagacggga   10500
tcgatttcat gatttttttt gtttcgttgc atagggtttg gtttgccctt ttcctttatt   10560
tcaatatatg ccgtgcactt gtttgtcggg tcatctttc atgctttttt ttgtcttggt   10620
tgtgatgatg tggtctggtt gggcggtcgt tctagatcgg agtagaattc tgtttcaaac   10680
tacctggtgg atttattaat tttggatctg tatgtgtgtg ccatacatat tcatagttac   10740
gaattgaaga tgatggatgg aaatatcgat ctaggatagg tatacatgtt gatgcgggtt   10800
ttactgatgc atatacagag atgctttttg ttcgcttggt tgtgatgatg tggtgtggtt   10860
gggcggtcgt tcattcgttc tagatcggag tagaatactg tttcaaacta cctggtgtat   10920
ttattaattt tggaactgta tgtgtgtgtc atacatcttc atagttacga gtttaagatg   10980
gatggaaata tcgatctagg ataggtatac atgttgatgt gggtttttact gatgcatata   11040 catgatggca tatgcagcat ctattcatat gctctaacct tgagtaccta tctattataa   11100
taaacaagta tgttttataa ttatttgat cttgatatac ttggatgatg gcatatgcag   11160
cagctatatg tggattttttt tagccctgcc ttcatacgct attttatttgc ttggtactgt   11220 ttcttttgtc gatgctcacc ctgttgtttg gtgttacttc tgcagggatc cggcagcagc   11280
catgcagaag ctgatcaaca gcgtgcagaa ctacgcctgg ggcagcaaga ccgccctgac   11340
cgagctgtac ggcatggaga accccagcag ccagcccatg gccgagctgt ggatgggcgc   11400
ccaccccaag agcagcagcc gcgtgcagaa cgccgccggc gacatcgtga gcctgcgcga   11460
cgtgatcgag agcgacaaga gcaccctgct gggcgaggcc gtggccaagc gcttcggcga   11520
gctgcccttc ctgttcaagg tgctgtgcgc cgcccagccc ctgagcatcc aggtgcaccc   11580
caacaagcac aacagcgaga tcggcttcgc caaggagaac gccgccggca tcccatgga   11640 cgccgccgag cgcaactaca aggaccccaa ccacaagccc gagctggtgt cgccctgac   11700 cccccttcctg gccatgaacg ccttccgcga gttcagcgag atcgtgagcc tgctgcagcc   11760
cgtggccggc gcccacccg ccatcgccca cttcctgcag cagcccgacg ccgagcgcct   11820
gagcgagctg ttcgccagcc tgctgaacat gcagggcgag gagaagagcc gcgccctggc   11880
catcctgaag agcgccctgg acagccagca gggcgagccc tggcagacca ccgcctgat   11940 cagcgagttc taccccgagg acagcggcct gttcagcccc ctgctgctga acgtggtgaa   12000
```

-continued

```
gctgaacccc ggcgaggcca tgttcctgtt cgccgagacc ccccacgcct acctgcaggg   12060
cgtggccctg gaggtgatgg ccaacagcga caacgtgctg cgcgccggcc tgacccccaa   12120
gtacatcgac atccccgagc tggtggccaa cgtgaagttc gaggccaagc ccgccaacca   12180
gctgctgacc cagcccgtga agcagggcgc cgagctggac ttccccatcc ccgtggacga   12240
cttcgccttc agcctgcacg acctgagcga caaggagacc accatcagcc agcagagcgc   12300
cgccatcctg ttctgcgtgg agggcgacgc caccctgtgg aagggcagcc agcagctgca   12360
gctgaagccc ggcgagagcg ccttcatcgc cgccaacgag agccccgtga ccgtgaaggg   12420
ccacggccgc ctggcccgcg tgtacaacaa gctgtgatag gagctcgatc cgtcgacctg   12480
cagatcgttc aaacatttgg caataaagtt tcttaagatt gaatcctgtt gccggtcttg   12540
cgatgattat catataattt ctgttgaatt acgttaagca tgtaataatt aacatgtaat   12600
gcatgacgtt atttatgaga tgggtttttta tgattagagt cccgcaatta tacatttaat   12660
acgcgataga aaacaaaata tagcgcgcaa actaggataa attatcgcgc gcggtgtcat   12720
ctatgttact agatcggcgc gccgcaattg aagtttgggc ggccagcatg gccgtatccg   12780
caatgtgtta ttaagttgtc taagcgtcaa tttgtttaca ccacaatata tcctgccacc   12840
agccagccaa cagctccccg accggcagct cggcacaaaa tcaccactcg atacaggcag   12900
cccatcagaa ttaattctca tgtttgacag cttatcatcg actgcacggt gcaccaatgc   12960
ttctggcgtc aggcagccat cggaagctgt ggtatggctg tgcaggtcgt aaatcactgc   13020
ataattcgtg tcgctcaagg cgcactcccg ttctggataa tgttttttgc gccgacatca   13080
taacggttct ggcaaatatt ctgaaatgag ctgttgacaa ttaatcatcc ggctcgtata   13140
atgtgtggaa ttgtgagcgg ataacaattt cacacaggaa acagaccatg agggaagcgt   13200
tgatcgccga agtatcgact caactatcag aggtagttgg cgtcatcgag cgccatctcg   13260
aaccgacgtt gctggccgta catttgtacg gctccgcagt ggatggcggc ctgaagccac   13320
acagtgatat tgatttgctg gttacggtga ccgtaaggct tgatgaaaca acgcggcgag   13380
ctttgatcaa cgaccttttg gaaacttcgg cttcccctgg agagagcgag attctccgcg   13440
ctgtagaagt caccattgtt gtgcacgacg acatcattcc gtggcgttat ccagctaagc   13500
gcgaactgca atttggagaa tggcagcgca atgacattct tgcaggtatc ttcgagccag   13560
ccacgatcga cattgatctg gctatcttgc tgacaaaagc aagagaacat agcgttgcct   13620
tggtaggtcc agcggcggag gaactctttg atccggttcc tgaacaggat ctatttgagg   13680
cgctaaatga aaccttaacg ctatggaact cgccgcccga ctgggctggc gatgagcgaa   13740
atgtagtgct tacgttgtcc cgcatttggt acagcgcagt aaccggcaaa atcgcgccga   13800
aggatgtcgc tgccgactgg gcaatggagc gcctgccggc ccagtatcag cccgtcatac   13860
ttgaagctag gcaggcttat cttggacaag aagatcgctt ggcctcgcgc gcagatcagt   13920
tggaagaatt tgttcactac gtgaaaggcg agatcaccaa agtagtcggc aaataaagct   13980
ctagtggatc tccgtacccg gggatctggc tcgcggcgga cgcacgacgc cggggcgaga   14040
ccataggcga tctcctaaat caatagtagc tgtaacctcg aagcgtttca cttgtaacaa   14100
cgattgagaa tttttgtcat aaaattgaaa tacttggttc gcattttgt catccgcggt    14160 cagccgcaat tctgacgaac tgcccattta gctggagatg attgtacatc cttcacgtga   14220
aaatttctca agcgctgtga acaagggttc agattttaga ttgaaaggtg agccgttgaa   14280
acacgttctt cttgtcgatg acgacgtcgc tatgcggcat cttattattg aataccttac   14340
gatccacgcc ttcaaagtga ccgcggtagc cgacagcacc cagttcacaa gagtactctc   14400
```

-continued

```
ttccgcgacg gtcgatgtcg tggttgttga tctagattta ggtcgtgaag atgggctcga   14460
gctaggagca agtgatttta tcgctaagcc gttcagtatc agagagtttc tagcacgcat   14520
tcgggttgcc ttgcgcgtgc gccccaacgt tgtccgctcc aaagaccgac ggtcttttg    14580 ttttactgac tggacactta atctcaggca acgtcgcttg atgtccgaag ctggcggtga   14640
ggtgaaactt acggcaggtg agttcaatct tctcctcgcg tttttagaga aaccccgcga   14700
cgttctatcg cgcgagcaac ttctcattgc cagtcgagta cgcgacgagg aggtttatga   14760
caggagtata gatgttctca ttttgaggct gcgccgcaaa cttgaggcag atccgtcaag   14820
ccctcaactg ataaaaacag caagaggtgc cggttatttc tttgacgcgg acgtgcaggt   14880
ttcgcacggg gggacgatgg cagcctgagc caattcccag atccccgagg aatcggcgtg   14940
agcggtcgca aaccatccgg cccggtacaa atcggcgcgg cgctgggtga tgacctggtg   15000
gagaagttga aggccgcgca ggccgcccag cggcaacgca tcgaggcaga agcacgcccc   15060
ggtgaatcgt ggcaagcggc cgctgatcga atccgcaaag aatcccggca accgccggca   15120
gccggtgcgc cgtcgattag gaagccgccc aagggcgacg agcaaccaga ttttttcgtt   15180
ccgatgctct atgacgtggg cacccgcgat agtcgcagca tcatggacgt ggccgttttc   15240
cgtctgtcga agcgtgaccg acgagctggc gaggtgatcc gctacgagct tccagacggg   15300
cacgtagagg tttccgcagg gccggccggc atggccagtg tgtgggatta cgacctggta   15360
ctgatggcgg tttcccatct aaccgaatcc atgaaccgat accgggaagg gaagggagac   15420
aagcccggcc gcgtgttccg tccacacgtt gcggacgtac tcaagttctg ccggcgagcc   15480
gatggcggaa agcagaaaga cgacctggta gaaacctgca ttcggttaaa caccacgcac   15540
gttgccatgc agcgtacgaa gaaggccaag aacggccgcc tggtgacggt atccgagggt   15600
gaagccttga ttagccgcta caagatcgta aagagcgaaa ccgggcggcc ggagtacatc   15660
gagatcgagc tagctgattg gatgtaccgc gagatcacag aaggcaagaa cccggacgtg   15720
ctgacggttc accccgatta cttttttgatc gatcccggca tcggccgttt tctctaccgc   15780
ctggcacgcc gcgccgcagg caaggcagaa gccagatggt tgttcaagac gatctacgaa   15840
cgcagtggca gcgccggaga gttcaagaag ttctgtttca ccgtgcgcaa gctgatcggg   15900
tcaaatgacc tgccggagta cgatttgaag gaggaggcgg ggcaggctgg cccgatccta   15960
gtcatgcgct accgcaacct gatcgagggc gaagcatccg ccggttccta atgtacggag   16020
cagatgctag ggcaaattgc cctagcaggg gaaaaaggtc gaaaaggtct ctttcctgtg   16080
gatagcacgt acattgggaa cccaaagccg tacattggga accggaaccc gtacattggg   16140
aacccaaagc cgtacattgg gaaccggtca cacatgtaag tgactgatat aaaagagaaa   16200
aaaggcgatt tttccgccta aaactcttta aaacttatta aaactcttaa aacccgcctg   16260
gcctgtgcat aactgtctgg ccagcgcaca gccgaagagc tgcaaaaagc gcctacccttt  16320 cggtcgctgc gctccctacg ccccgccgct tcgcgtcggc ctatcgcggc cgctggccgc   16380
tcaaaaatgg ctggcctacg gccaggcaat ctaccagggc gcggacaagc cgcgccgtcg   16440
ccactcgacc gccggcgctg aggtctgcct cgtgaagaag gtgttgctga ctcataccag   16500
gcctgaatcg ccccatcatc cagccagaaa gtgagggagc cacggttgat gagagctttg   16560
ttgtaggtgg accagttggt gattttgaac ttttgctttg ccacggaacg gtctgcgttg   16620
tcgggaagat gcgtgatctg atccttcaac tcagcaaaag ttcgatttat tcaacaaagc   16680
cgccgtcccg tcaagtcagc gtaatgctct gccagtgtta caaccaatta accaattctg   16740
```

```
attagaaaaa ctcatcgagc atcaaatgaa actgcaattt attcatatca ggattatcaa    16800
taccatattt ttgaaaaagc cgtttctgta atgaaggaga aaactcaccg aggcagttcc    16860
ataggatggc aagatcctgg tatcggtctg cgattccgac tcgtccaaca tcaatacaac    16920
ctattaattt cccctcgtca aaaataaggt tatcaagtga gaaatcacca tgagtgacga    16980
ctgaatccgg tgagaatggc aaaagctctg cattaatgaa tcggccaacg cgcggggaga    17040
ggcggtttgc gtattgggcg ctcttccgct tcctcgctca ctgactcgct gcgctcggtc    17100
gttcggctgc ggcgagcggt atcagctcac tcaaaggcgg taatacggtt atccacagaa    17160 tcagggggata acgcaggaaa gaacatgtga gcaaaaggcc agcaaaaggc caggaaccgt    17220
aaaaaggccg cgttgctggc gtttttccat aggctccgcc ccctgacga gcatcacaaa    17280 aatcgacgct caagtcagag gtggcgaaac ccgacaggac tataaagata ccaggcgttt    17340
ccccctggaa gctccctcgt gcgctctcct gttccgaccc tgccgcttac cggatacctg    17400 tccgccttc tcccttcggg aagcgtggcg ctttctcata gctcacgctg taggtatctc    17460
agttcggtgt aggtcgttcg ctccaagctg ggctgtgtgc acgaaccccc cgttcagccc    17520
gaccgctgcg ccttatccgg taactatcgt cttgagtcca acccggtaag acacgactta    17580
tcgccactgg cagcagccac tggtaacagg attagcagag cgaggtatgt aggcggtgct    17640
acagagttct tgaagtggtg gcctaactac ggctacacta gaagaacagt atttggtatc    17700
tgcgctctgc tgaagccagt taccttcgga aaaagagttg gtagctcttg atccggcaaa    17760
caaaccaccg ctggtagcgg tggtttttt gtttgcaagc agcagattac gcgcagaaaa    17820
aaaggatctc aagaagatcc tttgatcttt tctacggggt ctgacgctca gtggaacgaa    17880
aactcacgtt aagggatttt ggtcatgaga ttatcaaaaa ggatcttcac ctagatcctt    17940
ttgatccgga atta    17954
```

```
<210> SEQ ID NO 36
<211> LENGTH: 17045
<212> TYPE: DNA
<213> ORGANISM: Artificial Sequence
<220> FEATURE:
<223> OTHER INFORMATION: vector 24079
<220> FEATURE:
<221> NAME/KEY: misc_feature
<222> LOCATION: (4)..(259)
<220> FEATURE:
<221> NAME/KEY: promoter
<222> LOCATION: (312)..(2356)
<223> OTHER INFORMATION: prGRMZM2G146551-01
<220> FEATURE:
<221> NAME/KEY: gene
<222> LOCATION: (2358)..(6527)
<223> OTHER INFORMATION: cCas9-01
<220> FEATURE:
<221> NAME/KEY: mutation
<222> LOCATION: (5847)..(5849)
<223> OTHER INFORMATION: L to V mutation
<220> FEATURE:
<221> NAME/KEY: mutation
<222> LOCATION: (5892)..(5894)
<223> OTHER INFORMATION: I to V mutation
<220> FEATURE:
<221> NAME/KEY: terminator
<222> LOCATION: (6542)..(7860)
<223> OTHER INFORMATION: tGRMZM2G146551-01
<220> FEATURE:
<221> NAME/KEY: promoter
<222> LOCATION: (7874)..(8248)
<223> OTHER INFORMATION: prOsU3-01
<220> FEATURE:
<221> NAME/KEY: misc_feature
<222> LOCATION: (8249)..(8354)
```

```
<223> OTHER INFORMATION: rsgRNAZmVLHP-02
<220> FEATURE:
<221> NAME/KEY: misc_feature
<222> LOCATION: (8250)..(8269)
<223> OTHER INFORMATION: ZmVLHP2 target
<220> FEATURE:
<221> NAME/KEY: misc_feature
<222> LOCATION: (8270)..(8281)
<223> OTHER INFORMATION: rCrRNA-01
<220> FEATURE:
<221> NAME/KEY: misc_feature
<222> LOCATION: (8286)..(8354)
<223> OTHER INFORMATION: rTracrRNA-01
<220> FEATURE:
<221> NAME/KEY: promoter
<222> LOCATION: (8365)..(10356)
<223> OTHER INFORMATION: prUbi1-04
<220> FEATURE:
<221> NAME/KEY: gene
<222> LOCATION: (10373)..(11551)
<223> OTHER INFORMATION: cPMI-09
<220> FEATURE:
<221> NAME/KEY: terminator
<222> LOCATION: (11574)..(11826)
<223> OTHER INFORMATION: tNOS-05-01
<220> FEATURE:
<221> NAME/KEY: misc_feature
<222> LOCATION: (11870)..(11999)
<223> OTHER INFORMATION: bNLB-03
<220> FEATURE:
<221> NAME/KEY: gene
<222> LOCATION: (12279)..(13067)
<223> OTHER INFORMATION: cSpec-03
<220> FEATURE:
<221> NAME/KEY: promoter
<222> LOCATION: (13162)..(13292)
<223> OTHER INFORMATION: prVirG-01
<220> FEATURE:
<221> NAME/KEY: gene
<222> LOCATION: (13367)..(13999)
<223> OTHER INFORMATION: cVirG-09
<220> FEATURE:
<221> NAME/KEY: gene
<222> LOCATION: (14029)..(15102)
<223> OTHER INFORMATION: cRepA-01
<220> FEATURE:
<221> NAME/KEY: misc_feature
<222> LOCATION: (15145)..(15549)
<223> OTHER INFORMATION: oVS1-02
<220> FEATURE:
<221> NAME/KEY: misc_feature
<222> LOCATION: (16227)..(17033)
<223> OTHER INFORMATION: oCOLE-06

<400> SEQUENCE: 36
attcctgtgg ttggcatgca catacaaatg gacgaacgga taaacctttt cacgcccttt        60
taaatatccg attattctaa taaacgctct tttctcttag gtttacccgc caatatatcc       120
tgtcaaacac tgatagttta aactgaaggc gggaaacgac aatctgatca tgagcggaga       180
attaagggag tcacgttatg accccgccg atgacgcggg acaagccgtt ttacgtttgg        240
aactgacaga accgcaacgc tgcaggaatt ggccgcagcg gccatttaaa caaagcttgg       300
taccgggacc catgtagtat cacatgagtg agtcaaggac taagtattat gcattttgtt       360
tctcactcac ggattagctc gcaatcatca tagtgaaatc tagctactgg cactatcgaa       420
atctagctct ttgccgagtg cactttatcg agcactcgac aaagcattct ttatcgagtg       480
ccagtcttgg cgaaataaga ctctcgacaa agaccttgtt taccgaggga gaaacactcg       540
gcgtaaaaag acactcggca aagaagactt tgctgagtgt caaaccctca gcgaaatgcg       600
accctcggca aaggaccgtc agcagccatc tatagttgat ggctattaac ttcgcgagtg       660
tcaggcgttg acacacgaca aaatatcttt tttgtcgagt gtcactgggc aaacacttgg       720
```

```
taaacctatg ttttgccgag tgtctttcct tgacactcga caaagtatat ttgtttttc     780 ttttccccca aactttttgt ggtgtgtttc tacaatatat agacctattt gttcaatttt     840
ggcacaatta taaaagtgtt tgctataact atcagattta gtttgcttaa ttggatttct     900
ttggataatt cagatttgaa ctacaagcca cttgaaaaat ggaaaacagt gaatacaaaa     960
atgacattca tgttatttag cacaagttat gatctatttc aggaacatgc gagaattttc    1020
gaacaccatt ctcacaaaac atgattgcgg acttgtgatc aagttgtttt aaaattgtat    1080
aaaacaaaaa caaagtcaga aaatcatgaa acttgttgac atgtcatgat atcatatgta    1140
gagactctaa taaaaatttg agattgtttc atgaaagttg tcacgcgcta tgtgtagaaa    1200
cctagcccgt ctacattgag gttctatgat ttcatgtgaa ggacatctag gcatcaatgt    1260
ttatgataat atcttatgtt tgtttggacg aaatattaaa aacaaataaa aagggggtcct    1320 tgatcacttt gacgagcatt gcactcagca aagggtgcct ttgctgagtg caatggtcat    1380
agaactcggt agaaaaacat acatagacat agggaaactt gctttaccgc gtgctatggc    1440
caagacactc ggcaaactag gctcctttgt cgagttccat cccaagcact cgacattgga    1500
actgcgactg ggcctcacag aagctttctt tgccgagtgc cactaagcga ggaactcgga    1560
tgctcagcaa aggctctgtc atcgtcacga tgtctttgt ttgtcgtgta ccagttggca    1620
ctcggtaaag actttactga gtgcccgata gaaagtactc gacaaagaga ccgttgccaa    1680
cgtttggttc actgagggct ctttgctgcc ttttggactt gacaaagaag ccgtctccag    1740
tagtgtctcc tgggaggcgg gatttatgtt ttttcccgga gctctgtggg acatcatgga    1800
cggtccagtc tggtgatcta aaatagacgg tttgccaagc tcacagagaa gtctttaaga    1860
tcttccacga tgcacgcatg ctttaaggtt agttagtgtt tggtctgaaa aagcgtcaac    1920
aattaggaaa caagaactaa aattattaaa ggacagatca ggaagcatgc atgttcttct    1980
tctatagtgt gtgttgagcc tgagtttggc cttttaggct ttattagggg gctcacagtc    2040
taactaagga gttgtattga tgtgctgaca aatattatgt tcgatcgtca cagtgttctt    2100
atgcggatcg attaggcccg atcatggtga aataaactaa ccaccggtaa gcccgggcag    2160
ccctagagca tgcagcggcc tacgtgaagc ccgcacatcg catcgtcgtc cgtcaggcgc    2220
taacggccgg ccgctgcatg cgtcgccggc gaactctctg ctgagccacc cgtcctccct    2280
ataagtagct atcccagcac cgtcgtctat caaccacaca cagagcggca tttcgaataa    2340
cacaggtgag cgcgaccatg gacaagaagt acagcatcgg cctggacatc ggcaccaaca    2400
gcgtgggctg gccgtgatc accgacgagt acaaggtgcc gagcaagaag ttcaaggtgc    2460
tgggcaacac cgacaggcac agcatcaaga agaacctgat cggcgccctg ctgttcgaca    2520
gcggcgagac cgccgaggcc accaggctga agaggaccgc caggaggagg tacaccagga    2580
ggaagaacag gatctgctac ctgcaggaga tcttcagcaa cgagatggcc aaggtggacg    2640
acagcttctt ccacaggctg gaggagagct cctggtggga ggaggacaag aagcacgaga    2700
ggcacccgat cttcggcaac atcgtggacg aggtggccta ccacgagaag tacccgacca    2760
tctaccacct gaggaagaag ctggtggaca gcaccgacaa ggccgacctg aggctgatct    2820
acctggccct ggcccacatg atcaagttca ggggccactt cctgatcgag ggcgacctga    2880
acccggacaa cagcgacgtg gacaagctgt tcatccagct ggtgcagacc tacaaccagc    2940
tgttcgagga gaacccgatc aacgccagcg gcgtggacgc caaggccatc ctgagcgcca    3000
ggctgagcaa gagcaggagg ctggagaacc tgatcgccca gctgccgggc gagaagaaga    3060
```

-continued

```
acggcctgtt cggcaacctg atcgccctga gcctgggcct gaccccgaac ttcaagagca    3120
acttcgacct ggccgaggac gccaagctgc agctgagcaa ggacacctac gacgacgacc    3180
tggacaacct gctggcccag atcggcgacc agtacgccga cctgttcctg gccgccaaga    3240
acctgagcga cgccatcctg ctgagcgaca tcctgagggt gaacaccgag atcaccaagg    3300
ccccgctgag cgccagcatg atcaagaggt acgacgagca ccaccaggac ctgaccctgc    3360
tgaaggccct ggtgaggcag cagctgccgg agaagtacaa ggagatcttc ttcgaccaga    3420
gcaagaacgg ctacgccggc tacatcgacg gcggcgccag ccaggaggag ttctacaagt    3480
tcatcaagcc gatcctggag aagatggacg gcaccgagga gctgctggtg aagctgaaca    3540
gggaggacct gctgaggaag cagaggacct tcgacaacgg cagcatcccg caccagatcc    3600
acctgggcga gctgcacgcc atcctgagga ggcaggagga cttctacccg ttcctgaagg    3660
acaacaggga gaagatcgag aagatcctga ccttccgcat cccgtactac gtgggcccgc    3720
tggccagggg caacagcagg ttcgcctgga tgaccaggaa gagcgaggag accatcaccc    3780
cgtggaactt cgaggaggtg gtggacaagg cgccagcgc ccagagcttc atcgagagga    3840
tgaccaactt cgacaagaac ctgccgaacg agaaggtgct gccgaagcac agcctgctgt    3900
acgagtactt caccgtgtac aacgagctga ccaaggtgaa gtacgtgacc gagggcatga    3960
ggaagccggc cttcctgagc ggcgagcaga agaaggccat cgtggacctg ctgttcaaga    4020
ccaacaggaa ggtgaccgtg aagcagctga aggaggacta cttcaagaag atcgagtgct    4080
tcgacagcgt ggagatcagc ggcgtggagg acaggttcaa cgccagcctg ggcacctacc    4140
acgacctgct gaagatcatc aaggacaagg acttcctgga caacgaggag aacgaggaca    4200
tcctggagga catcgtgctg accctgaccc tgttcgagga cagggagatg atcgaggaga    4260
ggctgaagac ctacgcccac ctgttcgacg acaaggtgat gaagcagctg aagaggagga    4320
ggtacaccgg ctggggcagg ctgagcagga agctgatcaa cggcatcagg gacaagcaga    4380
gcggcaagac catcctggac ttcctgaaga gcgacggctt cgccaacagg aacttcatgc    4440
agctgatcca cgacgacagc ctgaccttca aggaggacat ccagaaggcc caggtgagcg    4500
gccagggcga cagcctgcac gagcacatcg ccaacctggc cggcagcccg gccatcaaga    4560
agggcatcct gcagaccgtg aaggtggtgg acgagctggt gaaggtgatg ggcaggcaca    4620
agccggagaa catcgtgatc gagatggcca gggagaacca gaccacccag aagggccaga    4680
agaacagcag ggagaggatg aagaggatcg aggagggcat caaggagctg ggcagccaga    4740
tcctgaagga gcaccggtg gagaacaccc agctgcagaa cgagaagctg tacctgtact    4800
acctgcagaa cggcagggac atgtacgtgg accaggagct ggacatcaac aggctgagcg    4860
actacgacgt ggaccacatc gtgccgcaga gcttcctgaa ggacgacagc atcgacaaca    4920
aggtgctgac caggagcgac aagaacaggg caagagcga caacgtgccg agcgaggagg    4980
tggtgaagaa gatgaaaaac tactggaggc agctgctgaa cgccaagctg atcacccaga    5040
ggaagttcga caacctgacc aaggccgaga ggggcggcct gagcgagctg gacaaggccg    5100
gcttcattaa aaggcagctg gtggagacca ggcagatcac caagcacgtg gcccagatcc    5160
tggacagcag gatgaacacc aagtacgacg agaacgacaa gctgatcagg gaggtgaagg    5220
tgatcaccct gaagagcaag ctggtgagcg acttcaggaa ggacttccag ttctacaagg    5280
tgagggagat caataattac caccacgccc acgacgccta cctgaacgcc gtggtgggca    5340
ccgccctgat taaaaagtac ccgaagctgg agagcgagtt cgtgtacggc gactacaagg    5400
tgtacgacgt gaggaagatg atcgccaaga gcgagcagga gatcggcaag gccaccgcca    5460
```

-continued

```
agtacttctt ctacagcaac atcatgaact tcttcaagac cgagatcacc ctggccaacg   5520
gcgagatcag gaagaggccg ctgatcgaga ccaacggcga gaccggcgag atcgtgtggg   5580
acaagggcag ggacttcgcc accgtgagga aggtgctgtc catgccgcag gtgaacatcg   5640
tgaagaagac cgaggtgcag accggcggct tcagcaagga gagcatcctg ccgaagagga   5700
acagcgacaa gctgatcgcc aggaagaagg actgggaccc gaagaagtac ggcggcttcg   5760
acagcccgac cgtggcctac agcgtgctgg tggtggccaa ggtggagaag ggcaagagca   5820
agaagctgaa gagcgtgaag gagctggtgg gcatcaccat catggagagg agcagcttcg   5880
agaagaaccc agtggacttc ctggaggcca agggctacaa ggaggtgaag aaggacctga   5940
tcattaaact gccgaagtac agcctgttcg agctggagaa cggcaggaag aggatgctgg   6000
ccagcgccgg cgagctgcag aagggcaacg agctggccct gccgagcaag tacgtgaact   6060
tcctgtacct ggccagccac tacgagaagc tgaagggcag cccggaggac aacgagcaga   6120
agcagctgtt cgtggagcag cacaagcact acctggacga gatcatcgag cagatcagcg   6180
agttcagcaa gagggtgatc ctggccgacg ccaacctgga caaggtgctg agcgcctaca   6240
acaagcacag ggacaagccg atcagggagc aggccgagaa catcatccac ctgttcaccc   6300
tgaccaacct gggcgccccg gccgccttca gtacttcga caccaccatc gacaggaaga   6360
ggtacaccag caccaaggag gtgctggacg ccaccctgat ccaccagagc atcaccggcc   6420
tgtacgagac caggatcgac ctgagccagc tgggcggcga cagcagcccg ccgaagaaga   6480
agaggaaggt gagctggaag gacgccagcg gctggagcag gatgtgacca tggagctcta   6540
aactttgaat tcccttcgat tcatccggca cagcgggcta tggaccttca gcagcaagct   6600
aattaagttg gcagcatgca ccgctaacct tatatactac tgagacttcc aaattctagt   6660
atatgtaatc cttttgttcg ggttcatgat cgaattccaa agagtggaaa acaagcaaaa   6720
ggttaaatat acatgccatt tttggaggca tttttttcat gagggcatgt ttcgatatat   6780
ggaccactaa atatacatat catttacttt cctacaaatt tgctacatcc ttggaaatgc   6840
atagtctgtc tccaagaaaa agatactctg attacatcac tagtacacac agcctctata   6900
gtggcggttc tagagacatt ttcactggcg cttttcagtg ccgccagtgt tagggggccag   6960 tggaaatcgc catttccatt caataaccgc cagtggaaaa agcatttcca ctggcggttt   7020
tcttaagcaa ccgccagtgg aaatgtttcc cgtctttttt taaattttcg tactgaaatt   7080
tatatattta cacacacaaa catatatata tatatattga tattgataaa catgtagtat   7140
tgatactaaa agcaacatga aattaaattc tatcatacat ttatatacat caaagtcttg   7200
tttacaacca tgtatgcatc acacattata tacatcaaag ttttcactta agctctaata   7260
actatctcgg ctaagagata gtctactaat ttctgttagt attctaaact ctggcaaagc   7320
taatgttccg gaagcatcgt gatatttccc ttctgcggga atgacctctt tcaatatgaa   7380
tgtgcacagt cctcaacta tgccatacaa tgcaccttca gtcaagttct ccgggcttcc   7440
tttttgaaat tgctgtaaag gaagtttata aacatcatct atttatactc aataataaca   7500
catttgcatc tttaatgaca taaatacata cgtgactatt actaataata ccttgccagg   7560
gttcgtgatg tatcgtccat tcattctcat aaactcgcac acgtagaacc cacataggac   7620
cgatccgggt ggttgcttgt ggcactacat aacgggagat tggttatta gttgcaacat   7680 tgtcctatgt acgtacatgt atgatatgta ttcataaatt cacatacta ctggccagtt   7740 ataatggatg tctagtggca cacctttttt ggacgtgtcg tactttccac catgtagctt   7800
```

-continued

```
ataaaaccta aatgccctgt gatctcaaat agaatcacca tgttattcta caattctcat      7860
gggacccttc gaagggatct ttaaacatac gaacagatca cttaaagttc ttctgaagca      7920
acttaaagtt atcaggcatg catggatctt ggaggaatca gatgtgcagt cagggaccat      7980
agcacaggac aggcgtcttc tactggtgct accagcaaat gctggaagcc gggaacactg      8040
ggtacgttgg aaaccacgtg atgtggagta agataaactg taggagaaaa gcatttcgta      8100
gtgggccatg aagcctttca ggacatgtat tgcagtatgg gccggcccat tacgcaattg      8160
gacgacaaca aagactagta ttagtaccac ctcggctatc cacatagatc aaagctggtt      8220
taaaagagtt gtgcagatga tccgtggcag ctggagctga gcttccgggg ttttagagct      8280
agaaatagca agttaaaata aggctagtcc gttatcaact tgaaaaagtg gcaccgagtc      8340
ggtgcttttt ttttcggacc gcgcctgcag tgcagcgtga cccggtcgtg cccctctcta      8400
gagataatga gcattgcatg tctaagttat aaaaaaattac cacatatttt ttttgtcaca      8460
cttgtttgaa gtgcagttta tctatcttta tacatatatt taaactttac tctacgaata      8520
atataatcta tagtactaca ataatatcag tgttttagag aatcatataa atgaacagtt      8580
agacatggtc taaaggacaa ttgagtattt tgacaacagg actctacagt tttatctttt      8640
tagtgtgcat gtgttctcct tttttttttgc aaatagcttc acctatataa tacttcatcc      8700
attttattag tacatccatt tagggtttag ggttaatggt ttttatagac taatttttttt      8760 agtacatcta ttttattcta ttttagcctc taaattaaga aaactaaaac tctattttag      8820 ttttttttatt taataattta gatataaaat agaataaaat aaagtgacta aaaattaaac      8880 aaatacccttt taagaaatta aaaaaactaa ggaaacattt ttcttgtttc gagtagataa      8940
tgccagcctg ttaaacgccg tcgacgagtc taacggacac caaccagcga accagcagcg      9000
tcgcgtcggg ccaagcgaag cagacggcac ggcatctctg tcgctgcctc tggacccctc      9060
tcgagagttc cgctccaccg ttggacttgc tccgctgtcg gcatccagaa attgcgtggc      9120
ggagcggcag acgtgagccg gcacggcagg cggcctcctc ctcctctcac ggcaccggca      9180
gctacggggg attcctttcc caccgctcct tcgctttccc ttcctcgccc gccgtaataa      9240
atagacaccc cctccacacc ctctttcccc aacctcgtgt tgttcggagc gcacacacac      9300
acaaccagat ctcccccaaa tccacccgtc ggcacctccg cttcaaggta cgccgctcgt      9360
cctccccccc ccccctctct accttctcta gatcggcgtt ccggtccatg gttagggccc      9420
ggtagttcta cttctgttca tgtttgtgtt agatccgtgt ttgtgttaga tccgtgctgc      9480
tagcgttcgt acacggatgc gacctgtacg tcagacacgt tctgattgct aacttgccag      9540
tgtttctctt tggggaatcc tgggatggct ctagccgttc cgcagacggg atcgatttca      9600
tgattttttt tgtttcgttg catagggttt ggtttgccct tttcctttat ttcaatatat      9660
gccgtgcact tgtttgtcgg gtcatctttt catgcttttt tttgtcttgg ttgtgatgat      9720
gtggtctggt tgggcggtcg ttctagatcg gagtagaatt ctgtttcaaa ctacctggtg      9780
gatttattaa ttttggatct gtatgtgtgt gccatacata ttcatagtta cgaattgaag      9840
atgatggatg gaaatatcga tctaggatag gtatacatgt tgatgcgggt tttactgatg      9900
catatacaga gatgcttttt gttcgcttgg ttgtgatgat gtggtgtggt tgggcggtcg      9960
ttcattcgtt ctagatcgga gtagaatact gtttcaaact acctggtgta tttattaatt     10020
ttggaactgt atgtgtgtgt catacatctt catagttacg agtttaagat ggatggaaat     10080
atcgatctag gataggtata catgttgatg tgggtttttac tgatgcatat acatgatggc     10140
atatgcagca tctattcata tgctctaacc ttgagtacct atctattata ataaacaagt     10200
```

-continued

```
atgtttata attattttga tcttgatata cttggatgat ggcatatgca gcagctatat   10260
gtggattttt ttagccctgc cttcatacgc tatttatttg cttggtactg tttcttttgt   10320
cgatgctcac cctgttgttt ggtgttactt ctgcagggat ccggcagcag ccatgcagaa   10380
gctgatcaac agcgtgcaga actacgcctg gggcagcaag accgccctga ccgagctgta   10440
cggcatggag aaccccagca gccagcccat ggccgagctg tggatgggcg cccaccccaa   10500
gagcagcagc cgcgtgcaga acgccgccgg cgacatcgtg agcctgcgcg acgtgatcga   10560
gagcgacaag agcaccctgc tgggcgaggc cgtggccaag cgcttcggcg agctgccctt   10620
cctgttcaag gtgctgtgcg ccgcccagcc cctgagcatc caggtgcacc ccaacaagca   10680
caacagcgag atcggcttcg ccaaggagaa cgccgccggc atccccatgg acgccgccga   10740
gcgcaactac aaggacccca accacaagcc cgagctggtg ttcgccctga cccccttcct   10800
ggccatgaac gccttccgcg agttcagcga gatcgtgagc ctgctgcagc ccgtggccgg   10860
cgcccacccc gccatcgccc acttcctgca gcagcccgac gccgagcgcc tgagcgagct   10920
gttcgccagc ctgctgaaca tgcagggcga ggagaagagc cgcgccctgg ccatcctgaa   10980
gagcgccctg gacagccagc agggcgagcc ctggcagacc atccgcctga tcagcgagtt   11040
ctaccccgag gacagcggcc tgttcagccc cctgctgctg aacgtggtga agctgaaccc   11100
cggcgaggcc atgttcctgt tcgccgagac cccccacgcc tacctgcagg gcgtggccct   11160
ggaggtgatg gccaacagcg acaacgtgct gcgcgccggc ctgacccca agtacatcga   11220 catccccgag ctggtggcca acgtgaagtt cgaggccaag cccgccaacc agctgctgac   11280
ccagcccgtg aagcagggcg ccgagctgga cttccccatc cccgtggacg acttcgcctt   11340
cagcctgcac gacctgagcg acaaggagac caccatcagc cagcagagcg ccgccatcct   11400
gttctgcgtg gagggcgacg ccaccctgtg gaagggcagc cagcagctgc agctgaagcc   11460
cggcgagagc gccttcatcg ccgccaacga gagcccccgtg accgtgaagg gccacggccg   11520
cctggcccgc gtgtacaaca agctgtgata ggagctcgat ccgtcgacct gcagatcgtt   11580
caaacatttg gcaataaagt ttcttaagat tgaatcctgt tgccggtctt gcgatgatta   11640
tcatataatt tctgttgaat tacgttaagc atgtaataat taacatgtaa tgcatgacgt   11700
tatttatgag atgggttttt atgattagag tcccgcaatt atacatttaa tacgcgatag   11760
aaaacaaaat atagcgcgca aactaggata aattatcgcg cgcggtgtca tctatgttac   11820
tagatcggcg cgccgcaatt gaagtttggg cggccagcat ggccgtatcc gcaatgtgtt   11880
attaagttgt ctaagcgtca atttgtttac accacaatat atcctgccac cagccagcca   11940
acagctcccc gaccggcagc tcggcacaaa atcaccactc gatacaggca gcccatcaga   12000
attaattctc atgtttgaca gcttatcatc gactgcacgg tgcaccaatg cttctggcgt   12060
caggcagcca tcggaagctg tggtatggct gtgcaggtcg taaatcactg cataattcgt   12120
gtcgctcaag gcgcactccc gttctggata atgttttttg cgccgacatc ataacggttc   12180
tggcaaatat tctgaaatga gctgttgaca attaatcatc cggctcgtat aatgtgtgga   12240
attgtgagcg gataacaatt tcacacagga aacagaccat gagggaagcg ttgatcgccg   12300
aagtatcgac tcaactatca gaggtagttg gcgtcatcga gcgccatctc gaaccgacgt   12360
tgctggccgt acatttgtac ggctccgcag tggatggcgg cctgaagcca cacagtgata   12420
ttgatttgct ggttacggtg accgtaaggc ttgatgaaac aacgcggcga gctttgatca   12480
acgacctttt ggaaacttcg gcttcccctg gagagagcga gattctccgc gctgtagaag   12540
```

-continued

```
tcaccattgt tgtgcacgac gacatcattc cgtggcgtta tccagctaag cgcgaactgc   12600
aatttggaga atggcagcgc aatgacattc ttgcaggtat cttcgagcca gccacgatcg   12660
acattgatct ggctatcttg ctgacaaaag caagagaaca tagcgttgcc ttggtaggtc   12720
cagcggcgga ggaactcttt gatccggttc ctgaacagga tctatttgag gcgctaaatg   12780
aaaccttaac gctatggaac tcgccgcccg actgggctgg cgatgagcga aatgtagtgc   12840
ttacgttgtc ccgcatttgg tacagcgcag taaccggcaa aatcgcgccg aaggatgtcg   12900
ctgccgactg ggcaatggag cgcctgccgg cccagtatca gcccgtcata cttgaagcta   12960
ggcaggctta tcttggacaa gaagatcgct tggcctcgcg cgcagatcag ttggaagaat   13020
ttgttcacta cgtgaaaggc gagatcacca aagtagtcgg caaataaagc tctagtggat   13080
ctccgtaccc ggggatctgg ctcgcggcgg acgcacgacg ccggggcgag accataggcg   13140
atctcctaaa tcaatagtag ctgtaacctc gaagcgtttc acttgtaaca acgattgaga   13200
atttttgtca taaaattgaa atacttggtt cgcatttttg tcatccgcgg tcagccgcaa   13260
ttctgacgaa ctgcccattt agctggagat gattgtacat ccttcacgtg aaaatttctc   13320
aagcgctgtg aacaagggtt cagattttag attgaaaggt gagccgttga aacacgttct   13380
tcttgtcgat gacgacgtcg ctatgcggca tcttattatt gaataccttta cgatccacgc   13440 cttcaaagtg accgcggtag ccgacagcac ccagttcaca agagtactct cttccgcgac   13500
ggtcgatgtc gtggttgttg atctagattt aggtcgtgaa gatgggctcg agctaggagc   13560
aagtgatttt atcgctaagc cgttcagtat cagagagttt ctagcacgca ttcgggttgc   13620
cttgcgcgtg cgccccaacg ttgtccgctc caaagaccga cggtcttttt gttttactga   13680
ctggacactt aatctcaggc aacgtcgctt gatgtccgaa gctggcggtg aggtgaaact   13740
tacggcaggt gagttcaatc ttctcctcgc gttttttagag aaaccccgcg acgttctatc   13800
gcgcgagcaa cttctcattg ccagtcgagt acgcgacgag gaggtttatg acaggagtat   13860
agatgttctc attttgaggc tgcgccgcaa acttgaggca gatccgtcaa gccctcaact   13920
gataaaaaca gcaagaggtg ccggttattt cttttgacgcg gacgtgcagg tttcgcacgg   13980
ggggacgatg gcagcctgag ccaattccca gatccccgag gaatcggcgt gagcggtcgc   14040
aaaccatccg gcccggtaca aatcggcgcg gcgctgggtg atgacctggt ggagaagttg   14100
aaggccgcgc aggccgccca gcggcaacgc atcgaggcag aagcacgccc cggtgaatcg   14160
tggcaagcgg ccgctgatcg aatccgcaaa gaatcccggc aaccgccggc agccggtgcg   14220
ccgtcgatta ggaagccgcc caagggcgac gagcaaccag attttttcgt tccgatgctc   14280
tatgacgtgg gcacccgcga tagtcgcagc atcatggacg tggccgtttt ccgtctgtcg   14340
aagcgtgacc gacgagctgg cgaggtgatc cgctacgagc ttccagacgg gcacgtagag   14400
gtttccgcag ggccggccgg catggccagt gtgtgggatt acgacctggt actgatggcg   14460
gtttcccatc taaccgaatc catgaaccga taccgggaag ggaagggaga caagcccggc   14520
cgcgtgttcc gtccacacgt tgcggacgta ctcaagttct gccggcgagc cgatggcgga   14580
aagcagaaag acgacctggt agaaacctgc attcggttaa acaccacgca cgttgccatg   14640
cagcgtacga agaaggccaa gaacggccgc ctggtgacgg tatccgaggg tgaagccttg   14700
attagccgct acaagatcgt aaagagcgaa accgggcggc cggagtacat cgagatcgag   14760
ctagctgatt ggatgtaccg cgagatcaca gaaggcaaga acccggacgt gctgacggtt   14820
caccccgatt acttttttgat cgatcccggc atcggccgtt ttctctaccg cctggcacgc   14880
cgcgccgcag gcaaggcaga agccagatgg ttgttcaaga cgatctacga acgcagtggc   14940
```

-continued

```
agcgccggag agttcaagaa gttctgtttc accgtgcgca agctgatcgg gtcaaatgac   15000
ctgccggagt acgatttgaa ggaggaggcg gggcaggctg gcccgatcct agtcatgcgc   15060
taccgcaacc tgatcgaggg cgaagcatcc gccggttcct aatgtacgga gcagatgcta   15120
gggcaaattg ccctagcagg ggaaaaaggt cgaaaaggtc tctttcctgt ggatagcacg   15180
tacattggga acccaaagcc gtacattggg aaccggaacc cgtacattgg gaacccaaag   15240
ccgtacattg ggaaccggtc acacatgtaa gtgactgata taaaagagaa aaaaggcgat   15300
ttttccgcct aaaactcttt aaaacttatt aaaactctta aaacccgcct ggcctgtgca   15360
taactgtctg gccagcgcac agccgaagag ctgcaaaaag cgcctaccct tcggtcgctg   15420
cgctccctac gccccgccgc ttcgcgtcgg cctatcgcgg ccgctggccg ctcaaaaatg   15480
gctggcctac ggccaggcaa tctaccaggg cgcggacaag ccgcgccgtc gccactcgac   15540
cgccggcgct gaggtctgcc tcgtgaagaa ggtgttgctg actcatacca ggcctgaatc   15600
gccccatcat ccagccagaa agtgagggag ccacggttga tgagagcttt gttgtaggtg   15660
gaccagttgg tgattttgaa cttttgcttt gccacggaac ggtctgcgtt gtcgggaaga   15720
tgcgtgatct gatccttcaa ctcagcaaaa gttcgattta ttcaacaaag ccgccgtccc   15780
gtcaagtcag cgtaatgctc tgccagtgtt acaaccaatt aaccaattct gattagaaaa   15840
actcatcgag catcaaatga aactgcaatt tattcatatc aggattatca ataccatatt   15900
tttgaaaaag ccgtttctgt aatgaaggag aaaactcacc gaggcagttc cataggatgg   15960
caagatcctg gtatcggtct gcgattccga ctcgtccaac atcaatacaa cctattaatt   16020
tcccctcgtc aaaaataagg ttatcaagtg agaaatcacc atgagtgacg actgaatccg   16080
gtgagaatgg caaaagctct gcattaatga atcggccaac gcgcggggag aggcggtttg   16140
cgtattgggc gctcttccgc ttcctcgctc actgactcgc tgcgctcggt cgttcggctg   16200
cggcgagcgg tatcagctca ctcaaaggcg gtaatacggt tatccacaga atcaggggat   16260
aacgcaggaa agaacatgtg agcaaaaggc cagcaaaagg ccaggaaccg taaaaaggcc   16320
gcgttgctgg cgtttttcca taggctccgc cccctgacg agcatcacaa aaatcgacgc   16380
tcaagtcaga ggtggcgaaa cccgacagga ctataaagat accaggcgtt ccccctgga   16440 agctccctcg tgcgctctcc tgttccgacc ctgccgctta ccggatacct gtccgccttt   16500
ctcccttcgg gaagcgtggc gctttctcat agctcacgct gtaggtatct cagttcggtg   16560
taggtcgttc gctccaagct gggctgtgtg cacgaacccc ccgttcagcc cgaccgctgc   16620
gccttatccg gtaactatcg tcttgagtcc aacccggtaa gacacgactt atcgccactg   16680
gcagcagcca ctggtaacag gattagcaga gcgaggtatg taggcggtgc tacagagttc   16740
ttgaagtggt ggcctaacta cggctacact agaagaacag tatttggtat ctgcgctctg   16800
ctgaagccag ttaccttcgg aaaaagagtt ggtagctctt gatccggcaa acaaaccacc   16860
gctggtagcg gtggtttttt tgtttgcaag cagcagatta cgcgcagaaa aaaggatct   16920 caagaagatc ctttgatctt ttctacgggg tctgacgctc agtggaacga aaactcacgt   16980
taagggattt tggtcatgag attatcaaaa aggatcttca cctagatcct tttgatccgg   17040
aatta                                                                17045
```

<210> SEQ ID NO 37
<211> LENGTH: 16776
<212> TYPE: DNA
<213> ORGANISM: artificial sequence
<220> FEATURE:

-continued

```
<223> OTHER INFORMATION: vector 24091
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (330)..(2417)
<223> OTHER INFORMATION: prZmGRMZM2G471240-01
<220> FEATURE:
<221> NAME/KEY: gene
<222> LOCATION: (2420)..(6589)
<223> OTHER INFORMATION: cCas9-01
<220> FEATURE:
<221> NAME/KEY: mutation
<222> LOCATION: (5909)..(5911)
<223> OTHER INFORMATION: L to V mutation
<220> FEATURE:
<221> NAME/KEY: mutation
<222> LOCATION: (5954)..(5956)
<223> OTHER INFORMATION: I to V mutation
<220> FEATURE:
<221> NAME/KEY: terminator
<222> LOCATION: (6596)..(7591)
<223> OTHER INFORMATION: tZmGRMZM2G471240-01
<220> FEATURE:
<221> NAME/KEY: promoter
<222> LOCATION: (7605)..(7979)
<223> OTHER INFORMATION: prOsU3-01
<220> FEATURE:
<221> NAME/KEY: misc_feature
<222> LOCATION: (7981)..(8085)
<223> OTHER INFORMATION: rsgRNAZmVLHP-02
<220> FEATURE:
<221> NAME/KEY: misc_feature
<222> LOCATION: (7981)..(8000)
<223> OTHER INFORMATION: xZmVLHP2
<220> FEATURE:
<221> NAME/KEY: misc_feature
<222> LOCATION: (8001)..(8012)
<223> OTHER INFORMATION: rCrRNA-01
<220> FEATURE:
<221> NAME/KEY: misc_feature
<222> LOCATION: (8017)..(8085)
<223> OTHER INFORMATION: rTracrRNA-01
<220> FEATURE:
<221> NAME/KEY: promoter
<222> LOCATION: (8096)..(10087)
<223> OTHER INFORMATION: prUbi1-04
<220> FEATURE:
<221> NAME/KEY: gene
<222> LOCATION: (10104)..(11282)
<223> OTHER INFORMATION: cPMI-09
<220> FEATURE:
<221> NAME/KEY: terminator
<222> LOCATION: (11305)..(11557)
<223> OTHER INFORMATION: tNOS-05-01
<220> FEATURE:
<221> NAME/KEY: misc_feature
<222> LOCATION: (11601)..(11730)
<223> OTHER INFORMATION: bNLB-03
<220> FEATURE:
<221> NAME/KEY: gene
<222> LOCATION: (12010)..(12798)
<223> OTHER INFORMATION: cSpec-03
<220> FEATURE:
<221> NAME/KEY: promoter
<222> LOCATION: (12893)..(13023)
<223> OTHER INFORMATION: prVirG-01
<220> FEATURE:
<221> NAME/KEY: gene
<222> LOCATION: (13098)..(13730)
<223> OTHER INFORMATION: cVirG-09
<220> FEATURE:
<221> NAME/KEY: gene
<222> LOCATION: (13760)..(14833)
<223> OTHER INFORMATION: cRepA-01
<220> FEATURE:
<221> NAME/KEY: misc_feature
```

-continued

```
<222> LOCATION: (14876)..(15280)
<223> OTHER INFORMATION: oVS1-02
<220> FEATURE:
<221> NAME/KEY: misc_feature
<222> LOCATION: (15958)..(16764)
<223> OTHER INFORMATION: oCOLE-06

<400> SEQUENCE: 37
attcctgtgg ttggcatgca catacaaatg gacgaacgga taaacctttt cacgcccttt        60
taaatatccg attattctaa taaacgctct tttctcttag gtttacccgc caatatatcc       120
tgtcaaacac tgatagttta aactgaaggc gggaaacgac aatctgatca tgagcggaga       180
attaagggag tcacgttatg accccgccg atgacgcggg acaagccgtt ttacgtttgg        240
aactgacaga accgcaacgc tgcaggaatt ggccgcagcg gccatttaaa caaagcttgg       300
tacctcgcga atgcatctag atgggaccct atttgtactc attccatgtc tcataaactt       360
tgggcaccat ccatccaaca catccaatct aaacacacca aacgatgggg aatggaaaga       420
gcagtattcg attcaacaat ggcaaacaaa tatcactgaa ttagaccaag aataaaccta       480
attagacaac gacctcccaa ccatcattcg tcaggctgta aagaagataa agctgccttg       540
gggcatggat caagcagaac accagagatg aatccaaaca cacagaaaat cacgcgcgct       600
gtctacaatg acaacaagcc ccacatttca ttgcagtaca ctgggctaca aaggcacgta       660
caacaaagag ctagggaaac attgcggagg gcacgagaga gcagctaact tgacaatata       720
gcagactgag cttgcactgt tagcaggcga ggaagggaat catggggacg gagaatgggg       780
tccatgcccg cgaaggagaa ggcggacgcc gccacggtgg caccggcgca cgcgcacaca       840
gggaacccgc acaggcagcc aaggatgctg cctcgccatt gcgccggtcg tctctgccac       900
gctcctctct ctctcccgct gcatcgccgt ggatggggca agcagagagc agggactgcg       960
acgatctggg cggaggactc gccttggaga gcgcggacgc agacgggatt ctagggagag      1020
agcgaagacg gggcgcgcgc ggcgctcgcg cggcgtggtg gcggcgagat tagcgggggt      1080
ggggggaggg cggagccgtg gtgagggtgt ggacgccctc cttaccctct taagtagtag      1140
tagagatata atccgttcca aaatatccat ccgttcaatt tatatttcgt ttgatctttt      1200
taccctaaat ttgattgact catcttatta aaaaagttca taactattat taatctttat      1260
tgagatatca tttagcatat aatatacttt aagtgtggtt ttagattttt tttaaaaaaa      1320
aaaattcgca aaaattaaat gaaacgaccc aatcaaactt gaaaagtaaa actaattata      1380
aatttgaacg gaaggagtaa gaggatgttt gaatgtacta gagctaatag ttggttgctt      1440
taaaatttgc tagtagaatt agctagctaa taaatatcta gataactatt agctaatttg      1500
ctaaaacagc taatagttga actattagct agattgtttg gatgtattcg gctaatttta      1560
atggctaact attagctata gtacaatatt caaacacctc ctaattaaaa tggacaaata      1620
tctcttcttt tggtcccttg cgttagattt ttcatatctc cttatttagt ataaaagaat      1680
catcaaaaag tggacaaccc ctagtggaac accattttag tagtggttgc atgaaacctt      1740
tcgcgcacca gtttctatgt gtcactctaa aaatgggaca gcatgtacgt agtgcctata      1800
tatatacaag tcatctatcg ttgcctcctc agttcatcac taatcacact tattgtgccc      1860
tcgacgagta tctatagcta gctcattaat cgattcgggg gtgtgttgtc gaaggcggca      1920
ttggcgagct actcgtcgcg gcgtccaagc aatacctgta gcacgaaggc gatcgccggg      1980
agcgtggtcg gcgagcccgt cgtgctgggg cagagggtga cggtgctgac ggtggacggc      2040
ggcggcgtcc ggggtctcat cccgggaacc atcctcgcct tcctggaggc caggctgcag      2100
```

-continued

```
gagctggacg caccggaggc gaggctggcg gactacttcg actacatcgc cggaaccagc   2160
accggcggtc tcatcaccgc cttgctgacc gcgcccggca aggacaagcg gcctctctag   2220
gctgccaagg acatcaacca cttttacatc cataactgcc cgcgcatctt tcctcagaag   2280
tgagtccgat gctgccgcca ttgttcttgc atccatccag catcgtacgt acgtcctcta   2340
tacatctgcg gatcatcatg tgcgcatgtt tgtggcatgc atgcatgcat gtgagcagga   2400
gcaggcttgc gaaaacccca tggacaagaa gtacagcatc ggcctggaca tcggcaccaa   2460
cagcgtgggc tgggccgtga tcaccgacga gtacaaggtg ccgagcaaga agttcaaggt   2520
gctgggcaac accgacaggc acagcatcaa gaagaacctg atcggcgccc tgctgttcga   2580
cagcggcgag accgccgagg ccaccaggct gaagaggacc gccaggagga ggtacaccag   2640
gaggaagaac aggatctgct acctgcagga gatcttcagc aacgagatgg ccaaggtgga   2700
cgacagcttc ttccacaggc tggaggagag cttcctggtg gaggaggaca agaagcacga   2760
gaggcacccg atcttcggca acatcgtgga cgaggtggcc taccacgaga gtacccgac    2820 catctaccac ctgaggaaga agctggtgga cagcaccgac aaggccgacc tgaggctgat   2880
ctacctggcc ctggcccaca tgatcaagtt caggggccac ttcctgatcg agggcgacct   2940
gaacccggac aacagcgacg tggacaagct gttcatccag ctggtgcaga cctacaacca   3000
gctgttcgag gagaacccga tcaacgccag cggcgtggac gccaaggcca tcctgagcgc   3060
caggctgagc aagagcagga ggctggagaa cctgatcgcc cagctgccgg gcgagaagaa   3120
gaacggcctg ttcggcaacc tgatcgccct gagcctgggc ctgacccga acttcaagag    3180 caacttcgac ctggccgagg acgccaagct gcagctgagc aaggacacct acgacgacga   3240
cctggacaac ctgctggccc agatcggcga ccagtacgcc gacctgttcc tggccgccaa   3300
gaacctgagc gacgccatcc tgctgagcga catcctgagg gtgaacaccg agatcaccaa   3360 ggcccgctg agcgccagca tgatcaagag gtacgacgag caccaccagg acctgaccct    3420
gctgaaggcc ctggtgaggc agcagctgcc ggagaagtac aaggagatct tcttcgacca   3480
gagcaagaac ggctacgccg gctacatcga cggcggcgcc agccaggagg agttctacaa   3540
gttcatcaag ccgatcctgg agaagatgga cggcaccgag gagctgctgg tgaagctgaa   3600 caggggaggac ctgctgagga agcagaggac cttcgacaac ggcagcatcc gcaccagat    3660 ccacctgggc gagctgcacg ccatcctgag gaggcaggag gacttctacc cgttcctgaa   3720
ggacaacagg gagaagatcg agaagatcct gaccttccgc atcccgtact acgtgggccc   3780
gctggccagg ggcaacagca ggttcgcctg gatgaccagg aagagcgagg agaccatcac   3840
cccgtggaac ttcgaggagg tggtggacaa gggcgccagc gcccagagct tcatcgagag   3900
gatgaccaac ttcgacaaga acctgccgaa cgagaaggtg ctgccgaagc acagcctgct   3960
gtacgagtac ttcaccgtgt acaacgagct gaccaaggtg aagtacgtga ccgagggcat   4020
gaggaagccg gccttcctga cgcggcgagca aagaagggcc atcgtggacc tgctgttcaa   4080
gaccaacagg aaggtgaccg tgaagcagct gaaggaggac tacttcaaga gatcgagtg    4140 cttcgacagc gtggagatca gcggcgtgga ggacaggttc aacgccagcc tgggcaccta   4200
ccacgacctg ctgaagatca tcaaggacaa ggacttcctg gacaacgagg agaacgagga   4260
catcctggag gacatcgtgc tgaccctgac cctgttcgag gacaggggaga tgatcgagga   4320 gaggctgaag acctacgccc acctgttcga cgacaaggtg atgaagcagc tgaagaggag   4380
gaggtacacc ggctggggca ggctgagcag gaagctgatc aacggcatca gggacaagca   4440
gagcggcaag accatcctgg acttcctgaa gagcgacggc ttcgccaaca ggaacttcat   4500
```

-continued

```
gcagctgatc cacgacgaca gcctgacctt caaggaggac atccagaagg cccaggtgag    4560
cggccagggc gacagcctgc acgagcacat cgccaacctg gccggcagcc cggccatcaa    4620
gaagggcatc ctgcagaccg tgaaggtggt ggacgagctg gtgaaggtga tgggcaggca    4680
caagccggag aacatcgtga tcgagatggc cagggagaac cagaccaccc agaagggcca    4740
gaagaacagc agggagagga tgaagaggat cgaggagggc atcaaggagc tgggcagcca    4800
gatcctgaag gagcacccgg tggagaacac ccagctgcag aacgagaagc tgtacctgta    4860
ctacctgcag aacggcaggg acatgtacgt ggaccaggag ctggacatca acaggctgag    4920
cgactacgac gtggaccaca tcgtgccgca gagcttcctg aaggacgaca gcatcgacaa    4980
caaggtgctg accaggagcg acaagaacag gggcaagagc gacaacgtgc cgagcgagga    5040
ggtggtgaag aagatgaaaa actactggag gcagctgctg aacgccaagc tgatcaccca    5100
gaggaagttc gacaacctga ccaaggccga gaggggcggc ctgagcgagc tggacaaggc    5160
cggcttcatt aaaaggcagc tggtggagac caggcagatc accaagcacg tggcccagat    5220
cctggacagc aggatgaaca ccaagtacga cgagaacgac aagctgatca gggaggtgaa    5280
ggtgatcacc ctgaagagca agctggtgag cgacttcagg aaggacttcc agttctacaa    5340
ggtgagggag atcaataatt accaccacgc ccacgacgcc tacctgaacg ccgtggtggg    5400
caccgccctg attaaaaagt acccgaagct ggagagcgag ttcgtgtacg gcgactacaa    5460
ggtgtacgac gtgaggaaga tgatcgccaa gagcgagcag gagatcggca aggccaccgc    5520
caagtacttc ttctacagca acatcatgaa cttcttcaag accgagatca ccctggccaa    5580
cggcgagatc aggaagaggc cgctgatcga gaccaacggc gagaccggcg agatcgtgtg    5640
ggacaagggc agggacttcg ccaccgtgag gaaggtgctg tccatgccgc aggtgaacat    5700
cgtgaagaag accgaggtgc agaccggcgg cttcagcaag gagagcatcc tgccgaagag    5760
gaacagcgac aagctgatcg ccaggaagaa ggactgggac ccgaagaagt acggcggctt    5820
cgacagcccg accgtggcct acagcgtgct ggtggtggcc aaggtggaga agggcaagag    5880
caagaagctg aagagcgtga aggagctggt gggcatcacc atcatggaga ggagcagctt    5940
cgagaagaac ccagtggact tcctggaggc caagggctac aaggaggtga agaaggacct    6000
gatcattaaa ctgccgaagt acagcctgtt cgagctggag aacggcagga gaggatgct    6060 ggccagcgcc ggcgagctgc agaagggcaa cgagctggcc ctgccgagca gtacgtgaa    6120 cttcctgtac ctggccagcc actacgagaa gctgaagggc agcccggagg acaacgagca    6180
gaagcagctg ttcgtggagc agcacaagca ctacctggac gagatcatcg agcagatcag    6240
cgagttcagc aagagggtga tcctggccga cgccaacctg gacaaggtgc tgagcgccta    6300
caacaagcac agggacaagc cgatcaggga gcaggccgag aacatcatcc acctgttcac    6360
cctgaccaac ctgggcgccc cggccgcctt caagtacttc gacaccacca tcgacaggaa    6420
gaggtacacc agcaccaagg aggtgctgga cgccaccctg atccaccaga gcatcaccgg    6480
cctgtacgag accaggatcg acctgagcca gctgggcggc gacagcagcc gccgaagaa    6540 gaagaggaag gtgagctgga aggacgccag cggctggagc aggatgtgac catgggacaa    6600
gtggctttac tgtcagtcac atgcttgtaa ataagtagac tttattttaa taaaacataa    6660
aaatatatat atgttcttga atataaaatt gataaccaaa ttaaaattcg aaccatcact    6720
tatacataat tttactttat tttttataaa acgtgaacgg gaaggactac cgtgaatgac    6780
tatagaacca atcatactag tataaaatat atgatgacac tacgggagag acaaactttg    6840
```

-continued

```
tctggcgcta aatattttgc cgagtgtgaa ttcacgggca ctaggcaaag atcttctttg      6900
ccgagtgtta cgctgggcaa agtaagacac taggtaaatc agtcatttgc cgagtgtccg      6960
ccactaggca aagcaaaaca ctggcaaatc aaaagtttac ctagtgccag acactaggca      7020
aaaaaaaaac gctcggcaaa tcggaagttt ccctagtgcc agacactaga caaagaaaaa      7080
cacttgataa actagcgtcg tcagctaaca ccatccacca accgttaacg ttgccgagta      7140
tctgacttcg acactcggca aagaaggtct ctttgcctag tgtcggtctg gaacactagg      7200
caaagaggca ctttacctag tgtcgtattt tgacactcag taaaataatt ttttttcttt      7260
ctgcttccaa actttttatg atgtgttcct atagcaccta gaactacatg tcaagttttg      7320
gtaaaatttt tgaagttttt gctatattta cttaatttat tttatttaat tgaatttctt      7380
ttgataattc aaatttgaac tcggcaaggt aagaagcgag ggtagcctgg aaacacactt      7440
tgcctagtgt tacactcggt acaggagcct cccctgccta gtgctgcact cgacaaaaga      7500
ttcgcctttg cctagcgctg cactcggcac aggagtcgcc tttgcctagt gctgcactag      7560
gcaaagcctc cgttaccgtg ccttccatcg tcggacccctt cgaagggatc tttaaacata      7620
cgaacagatc acttaaagtt cttctgaagc aacttaaagt tatcaggcat gcatggatct      7680
tggaggaatc agatgtgcag tcagggacca tagcacagga caggcgtctt ctactggtgc      7740
taccagcaaa tgctggaagc cgggaacact gggtacgttg gaaaccacgt gatgtggagt      7800
aagataaact gtaggagaaa agcatttcgt agtgggccat gaagcctttc aggacatgta      7860
ttgcagtatg ggccggccca ttacgcaatt ggacgacaac aaagactagt attagtacca      7920
cctcggctat ccacatagat caaagctggt ttaaaagagt tgtgcagatg atccgtggca      7980
gctggagctg agcttccggg gttttagagc tagaaatagc aagttaaaat aaggctagtc      8040
cgttatcaac ttgaaaaagt ggcaccgagt cggtgctttt tttttcggac cgcgcctgca      8100
gtgcagcgtg acccggtcgt gcccctctct agagataatg agcattgcat gtctaagtta      8160
taaaaaatta ccacatattt tttttgtcac acttgtttga agtgcagttt atctatcttt      8220
atacatatat ttaaactta ctctacgaat aatataatct atagtactac aataatatca      8280
gtgttttaga gaatcatata aatgaacagt tagacatggc ctaaaggaca attgagtatt      8340
ttgacaacag gactctacag ttttatcttt ttagtgtgca tgtgttctcc ttttttttttg      8400 caaatagctt cacctatata atacttcatc cattttatta gtacatccat ttagggttta      8460
gggttaatgg ttttttataga ctaattttttt tagtacatct attttattct attttagcct      8520
ctaaattaag aaaactaaaa ctctatttta gtttttttat ttaataattt agatataaaa      8580
tagaataaaa taaagtgact aaaaattaaa caaatacccct ttaagaaatt aaaaaaacta      8640
aggaaacatt tttcttgttt cgagtagata atgccagcct gttaaacgcc gtcgacgagt      8700
ctaacggaca ccaaccagcg aaccagcagc gtcgcgtcgg ccaagcgaa gcagacggca       8760 cggcatctct gtcgctgcct ctggaccccct ctcgagagtt ccgctccacc gttggacttg      8820
ctccgctgtc ggcatccaga aattgcgtgg cggagcggca gacgtgagcc ggcacggcag      8880
gcggcctcct cctcctctca cggcaccggc agctacgggg gattcctttc ccaccgctcc      8940
ttcgctttcc cttcctcgcc cgccgtaata aatagacacc ccctccacac cctctttccc      9000
caacctcgtg ttgttcggag cgcacacaca cacaaccaga tctcccccaa atccacccgt      9060
cggcacctcc gcttcaaggt acgccgctcg tcctcccccc cccccctctc taccttctct      9120
agatcggcgt tccggtccat ggttaggggcc cggtagttct acttctgttc atgtttgtgt      9180
tagatccgtg tttgtgttag atccgtgctg ctagcgttcg tacacggatg cgacctgtac      9240
```

-continued

```
gtcagacacg ttctgattgc taacttgcca gtgtttctct ttggggaatc ctgggatggc    9300
tctagccgtt ccgcagacgg gatcgatttc atgatttttt ttgtttcgtt gcatagggtt    9360
tggtttgccc ttttccttta tttcaatata tgccgtgcac ttgtttgtcg ggtcatcttt    9420
tcatgctttt ttttgtcttg gttgtgatga tgtggtctgg ttgggcggtc gttctagatc    9480
ggagtagaat tctgtttcaa actacctggt ggatttatta attttggatc tgtatgtgtg    9540
tgccatacat attcatagtt acgaattgaa gatgatggat ggaaatatcg atctaggata    9600
ggtatacatg ttgatgcggg ttttactgat gcatatacag agatgctttt tgttcgcttg    9660
gttgtgatga tgtggtgtgg ttgggcggtc gttcattcgt tctagatcgg agtagaatac    9720
tgtttcaaac tacctggtgt atttattaat tttggaactg tatgtgtgtg tcatacatct    9780
tcatagttac gagtttaaga tggatggaaa tatcgatcta ggataggtat acatgttgat    9840
gtgggtttta ctgatgcata tacatgatgg catatgcagc atctattcat atgctctaac    9900
cttgagtacc tatctattat aataaacaag tatgttttat aattattttg atcttgatat    9960
acttggatga tggcatatgc agcagctata tgtggatttt tttagccctg ccttcatacg   10020
ctatttattt gcttggtact gtttcttttg tcgatgctca ccctgttgtt tggtgttact   10080
tctgcaggga tccggcagca gccatgcaga agctgatcaa cagcgtgcag aactacgcct   10140
ggggcagcaa gaccgccctg accgagctgt acggcatgga gaaccccagc agccagccca   10200
tggccgagct gtggatgggc gcccacccca agagcagcag ccgcgtgcag aacgccgccg   10260
gcgacatcgt gagcctgcgc gacgtgatcg agagcgacaa gagcaccctg ctgggcgagg   10320
ccgtggccaa gcgcttcggc gagctgccct tcctgttcaa ggtgctgtgc gccgcccagc   10380
ccctgagcat ccaggtgcac cccaacaagc acaacagcga gatcggcttc gccaaggaga   10440
acgccgccgg catccccatg gacgccgccg agcgcaacta caaggacccc aaccacaagc   10500
ccgagctggt gttcgccctg acccccttcc tggccatgaa cgccttccgc gagttcagcg   10560
agatcgtgag cctgctgcag cccgtggccg gcgcccaccc cgccatcgcc cacttcctgc   10620
agcagcccga cgccgagcgc ctgagcgagc tgttcgccag cctgctgaac atgcagggcg   10680
aggagaagag ccgcgccctg gccatcctga agagcgccct ggacagccag cagggcgagc   10740
cctggcagac catccgcctg atcagcgagt ctacccccga ggacagcggc ctgttcagcc   10800
ccctgctgct gaacgtggtg aagctgaacc ccggcgaggc catgttcctg ttcgccgaga   10860
ccccccacgc ctacctgcag ggcgtggccc tggaggtgat ggccaacagc gacaacgtgc   10920
tgcgcgccgg cctgaccccc aagtacatcg acatccccga gctggtggcc aacgtgaagt   10980
tcgaggccaa gcccgccaac cagctgctga cccagcccgt gaagcagggc gccgagctgg   11040
acttccccat ccccgtggac gacttcgcct tcagcctgca cgacctgagc gacaaggaga   11100
ccaccatcag ccagcagagc gccgccatcc tgttctgcgt ggagggcgac gccaccctgt   11160
ggaagggcag ccagcagctg cagctgaagc ccggcgagag cgccttcatc gccgccaacg   11220 agagcccgt gaccgtgaag ggccacggcc gcctggcccg cgtgtacaac aagctgtgat   11280
aggagctcga tccgtcgacc tgcagatcgt tcaaacattt ggcaataaag tttcttaaga   11340
ttgaatcctg ttgccggtct tgcgatgatt atcatataat ttctgttgaa ttacgttaag   11400
catgtaataa ttaacatgta atgcatgacg ttatttatga gatgggtttt tatgattaga   11460
gtcccgcaat tatacattta atacgcgata gaaaacaaaa tatagcgcgc aaactaggat   11520
aaattatcgc gcgcggtgtc atctatgtta ctagatcggc gcgccgcaat tgaagtttgg   11580
```

-continued

```
gcggccagca tggccgtatc cgcaatgtgt tattaagttg tctaagcgtc aatttgttta   11640
caccacaata tatcctgcca ccagccagcc aacagctccc cgaccggcag ctcggcacaa   11700
aatcaccact cgatacaggc agcccatcag aattaattct catgtttgac agcttatcat   11760
cgactgcacg gtgcaccaat gcttctggcg tcaggcagcc atcggaagct gtggtatggc   11820
tgtgcaggtc gtaaatcact gcataattcg tgtcgctcaa ggcgcactcc cgttctggat   11880
aatgtttttt gcgccgacat cataacggtt ctggcaaata ttctgaaatg agctgttgac   11940
aattaatcat ccggctcgta taatgtgtgg aattgtgagc ggataacaat ttcacacagg   12000
aaacagacca tgagggaagc gttgatcgcc gaagtatcga ctcaactatc agaggtagtt   12060
ggcgtcatcg agcgccatct cgaaccgacg ttgctggccg tacatttgta cggctccgca   12120
gtggatggcg gcctgaagcc acacagtgat attgatttgc tggttacggt gaccgtaagg   12180
cttgatgaaa caacgcggcg agctttgatc aacgaccttt tggaaacttc ggcttcccct   12240
ggagagagcg agattctccg cgctgtagaa gtcaccattg ttgtgcacga cgacatcatt   12300
ccgtggcgtt atccagctaa gcgcgaactg caatttggag aatggcagcg caatgacatt   12360
cttgcaggta tcttcgagcc agccacgatc gacattgatc tggctatctt gctgacaaaa   12420
gcaagagaac atagcgttgc cttggtaggt ccagcggcgg aggaactctt tgatccggtt   12480
cctgaacagg atctatttga ggcgctaaat gaaaccttaa cgctatggaa ctcgccgccc   12540
gactgggctg gcgatgagcg aaatgtagtg cttacgttgt cccgcatttg gtacagcgca   12600
gtaaccggca aaatcgcgcc gaaggatgtc gctgccgact gggcaatgga gcgcctgccg   12660
gcccagtatc agcccgtcat acttgaagct aggcaggctt atcttggaca agaagatcgc   12720
ttggcctcgc gcgcagatca gttggaagaa tttgttcact acgtgaaagg cgagatcacc   12780
aaagtagtcg gcaaataaag ctctagtgga tctccgtacc cggggatctg ctcgcggcg   12840 gacgcacgac gccggggcga gaccataggc gatctcctaa atcaatagta gctgtaacct   12900
cgaagcgttt cacttgtaac aacgattgag aatttttgtc ataaaattga aatacttggt   12960
tcgcattttt gtcatccgcg gtcagccgca attctgacga actgcccatt tagctggaga   13020
tgattgtaca tccttcacgt gaaaatttct caagcgctgt gaacaagggt tcagatttta   13080
gattgaaagg tgagccgttg aaacacgttc ttcttgtcga tgacgacgtc gctatgcggc   13140
atcttattat tgaatacctt acgatccacg ccttcaaagt gaccgcggta gccgacagca   13200
cccagttcac aagagtactc tcttccgcga cggtcgatgt cgtggttgtt gatctagatt   13260
taggtcgtga agatgggctc gagctaggag caagtgattt tatcgctaag ccgttcagta   13320
tcagagagtt tctagcacgc attcgggttg ccttgcgcgt gcgccccaac gttgtccgct   13380
ccaaagaccg acggtctttt tgtttactg actggacact taatctcagg caacgtcgct   13440
tgatgtccga agctggcggt gaggtgaaac ttacggcagg tgagttcaat cttctcctcg   13500 cgttttaga gaaaccccgc gacgttctat cgcgcgagca acttctcatt gccagtcgag   13560
tacgcgacga ggaggtttat gacaggagta tagatgttct cattttgagg ctgcgccgca   13620
aacttgaggc agatccgtca agccctcaac tgataaaaac agcaagaggt gccggttatt   13680
tctttgacgc ggacgtgcag gtttcgcacg ggggacgat ggcagcctga gccaattccc   13740
agatccccga ggaatcggcg tgagcggtcg caaaccatcc ggcccggtac aaatcggcgc   13800
ggcgctgggt gatgacctgg tggagaagtt gaaggccgcg caggccgccc agcggcaacg   13860
catcgaggca gaagcacgcc ccggtgaatc gtggcaagcg gccgctgatc gaatccgcaa   13920
agaatcccgg caaccgccgg cagccggtgc gccgtcgatt aggaagccgc ccaagggcga   13980
```

-continued

```
cgagcaacca gatttttttcg ttccgatgct ctatgacgtg ggcacccgcg atagtcgcag   14040
catcatggac gtggccgttt tccgtctgtc gaagcgtgac cgacgagctg gcgaggtgat   14100
ccgctacgag cttccagacg ggcacgtaga ggtttccgca gggccggccg gcatggccag   14160
tgtgtgggat tacgacctgg tactgatggc ggtttcccat ctaaccgaat ccatgaaccg   14220
ataccgggaa gggaagggag acaagcccgg ccgcgtgttc cgtccacacg ttgcggacgt   14280
actcaagttc tgccggcgag ccgatggcgg aaagcagaaa gacgacctgg tagaaacctg   14340
cattcggtta aacaccacgc acgttgccat gcagcgtacg aagaaggcca agaacggccg   14400
cctggtgacg gtatccgagg gtgaagcctt gattagccgc tacaagatcg taaagagcga   14460
aaccgggcgg ccggagtaca tcgagatcga gctagctgat tggatgtacc gcgagatcac   14520
agaaggcaag aacccggacg tgctgacggt tcaccccgat tacttttttga tcgatcccgg   14580 catcggccgt tttctctacc gcctggcacg ccgcgccgca ggcaaggcag aagccagatg   14640
gttgttcaag acgatctacg aacgcagtgg cagcgccgga gagttcaaga agttctgttt   14700
caccgtgcgc aagctgatcg ggtcaaatga cctgccggag tacgatttga aggaggaggc   14760
ggggcaggct ggcccgatcc tagtcatgcg ctaccgcaac ctgatcgagg gcgaagcatc   14820
cgccggttcc taatgtacgg agcagatgct agggcaaatt gccctagcag gggaaaaagg   14880 tcgaaaggt ctctttcctg tggatagcac gtacattggg aacccaaagc cgtacattgg   14940
gaaccggaac ccgtacattg ggaacccaaa gccgtacatt gggaaccggt cacacatgta   15000
agtgactgat ataaaagaga aaaaggcga tttttccgcc taaaactctt taaaacttat   15060
taaaactctt aaaacccgcc tggcctgtgc ataactgtct ggccagcgca cagccgaaga   15120
gctgcaaaaa gcgcctaccc ttcggtcgct gcgctcccta cgccccgccg cttcgcgtcg   15180
gcctatcgcg gccgctggcc gctcaaaaat ggctggccta cggccaggca atctaccagg   15240
gcgcggacaa gccgcgccgt cgccactcga ccgccggcgc tgaggtctgc ctcgtgaaga   15300
aggtgttgct gactcatacc aggcctgaat cgccccatca tccagccaga aagtgaggga   15360
gccacggttg atgagagctt tgttgtaggt ggaccagttg gtgattttga acttttgctt   15420
tgccacggaa cggtctgcgt tgtcgggaag atgcgtgatc tgatccttca actcagcaaa   15480
agttcgattt attcaacaaa gccgccgtcc cgtcaagtca gcgtaatgct ctgccagtgt   15540
tacaaccaat taaccaattc tgattagaaa aactcatcga gcatcaaatg aaaactgcaat  15600 ttattcatat caggattatc aataccatat ttttgaaaaa gccgtttctg taatgaagga   15660
gaaaactcac cgaggcagtt ccataggatg gcaagatcct ggtatcggtc tgcgattccg   15720
actcgtccaa catcaataca acctattaat ttcccctcgt caaaaataag gttatcaagt   15780
gagaaatcac catgagtgac gactgaatcc ggtgagaatg gcaaaagctc tgcattaatg   15840
aatcggccaa cgcgcgggga gaggcggttt gcgtattggg cgctcttccg cttcctcgct   15900
cactgactcg ctgcgctcgg tcgttcggct gcggcgagcg gtatcagctc actcaaaggc   15960
ggtaatacgg ttatccacag aatcagggga taacgcagga agaacatgt gagcaaaagg   16020 ccagcaaaag gccaggaacc gtaaaaaggc cgcgttgctg gcgtttttcc ataggctccg   16080
cccccctgac gagcatcaca aaaatcgacg ctcaagtcag aggtggcgaa acccgacagg   16140
actataaaga taccaggcgt ttccccctgg aagctccctc gtgcgctctc ctgttccgac   16200
cctgccgctt accggatacc tgtccgcctt tctcccttcg ggaagcgtgg cgctttctca   16260
tagctcacgc tgtaggtatc tcagttcggt gtaggtcgtt cgctccaagc tgggctgtgt   16320
```

-continued

```
gcacgaaccc cccgttcagc ccgaccgctg cgccttatcc ggtaactatc gtcttgagtc    16380
caacccggta agacacgact tatcgccact ggcagcagcc actggtaaca ggattagcag    16440
agcgaggtat gtaggcggtg ctacagagtt cttgaagtgg tggcctaact acggctacac    16500
tagaagaaca gtatttggta tctgcgctct gctgaagcca gttaccttcg gaaaaagagt    16560
tggtagctct tgatccggca aacaaaccac cgctggtagc ggtggttttt ttgtttgcaa    16620
gcagcagatt acgcgcagaa aaaaaggatc tcaagaagat cctttgatct ttttctacggg    16680 gtctgacgct cagtggaacg aaaactcacg ttaagggatt ttggtcatga gattatcaaa    16740
aaggatcttc acctagatcc ttttgatccg gaatta                              16776
```

<210> SEQ ID NO 38
<211> LENGTH: 17475
<212> TYPE: DNA
<213> ORGANISM: Artificial Sequence
<220> FEATURE:
<223> OTHER INFORMATION: vector 24094
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (330)..(2417)
<223> OTHER INFORMATION: prZmGRMZM2G471240-01
<220> FEATURE:
<221> NAME/KEY: gene
<222> LOCATION: (2420)..(7288)
<223> OTHER INFORMATION: cAmCyanCas9-01
<220> FEATURE:
<221> NAME/KEY: terminator
<222> LOCATION: (7295)..(8290)
<223> OTHER INFORMATION: tZmGRMZM2G471240-01
<220> FEATURE:
<221> NAME/KEY: promoter
<222> LOCATION: (8304)..(8678)
<223> OTHER INFORMATION: prOsU3-01
<220> FEATURE:
<221> NAME/KEY: misc_feature
<222> LOCATION: (8679)..(8784)
<223> OTHER INFORMATION: rsgRNAZmVLHP-02
<220> FEATURE:
<221> NAME/KEY: misc_feature
<222> LOCATION: (8680)..(8699)
<223> OTHER INFORMATION: ZmVLHP2 target
<220> FEATURE:
<221> NAME/KEY: misc_feature
<222> LOCATION: (8700)..(8711)
<223> OTHER INFORMATION: rCrRNA-01
<220> FEATURE:
<221> NAME/KEY: misc_feature
<222> LOCATION: (8716)..(8784)
<223> OTHER INFORMATION: rTracrRNA-01
<220> FEATURE:
<221> NAME/KEY: promoter
<222> LOCATION: (8795)..(10786)
<223> OTHER INFORMATION: prUbi1-04
<220> FEATURE:
<221> NAME/KEY: gene
<222> LOCATION: (10803)..(11981)
<223> OTHER INFORMATION: cPMI-09
<220> FEATURE:
<221> NAME/KEY: terminator
<222> LOCATION: (12004)..(12256)
<223> OTHER INFORMATION: tNOS-05-01
<220> FEATURE:
<221> NAME/KEY: misc_feature
<222> LOCATION: (12300)..(12429)
<223> OTHER INFORMATION: bNLB-03
<220> FEATURE:
<221> NAME/KEY: gene
<222> LOCATION: (12709)..(13497)
<223> OTHER INFORMATION: cSpec-03

```
<220> FEATURE:
<221> NAME/KEY: promoter
<222> LOCATION: (13592)..(13722)
<223> OTHER INFORMATION: prVirG-01
<220> FEATURE:
<221> NAME/KEY: gene
<222> LOCATION: (13797)..(14429)
<223> OTHER INFORMATION: cVirG-09
<220> FEATURE:
<221> NAME/KEY: gene
<222> LOCATION: (14459)..(15532)
<223> OTHER INFORMATION: cRepA-01
<220> FEATURE:
<221> NAME/KEY: misc_feature
<222> LOCATION: (15575)..(15979)
<223> OTHER INFORMATION: oVS1-02
<220> FEATURE:
<221> NAME/KEY: misc_feature
<222> LOCATION: (16657)..(17463)
<223> OTHER INFORMATION: oCOLE-06

<400> SEQUENCE: 38
attcctgtgg ttggcatgca catacaaatg gacgaacgga taaacctttt cacgcccttt        60
taaatatccg attattctaa taaacgctct tttctcttag gtttacccgc caatatatcc       120
tgtcaaacac tgatagttta aactgaaggc gggaaacgac aatctgatca tgagcggaga       180
attaagggag tcacgttatg accccgccg atgacgcggg acaagccgtt ttacgtttgg        240
aactgacaga accgcaacgc tgcaggaatt ggccgcagcg gccatttaaa caaagcttgg       300
tacctcgcga atgcatctag atgggaccct atttgtactc attccatgtc tcataaactt       360
tgggcaccat ccatccaaca catccaatct aaacacacca aacgatgggg aatggaaaga       420
gcagtattcg attcaacaat ggcaaacaaa tatcactgaa ttagaccaag aataaaccta       480
attagacaac gacctcccaa ccatcattcg tcaggctgta aagaagataa agctgccttg       540
gggcatggat caagcagaac accagagatg aatccaaaca cacagaaaat cacgcgcgct       600
gtctacaatg acaacaagcc ccacatttca ttgcagtaca ctgggctaca aaggcacgta       660
caacaaagag ctagggaaac attgcggagg gcacgagaga gcagctaact tgacaatata       720
gcagactgag cttgcactgt tagcaggcga ggaaggaat catggggacg gagaatgggg        780
tccatgcccg cgaaggagaa ggcggacgcc gccacggtgg caccggcgca cgcgcacaca       840
gggaacccgc acaggcagcc aaggatgctg cctcgccatt gcgccggtcg tctctgccac       900
gctcctctct ctctcccgct gcatcgccgt ggatggggca agcagagagc agggactgcg       960
acgatctggg cggaggactc gccttggaga gcgcggacgc agacgggatt ctaggagag      1020 agcgaagacg gggcgcgcgc ggcgctcgcg cggcgtggtg gcggcgagat tagcgggggt      1080
gggggagggg cggagccgtg gtgagggtgt ggacgccctc cttaccctct taagtagtag      1140
tagagatata atccgttcca aaatatccat ccgttcaatt tatatttcgt ttgatctttt      1200
taccctaaat ttgattgact catcttatta aaaaagttca taactattat taatctttat      1260
tgagatatca tttagcatat aatatacttt aagtgtggtt ttagattttt tttaaaaaaa      1320
aaaattcgca aaaattaaat gaaacgaccc aatcaaactt gaaaagtaaa actaattata      1380
aatttgaacg gaaggagtaa gaggatgttt gaatgtacta gagctaatag ttggttgctt      1440
taaaatttgc tagtagaatt agctagctaa taaatatcta gataactatt agctaatttg      1500
ctaaaacagc taatagttga actattagct agattgtttg gatgtattcg gctaattttta     1560 atggctaact attagctata gtacaatatt caaacacctc ctaattaaaa tggacaaata     1620
tctcttcttt tggtcccttg cgttagattt ttcatatctc cttatttagt ataaaagaat     1680
```

-continued

```
catcaaaaag tggacaaccc ctagtggaac accattttag tagtggttgc atgaaacctt       1740
tcgcgcacca gtttctatgt gtcactctaa aaatgggaca gcatgtacgt agtgcctata       1800
tatatacaag tcatctatcg ttgcctcctc agttcatcac taatcacact tattgtgccc       1860
tcgacgagta tctatagcta gctcattaat cgattcgggg gtgtgttgtc gaaggcggca       1920
ttggcgagct actcgtcgcg gcgtccaagc aatacctgta gcacgaaggc gatcgccggg       1980
agcgtggtcg gcgagcccgt cgtgctgggg cagagggtga cggtgctgac ggtggacggc       2040
ggcggcgtcc ggggtctcat cccgggaacc atcctcgcct tcctggaggc caggctgcag       2100
gagctggacg caccggaggc gaggctggcg gactacttcg actacatcgc cggaaccagc       2160
accggcggtc tcatcaccgc cttgctgacc gcgcccggca aggacaagcg gcctctctag       2220
gctgccaagg acatcaacca cttttacatc cataactgcc cgcgcatctt tcctcagaag       2280
tgagtccgat gctgccgcca ttgttcttgc atccatccag catcgtacgt acgtcctcta       2340
tacatctgcg gatcatcatg tgcgcatgtt tgtggcatgc atgcatgcat gtgagcagga       2400
gcaggcttgc gaaaacccca tggccctgtc caacaagttc atcggcgacg acatgaagat       2460
gacctaccac atggacggct gcgtgaacgg ccactacttc accgtgaagg gcgagggcag       2520
cggcaagccc tacgagggca cccagacctc caccttcaag gtgaccatgg ccaacggcgg       2580 cccctggcc ttctccttcg acatcctgtc caccgtgttc atgtacggca accgctgctt       2640
caccgcctac cccaccagca tgcccgacta cttcaagcag gccttccccg acggcatgtc       2700
ctacgagaga accttcacct acgaggacgg cggcgtggcc accgccagct gggagatcag       2760
cctgaagggc aactgcttcg agcacaagtc caccttccac ggcgtgaact cccccgccga       2820
cggccccgtg atggccaaga agaccaccgg ctgggacccc tccttcgaga agatgaccgt       2880
gtgcgacggc atcttgaagg gcgacgtgac cgccttcctg atgctgcagg gcggcggcaa       2940
ctacagatgc cagttccaca cctcctacaa gaccaagaag cccgtgacca tgcccccaa       3000 ccacgtggtg gagcaccgca tcgccagaac cgacctggac aagggcggca acagcgtgca       3060
gctgaccgag cacgccgtgg cccacatcac ctccgtggtg cccttcggcg cggcggatc        3120 cgacaagaag tacagcatcg gcctggacat cggcaccaac agcgtgggct gggccgtgat       3180
caccgacgag tacaaggtgc gagcaagaa gttcaaggtg ctgggcaaca ccgacaggca       3240
cagcatcaag aagaacctga tcggcgccct gctgttcgac agcggcgaga ccgccgaggc       3300
caccaggctg aagaggaccg ccaggaggag gtacaccagg aggaagaaca ggatctgcta       3360
cctgcaggag atcttcagca acgagatggc caaggtggac gacagcttct tccacaggct       3420
ggaggagagc ttcctggtgg aggaggacaa gaagcacgag aggcacccga tcttcggcaa       3480
catcgtggac gaggtggcct accacgagaa gtacccgacc atctaccacc tgaggaagaa       3540
gctggtggac agcaccgaca aggccgacct gaggctgatc tacctggccc tggcccacat       3600
gatcaagttc aggggccact tcctgatcga gggcgacctg aacccggaca cagcgacgt        3660 ggacaagctg ttcatccagc tggtgcagac ctacaaccag ctgttcgagg agaacccgat       3720
caacgccagc ggcgtggacg ccaaggccat cctgagcgcc aggctgagca gagcaggag        3780 gctggagaac ctgatcgccc agctgccggg cgagaagaag aacggcctgt tcggcaacct       3840
gatcgccctg agcctgggcc tgaccccgaa cttcaagagc aacttcgacc tggccgagga       3900
cgccaagctg cagctgagca aggacaccta cgacgacgac ctggacaacc tgctggccca       3960
gatcggcgac cagtacgccg acctgttcct ggccgccaag aacctgagcg acgccatcct       4020
gctgagcgac atcctgaggg tgaacaccga gatcaccaag gccccgctga gcgccagcat       4080
```

-continued

```
gatcaagagg tacgacgagc accaccagga cctgaccctg ctgaaggccc tggtgaggca    4140
gcagctgccg gagaagtaca aggagatctt cttcgaccag agcaagaacg gctacgccgg    4200
ctacatcgac ggcggcgcca gccaggagga gttctacaag ttcatcaagc cgatcctgga    4260
gaagatggac ggcaccgagg agctgctggt gaagctgaac agggaggacc tgctgaggaa    4320
gcagaggacc ttcgacaacg gcagcatccc gcaccagatc cacctgggcg agctgcacgc    4380
catcctgagg aggcaggagg acttctaccc gttcctgaag gacaacaggg agaagatcga    4440
gaagatcctg accttccgca tcccgtacta cgtgggcccg ctggccaggg gcaacagcag    4500
gttcgcctgg atgaccagga agagcgagga gaccatcacc ccgtggaact tcgaggaggt    4560
ggtggacaag ggcgccagcg cccagagctt catcgagagg atgaccaact tcgacaagaa    4620
cctgccgaac gagaaggtgc tgccgaagca cagcctgctg tacgagtact tcaccgtgta    4680
caacgagctg accaaggtga agtacgtgac cgagggcatg aggaagccgg ccttcctgag    4740
cggcgagcag aagaaggcca tcgtggacct gctgttcaag accaacagga aggtgaccgt    4800
gaagcagctg aaggaggact acttcaagaa gatcgagtgc ttcgacagcg tggagatcag    4860
cggcgtggag gacaggttca acgccagcct gggcacctac cacgacctgc tgaagatcat    4920
caaggacaag gacttcctgg acaacgagga gaacgaggac atcctggagg acatcgtgct    4980
gaccctgacc ctgttcgagg acagggagat gatcgaggag aggctgaaga cctacgccca    5040
cctgttcgac gacaaggtga tgaagcagct gaagaggagg aggtacaccg gctggggcag    5100
gctgagcagg aagctgatca cggcatcag ggacaagcag agcggcaaga ccatcctgga    5160
cttcctgaag agcgacggct tcgccaacag gaacttcatg cagctgatcc acgacgacag    5220
cctgaccttc aaggaggaca tccagaaggc ccaggtgagc ggccagggcg acagcctgca    5280
cgagcacatc gccaacctgg ccggcagccc ggccatcaag aagggcatcc tgcagaccgt    5340
gaaggtggtg gacgagctgg tgaaggtgat gggcaggcac aagccggaga acatcgtgat    5400
cgagatggcc agggagaacc agaccaccca gaagggccag aagaacagca gggagaggat    5460
gaagaggatc gaggagggca tcaaggagct gggcagccag atcctgaagg agcacccggt    5520
ggagaacacc cagctgcaga acgagaagct gtacctgtac tacctgcaga acggcaggga    5580
catgtacgtg gaccaggagc tggacatcaa caggctgagc gactacgacg tggaccacat    5640
cgtgccgcag agcttcctga aggacgacag catcgacaac aaggtgctga ccaggagcga    5700
caagaacagg ggcaagagcg acaacgtgcc gagcgaggag gtggtgaaga agatgaaaaa    5760
ctactggagg cagctgctga acgccaagct gatcacccag aggaagttcg acaacctgac    5820
caaggccgag aggggcggcc tgagcgagct ggacaaggcc ggcttcatta aaaggcagct    5880
ggtggagacc aggcagatca ccaagcacgt ggcccagatc ctggacagca ggatgaacac    5940
caagtacgac gagaacgaca agctgatcag ggaggtgaag gtgatcaccc tgaagagcaa    6000
gctggtgagc gacttcagga aggacttcca gttctacaag gtgagggaga tcaataatta    6060
ccaccacgcc cacgacgcct acctgaacgc cgtggtgggc accgccctga ttaaaaagta    6120
cccgaagctg gagagcgagt cgtgtacgg cgactacaag gtgtacgacg tgaggaagat    6180
gatcgccaag agcgagcagg agatcggcaa ggccaccgcc aagtacttct ctacagcaa    6240 catcatgaac ttcttcaaga ccgagatcac cctggccaac ggcgagatca ggaagaggcc    6300
gctgatcgag accaacggcg agaccggcga gatcgtgtgg gacaagggca gggacttcgc    6360
caccgtgagg aaggtgctgt ccatgccgca ggtgaacatc gtgaagaaga ccgaggtgca    6420
```

-continued

```
gaccggcggc ttcagcaagg agagcatcct gccgaagagg aacagcgaca agctgatcgc      6480
caggaagaag gactgggacc cgaagaagta cggcggcttc gacagcccga ccgtggccta      6540
cagcgtgctg gtggtggcca aggtggagaa gggcaagagc aagaagctga agagcgtgaa      6600
ggagctggtg ggcatcacca tcatggagag gagcagcttc gagaagaacc cagtggactt      6660
cctggaggcc aagggctaca aggaggtgaa gaaggacctg atcattaaac tgccgaagta      6720
cagcctgttc gagctggaga acggcaggaa gaggatgctg gccagcgccg gcgagctgca      6780
gaagggcaac gagctggccc tgccgagcaa gtacgtgaac ttcctgtacc tggccagcca      6840
ctacgagaag ctgaagggca gcccggagga caacagcagc aagcagctgt cgtggagca       6900 gcacaagcac tacctggacg agatcatcga gcagatcagc gagttcagca agagggtgat      6960
cctggccgac gccaacctgg acaaggtgct gagcgcctac aacaagcaca gggacaagcc      7020
gatcagggag caggccgaga acatcatcca cctgttcacc ctgaccaacc tgggcgcccc      7080
ggccgccttc aagtacttcg acaccaccat cgacaggaag aggtacacca gcaccaagga      7140
ggtgctggac gccaccctga tccaccagag catcaccggc ctgtacgaga ccaggatcga      7200
cctgagccag ctgggcggcg acagcagccc gccgaagaag aagaggaagg tgagctggaa      7260
ggacgccagc ggctggagca ggatgtgacc atgggacaag tggctttact gtcagtcaca      7320
tgcttgtaaa taagtagact ttattttaat aaaacataaa aatatatata tgttcttgaa      7380
tataaaattg ataaccaaat taaaattcga accatcactt atacataatt ttactttatt      7440
ttttataaaa cgtgaacggg aaggactacc gtgaatgact atagaaccaa tcatactagt      7500
ataaaatata tgatgacact acgggagaga caaactttgt ctggcgctaa atattttgcc      7560
gagtgtgaat tcacgggcac taggcaaaga tcttcttttgc cgagtgttac gctgggcaaa      7620
gtaagacact aggtaaatca gtcatttgcc gagtgtccgc cactaggcaa agcaaaacac      7680
tggcaaatca aaagtttacc tagtgccaga cactaggcaa aaaaaaaacg ctcggcaaat      7740
cggaagtttc cctagtgcca gacactagac aaagaaaaac acttgataaa ctagcgtcgt      7800
cagctaacac catccaccaa ccgttaacgt tgccgagtat ctgacttcga cactcggcaa      7860
agaaggtctc tttgcctagt gtcggtctgg aacactaggc aaagaggcac tttacctagt      7920
gtcgtatttt gacactcagt aaaataattt tttttctttc tgcttccaaa cttttttatga      7980 tgtgttccta tagcacctag aactacatgt caagttttgg taaaattttt gaagtttttg      8040
ctatatttac ttaatttatt ttatttaatt gaatttcttt tgataattca aatttgaact      8100
cggcaaggta agaagcgagg gtagcctgga aacacacttt gcctagtgtt acactcggta      8160
caggagcctc ccctgcctag tgctgcactc gacaaaagat tcgcctttgc ctagcgctgc      8220
actcggcaca ggagtcgcct ttgcctagtg ctgcactagg caaagcctcc gttaccgtgc      8280
cttccatcgt cggacccttc gaagggatct ttaaacatac gaacagatca cttaaagttc      8340
ttctgaagca acttaaagtt atcaggcatg catggatctt ggaggaatca gatgtgcagt      8400
cagggaccat agcacaggac aggcgtcttc tactggtgct accagcaaat gctggaagcc      8460
gggaacactg ggtacgttgg aaaccacgtg atgtggagta agataaactg taggagaaaa      8520
gcatttcgta gtgggccatg aagcctttca ggacatgtat tgcagtatgg gccggcccat      8580
tacgcaattg gacgacaaca aagactagta ttagtaccac ctcggctatc cacatagatc      8640
aaagctggtt taaaagagtt gtgcagatga tccgtggcag ctggagctga gcttccgggg      8700
ttttagagct agaaatagca agttaaaata aggctagtcc gttatcaact tgaaaaagtg      8760
gcaccgagtc ggtgcttttt ttttcggacc gcgcctgcag tgcagcgtga cccggtcgtg      8820
```

-continued

```
cccctctcta gagataatga gcattgcatg tctaagttat aaaaaattac cacatatttt    8880
ttttgtcaca cttgtttgaa gtgcagttta tctatcttta tacatatatt taaactttac    8940
tctacgaata atataatcta tagtactaca ataatatcag tgttttagag aatcatataa    9000
atgaacagtt agacatggtc taaaggacaa ttgagtattt tgacaacagg actctacagt    9060
tttatctttt tagtgtgcat gtgttctcct tttttttttgc aaatagcttc acctatataa    9120
tacttcatcc attttattag tacatccatt tagggtttag ggttaatggt ttttatagac    9180
taattttttt agtacatcta ttttattcta ttttagcctc taaattaaga aaactaaaac    9240
tctattttag ttttttttatt taataattta gatataaaat agaataaaat aaagtgacta    9300
aaaattaaac aaatacccctt taagaaatta aaaaaactaa ggaaacattt ttcttgtttc    9360
gagtagataa tgccagcctg ttaaacgccg tcgacgagtc taacggacac caaccagcga    9420
accagcagcg tcgcgtcggg ccaagcgaag cagacggcac ggcatctctg tcgctgcctc    9480
tggacccctc tcgagagttc cgctccaccg ttggacttgc tccgctgtcg gcatccagaa    9540
attgcgtggc ggagcggcag acgtgagccg gcacggcagg cggcctcctc ctcctctcac    9600
ggcaccggca gctacggggg attcctttcc caccgctcct tcgctttccc ttcctcgccc    9660
gccgtaataa atagacaccc cctccacacc ctctttcccc aacctcgtgt tgttcggagc    9720
gcacacacac acaaccagat ctcccccaaa tccacccgtc ggcacctccg cttcaaggta    9780
cgccgctcgt cctccccccc cccctctct accttctcta gatcggcgtt ccggtccatg    9840
gttagggccc ggtagttcta cttctgttca tgtttgtgtt agatccgtgt ttgtgttaga    9900
tccgtgctgc tagcgttcgt acacggatgc gacctgtacg tcagacacgt tctgattgct    9960
aacttgccag tgtttctctt tggggaatcc tgggatggct ctagccgttc cgcagacggg   10020
atcgatttca tgattttttt tgtttcgttg catagggttt ggtttgccct tttcctttat   10080
ttcaatatat gccgtgcact tgtttgtcgg gtcatctttt catgcttttt tttgtcttgg   10140
ttgtgatgat gtggtctggt tgggcggtcg ttctagatcg gagtagaatt ctgtttcaaa   10200
ctacctggtg gatttattaa ttttggatct gtatgtgtgt gccatacata ttcatagtta   10260
cgaattgaag atgatggatg gaaatatcga tctaggatag gtatacatgt tgatgcgggt   10320
tttactgatg catatacaga gatgcttttt gttcgcttgg ttgtgatgat gtggtgtggt   10380
tgggcggtcg ttcattcgtt ctagatcgga gtagaatact gtttcaaact acctggtgta   10440
tttattaatt ttggaactgt atgtgtgtgt catacatctt catagttacg agtttaagat   10500
ggatggaaat atcgatctag gataggtata catgttgatg tgggttttac tgatgcatat   10560
acatgatggc atatgcagca tctattcata tgctctaacc ttgagtacct atctattata   10620
ataaacaagt atgttttata attattttga tcttgatata cttggatgat ggcatatgca   10680
gcagctatat gtggattttt ttagccctgc cttcatacgc tatttatttg cttggtactg   10740
tttcttttgt cgatgctcac cctgttgttt ggtgttactt ctgcagggat ccggcagcag   10800
ccatgcagaa gctgatcaac agcgtgcaga actacgcctg gggcagcaag accgccctga   10860
ccgagctgta cggcatggag aaccccagca gccagcccat ggccgagctg tggatgggcg   10920 cccacccaa gagcagcagc cgcgtgcaga acgccgccgg cgacatcgtg agcctgcgcg   10980
acgtgatcga gagcgacaag agcacccctgc tgggcgaggc cgtggccaag cgcttcggcg   11040 agctgcccctt cctgttcaag gtgctgtgcg ccgcccagcc cctgagcatc caggtgcacc   11100
ccaacaagca caacagcgag atcggcttcg ccaaggagaa cgccgccggc atccccatgg   11160
```

-continued

```
acgccgccga gcgcaactac aaggacccca accacaagcc cgagctggtg ttcgccctga   11220
cccccttcct ggccatgaac gccttccgcg agttcagcga gatcgtgagc ctgctgcagc   11280
ccgtggccgg cgcccacccc gccatcgccc acttcctgca gcagcccgac gccgagcgcc   11340
tgagcgagct gttcgccagc ctgctgaaca tgcaggggcga ggagaagagc cgcgccctgg   11400
ccatcctgaa gagcgccctg gacagccagc agggcgagcc ctggcagacc atccgcctga   11460
tcagcgagtt ctaccccgag gacagcggcc tgttcagccc cctgctgctg aacgtggtga   11520
agctgaaccc cggcgaggcc atgttcctgt tcgccgagac cccccacgcc tacctgcagg   11580
gcgtggccct ggaggtgatg gccaacagcg acaacgtgct gcgcgccggc ctgaccccca   11640
agtacatcga catccccgag ctggtggcca acgtgaagtt cgaggccaag cccgccaacc   11700
agctgctgac ccagcccgtg aagcagggcg ccgagctgga cttccccatc cccgtggacg   11760
acttcgcctt cagcctgcac gacctgagcg acaaggagac caccatcagc cagcagagcg   11820
ccgccatcct gttctgcgtg gagggcgacg ccaccctgtg aagggcagc cagcagctgc   11880 agctgaagcc cggcgagagc gccttcatcg ccgccaacga gagccccgtg accgtgaagg   11940
gccacggccg cctggcccgc gtgtacaaca agctgtgata ggagctcgat ccgtcgacct   12000
gcagatcgtt caaacatttg gcaataaagt ttcttaagat tgaatcctgt tgccggtctt   12060
gcgatgatta tcatataatt tctgttgaat tacgttaagc atgtaataat aacatgtaa   12120 tgcatgacgt tatttatgag atgggttttt atgattagag tcccgcaatt atacatttaa   12180
tacgcgatag aaaacaaaat atagcgcgca aactaggata aattatcgcg cgcggtgtca   12240
tctatgttac tagatcggcg cgccgcaatt gaagtttggg cggccagcat ggccgtatcc   12300
gcaatgtgtt attaagttgt ctaagcgtca atttgtttac accacaatat atcctgccac   12360
cagccagcca acagctcccc gaccggcagc tcggcacaaa atcaccactc gatacaggca   12420
gcccatcaga attaattctc atgtttgaca gcttatcatc gactgcacgg tgcaccaatg   12480
cttctggcgt caggcagcca tcggaagctg tggtatggct gtgcaggtcg taaatcactg   12540
cataattcgt gtcgctcaag cgcactcccc gttctggata atgtttttg cgccgacatc   12600 ataacggttc tggcaaatat tctgaaatga gctgttgaca attaatcatc cggctcgtat   12660
aatgtgtgga attgtgagcg ataacaatt tcacacagga aacagaccat gagggaagcg   12720
ttgatcgccg aagtatcgac tcaactatca gaggtagttg gcgtcatcga cgccatctc   12780 gaaccgacgt tgctggccgt acatttgtac ggctccgcag tggatggcgg cctgaagcca   12840
cacagtgata ttgatttgct ggttacggtg accgtaaggc ttgatgaaac aacgcggcga   12900
gctttgatca acgacctttt ggaaacttcg gcttcccctg gagagagcga gattctccgc   12960
gctgtagaag tcaccattgt tgtgcacgac gacatcattc cgtggcgtta ccagctaag   13020 cgcgaactgc aatttggaga atggcagcgc aatgacattc ttgcaggtat cttcgagcca   13080
gccacgatcg acattgatct ggctatcttg ctgacaaaag caagagaaca tagcgttgcc   13140
ttggtaggtc cagcggcgga ggaactcttt gatccggttc ctgaacagga tctatttgag   13200
gcgctaaatg aaaccttaac gctatggaac tcgccgcccg actgggctgg cgatgagcga   13260
aatgtagtgc ttacgttgtc ccgcatttgg tacagcgcag taaccggcaa aatcgcgccg   13320
aaggatgtcg ctgccgactg ggcaatggag cgcctgccgg cccagtatca gcccgtcata   13380
cttgaagcta ggcaggctta tcttggacaa gaagatcgct tggcctcgcg cgcagatcag   13440
ttggaagaat ttgttcacta cgtgaaaggc gagatcacca aagtagtcgg caaataaagc   13500
tctagtggat ctccgtaccc ggggatctgg ctcgcggcgg acgcacgacg ccggggcgag   13560
```

-continued

```
accataggcg atctcctaaa tcaatagtag ctgtaacctc gaagcgtttc acttgtaaca   13620
acgattgaga atttttgtca taaaattgaa atacttggtt cgcatttttg tcatccgcgg   13680
tcagccgcaa ttctgacgaa ctgcccattt agctggagat gattgtacat ccttcacgtg   13740
aaaatttctc aagcgctgtg aacaagggtt cagatttttag attgaaaggt gagccgttga   13800
aacacgttct tcttgtcgat gacgacgtcg ctatgcggca tcttattatt gaatacctta   13860
cgatccacgc cttcaaagtg accgcggtag ccgacagcac ccagttcaca agagtactct   13920
cttccgcgac ggtcgatgtc gtggttgttg atctagattt aggtcgtgaa gatgggctcg   13980
agctaggagc aagtgatttt atcgctaagc cgttcagtat cagagagttt ctagcacgca   14040
ttcgggttgc cttgcgcgtg cgccccaacg ttgtccgctc caaagaccga cggtcttttt   14100
gttttactga ctggacactt aatctcaggc aacgtcgctt gatgtccgaa gctggcggtg   14160
aggtgaaact tacggcaggt gagttcaatc ttctcctcgc gttttttagag aaaccccgcg   14220 acgttctatc gcgcgagcaa cttctcattg ccagtcgagt acgcgacgag gaggtttatg   14280
acaggagtat agatgttctc attttgaggc tgcgccgcaa acttgaggca gatccgtcaa   14340
gccctcaact gataaaaaca gcaagaggtg ccggttattt ctttgacgcg gacgtgcagg   14400
tttcgcacgg ggggacgatg gcagcctgag ccaattccca gatccccgag gaatcggcgt   14460
gagcggtcgc aaaccatccg gcccggtaca aatcggcgcg cgcgctgggtg atgacctggt   14520 ggagaagttg aaggccgcgc aggccgccca gcggcaacgc atcgaggcag aagcacgccc   14580
cggtgaatcg tggcaagcgg ccgctgatcg aatccgcaaa gaatcccggc aaccgccggc   14640
agccggtgcg ccgtcgatta ggaagccgcc caagggcgac gagcaaccag atttttttcgt   14700 tccgatgctc tatgacgtgg gcacccgcga tagtcgcagc atcatggacg tggccgtttt   14760
ccgtctgtcg aagcgtgacc gacgagctgg cgaggtgatc cgctacgagc ttccagacgg   14820
gcacgtagag gtttccgcag ggccggccgg catggccagt gtgtgggatt acgacctggt   14880
actgatggcg gtttcccatc taaccgaatc catgaaccga taccgggaag ggaagggaga   14940
caagcccggc cgcgtgttcc gtccacacgt tgcggacgta ctcaagttct gccggcgagc   15000
cgatggcgga aagcagaaag acgacctggt agaaacctgc attcggttaa acaccacgca   15060
cgttgccatg cagcgtacga agaaggccaa gaacggccgc ctggtgacgg tatccgaggg   15120
tgaagccttg attagccgct acaagatcgt aaagagcgaa accgggcggc cggagtacat   15180
cgagatcgag ctagctgatt ggatgtaccg cgagatcaca gaaggcaaga acccggacgt   15240
gctgacggtt caccccgatt acttttttgat cgatcccggc atcggccgtt ttctctaccg   15300
cctggcacgc cgcgccgcag gcaaggcaga agccagatgg ttgttcaaga cgatctacga   15360
acgcagtggc agcgccggag agttcaagaa gttctgtttc accgtgcgca agctgatcgg   15420
gtcaaatgac ctgccggagt acgatttgaa ggaggaggcg gggcaggctg gcccgatcct   15480
agtcatgcgc taccgcaacc tgatcgaggg cgaagcatcc gccggttcct aatgtacgga   15540
gcagatgcta gggcaaattg ccctagcagg ggaaaaaggt cgaaaaggtc tctttcctgt   15600
ggatagcacg tacattggga acccaaagcc gtacattggg aaccggaacc cgtacattgg   15660
gaacccaaag ccgtacattg ggaaccggtc acacatgtaa gtgactgata taaaagagaa   15720
aaaaggcgat ttttccgcct aaaactcttt aaaacttatt aaaactctta aaacccgcct   15780
ggcctgtgca taactgtctg ccagcgcac agccgaagag ctgcaaaaag cgcctaccct   15840
tcggtcgctg cgctccctac gccccgccgc ttcgcgtcgg cctatcgcgg ccgctggccg   15900
```

-continued

```
ctcaaaaatg gctggcctac ggccaggcaa tctaccaggg cgcggacaag ccgcgccgtc   15960
gccactcgac cgccggcgct gaggtctgcc tcgtgaagaa ggtgttgctg actcatacca   16020
ggcctgaatc gccccatcat ccagccagaa agtgagggag ccacggttga tgagagcttt   16080
gttgtaggtg gaccagttgg tgattttgaa cttttgcttt gccacggaac ggtctgcgtt   16140
gtcgggaaga tgcgtgatct gatccttcaa ctcagcaaaa gttcgattta ttcaacaaag   16200
ccgccgtccc gtcaagtcag cgtaatgctc tgccagtgtt acaaccaatt aaccaattct   16260
gattagaaaa actcatcgag catcaaatga aactgcaatt tattcatatc aggattatca   16320
ataccatatt tttgaaaaag ccgtttctgt aatgaaggag aaaactcacc gaggcagttc   16380
cataggatgg caagatcctg gtatcggtct gcgattccga ctcgtccaac atcaatacaa   16440
cctattaatt tcccctcgtc aaaaataagg ttatcaagtg agaaatcacc atgagtgacg   16500
actgaatccg gtgagaatgg caaaagctct gcattaatga atcggccaac gcgcggggag   16560
aggcggtttg cgtattgggc gctcttccgc ttcctcgctc actgactcgc tgcgctcggt   16620
cgttcggctg cggcgagcgg tatcagctca ctcaaaggcg gtaatacggt tatccacaga   16680
atcaggggat aacgcaggaa agaacatgtg agcaaaaggc cagcaaaagg ccaggaaccg   16740
taaaaaggcc gcgttgctgg cgtttttcca taggctccgc ccccctgacg agcatcacaa   16800
aaatcgacgc tcaagtcaga ggtggcgaaa cccgacagga ctataaagat accaggcgtt   16860
tccccctgga agctccctcg tgcgctctcc tgttccgacc ctgccgctta ccggatacct   16920
gtccgccttt ctcccttcgg gaagcgtggc gctttctcat agctcacgct gtaggtatct   16980
cagttcggtg taggtcgttc gctccaagct gggctgtgtg cacgaacccc ccgttcagcc   17040
cgaccgctgc gccttatccg gtaactatcg tcttgagtcc aacccggtaa gacacgactt   17100
atcgccactg gcagcagcca ctggtaacag gattagcaga gcgaggtatg taggcggtgc   17160
tacagagttc ttgaagtggt ggcctaacta cggctacact agaagaacag tatttggtat   17220
ctgcgctctg ctgaagccag ttaccttcgg aaaaagagtt ggtagctctt gatccggcaa   17280
acaaaccacc gctggtagcg gtggtttttt tgtttgcaag cagcagatta cgcgcagaaa   17340
aaaaggatct caagaagatc ctttgatctt ttctacgggg tctgacgctc agtggaacga   17400
aaactcacgt taagggattt ggtcatgag attatcaaaa aggatcttca cctagatcct   17460
tttgatccgg aatta                                                    17475
```

```
<210> SEQ ID NO 39
<211> LENGTH: 19
<212> TYPE: DNA
<213> ORGANISM: Artificial Sequence
<220> FEATURE:
<223> OTHER INFORMATION: primer

<400> SEQUENCE: 39
ttgtgctgct ccacgaaca                                                       19

<210> SEQ ID NO 40
<211> LENGTH: 20
<212> TYPE: DNA
<213> ORGANISM: artificial sequence
<220> FEATURE:
<223> OTHER INFORMATION: primer

<400> SEQUENCE: 40
gccagccact acgagaagct                                                      20
```

-continued

```
<210> SEQ ID NO 41
<211> LENGTH: 24
<212> TYPE: DNA
<213> ORGANISM: Artificial Sequence
<220> FEATURE:
<223> OTHER INFORMATION: probe

<400> SEQUENCE: 41
ctgcttctgc tcgttgtcct ccgg                                          24

<210> SEQ ID NO 42
<211> LENGTH: 17
<212> TYPE: DNA
<213> ORGANISM: Artificial Sequence
<220> FEATURE:
<223> OTHER INFORMATION: promer

<400> SEQUENCE: 42
gcggatgctg gcacagc                                                  17

<210> SEQ ID NO 43
<211> LENGTH: 19
<212> TYPE: DNA
<213> ORGANISM: Artificial Sequence
<220> FEATURE:
<223> OTHER INFORMATION: primer

<400> SEQUENCE: 43
ggcattgctt ccttctccg                                                19

<210> SEQ ID NO 44
<211> LENGTH: 15
<212> TYPE: DNA
<213> ORGANISM: Artificial Sequence
<220> FEATURE:
<223> OTHER INFORMATION: probe

<400> SEQUENCE: 44
cagggagcga ggtac                                                    15

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
ctggtggcca acgtgaagtt                                               20

<210> SEQ ID NO 46
<211> LENGTH: 17
<212> TYPE: DNA
<213> ORGANISM: Artificial Sequence
<220> FEATURE:
<223> OTHER INFORMATION: primer

<400> SEQUENCE: 46
gcttcacggg ctgggtc                                                  17

<210> SEQ ID NO 47
<211> LENGTH: 20
<212> TYPE: DNA
<213> ORGANISM: Artificial Sequence
<220> FEATURE:
<223> OTHER INFORMATION: probe
```

<400> SEQUENCE: 47
aggccaagcc cgccaaccag                                                          20

<210> SEQ ID NO 48
<211> LENGTH: 17
<212> TYPE: DNA
<213> ORGANISM: Artificial Sequence
<220> FEATURE:
<223> OTHER INFORMATION: primer

<400> SEQUENCE: 48
gcggatgctg gcacaga                                                             17

<210> SEQ ID NO 49
<211> LENGTH: 18
<212> TYPE: DNA
<213> ORGANISM: Artificial Sequence
<220> FEATURE:
<223> OTHER INFORMATION: primer

<400> SEQUENCE: 49
gcattgcttc cttcgcca                                                            18

<210> SEQ ID NO 50
<211> LENGTH: 16
<212> TYPE: DNA
<213> ORGANISM: Artificial Sequence
<220> FEATURE:
<223> OTHER INFORMATION: probe

<400> SEQUENCE: 50
cagggaggta cgaacc                                                              16

<210> SEQ ID NO 51
<211> LENGTH: 16
<212> TYPE: DNA
<213> ORGANISM: Artificial Sequence
<220> FEATURE:
<223> OTHER INFORMATION: primer

<400> SEQUENCE: 51
gcggcgaaga agcgaa                                                              16

<210> SEQ ID NO 52
<211> LENGTH: 17
<212> TYPE: DNA
<213> ORGANISM: Artificial Sequence
<220> FEATURE:
<223> OTHER INFORMATION: primer

<400> SEQUENCE: 52
gcggcgtctc cagcttc                                                             17

<210> SEQ ID NO 53
<211> LENGTH: 12
<212> TYPE: DNA
<213> ORGANISM: Artificial Sequence
<220> FEATURE:
<223> OTHER INFORMATION: probe

<400> SEQUENCE: 53
ccaggaactg cg                                                                  12

<210> SEQ ID NO 54
<211> LENGTH: 18

-continued

```
<212> TYPE: DNA
<213> ORGANISM: Artificial Sequence
<220> FEATURE:
<223> OTHER INFORMATION: primer

<400> SEQUENCE: 54
aagaaacgcc ggctgagt                                                    18

<210> SEQ ID NO 55
<211> LENGTH: 15
<212> TYPE: DNA
<213> ORGANISM: Artificial Sequence
<220> FEATURE:
<223> OTHER INFORMATION: primer

<400> SEQUENCE: 55
accttgcggg gcgtt                                                       15

<210> SEQ ID NO 56
<211> LENGTH: 12
<212> TYPE: DNA
<213> ORGANISM: Artificial Sequence
<220> FEATURE:
<223> OTHER INFORMATION: probe

<400> SEQUENCE: 56
ccaggaactg cg                                                          12

<210> SEQ ID NO 57
<211> LENGTH: 18
<212> TYPE: DNA
<213> ORGANISM: Artificial Sequence
<220> FEATURE:
<223> OTHER INFORMATION: primer

<400> SEQUENCE: 57
aagaaacgcc ggctgagt                                                    18

<210> SEQ ID NO 58
<211> LENGTH: 14
<212> TYPE: DNA
<213> ORGANISM: Artificial Sequence
<220> FEATURE:
<223> OTHER INFORMATION: primer

<400> SEQUENCE: 58
ccttgcgcgg cgtc                                                        14

<210> SEQ ID NO 59
<211> LENGTH: 12
<212> TYPE: DNA
<213> ORGANISM: Artificial Sequence
<220> FEATURE:
<223> OTHER INFORMATION: probe

<400> SEQUENCE: 59
ccaggaactg cg                                                          12

<210> SEQ ID NO 60
<211> LENGTH: 19
<212> TYPE: DNA
<213> ORGANISM: Artificial Sequence
<220> FEATURE:
<223> OTHER INFORMATION: primer

<400> SEQUENCE: 60
```

-continued tgatcctcga ggccaagct                                                                    19

<210> SEQ ID NO 61
<211> LENGTH: 18
<212> TYPE: DNA
<213> ORGANISM: Artificial Sequence
<220> FEATURE:
<223> OTHER INFORMATION: primer

<400> SEQUENCE: 61
aggtcgaggt cccctcca                                                                     18

<210> SEQ ID NO 62
<211> LENGTH: 14
<212> TYPE: DNA
<213> ORGANISM: Artificial Sequence
<220> FEATURE:
<223> OTHER INFORMATION: probe

<400> SEQUENCE: 62
cctgctaccc gggc                                                                         14

<210> SEQ ID NO 63
<211> LENGTH: 15
<212> TYPE: DNA
<213> ORGANISM: Artificial Sequence
<220> FEATURE:
<223> OTHER INFORMATION: primer

<400> SEQUENCE: 63
cgcgccctgc taccc                                                                        15

<210> SEQ ID NO 64
<211> LENGTH: 17
<212> TYPE: DNA
<213> ORGANISM: Artificial Sequence
<220> FEATURE:
<223> OTHER INFORMATION: primer

<400> SEQUENCE: 64
gcgcgtgctt accagga                                                                      17

<210> SEQ ID NO 65
<211> LENGTH: 13
<212> TYPE: DNA
<213> ORGANISM: Artificial Sequence
<220> FEATURE:
<223> OTHER INFORMATION: probe

<400> SEQUENCE: 65
tcgaggagtg ccc                                                                          13

<210> SEQ ID NO 66
<211> LENGTH: 16
<212> TYPE: DNA
<213> ORGANISM: Artificial Sequence
<220> FEATURE:
<223> OTHER INFORMATION: primer

<400> SEQUENCE: 66
caccgatgag caggcg                                                                       16

<210> SEQ ID NO 67
<211> LENGTH: 18
<212> TYPE: DNA
<213> ORGANISM: Artificial Sequence
<220> FEATURE:
<223> OTHER INFORMATION: primer

<400> SEQUENCE: 67
agatacacct tccggccg                                                      18

<210> SEQ ID NO 68
<211> LENGTH: 14
<212> TYPE: DNA
<213> ORGANISM: Artificial Sequence
<220> FEATURE:
<223> OTHER INFORMATION: probe

<400> SEQUENCE: 68
ttcctcccgg aagc                                                          14

<210> SEQ ID NO 69
<211> LENGTH: 16
<212> TYPE: DNA
<213> ORGANISM: Artificial Sequence
<220> FEATURE:
<223> OTHER INFORMATION: primer

<400> SEQUENCE: 69
caccgatgag caggcg                                                        16

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
agatacacct tccggccagt                                                    20

<210> SEQ ID NO 71
<211> LENGTH: 14
<212> TYPE: DNA
<213> ORGANISM: Artificial Sequence
<220> FEATURE:
<223> OTHER INFORMATION: probe

<400> SEQUENCE: 71
ctcctcccgg aagc                                                          14

<210> SEQ ID NO 72
<211> LENGTH: 25
<212> TYPE: DNA
<213> ORGANISM: Artificial Sequence
<220> FEATURE:
<223> OTHER INFORMATION: primer

<400> SEQUENCE: 72
caagtttctg gacaaggaga ttctc                                              25

<210> SEQ ID NO 73
<211> LENGTH: 27
<212> TYPE: DNA
<213> ORGANISM: Artificial Sequence
<220> FEATURE:
<223> OTHER INFORMATION: primer

<400> SEQUENCE: 73
aagaattccc ttcttaatag ctggaga                                            27

-continued

```
<210> SEQ ID NO 74
<211> LENGTH: 26
<212> TYPE: DNA
<213> ORGANISM: Artificial Sequence
<220> FEATURE:
<223> OTHER INFORMATION: probe

<400> SEQUENCE: 74
cacgagcaca ttgctaacct tgctgg                                    26

<210> SEQ ID NO 75
<211> LENGTH: 17
<212> TYPE: DNA
<213> ORGANISM: Artificial Sequence
<220> FEATURE:
<223> OTHER INFORMATION: primer

<400> SEQUENCE: 75
tcaccgatga gcaggca                                              17

<210> SEQ ID NO 76
<211> LENGTH: 18
<212> TYPE: DNA
<213> ORGANISM: Artificial Sequence
<220> FEATURE:
<223> OTHER INFORMATION: primer

<400> SEQUENCE: 76
atacaccttc cggccagc                                             18

<210> SEQ ID NO 77
<211> LENGTH: 14
<212> TYPE: DNA
<213> ORGANISM: Artificial Sequence
<220> FEATURE:
<223> OTHER INFORMATION: probe

<400> SEQUENCE: 77
ttcctcccgg aagc                                                 14

<210> SEQ ID NO 78
<211> LENGTH: 24
<212> TYPE: DNA
<213> ORGANISM: Artificial Sequence
<220> FEATURE:
<223> OTHER INFORMATION: primer

<400> SEQUENCE: 78
gatagggcta aagagatgtg ggaa                                      24

<210> SEQ ID NO 79
<211> LENGTH: 26
<212> TYPE: DNA
<213> ORGANISM: Artificial Sequence
<220> FEATURE:
<223> OTHER INFORMATION: primer

<400> SEQUENCE: 79
ctttgttcac attagggctc aaataa                                    26

<210> SEQ ID NO 80
<211> LENGTH: 16
<212> TYPE: DNA
<213> ORGANISM: Artificial Sequence
<220> FEATURE:
<223> OTHER INFORMATION: probe
```

-continued

```
<400> SEQUENCE: 80
tagactgaga tggatg                                                16

<210> SEQ ID NO 81
<211> LENGTH: 20
<212> TYPE: DNA
<213> ORGANISM: Artificial Sequence
<220> FEATURE:
<223> OTHER INFORMATION: primer

<400> SEQUENCE: 81
aaaaccaccg gagaagacga                                            20

<210> SEQ ID NO 82
<211> LENGTH: 17
<212> TYPE: DNA
<213> ORGANISM: Artificial Sequence
<220> FEATURE:
<223> OTHER INFORMATION: primer

<400> SEQUENCE: 82
aggtgtggcg gcagtga                                               17

<210> SEQ ID NO 83
<211> LENGTH: 14
<212> TYPE: DNA
<213> ORGANISM: Artificial Sequence
<220> FEATURE:
<223> OTHER INFORMATION: probe

<400> SEQUENCE: 83
caccgtcatt gttc                                                  14

<210> SEQ ID NO 84
<211> LENGTH: 25
<212> TYPE: DNA
<213> ORGANISM: Artificial Sequence
<220> FEATURE:
<223> OTHER INFORMATION: primer

<400> SEQUENCE: 84
caagtttctg gacaaggaga ttctc                                      25

<210> SEQ ID NO 85
<211> LENGTH: 27
<212> TYPE: DNA
<213> ORGANISM: Artificial Sequence
<220> FEATURE:
<223> OTHER INFORMATION: primer

<400> SEQUENCE: 85
aagaattccc ttcttaatag ctggaga                                    27

<210> SEQ ID NO 86
<211> LENGTH: 26
<212> TYPE: DNA
<213> ORGANISM: Artificial Sequence
<220> FEATURE:
<223> OTHER INFORMATION: probe

<400> SEQUENCE: 86
cacgagcaca ttgctaacct tgctgg                                     26

<210> SEQ ID NO 87
```

```
<211> LENGTH: 15
<212> TYPE: DNA
<213> ORGANISM: Artificial Sequence
<220> FEATURE:
<223> OTHER INFORMATION: primer

<400> SEQUENCE: 87
gcgacgccgg aaagg                                                    15

<210> SEQ ID NO 88
<211> LENGTH: 21
<212> TYPE: DNA
<213> ORGANISM: Artificial Sequence
<220> FEATURE:
<223> OTHER INFORMATION: primer

<400> SEQUENCE: 88
tggcgtggtt tcgtcttctt a                                             21

<210> SEQ ID NO 89
<211> LENGTH: 25
<212> TYPE: DNA
<213> ORGANISM: Artificial Sequence
<220> FEATURE:
<223> OTHER INFORMATION: probe

<400> SEQUENCE: 89
aagagcggcg tctggaggtg actca                                         25

<210> SEQ ID NO 90
<211> LENGTH: 20
<212> TYPE: DNA
<213> ORGANISM: Artificial Sequence
<220> FEATURE:
<223> OTHER INFORMATION: primer

<400> SEQUENCE: 90
aaccgcatcg tcagaaaaac                                               20

<210> SEQ ID NO 91
<211> LENGTH: 20
<212> TYPE: DNA
<213> ORGANISM: Artificial Sequence
<220> FEATURE:
<223> OTHER INFORMATION: primer

<400> SEQUENCE: 91
tcaacttaac cggccaaatc                                               20

<210> SEQ ID NO 92
<211> LENGTH: 21
<212> TYPE: DNA
<213> ORGANISM: Artificial Sequence
<220> FEATURE:
<223> OTHER INFORMATION: primer

<400> SEQUENCE: 92
catcccttct cttccctcct g                                             21

<210> SEQ ID NO 93
<211> LENGTH: 23
<212> TYPE: DNA
<213> ORGANISM: Artificial Sequence
<220> FEATURE:
<223> OTHER INFORMATION: primer

<400> SEQUENCE: 93
```
gccagtgtga gtgtgtatga gca                                          23

<210> SEQ ID NO 94
<211> LENGTH: 21
<212> TYPE: DNA
<213> ORGANISM: Artificial Sequence
<220> FEATURE:
<223> OTHER INFORMATION: primer

<400> SEQUENCE: 94
catcgttttc tccctcctc a                                            21

<210> SEQ ID NO 95
<211> LENGTH: 19
<212> TYPE: DNA
<213> ORGANISM: Artificial Sequence
<220> FEATURE:
<223> OTHER INFORMATION: primer

<400> SEQUENCE: 95
actgatatgc acggcgcca                                              19

<210> SEQ ID NO 96
<211> LENGTH: 22
<212> TYPE: DNA
<213> ORGANISM: Artificial Sequence
<220> FEATURE:
<223> OTHER INFORMATION: primer

<400> SEQUENCE: 96
tgcagtagct tcattttcac cg                                          22

<210> SEQ ID NO 97
<211> LENGTH: 22
<212> TYPE: DNA
<213> ORGANISM: Artificial Sequence
<220> FEATURE:
<223> OTHER INFORMATION: primer

<400> SEQUENCE: 97
aggaattgat atgtacgccc gt                                          22

<210> SEQ ID NO 98
<211> LENGTH: 16279
<212> TYPE: DNA
<213> ORGANISM: Artificial Sequence
<220> FEATURE:
<223> OTHER INFORMATION: vector 24075
<220> FEATURE:
<221> NAME/KEY: misc_feature
<222> LOCATION: (1)..(517)
<223> OTHER INFORMATION: bNRB-07
<220> FEATURE:
<221> NAME/KEY: promoter
<222> LOCATION: (538)..(1697)
<223> OTHER INFORMATION: prAtEFaA1-02
<220> FEATURE:
<221> NAME/KEY: gene
<222> LOCATION: (1716)..(5885)
<223> OTHER INFORMATION: cCas9-05
<220> FEATURE:
<221> NAME/KEY: mutation
<222> LOCATION: (5205)..(5207)
<223> OTHER INFORMATION: L to V mutation
<220> FEATURE:
<221> NAME/KEY: mutation
<222> LOCATION: (5250)..(5252)
<223> OTHER INFORMATION: I to V mutation
<220> FEATURE:

```
<221> NAME/KEY: terminator
<222> LOCATION: (5894)..(6146)
<223> OTHER INFORMATION: tNOS-05-01
<220> FEATURE:
<221> NAME/KEY: promoter
<222> LOCATION: (6173)..(6620)
<223> OTHER INFORMATION: prAtU6-01
<220> FEATURE:
<221> NAME/KEY: misc_feature
<222> LOCATION: (6621)..(6640)
<223> OTHER INFORMATION: AtGL1 target1
<220> FEATURE:
<221> NAME/KEY: misc_feature
<222> LOCATION: (6621)..(6725)
<223> OTHER INFORMATION: rsgRNA AtGL1-01
<220> FEATURE:
<221> NAME/KEY: misc_feature
<222> LOCATION: (6641)..(6652)
<223> OTHER INFORMATION: rCrRNA-01
<220> FEATURE:
<221> NAME/KEY: misc_feature
<222> LOCATION: (6657)..(6725)
<223> OTHER INFORMATION: rTracrRNA-01
<220> FEATURE:
<221> NAME/KEY: promoter
<222> LOCATION: (6726)..(7173)
<223> OTHER INFORMATION: prAtU6-01
<220> FEATURE:
<221> NAME/KEY: misc_feature
<222> LOCATION: (7174)..(7193)
<223> OTHER INFORMATION: AtGl1 target 2
<220> FEATURE:
<221> NAME/KEY: misc_feature
<222> LOCATION: (7174)..(7278)
<223> OTHER INFORMATION: rsgRNA AtGL1-02
<220> FEATURE:
<221> NAME/KEY: misc_feature
<222> LOCATION: (7194)..(7205)
<223> OTHER INFORMATION: rCrRNA-01
<220> FEATURE:
<221> NAME/KEY: misc_feature
<222> LOCATION: (7210)..(7278)
<223> OTHER INFORMATION: rTracrRNA-01
<220> FEATURE:
<221> NAME/KEY: promoter
<222> LOCATION: (7295)..(7640)
<223> OTHER INFORMATION: prCMP-02
<220> FEATURE:
<221> NAME/KEY: gene
<222> LOCATION: (7653)..(8447)
<223> OTHER INFORMATION: cNpt2-10
<220> FEATURE:
<221> NAME/KEY: terminator
<222> LOCATION: (8476)..(8728)
<223> OTHER INFORMATION: tNOS-05-01
<220> FEATURE:
<221> NAME/KEY: promoter
<222> LOCATION: (8755)..(10752)
<223> OTHER INFORMATION: prGmUBI-01
<220> FEATURE:
<221> NAME/KEY: gene
<222> LOCATION: (10765)..(11454)
<223> OTHER INFORMATION: cAmCyan-06
<220> FEATURE:
<221> NAME/KEY: terminator
<222> LOCATION: (11477)..(12119)
<223> OTHER INFORMATION: tPsE9-01
<220> FEATURE:
<221> NAME/KEY: misc_feature
<222> LOCATION: (12193)..(12311)
<223> OTHER INFORMATION: bNLB-03
<220> FEATURE:
<221> NAME/KEY: gene
<222> LOCATION: (12928)..(13716)
<223> OTHER INFORMATION: cSpec-03
<220> FEATURE:
<221> NAME/KEY: gene
<222> LOCATION: (13751)..(14824)
<223> OTHER INFORMATION: cRepA-08
```

-continued

```
<220> FEATURE:
<221> NAME/KEY: misc_feature
<222> LOCATION: (14867)..(15271)
<223> OTHER INFORMATION: oVC1-04
<220> FEATURE:
<221> NAME/KEY: misc_feature
<222> LOCATION: (15441)..(16247)
<223> OTHER INFORMATION: oCOLE-06

<400> SEQUENCE: 98
gccaggacgt cggccgaaag agcgacaagc agatcacgct tttcgacagc gtcggatttg      60
cgatcgagga tttttcggcg ctgcgctacg tccgcgaccg cgttgaggga tcaagccaca     120
gcagcccact cgaccttcta gccgacccag acgagccaag ggatcttttt ggaatgctgc     180
tccgtcgtca ggctttccga cgtttgggtg gttgaacaga agtcattatc gcacggaatg     240
ccaagcactc ccgaggggaa ccctgtggtt ggcatgcaca tacaaatgga cgaacggata     300 aacctttttca cgcccttttta aatatccgat tattctaata aacgctcttt tctcttaggt     360
ttacccgcca atatatcctg tcaaacactg atagtttaaa ctgaaggcgg gaaacgacaa     420
tctgatcatg agcggagaat taagggagtc acgttatgac ccccgccgat gacgcgggac     480
aagccgtttt acgtttggaa ctgacagaac cgcaacgttg aaggcgcgcc actcagcaag     540
cttgatatcg gaagtttctc tcttgaggga ggttgctcgt ggaatgggac acatatggtt     600
gttataataa accatttcca ttgtcatgag attttgaggt taatatatac tttacttgtt     660
cattatttta tttggtgttt gaataaatga tataaatggc tcttgataat ctgcattcat     720
tgagatatca aatatttact ctagagaaga gtgtcatata gattgatggt ccacaatcaa     780
tgaaattttt gggagacgaa catgtataac catttgcttg aataaccttta attaaaaggt     840 gtgattaaat gatgtttgta acatgtagta ctaaacattc ataaaacaca accaacccaa     900
gaggtattga gtattcacgg ctaaacaggg gcataatggt aatttaaaga atgatattat     960
tttatgttaa accctaacat tggtttcgga ttcaacgcta taaataaaac cactctcgtt    1020
gctgattcca tttatcgttc ttattgaccc tagccgctac acacttttct gcgatatctc    1080
tgaggtaagc gttaacgtac ccttagatcg ttcttttttct ttttcgtctg ctgatcgttg    1140
ctcatattat ttcgatgatt gttggattcg atgctctttg ttgattgatc gttctgaaaa    1200
ttctgatctg ttgtttagat tttatcgatt gttaatatca acgtttcact gcttctaaac    1260
gataatttat tcatgaaact attttcccat tctgatcgat cttgttttga gattttaatt    1320
tgttcgattg attgttggtt ggtggatcta tatacgagtg aacttgttga tttgcgtatt    1380
taagatgtat gtcgatttga attgtgattg ggtaattctg gagtagcata acaaatccag    1440
tgttcccttt ttctaagggt aattctcgga ttgtttgctt tatatctctt gaaattgccg    1500
atttgattga atttagctcg cttagctcag atgatagagc accacaattt ttgtggtaga    1560
aatcggtttg actccgatag cggcttttta ctatgattgt tttgtgttaa agatgatttt    1620
cataatggtt atatatgtct actgttttta ttgattcaat atttgattgt tctttttttt    1680
gcagatttgt tgaccaggga tccgcggccg ctaaaatgga taagaagtat tctattggac    1740
ttgatattgg aaccaactct gtgggatggg ctgttattac tgacgagtat aaggttccat    1800
ctaagaagtt caaggttctt ggaaacactg atagacactc tattaagaag aaccttattg    1860
gtgctcttct tttcgattct ggagagactg ctgaggctac tagacttaag agaactgcta    1920
gaagaagata tactagaaga aagaacagaa tttgctatct tcaagagatt ttctctaacg    1980
agatggctaa ggttgacgat tctttcttcc acagacttga ggagtctttc cttgttgagg    2040
```

-continued

```
aggataagaa gcacgagaga cacccaattt tcggaaacat tgttgacgag gttgcttatc      2100
acgagaagta tccaactatt tatcacctta gaaagaagct cgttgattct actgataagg      2160
ctgatcttag acttatttat cttgctcttg ctcacatgat taagttcaga ggacacttcc      2220
ttattgaggg agatcttaac ccagataact ctgacgttga taagctcttc attcaacttg      2280
ttcaaactta taaccaactt ttcgaggaga acccaattaa cgcttctgga gttgacgcta      2340
aggctattct ttctgctaga ctttctaagt ctagaaggct tgagaacctt attgctcaac      2400
ttccaggaga gaagaagaac ggactttctcg gaaaccttat tgctctttct cttggactta      2460
ctccaaactt caagtctaac ttcgatcttg ctgaggacgc taagctccaa ctttctaagg      2520
atacttacga cgatgatctt gataaccttc ttgctcaaat tggagatcaa tacgctgatc      2580
ttttccttgc tgctaagaac ctttctgacg ctattcttct ttctgatatt cttagagtta      2640
acactgagat tactaaggct ccactttctg cttctatgat taagagatac gacgagcacc      2700
accaagatct tactcttctt aaggctcttg ttagacaaca acttccagag aagtataagg      2760
agattttctt cgatcaatct aagaacggat acgctggata tattgacgga ggagcttctc      2820
aagaggagtt ctataagttc attaagccaa ttcttgagaa gatggacgga actgaggagc      2880
ttcttgttaa gctcaacaga gaggatcttc ttagaaagca aagaactttc gataacggat      2940
ctattccaca ccaaattcac cttggagagc ttcacgctat tcttagaagg caagaggatt      3000
tctatccatt ccttaaggat aacagagaga agattgagaa gattcttact ttccgtattc      3060
catattacgt tggaccactt gctagaggaa actctagatt cgcttggatg actagaaagt      3120
ctgaggagac tattactcct tggaacttcg aggaggttgt tgataaggga gcttctgctc      3180
aatctttcat tgagagaatg actaacttcg ataagaacct tccaaacgag aaggttcttc      3240
caaagcactc tcttctttac gagtatttca ctgtttataa cgagcttact aaggttaagt      3300
acgttactga gggaatgaga aagccagctt tcctttctgg agagcaaaag aaggctattg      3360
ttgatcttct tttcaagact aacagaaagg ttactgttaa gcaacttaag gaggattatt      3420
tcaagaagat tgagtgcttc gattctgttg agatttctgg agttgaggat agattcaacg      3480
cttctcttgg aacttatcac gatcttctta agattattaa ggataaggat ttccttgata      3540
acgaggagaa cgaggatatt cttgaggata ttgttcttac tcttactctt ttcgaggata      3600
gagagatgat tgaggagaga cttaagacttc acgctcacct tttcgacgat aaggttatga      3660
agcaacttaa gagaagaaga tatactggat ggggtagact ttctagaaag ctcattaacg      3720
gaattagaga taagcaatct ggaaagacta ttcttgattt ccttaagtct gacggattcg      3780
ctaacagaaa cttcatgcaa cttattcacg acgattctct tactttcaag gaggatattc      3840
aaaaggctca agtttctgga caaggagatt ctcttcacga gcacattgct aaccttgctg      3900
gatctccagc tattaagaag ggaattcttc aaactgttaa ggttgttgac gagcttgtta      3960
aggttatggg tagacacaag ccagagaaca ttgttattga tggctagaga gagaaccaaa      4020
ctactcaaaa gggacaaaag aactctagag agagaatgaa gagaattgag gagggaatta      4080
aggagcttgg atctcaaatt cttaaggagc acccagttga gaacactcaa cttcaaaacg      4140
agaagctcta tctttattat cttcaaaacg gaagagatat gtacgttgat caagagcttg      4200
atattaacag actttctgat tacgacgttg atcacattgt tccacaatct ttccttaagg      4260
acgattctat tgataacaag gttcttacta gatctgataa gaacagagga aagtctgata      4320
acgttccatc tgaggaggtt gttaagagag tgaagaacta ttggagacaa cttcttaacg      4380
ctaagctcat tactcaaaga aagttcgata accttactaa ggctgagaga ggaggacttt      4440
```

```
ctgagcttga taaggctgga ttcattaaga gacaacttgt tgagactaga caaattacta    4500
agcacgttgc tcaaattctt gattctagaa tgaacactaa gtacgacgag aacgataagc    4560
tcattagaga ggttaaggtt attactctta agtctaagct cgtttctgat ttcagaaagg    4620
atttccaatt ctataaggtt agagagatta acaactatca ccacgctcac gacgcttatc    4680
ttaacgctgt tgttggaact gctcttatta agaagtatcc aaaacttgag tctgagttcg    4740
tttacggaga ttataaggtt tacgacgtta gaaagatgat tgctaagtct gagcaagaga    4800
ttggaaaggc tactgctaag tatttcttct attctaacat tatgaacttc ttcaagactg    4860
agattactct tgctaacgga gagattagaa agaggccact tattgagact aacggagaga    4920
ctggagagat tgtttgggat aagggaagag atttcgctac tgttagaaag gttctttcta    4980
tgccacaagt taacattgtt aagaaaactg aggttcaaac tggaggattc tctaaggagt    5040
ctattcttcc aaagagaaac tctgataagc tcattgctag aaagaaggat tgggacccaa    5100
agaagtacgg aggattcgat tctccaactg ttgcttattc tgttcttgtt gttgctaagg    5160
ttgagaaggg aaagtctaag aagctcaagt ctgttaagga gcttgttgga attactatta    5220
tggagagatc ttctttcgag aagaacccag ttgatttcct tgaggctaag ggatataagg    5280
aggttaagaa ggatcttatt attaagctcc caaagtattc tcttttcgag cttgagaacg    5340
gaagaaagag aatgcttgct tctgctggag agcttcaaaa gggaaacgag cttgctcttc    5400
catctaagta cgttaacttc ctttatcttg cttctcacta cgagaagctc aagggatctc    5460
cagaggataa cgagcaaaag caacttttcg ttgagcaaca caagcactat cttgacgaga    5520
ttattgagca aatttctgag ttctctaaga gagttattct tgctgacgct aaccttgata    5580
aggttctttc tgcttataac aagcacagag ataagccaat tagagagcaa gctgagaaca    5640
ttattcacct tttcactctt actaaccttg gtgctccagc tgctttcaag tatttcgata    5700
ctactattga tagaaagaga tatacttcta ctaaggaggt tcttgacgct actcttattc    5760
accaatctat tactggactt tacgagacta gaattgatct ttctcaactt ggaggagatt    5820
cttctccacc aaagaagaag agaaaggttt cttggaagga cgcttctgga tggtctagaa    5880
tgtgacgtcg cgtgatcgtt caaacatttg gcaataaagt ttcttaagat tgaatcctgt    5940
tgccggtctt gcgatgatta tcatataatt tctgttgaat tacgttaagc atgtaataat    6000
taacatgtaa tgcatgacgt tatttatgag atgggttttt atgattagag tcccgcaatt    6060
atacatttaa tacgcgatag aaaacaaaat atagcgcgca aactaggata aattatcgcg    6120
cgcggtgtca tctatgttac tagatctgca gatcggaccc ctaattagct aaaagcttcg    6180
ttgaacaacg gaaactcgac ttgccttccg cacaatacat catttcttct tagctttttt    6240
tcttcttctt cgttcataca gttttttttt gtttatcagc ttacattttc ttgaaccgta    6300
gctttcgttt tcttcttttt aactttccat tcggagtttt tgtatcttgt ttcatagttt    6360
gtcccaggat tagaatgatt aggcatcgaa ccttcaagaa tttgattgaa taaaacatct    6420
tcattcttaa gatatgaaga taatcttcaa aaggcccctg ggaatctgaa agaagagaag    6480
caggcccatt tatatgggaa agaacaatag tatttcttat ataggcccat ttaagttgaa    6540
aacaatcttc aaaagtccca catcgcttag ataagaaaac gaagctgagt ttatatacag    6600
ctagagtcga gtagtgatt ggaaaagttg tagactgaga gttttagagc tagaaatagc    6660
aagttaaaat aaggctagtc cgttatcaac ttgaaaaagt ggcaccgagt cggtgctttt    6720
tttttaagct tcgttgaaca acggaaactc gacttgcctt ccgcacaata catcatttct    6780
```

-continued

```
tcttagcttt ttttcttctt cttcgttcat acagtttttt tttgtttatc agcttacatt   6840
ttcttgaacc gtagctttcg ttttcttctt tttaactttc cattcggagt ttttgtatct   6900
tgtttcatag tttgtcccag gattagaatg attaggcatc gaaccttcaa gaatttgatt   6960
gaataaaaca tcttcattct taagatatga agataatctt caaaaggccc ctgggaatct   7020
gaaagaagag aagcaggccc atttatatgg gaaagaacaa tagtatttct tatataggcc   7080
catttaagtt gaaaacaatc ttcaaaagtc ccacatcgct tagataagaa aacgaagctg   7140
agtttatata cagctagagt cgaagtagtg attgcagtga tgaacaatga cgggttttag   7200
agctagaaat agcaagttaa aataaggcta gtccgttatc aacttgaaaa agtggcaccg   7260
agtcggtgct ttttttttgg cgcgcctaaa gcttctggca gacaaagtgg cagacatact   7320
gtcccacaaa tgaagatgga atctgtaaaa gaaaacgcgt gaaataatgc gtctgacaaa   7380
ggttaggtcg gctgccttta atcaatacca aagtggtccc taccacgatg gaaaaactgt   7440
gcagtcggtt tggcttttc tgacgaacaa ataagattcg tggccgacag gtgggggtcc   7500
accatgtgaa ggcatcttca gactccaata atggagcaat gacgtaaggg cttacgaaat   7560
aagtaagggt agtttgggaa atgtccactc acccgtcagt ctataaatac ttagcccctc   7620
cctcattgtt aagggagcaa ggatcctaaa ccatgattga acaagatgga ttgcacgcag   7680
gttctccggc cgcttgggtg gagaggctat tcggctatga ctgggcacaa cagacaatcg   7740
gctgctctga tgccgccgtg ttccggctgt cagcgcaggg gcgcccggtt cttttttgtca   7800 agaccgacct gtccggtgcc ctgaatgaac tgcaggacga ggcagcgcgg ctatcgtggc   7860
tggccacgac gggcgttcct tgcgcagctg tgctcgacgt tgtcactgaa gcgggaaggg   7920
actggctgct attgggcgaa gtgccggggc aggatctcct gtcatctcac cttgctcctg   7980
ccgagaaagt atccatcatg gctgatgcaa tgcggcggct gcatacgctt gatccggcta   8040
cctgcccatt cgaccaccaa gcgaaacatc gcatcgagcg agcacgtact cggatggaag   8100
ccggtcttgt cgatcaggat gatctggacg aagagcatca ggggctcgcg ccagccgaac   8160
tgttcgccag gctcaaggcg cgcatgcccg acggcgagga tctcgtcgtg acccatggcg   8220
atgcctgctt gccgaatatc atggtggaaa atggccgctt ttctggattc atcgactgtg   8280
gccggctggg tgtggcggac cgctatcagg acatagcgtt ggctacccgt gatattgctg   8340
aagagcttgg cggcgaatgg gctgaccgct tcctcgtgct ttacggtatc gccgctcccg   8400
attcgcagcg catcgccttc tatcgccttc ttgacgagtt cttctgatga gagctctaga   8460
tccccgaatt tccccgatcg ttcaaacatt tggcaataaa gtttcttaag attgaatcct   8520
gttgccggtc ttgcgatgat tatcatataa tttctgttga attacgttaa gcatgtaata   8580
attaacatgt aatgcatgac gttatttatg agatgggttt ttatgattag agtcccgcaa   8640
ttatacattt aatacgcgat agaaaacaaa atatagcgcg caaactagga taaattatcg   8700
cgcgcggtgt catctatgtt actagatcgg gaattgggta ccctaattag ctaaattcca   8760
aaattttcag ttagtcctta ctaattatta aattatagta ttaatccaat gtgattgcgg   8820
ttacatcatg tacggaaaaa taattctaat ccttgattta aatttgatct tgactatta   8880 tttattcttt atttcatttt gtaaatcatt ttatgtatct cctggcaagc aattttatcc   8940
accttgcacc aacaccttcg ggttccataa tcaaaccacc ttaacttcac accatgctgt   9000
aactcacacc gcccagcatc tccaatgtga aagaagctaa aatttaataa acaatcatac   9060
gaagcagtga caaaatacca gatggtatta atgctttgat aaaattaatt ggaaagtata   9120
aaatggtaga aaataataaa ttataattaa tttaaataag ataaaaaata attaaaaact   9180
```

```
aaaatgttaa aattttaaaa aaattatttt aaataatatt taaaaacatt aaaaatcatt    9240
ttaaaaaatt tatttataga acaattaaat aaatatttca gctaataaaa aacaaaagct    9300
tacctagcct tagaagacaa cttgtccaac aattagatga tacccattgc ccttacgttt    9360
tctttaacat caattattgt ttttgtcaac aagctatctt ttagtttta tttattggta    9420 aaaaatatgt cgccttcaag ttgcatcatt taacacatct cgtcattaga aaaataaaac    9480
tcttccctaa acgattagta gaaaaaatca ttcgataata aataagaaag aaaaattaga    9540
aaaaaataac ttcattttaa aaaaatcatt aaggctatat tttttaaatg actaattta    9600 tatagactgt aactaaaagt atacaattta ttatgctatg tatcttaaag aattacttat    9660
aaaaatctac ggaagaatat cttacaaagt gaaaaacaaa tgagaaagaa tttagtggga    9720
tgattatgat tttatttgaa aattgaaaaa ataattatta aagactttag tggagtaaga    9780
aagctttcct attagtcttt tcttatccat aaaaaaaaaa aaaaatctag cgtgacagct    9840
tttccataga ttttaataat gtaaaatact ggtagcagcc gaccgttcag gtaatggaca    9900
ctgtggtcct aacttgcaac gggtgcgggc ccaatttaat aacgccgtgg taacggataa    9960
agccaagcgt gaagcggtga aggtacatct ctgactccgt caagattacg aaaccgtcaa   10020
ctacgaagga ctccccgaaa tatcatctgt gtcataaaca ccaagtcaca ccatacatgg   10080
gcacgcgtca caatatgatt ggagaacggt tccaccgcat atgctataaa atgccccac    10140 accCctcgac cctaatcgca cttcaattgc aatcaaatta gttcattctc tttgcgcagt   10200
tccctacctc tcctttcaag gttcgtagat ttcttctgtt ttttttttctt cttctttatt   10260 gtttgttcta catcagcatg atgttgattt gattgtgttt tctatcgttt catcgattat   10320
aaattttcat aatcagaaga ttcagctttt attaatgcaa gaacgtcctt aattgatgat   10380
tttataaccg taaattaggt ctaattagag tttttttcat aaagattttc agatccgttt   10440
acaacaagcc ttaattgttg attctgtagt cgtagattaa ggttttttttc atgaactact   10500 tcagatccgt taaacaacag ccttatttgt tgatacttca gtcgtttttc aagaaattgt   10560
tcagatccgt tgataaaagc cttattcgtt gattctgtat ggtatttcaa gagatattgc   10620
tcaggtcctt tagcaactac cttatttgtt gattctgtgg ccatagatta ggattttttt   10680
tcacgaaatt gcttcttgaa attacgtgat ggattttgat tctgatttat cttgtgattg   10740
ttgactctac agagatctaa aaaaatggcc ctgtccaaca agttcatcgg cgacgacatg   10800
aagatgacct accacatgga cggctgcgtg aacggccact acttcaccgt gaagggcgag   10860
ggcagcggca agccctacga gggcacccag acctccacct tcaaggtgac gatggccaac   10920
ggcggccccc tggccttctc cttcgacatc ctgtccaccg tgttcatgta cggcaaccgc   10980
tgcttcaccg cctaccccac cagcatgccc gactacttca gcaggccctt ccccgacggc   11040
atgtcctacg agagaacctt cacctacgag gacggcggcg tggccaccgc cagctgggag   11100
atcagcctga agggcaactg cttcgagcac aagtccacct ccacggcgt gaacttcccc   11160 gccgacggcc ccgtgatggc caagaagacc accggctggg atccctcctt cgagaagatg   11220
accgtgtgcg acggcatctt gaagggcgac gtgaccgcct tcctgatgct gcagggcggc   11280
ggcaactaca gatgccagtt ccacacctcc tacaagacca agaagcccgt gaccatgccc   11340
cccaaccacg tggtggagca ccgcatcgcc agaaccgacc tggacaaggg cggcaacagc   11400
gtgcagctga ccgagcacgc cgtggcccac atcacctccg tggtgccctt ctgatgaact   11460
agtgaattcg agctcaagct ttcgttcgta tcatcggttt cgacaacgtt cgtcaagttc   11520
```

```
aatgcatcag tttcattgcg cacacaccag aatcctactg agtttgagta ttatggcatt   11580
gggaaaactg ttttctttgt accatttgtt gtgcttgtaa tttactgtgt tttttattcg   11640
gttttcgcta tcgaactgtg aaatggaaat ggatggagaa gagttaatga atgatatggt   11700
ccttttgttc attctcaaat taatattatt tgtttttttct cttatttgtt gtgtgttgaa   11760
tttgaaatta taagagatat gcaaacattt tgttttgagt aaaaatgtgt caaatcgtgg   11820
cctctaatga ccgaagttaa tatgaggagt aaaacacttg tagttgtacc attatgctta   11880
ttcactaggc aacaaatata ttttcagacc tagaaaagct gcaaatgtta ctgaatacaa   11940
gtatgtcctc ttgtgtttta gacatttatg aactttcctt tatgtaattt tccagaatcc   12000
ttgtcagatt ctaatcattg ctttataatt atagttatac tcatggattt gtagttgagt   12060
atgaaaatat tttttaatgc attttatgac ttgccaattg attgacaaca tgcatcaatc   12120
ggaccgttaa ctagctagac ggccaggatc gccgcgtgag cctttagcaa ctagctagat   12180
taattaaacg tccgcaatgt gttattaagt tgtctaagcg tcaatttgtt tacaccacaa   12240
tatatcctgc caccagccag ccaacagctc cccgaccggc agctcggcac aaaatcacca   12300
ctcgatacag gcagcccatc agtccgggac ggcgtcagcg ggagagccgt tgtaaggcgg   12360
cagactttgc tcatgttacc gatgctattc ggaagaacgg caactaagct gccgggtttg   12420
aaacacggat gatctcgcgg agggtagcat gttgattgta acgatgacag agcgttgctg   12480
cctgtgatca aatatcatct ccctcgcaga gatccgaatt atcagccttc ttattcattt   12540
ctcgcttaac cgtgacaggc tgtcgatctt gagaactatg ccgacataat aggaaatcgc   12600
tggataaagc cgctgaggaa gctgagtggc gctatttctt tagaagtgaa cgtcgactca   12660
tgtttgacag cttatcatcg actgcacggt gcaccaatgc ttctggcgtc aggcagccat   12720
cggaagctgt ggtatggctg tgcaggtcgt aaatcactgc ataattcgtg tcgctcaagg   12780
cgcactcccg ttctggataa tgtttttttgc gccgacatca taacggttct ggcaaatatt   12840
ctgaaatgag ctgttgacaa ttaatcatcc ggctcgtata atgtgtggaa ttgtgagcgg   12900
ataacaattt cacacaggaa acagaccatg agggaagcgt tgatcgccga agtatcgact   12960
caactatcag aggtagttgg cgtcatcgag cgccatctcg aaccgacgtt gctggccgta   13020
catttgtacg gctccgcagt ggatggcggc ctgaagccac acagtgatat tgatttgctg   13080
gttacggtga ccgtaaggct tgatgaaaca acgcggcgag ctttgatcaa cgaccttttg   13140
gaaacttcgg cttcccctgg agagagcgag attctccgcg ctgtagaagt caccattgtt   13200
gtgcacgacg acatcattcc gtggcgttat ccagctaagc gcgaactgca atttggagaa   13260
tggcagcgca atgacattct tgcaggtatc ttcgagccag ccacgatcga cattgatctg   13320
gctatcttgc tgacaaaagc aagagaacat agcgttgcct tggtaggtcc agcggcggag   13380
gaactctttg atccggttcc tgaacaggat ctatttgagg cgctaaatga aaccttaacg   13440
ctatggaact cgccgcccga ctgggctggc gatgagcgaa atgtagtgct tacgttgtcc   13500
cgcatttggt acagcgcagt aaccggcaaa atcgcgccga aggatgtcgc tgccgactgg   13560
gcaatggagc gcctgccggc ccagtatcag cccgtcatac ttgaagctag gcaggcttat   13620
cttggacaag aagatcgctt ggcctcgcgc gcagatcagt tggaagaatt tgttcactac   13680
gtgaaaggcg agatcaccaa agtagtcggc aaataaagct ctagtggatc tccgtacccg   13740
aggaatcggc gtgagcggtc gcaaaccatc cggcccggta caaatcggcg cggcgctggg   13800
tgatgacctg gtggagaagt tgaaggccgc gcaggccgcc cagcggcaac gcatcgaggc   13860
agaagcacgc cccggtgaat cgtggcaagc ggccgctgat cgaatccgca aagaatcccg   13920
```

-continued

```
gcaaccgccg gcagccggtg cgccgtcgat taggaagccg cccaagggcg acgagcaacc   13980
agattttttc gttccgatgc tctatgacgt gggcacccgc gatagtcgca gcatcatgga   14040
cgtggccgtt ttccgtctgt cgaagcgtga ccgacgagct ggcgaggtga tccgctacga   14100
gcttccagac gggcacgtag aggtttccgc agggccggcc ggcatggcca gtgtgtggga   14160
ttacgacctg gtactgatgg cggtttccca tctaaccgaa tccatgaacc gataccggga   14220
agggaaggga gacaagcccg gccgcgtgtt ccgtccacac gttgcggacg tactcaagtt   14280
ctgccggcga gccgatggcg gaaagcagaa agacgacctg gtagaaacct gcattcggtt   14340
aaacaccacg cacgttgcca tgcagcgtac caagaaggcc aagaacggcc gcctggtgac   14400
ggtatccgag ggtgaagcct tgattagccg ctacaagatc gtaaagagcg aaaccgggcg   14460
gccggagtac atcgagatcg agctggctga ttggatgtac cgcgagatca cagaaggcaa   14520
gaacccggac gtgctgacgg ttcaccccga ttactttttg atcgatcccg gcatcggccg   14580
ttttctctac cgcctggcac gccgcgccgc aggcaaggca gaagccagat ggttgttcaa   14640
gacgatctac gaacgcagtg gcagcgccgg agagttcaag aagttctgtt tcaccgtgcg   14700
caagctgatc gggtcaaatg acctgccgga gtacgatttg aaggaggagg cggggcaggc   14760
tggcccgatc ctagtcatgc gctaccgcaa cctgatcgag ggcgaagcat ccgccggttc   14820
ctaatgtacg gagcagatgc tagggcaaat tgccctagca ggggaaaaag gtcgaaaagg   14880
actctttcct gtggatagca cgtacattgg gaacccaaag ccgtacattg ggaaccggaa   14940
cccgtacatt gggaacccaa agccgtacat tgggaaccgg acacacatgt aagtgactga   15000
tataaaagag aaaaaaggcg attttttccgc ctaaaactct ttaaaactta ttaaaactct   15060
taaaacccgc ctggcctgtg cataactgtc tggccagcgc acagccgaag agctgcaaaa   15120
agcgcctacc cttcggtcgc tgcgctccct acgccccgcc gcttcgcgtc ggcctatcgc   15180
ggccgctggc cgctcaaaaa tggctggcct acggccaggc aatctaccag ggcgcggaca   15240
agccgcgccg tcgccactcg accgccggcg ctgaggtctg cctcgtgaag aaggtgttgc   15300
tgactcatac caggccatta atgaatcggc caacgcgcgg ggagaggcgg tttgcgtatt   15360
gggcgctctt ccgcttcctc gctcactgac tcgctgcgct cggtcgttcg gctgcggcga   15420
gcggtatcag ctcactcaaa ggcggtaata cggttatcca cagaatcagg ggataacgca   15480
ggaaagaaca tgtgagcaaa aggccagcaa aaggccagga accgtaaaaa ggccgcgttg   15540
ctggcgtttt tccataggct ccgcccccct gacgagcatc acaaaaatcg acgctcaagt   15600
cagaggtggc gaaacccgac aggactataa agataccagg cgtttccccc tggaagctcc   15660
ctcgtgcgct ctcctgttcc gaccctgccg cttaccggat acctgtccgc ctttctccct   15720
tcgggaagcg tggcgctttc tcatagctca cgctgtaggt atctcagttc ggtgtaggtc   15780
gttcgctcca agctgggctg tgtgcacgaa ccccccgttc agcccgaccg ctgcgcctta   15840
tccggtaact atcgtcttga gtccaacccg gtaagacacg acttatcgcc actggcagca   15900
gccactggta acaggattag cagagcgagg tatgtaggcg gtgctacaga gttcttgaag   15960
tggtggccta actacggcta cactagaaga acagtatttg gtatctgcgc tctgctgaag   16020
ccagttacct tcggaaaaag agttggtagc tcttgatccg gcaaacaaac caccgctggt   16080
agcggtggtt tttttgtttg caagcagcag attacgcgca gaaaaaaagg atctcaagaa   16140
gatcctttga tcttttctac ggggtctgac gctcagtgga acgaaaactc acgttaaggg   16200
attttggtca tgagattatc aaaaaggatc ttcacctaga tccttttgat ccggacaaac   16260
```

-continued

```
aaacaaatac agtaattta                                              16279

<210> SEQ ID NO 99
<211> LENGTH: 100
<212> TYPE: DNA
<213> ORGANISM: Zea mays

<400> SEQUENCE: 99
aagctgcgca agctcatcct cgaggccaag ctcgcgccct gctacccggg cgccgacgac    60
gccgcgcccg gcggagggga cctcgaggag tgccccatct                         100

<210> SEQ ID NO 100
<211> LENGTH: 100
<212> TYPE: DNA
<213> ORGANISM: Zea mays

<400> SEQUENCE: 100
agatggggca ctcctcgagg tcccctccgc cgggcgcggc gtcgtcggcg cccgggtagc    60
agggcgcgag cttggcctcg aggatgagct tgcgcagctt                         100

<210> SEQ ID NO 101
<211> LENGTH: 420
<212> TYPE: DNA
<213> ORGANISM: Triticum aestivum
<220> FEATURE:
<221> NAME/KEY: misc_feature
<222> LOCATION: (15)..(15)
<223> OTHER INFORMATION: n is a, c, g, or t

<400> SEQUENCE: 101
ctcatcgagt gttcnccgca atgcgctgtt gctgattctc aagtgcgtgt gggtgcaggt    60
ggagagcaga agaaggccgg ccggcagcgg cggaggagga gggcgaggca ggcagcggca    120
ggcgaaggcg cgggagggga cgatgcggcg aagaaacgcc ggctgagtga cgagcaggcg    180
cagttcctgg agatgagctt caggaaggaa cgtaaactgg aaacgccccg caaggtgcag    240
ctcgccgcgg agctgggcct ggacaccaag caggtcgcgg tgtggttcca gaaccgccgc    300
gcccgctaca agagcaagct catcgaggag gagttctcca agctccgcgc ggcacacgac    360
gccgtcgtcg tccacaactg ccacctcgag gccgaggtac agtgcaacag tccggctgcc    420

<210> SEQ ID NO 102
<211> LENGTH: 23
<212> TYPE: DNA
<213> ORGANISM: Artificial Sequence
<220> FEATURE:
<223> OTHER INFORMATION: gRNA target sequence

<400> SEQUENCE: 102
ggaaaagttg tagactgaga tgg                                          23

<210> SEQ ID NO 103
<211> LENGTH: 85
<212> TYPE: DNA
<213> ORGANISM: Arabidopsis thaliana

<400> SEQUENCE: 103
taaatttgat tcgttgatag ggctaaagag atgtgggaaa agttgtagac tgagatggat    60
gaattatttg agccctaatg tgaac                                        85

<210> SEQ ID NO 104
<211> LENGTH: 84
```

```
<212> TYPE: DNA
<213> ORGANISM: Arabidopsis thaliana

<400> SEQUENCE: 104
taaatttgat tcgttgatag ggctaaagag atgtgggaaa agttgtagac tagatggatg      60
aattatttga gccctaatgt gaac                                              84

<210> SEQ ID NO 105
<211> LENGTH: 86
<212> TYPE: DNA
<213> ORGANISM: Arabidopsis thaliana

<400> SEQUENCE: 105
taaatttgat tcgttgatag ggctaaagag atgtgggaaa agttgtagac tgtagatgga      60
tgaattattt gagccctaat gtgaac                                            86

<210> SEQ ID NO 106
<211> LENGTH: 85
<212> TYPE: DNA
<213> ORGANISM: Arabidopsis thaliana

<400> SEQUENCE: 106
taaatttgat tcgttgatag ggctaaagag atgtgggaaa agttgtagac tgagatggat      60
gaattatttg agccctaatg tgaac                                             85

<210> SEQ ID NO 107
<211> LENGTH: 86
<212> TYPE: DNA
<213> ORGANISM: Arabidopsis thaliana

<400> SEQUENCE: 107
taaatttgat tcgttgatag ggctaaagag atgtgggaaa agttgtagac tgaagatgga      60
tgaattattt gagccctaat gtgaac                                            86

<210> SEQ ID NO 108
<211> LENGTH: 86
<212> TYPE: DNA
<213> ORGANISM: Arabidopsis thaliana

<400> SEQUENCE: 108
taaatttgat tcgttgatag ggctaaagag atgtgggaaa agttgtagac tgtagatgga      60
tgaattattt gagccctaat gtgaac                                            86

<210> SEQ ID NO 109
<211> LENGTH: 82
<212> TYPE: DNA
<213> ORGANISM: Arabidopsis thaliana

<400> SEQUENCE: 109
taaatttgat tcgttgatag ggctaaagag atgtgggaaa agttgtagaa gatggatgaa      60
ttatttgagc cctaatgtga ac                                                82

<210> SEQ ID NO 110
<211> LENGTH: 86
<212> TYPE: DNA
<213> ORGANISM: Arabidopsis thaliana

<400> SEQUENCE: 110
taaatttgat tcgttgatag ggctaaagag atgtgggaaa agttgtagac tgaagatgga      60
```

-continued

```
tgaattattt gagccctaat gtgaac                                           86

<210> SEQ ID NO 111
<211> LENGTH: 84
<212> TYPE: DNA
<213> ORGANISM: Arabidopsis thaliana

<400> SEQUENCE: 111
taaatttgat tcgttgatag ggctaaagag atgtgggaaa agttgtagac tagatggatg      60
aattatttga gccctaatgt gaac                                             84

<210> SEQ ID NO 112
<211> LENGTH: 83
<212> TYPE: DNA
<213> ORGANISM: Arabidopsis thaliana

<400> SEQUENCE: 112
taaatttgat tcgttgatag ggctaaagag atgtgggaaa agttgtagac tgatggatga      60
attatttgag ccctaatgtg aac                                              83

<210> SEQ ID NO 113
<211> LENGTH: 83
<212> TYPE: DNA
<213> ORGANISM: Arabidopsis thaliana

<400> SEQUENCE: 113
taaatttgat tcgttgatag ggctaaagag atgtgggaaa agttgtagac agatggatga      60
attatttgag ccctaatgtg aac                                              83

<210> SEQ ID NO 114
<211> LENGTH: 86
<212> TYPE: DNA
<213> ORGANISM: Arabidopsis thaliana

<400> SEQUENCE: 114
taaatttgat tcgttgatag ggctaaagag atgtgggaaa agttgtagac tgtagatgga      60
tgaattattt gagccctaat gtgaac                                           86

<210> SEQ ID NO 115
<211> LENGTH: 86
<212> TYPE: DNA
<213> ORGANISM: Arabidopsis thaliana

<400> SEQUENCE: 115
taaatttgat tcgttgatag ggctaaagag atgtgggaaa agttgtagac tgaagatgga      60
tgaattattt gagccctaat gtgaac                                           86

<210> SEQ ID NO 116
<211> LENGTH: 86
<212> TYPE: DNA
<213> ORGANISM: Arabidopsis thaliana

<400> SEQUENCE: 116
taaatttgat tcgttgatag ggctaaagag atgtgggaaa agttgtagac tgtagatgga      60
tgaattattt gagccctaat gtgaac                                           86

<210> SEQ ID NO 117
<211> LENGTH: 78
<212> TYPE: DNA
<213> ORGANISM: Arabidopsis thaliana
```

<400> SEQUENCE: 117
taaatttgat tcgttgatag ggctaaagag atgtgggcta aacatagatg gatgaattat    60
ttgagcccta atgtgaac                                                  78

<210> SEQ ID NO 118
<211> LENGTH: 432
<212> TYPE: PRT
<213> ORGANISM: Oryza sativa

<400> SEQUENCE: 118

Met Ala Ala Ser Tyr Ser Cys Arg Arg Thr Cys Glu Ala Cys Ser Thr
1               5                   10                  15

Arg Ala Met Ala Gly Cys Val Val Gly Glu Pro Ala Ser Ala Pro Gly
            20                  25                  30

Gln Arg Val Thr Leu Leu Ala Ile Asp Gly Gly Gly Ile Arg Gly Leu
        35                  40                  45

Ile Pro Gly Thr Ile Leu Ala Phe Leu Glu Ala Arg Leu Gln Glu Leu
    50                  55                  60

Asp Gly Pro Asp Ala Arg Leu Ala Asp Tyr Phe Asp Cys Ile Ala Gly
65                  70                  75                  80

Thr Ser Thr Gly Gly Leu Ile Thr Ala Met Leu Ala Ala Pro Gly Asp
                85                  90                  95

His Gly Arg Pro Leu Phe Ala Ala Ser Asp Ile Asn Arg Phe Tyr Leu
            100                 105                 110

Asp Asn Gly Pro Leu Ile Phe Pro Gln Lys Arg Cys Gly Met Ala Ala
        115                 120                 125

Ala Met Ala Ala Leu Thr Arg Pro Arg Tyr Asn Gly Lys Tyr Leu Gln
    130                 135                 140

Gly Lys Ile Arg Lys Met Leu Gly Glu Thr Arg Val Arg Asp Thr Leu
145                 150                 155                 160

Thr Asn Val Val Ile Pro Thr Phe Asp Val Arg Leu Leu Gln Pro Thr
                165                 170                 175

Ile Phe Ser Thr Tyr Asp Ala Lys Ser Met Pro Leu Lys Asn Ala Leu
            180                 185                 190

Leu Ser Asp Ile Cys Ile Ser Thr Ser Ala Ala Pro Thr Tyr Leu Pro
        195                 200                 205

Ala His Cys Phe Gln Thr Thr Asp Asp Ala Thr Gly Lys Val Arg Glu
    210                 215                 220

Phe Asp Leu Ile Asp Gly Gly Val Ala Ala Asn Asn Pro Thr Met Val
225                 230                 235                 240

Ala Met Thr Gln Ile Thr Lys Lys Ile Met Val Lys Asp Lys Glu Glu
                245                 250                 255

Leu Tyr Pro Val Lys Pro Ser Asp Cys Gly Lys Phe Leu Val Leu Ser
            260                 265                 270

Val Gly Thr Gly Ser Thr Ser Asp Gln Gly Met Tyr Thr Ala Arg Gln
        275                 280                 285

Cys Ser Arg Trp Gly Ile Val Arg Trp Leu Arg Asn Lys Gly Met Ala
    290                 295                 300

Pro Ile Ile Asp Ile Phe Met Ala Ala Ser Ser Asp Leu Val Asp Ile
305                 310                 315                 320

His Ala Ala Val Met Phe Gln Ser Leu His Ser Asp Gly Asp Tyr Leu
                325                 330                 335

Arg Ile Gln Asp Asn Thr Leu His Gly Asp Ala Ala Thr Val Asp Ala

-continued

```
              340             345             350
Ala Thr Arg Asp Asn Met Arg Ala Leu Val Gly Ile Gly Glu Arg Met
            355             360             365
Leu Ala Gln Arg Val Ser Arg Val Asn Val Glu Thr Gly Arg Tyr Val
        370             375             380
Glu Val Pro Gly Ala Gly Ser Asn Ala Asp Ala Leu Arg Gly Phe Ala
385             390             395             400
Arg Gln Leu Ser Glu Glu Arg Arg Ala Arg Leu Gly Arg Arg Asn Ala
                405             410             415
Cys Gly Gly Gly Gly Glu Gly Glu Pro Ser Gly Val Ala Cys Lys Arg
            420             425             430

<210> SEQ ID NO 119
<211> LENGTH: 414
<212> TYPE: PRT
<213> ORGANISM: Oryza sativa

<400> SEQUENCE: 119

Met Ala Gly Cys Val Val Gly Glu Pro Ala Ser Ala Pro Gly Gln Arg
1               5                   10                  15
Val Thr Leu Leu Ala Ile Asp Gly Gly Gly Ile Arg Gly Leu Ile Pro
            20                  25                  30
Gly Thr Ile Leu Ala Phe Leu Glu Ala Arg Leu Gln Glu Leu Asp Gly
            35                  40                  45
Pro Asp Ala Arg Leu Ala Asp Tyr Phe Asp Cys Ile Ala Gly Thr Ser
        50                  55                  60
Thr Gly Gly Leu Ile Thr Ala Met Leu Ala Ala Pro Gly Asp His Gly
65                  70                  75                  80
Arg Pro Leu Phe Ala Ala Ser Asp Ile Asn Arg Phe Tyr Leu Asp Asn
                85                  90                  95
Gly Pro Arg Ile Phe Pro Gln Lys Arg Cys Gly Met Ala Ala Ala Met
            100             105             110
Ala Ala Leu Thr Arg Pro Arg Tyr Asn Gly Lys Tyr Leu Gln Gly Lys
        115             120             125
Ile Arg Lys Met Leu Gly Glu Thr Arg Val Arg Asp Thr Leu Thr Asn
        130             135             140
Val Val Ile Pro Thr Phe Asp Val Arg Leu Leu Gln Pro Thr Ile Phe
145             150             155             160
Ser Thr Tyr Asp Ala Lys Ser Met Pro Leu Lys Asn Ala Leu Leu Ser
                165             170             175
Asp Ile Cys Ile Ser Thr Ser Ala Ala Pro Thr Tyr Leu Pro Ala His
            180             185             190
Cys Phe Gln Thr Thr Asp Asp Ala Thr Gly Lys Val Arg Glu Phe Asp
        195             200             205
Leu Ile Asp Gly Gly Val Ala Ala Asn Asn Pro Thr Met Val Ala Met
        210             215             220
Thr Gln Ile Thr Lys Lys Ile Met Val Lys Asp Lys Glu Glu Leu Tyr
225             230             235             240
Pro Val Lys Pro Ser Asp Cys Gly Lys Phe Leu Val Leu Ser Leu Gly
                245             250             255
Thr Gly Ser Thr Ser Asp Gln Gly Met Tyr Thr Ala Arg Gln Cys Ser
            260             265             270
Arg Trp Gly Ile Val Arg Trp Leu Arg Asn Lys Gly Met Ala Pro Ile
        275             280             285
```

-continued

```
Ile Asp Ile Phe Met Ala Ala Ser Ser Asp Leu Val Asp Ile His Ala
    290             295                 300

Ala Val Met Phe Gln Ser Leu His Ser Asp Gly Asp Tyr Leu Arg Ile
305             310                 315                 320

Gln Asp Asn Thr Leu His Gly Asp Ala Ala Thr Val Asp Ala Ala Thr
            325                 330                 335

Arg Asp Asn Met Arg Ala Leu Val Gly Ile Gly Glu Arg Met Leu Ala
            340                 345                 350

Gln Arg Val Ser Arg Val Asn Val Glu Thr Gly Arg Tyr Val Glu Val
        355                 360                 365

Pro Gly Ala Gly Ser Asn Ala Asp Ala Leu Arg Gly Phe Ala Arg Gln
    370                 375                 380

Leu Ser Glu Glu Arg Arg Ala Arg Leu Gly Arg Arg Asn Ala Cys Gly
385                 390                 395                 400

Gly Gly Gly Glu Gly Glu Pro Ser Gly Val Ala Cys Lys Arg
            405                 410
```

SIMULTANEOUS GENE EDITING AND HAPLOID INDUCTION

This application is a § 371 of International Application No. PCT/US2017/064512, filed Dec. 4, 2017 and designating the U.S., which claims the benefit of U.S. Provisional Application 62/429,260, filed Dec. 2, 2016, all of which are incorporated herein by reference in their entirety.

FIELD OF THE INVENTION

This invention is related to the field of plant biotechnology, specifically agriculture biotechnology and gene editing, as well as plant breeding. The presently disclosed subject matter relates to using a haploid inducing line (whether existing or created) and transforming the haploid inducing line so that it contains DNA coding for cellular machinery capable of editing genes.

SEQUENCE LISTING

This application is accompanied by a sequence listing entitled 81189_USPCT_371_Substitute_Sequence_ST25_txt, created Dec. 4, 2023, which is approximately 344 kilobytes in size. This sequence listing is incorporated herein by reference in its entirety. This sequence listing is submitted herewith via Patent Center, and is in compliance with 37 C.F.R. § 1.824(a) (2) (6) and (b).

BACKGROUND

Targeted mutagenesis (also known as "gene editing") is a very important technology to crop breeding. There are numerous methods to edit specific gene targets now, including CRISPR, TALEN, meganucleases, and zinc fingers. One method to introduce editing machinery into plants is to use *Agrobacterium* or biolistic transformation of plant tissue. In transformation, DNA coding for the editing machinery (e.g., CAS9 and guide RNA) is introduced into plant callus, seed or embryonic tissue. Stably-transformed plants ("events") are then recovered, optionally with the help of a selectable marker. But because tissue culture is genotype-dependent, this route will not work for all crops, or even all varieties of the crops for which it does work. These are known as transformation-recalcitrant crops or varieties. These crops or varieties may be valued for their performance but it is a challenge for biotechnology that they cannot be transformed and thus cannot be directly edited via transformation. For recalcitrant varieties, one of two alternative approaches could be used to introduce desirable mutations. First, one could introduce the edits via trait introgression. This route is expensive, laborious, and time-consuming. It also means impurity of the final product because of genetic linkage— that is, there will be a linked block surrounding the introgressed edits, containing genes and alleles from the transformable donor line. This linkage can be an issue if any of those genes or alleles impact the performance of the transformation-recalcitrant line (may also be referred to as an "elite line"). Secondly, one could introduce the editing machinery transiently to the growing plant without tissue culture, such as floral dipping for *Arabidopsis* transformation. The challenge is ensuring edits end up in cells that contribute to the germ-line, so they are passed on to progeny seed. There are few established or routine methods to do this in crops.

Here we show a new method to transiently introduce editing machinery during haploid induction. Haploid induction ("HI") is a class of plant phenomena characterized by loss of one parent's set of chromosomes (the chromosomes from the haploid inducer parent) from the embryo at some time during or after fertilization, often during early embryo development. Haploid induction is also known as gynogenesis if the inducer line is used as the male in the cross, or androgenesis if the inducer line is used as the female in the cross. Haploid induction has been observed in numerous plant species, such as sorghum, barley, wheat, maize, *Arabidopsis*, and many other species.

Commonly, during haploid induction, both parent lines used in the induction cross are both diploids, so their gametes (egg cells and sperm cells) are haploids. Haploid induction is frequently a medium to low penetrance trait of the inducer line, so the resulting progeny, depending on the species or situation, may be either diploid (if no genome loss takes place) or haploids (if genome loss does indeed take place). If the parent line that is crossed to the haploid inducer is not diploid, but rather a tetraploid, hexaploid, or other plant of higher ploidy, the term haploid induction is something of a misnomer, because the "haploid" progeny produced will have a gametic chromosome number, and thus would not really be haploids, but rather diploids (if the parent is tetraploid) or triploids (if the parent is hexaploid) and so on. Therefore, as used herein, "haploids" possess half the number of chromosomes of either parent; thus haploids of diploid organisms (e.g., maize) exhibit monoploidy; haploids of tetraploid organisms (e.g., ryegrasses) exhibit diploidy; haploids of hexaploid organisms (e.g., wheat) exhibit triploidy.

Haploid induction can occur during self-pollination or intercrossing of two lines within the same species, or it can occur during wide crosses, where it can be viewed as a hybridization barrier, preventing the formation of interspecific hybrids. In maize, the most commonly employed method of inducing haploids is through the use of an intraspecific haploid inducer male line, which is primarily triggered by rearrangements of, mutations in, and/or recombinations, insertion, or deletions within a region of chromosome 1, specifically the MATRILINEAL (MATL) gene, also known as NOT LIKE DAD1 (NLD1) and PHOSPHOLIPASE A1 (PLA1) (with the notable exception of the ig type haploid induction, which is a result of a mutation in the INDETERMINATE GAMETOPHYTE1 gene on chromosome 3). In wheat, the most common method of inducting haploids is by wide cross to maize pollen—regardless of parent genotype or lineage, this works with almost any wheat crossed by almost any maize pollen.

HI maize lines contain a quantitative trait locus ("QTL") on Chromosome 1 responsible for at least 66% of the variation in haploid induction. The QTL causes haploid induction at different rates when it is introgressed into various backgrounds. All maize haploid inducer lines used in the seed industry are derivatives of the founding HI line, known as Stock6, and all have the haploid inducer chromosome 1 QTL mutation.

In maize, haploid seed or embryos are specifically produced by making crosses between a haploid inducer male (i.e., "haploid inducer pollen") and virtually any ear that one chooses—the ear could be of any inbred, hybrid, or other germplasm. Haploids are produced when the haploid inducer pollen DNA is not fully transmitted and/or maintained through the first cell divisions of the embryos. The resulting phenotype is not fully penetrant, with some ovules containing haploid embryos, and others containing diploid embryos, aneuploid embryos, chimeric embryos, or aborted embryos. The haploid kernels have embryos that contain only the maternal DNA plus normal triploid endosperm. After haploid induction, haploid embryos or seed are typically segregated from diploid and aneuploid siblings using a phenotypic or genetic marker screen and grown or cultured into haploid plants. These plants are then converted either naturally or via chemical manipulation (e.g., using an anti-microtubule agent such as colchicine) into doubled haploid ("DH") plants which then produce inbred seed.

Plant breeding is facilitated by the use of doubled haploid (DH) plants. The production of DH plants enables plant breeders to obtain inbred lines without multigenerational inbreeding, thus decreasing the time required to produce homozygous plants. DH plants provide an invaluable tool to plant breeders, particularly for generating inbred lines, QTL mapping, cytoplasmic conversions, trait introgression, and F2 screening for high throughput trait improvement. A great deal of time is spared as homozygous lines are essentially generated in one generation, negating the need for multi-generational single-seed decent (conventional inbreeding). In particular, because DH plants are entirely homozygous, they are very amenable to quantitative genetics studies. The production of haploid seed is critical for the doubled haploid breeding process. Haploid seed are produced on maternal germplasm when fertilized with pollen from a gynogenetic inducer, such as Stock 6 and Stock 6-derivative lines.

Here, we describe a novel method in which the in vivo haploid induction process can be co-opted to transiently introduce editing machinery into any germplasm by including it in the haploid inducer parent, either stably integrated as a transgene, or transiently expressed. Simultaneous editing plus haploid induction can be done in almost any crop via wide cross or de novo haploid induction for instance via CENH3 mutation (i.e., CENH3-modified haploid inducer; see, e.g., WO 2017/004375, incorporated herein by reference in its entirety) or via lipid spray (see P.C.T. Patent Application No. PCT/US2016/62548, incorporated herein by reference in its entirety). We show examples of HI in maize, both field corn and sweet corn, using a haploid inducer male as the editing donor line. Further, we show examples of HI in *Arabidopsis* using CENH3-modified haploid inducer lines.

We also show examples of HI in wheat using maize pollen as the editing donor line in a wide cross. In wheat, rice, barley, *brassica*, and other crops, the route to haploid induction would be to use a pollen donor that induces haploids via wide cross. For example, one could use corn pollen on wheat, millet pollen on wheat, barley pollen on other barley species, or any other wide crossing method. In those cases of gynogenetic haploid induction it would be preferable for the male line to contain the editing machinery, because it is the male (pollen-derived) DNA that is eliminated in the haploid induction process. In cases of andro-genic haploid induction, for instance in the ig1 system in maize or via altered CENH3 in any crop (which can work via either the male or the female), the editing machinery would be optimally present in the female parent, because the female chromosomes are eliminated in the haploid induction process.

In simultaneous editing plus haploid induction, the goal is to rapidly and cost-effectively edit crops and elite lines ("editing destination lines") without tissue culture. The line that receives the edits could be elite germplasm, and the editing machinery itself would be eliminated during the haploid induction process. At the same time, edited doubled haploid lines are produced.

SUMMARY

Tissue culture recalcitrance is a major challenge to rapid elite line editing across crops. Using haploid inducing lines to deliver the targeted mutagenesis machinery to elite lines and simultaneously induce haploids represents the surmounting of this major obstacle. Next-generation breeding programs may come to depend on this process.

The editing machinery is delivered via the inducer line. The editing machinery is most often DNA-binding proteins combined in some cases with RNA and in some cases also with DNA. The DNA, RNA, and proteins that make up the editing machinery are encoded by and are present in the inducer line because they have been stably inserted in the inducer, for example, via bombardment or *agrobacterium* mediated transformation. In other examples, the editing machinery is transiently introduced (through exogenous application) or transiently expressed in the gametophyte prior to fertilization. After fertilization, edits are made by the editing machinery in the non-inducer target genes prior to or during elimination of the inducer chromosomes. The result is a haploid embryo or plant or seed that contains the chromosome set only from the non-inducer parent, where that chromosome set contains DNA sequences that have been edited. These edited haploids can be identified, grown, and their chromosomes doubled, preferably by colchicine or other mitotic inhibitor. This line can then be directly used in downstream breeding programs.

In one embodiment, the invention provides a method of editing a plant's genomic DNA. This is done by taking a first plant—which is a haploid inducing plant and which also has encoded into its DNA the machinery necessary for accomplishing the editing (for example, a Cas9 enzyme and a guide RNA)—and using that first plant's pollen to pollinate a second plant. The second plant is the plant to be edited. From that pollination event, progeny (e.g., embryos or seeds) are produced; at least one of which will be a haploid seed. This haploid seed will only contain the chromosomes of the second plant; the first plant's chromosomes have vanished (having been eliminated, lost or degraded), but before doing so, the first plant's chromosomes permitted the gene-editing machinery to be expressed. Alternately, and without wishing to be bound by theory, the first plant delivers the already-expressed editing machinery upon pollination via the pollen tube. Or, in the case that the haploid inducer line is the female in the cross, the haploid inducing plant's egg cell contains the editing machinery that is present and perhaps already being expressed, upon fertilization with the "wild type" or non-haploid inducing pollen grain. Through any of these routes, the haploid progeny obtained by the cross will also have had its genome edited.

In one aspect, the editing machinery is any DNA modification enzyme, but is preferably a site-directed nuclease. The site-directed nuclease is preferably CRISPR-based, but could also be a meganuclease, a transcription-activator like effector nuclease (TALEN), or a zinc finger nuclease. The nuclease used in this invention could be Cas9, Cfp1, dCas9-FokI, chimeric FEN1-FokI. In one aspect, the DNA modification enzyme is a site-directed base editing enzyme such as Cas9-cytidine deaminase or Cas9-adeninie deaminase, wherein the Cas9 can have one or both of its nuclease activity inactivated, i.e. chimeric Cas9 nickase (nCas9) or deactivated Cas9 (dCas9) fused to cytidine deaminase or adenine deaminase. The optional guide RNA targets the genome at the specific site intended to be edited. In one aspect, the optional guide RNA comprises an 18-21 nucleotide sequence with homology to any of SEQ ID NOs: 2, 4, 8, 21, 23, 25, 29, 32, and 33.

Once the edited haploid progeny is obtained, it may optionally have its chromosomes doubled by a chromosome doubling agent (for example colchicine, pronamide, dithipyr, trifluralin, or another known anti-microtubule agent).

In one embodiment, the first plant is a monocot or a dicot. Aspects of the first plant include maize, wheat, rice, barley, oats, triticale, sorghum, pearl millet, teosinte, bamboo, sugar cane, asparagus, onion, and garlic. In one embodiment, the second plant is a monocot or a dicot. Aspects of the second plant include maize, wheat, rice, barley, oats, triticale, sorghum, pearl millet, teosinte, bamboo, sugar cane, asparagus, onion, and garlic. In one embodiment, the first plant is a monocot or a dicot of a different species than the second plant. For example, in one aspect, the first plant is maize and the second plant is wheat. In another aspect, the first plant is wheat and the second plant is maize. In another embodiment, the first plant is a maize plant selected and/or derived from the lines Stock 6, RWK, RWS, UH400, AX5707RS, NP2222-matl, or any of the several other known HI lines. In yet another embodiment, the first plant comprises a mutation in a CENH3 gene, an ig1 gene, or another mutation conferring paternal-haploid inducing systems. In another embodiment, the first plant is a rice plant with the MATL gene modified or knocked out which makes it a haploid inducer line.

In another embodiment, the first plant is not necessarily a haploid inducer, yet the first plant comprises the genes necessary for encoding the gene editing machinery. In this embodiment, haploid induction is produced by administering a compound during, immediately before, or immediately following pollination. In one aspect, the composition comprises a lipid or a phospholipase inhibitor. In another aspect, the composition comprises methyl alpha-linolenoyl fluoro-phosphonate (MALFP), linoleic acid ethyl ester (LLAEE), linoleic acid (LLA), corn oil, distearoyl-phosphatidyl choline (DSPC), methyl arachidonyl fluorophosphonate (MAFP), Palmityl trifluoromethylketone (PACOCF3), Arachidonyl trifluoromethylketone (AACOCF3), Manoalide, Linolenic acid ethyl ester (LNAEE), Linolenic acid ethyl ester (LNAEE), Oleic acid methyl ester (OAME), Oleic acid ethyl ester (OAEE), Palmitic acid ethyl ester (PAEE), Palmitoleic acid ethyl ester (PLAEE), Linseed oil, corn oil, alpha-Linolenic acid (aLNA), gamma-Linolenic acid (gLNA), Oleic acid, Arachidonic acid, Stearic Acid, 9(Z)-11(E)-conjugated Linoleic acid, or 2-oleoyl-1-palmitoyl-sn-glycero-3-phospho-ethanolamine.

BRIEF DESCRIPTION OF THE SEQUENCES IN THE SEQUENCE LISTING

SEQ ID NO: 1 is a nucleotide sequence for vector 23396.

SEQ ID NO: 2 is the nucleotide sequence encoding the gRNA sequence for editing VLHP1 in maize.

SEQ ID NO: 3 is a nucleotide sequence for vector 23399.

SEQ ID NO: 4 is the gRNA sequence for editing GW2-2 in maize.

SEQ ID NO: 5 is the nucleotide sequence for vector 22808, comprising a TALEN construct.

SEQ ID NO: 6 is the target sequence for the TALEN of 22808.

SEQ ID NO: 7 is the nucleotide sequence for vector 23123 comprising a Cas9 construct.

SEQ ID NO: 8 is the gRNA for editing MATL in maize.

SEQ ID NO: 9 is nucleotide sequence for the relevant portion of MATL in NP2222.

SEQ ID NO: 10 is nucleotide sequence for the relevant portion of MATL in Stock6.

SEQ ID NO: 11 is nucleotide sequence for the relevant portion of MATL in USR01350333-3 Allele 1.

SEQ ID NO: 12 is nucleotide sequence for the relevant portion of MATL in USR01350333-3 Allele 2.

SEQ ID NO: 13 is nucleotide sequence for the relevant portion of MATL in USR01350344-2 Allele 1.

SEQ ID NO: 14 is nucleotide sequence for the relevant portion of MATL in USR01350344-2 Allele 2.

SEQ ID NO: 15 is nucleotide sequence for the relevant portion of MATL in USR01350343-1 Allele 1.

SEQ ID NO: 16 is nucleotide sequence for the relevant portion of MATL in USR01350328-1 Allele 1.

SEQ ID NO: 17 is nucleotide sequence for the relevant portion of MATL in USR01350337-2 Allele 1.

SEQ ID NO: 18 is nucleotide sequence for the relevant portion of MATL in USR01350337-2 Allele 2.

SEQ ID NO: 19 is the nucleotide sequence of cDNA wildtype MATL.

SEQ ID NO: 20 is the nucleotide sequence for vector 23397.

SEQ ID NO: 21 is the gRNA sequence for editing VLHP2 in maize.

SEQ ID NO: 22 is the nucleotide sequence for vector 23398.

SEQ ID NO: 23 is the gRNA sequence for editing GW2-1 in maize.

SEQ ID NO: 24 is the nucleotide sequence for vector 23763.

SEQ ID NO: 25 is the gRNA sequence for VLHP1 in wheat.

SEQ ID NO: 26 is the wheat VLHP target sequence for TaVLHP2.

SEQ ID NO: 27 is the wheat VLHP target sequence for TaVLHP3.

SEQ ID NO: 28 is the target sequence in ZmVLHP2-03 for editing.

SEQ ID NO: 29 is the edited sequence in ZmVLHP2-03.

SEQ ID NO: 30 is the repair donor template sequence for creating E149L mutation in ZmPYL-D.

SEQ ID NO: 31 is the nucleotide sequence for vector 23136.

SEQ ID NO: 32 is the gRNA of vector 23136.

SEQ ID NO: 33 is the nucleotide sequence of rice PLA gene Os03g27610.

SEQ ID NO: 34 is the nucleotide sequence for vector 24038.

SEQ ID NO: 35 is the nucleotide sequence for vector 24039.

SEQ ID NO: 36 is the nucleotide sequence for vector 24079.

SEQ ID NO: 37 is the nucleotide sequence for vector 24091.

SEQ ID NO: 38 is the nucleotide sequence for vector 24094.

SEQ ID NOs: 39 through 97 are primers and probes used in the identified PCR Taqman assays.

SEQ ID NO: 98 is the nucleotide sequence for vector 24075.

SEQ ID NO: 99 is a portion of the edited GW2-02 target site in haploid sweet corn line JSER82A063, shown in FIG. 13.

SEQ ID NO: 100 is the reverse complement of SEQ ID NO: 99 shown in FIG. 13.

SEQ ID NO: 101 is a portion of the edited TaVLHP1-4B target site in haploid wheat line JSWER30A22, shown in FIG. 16.

SEQ ID NO: 102 is the nucleotide sequence of the gRNA used in editing the *Arabidopsis* GL1 gene.

SEQ ID NO: 103 is the relevant portion of the wildtype *Arabidopsis* GL1 gene.

SEQ ID NO: 104 is the relevant portion of the edited GL1 gene (by single nucleotide deletion) in individual 135.

SEQ ID NO: 105 is the relevant portion of the edited GL1 gene (by single nucleotide insertion) in individual 135.

SEQ ID NO: 106 is the relevant portion of the unedited GL1 gene in individual 1033-A3 (product of cross between USR01424135 and Ler-425).

SEQ ID NO: 107 is the relevant portion of the edited GL1 gene (by single nucleotide insertion) in individual 1033-C3 (product of cross between USR01424135 and Ler-427).

SEQ ID NO: 108 is the relevant portion of the edited GL1 gene (by single nucleotide insertion) in individual 1033-E4 (product of cross between USR01424135 and Ler-437).

SEQ ID NO: 109 is the relevant portion of the edited GL1 gene (by deletion of three nucleotides) in individual 1041-H12.

SEQ ID NO: 110 is the relevant portion of the edited GL1 gene (by single nucleotide insertion) in individual 1042-E5 (product of cross between USR01424136 and Ler-25).

SEQ ID NO: 111 is the relevant portion of the edited GL1 gene (by single nucleotide deletion) in individual 1042-G12 (product of cross between USR01424136 and Ler-83).

SEQ ID NO: 112 is the relevant portion of the edited GL1 gene (by deletion of two nucleotides) in individual 1042-G10 (product of cross between USR01424136 and Ler-67).

SEQ ID NO: 113 is the relevant portion of the edited GL1 gene (by deletion of two nucleotides) in individual 1045-E3 (product of cross between USR01424136 and Ler-261).

SEQ ID NO: 114 is the relevant portion of the edited GL1 gene (by single nucleotide insertion) in individual 1045-D3 (product of cross between USR01424136 and Ler-260).

SEQ ID NO: 115 is the relevant portion of the edited GL1 gene (by single nucleotide insertion) in individual 1046-D11 (product of cross between USR01431609 and Ler-111).

SEQ ID NO: 116 is the relevant portion of the edited GL1 gene (by single nucleotide insertion) in individual 1046-G12 (product of cross between USR01431609 and Ler-122).

SEQ ID NO: 117 is the relevant portion of the edited GL1 gene (by deletion of sixteen nucleotides and insertion of eight nucleotides) in individual 1045-F2 (product of cross between USR01424136 and Ler-254).

SEQ ID NO: 118 is the amino acid sequence encoded by Os03g27610.

SEQ ID NO: 119 is the amino acid sequence for a maize MATL ortholog found in *Oryza sativa* v. indica.

DEFINITIONS

Figure 1:
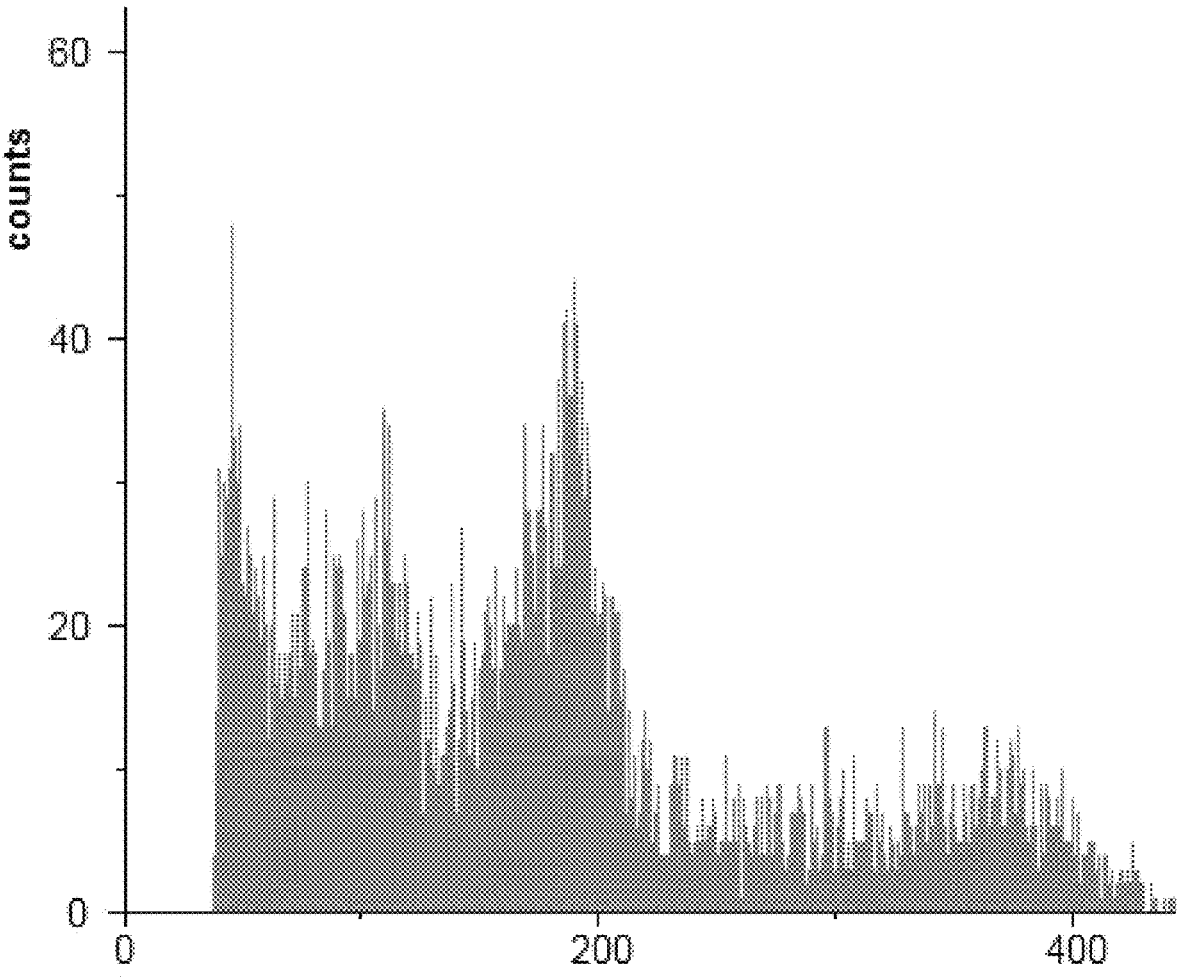
FIG. 1 shows the ploidy analysis (flow cytometry) data for USR01350334-3: DIPLOID (major peak at 200, secondary peak at 400).
Figure 2:
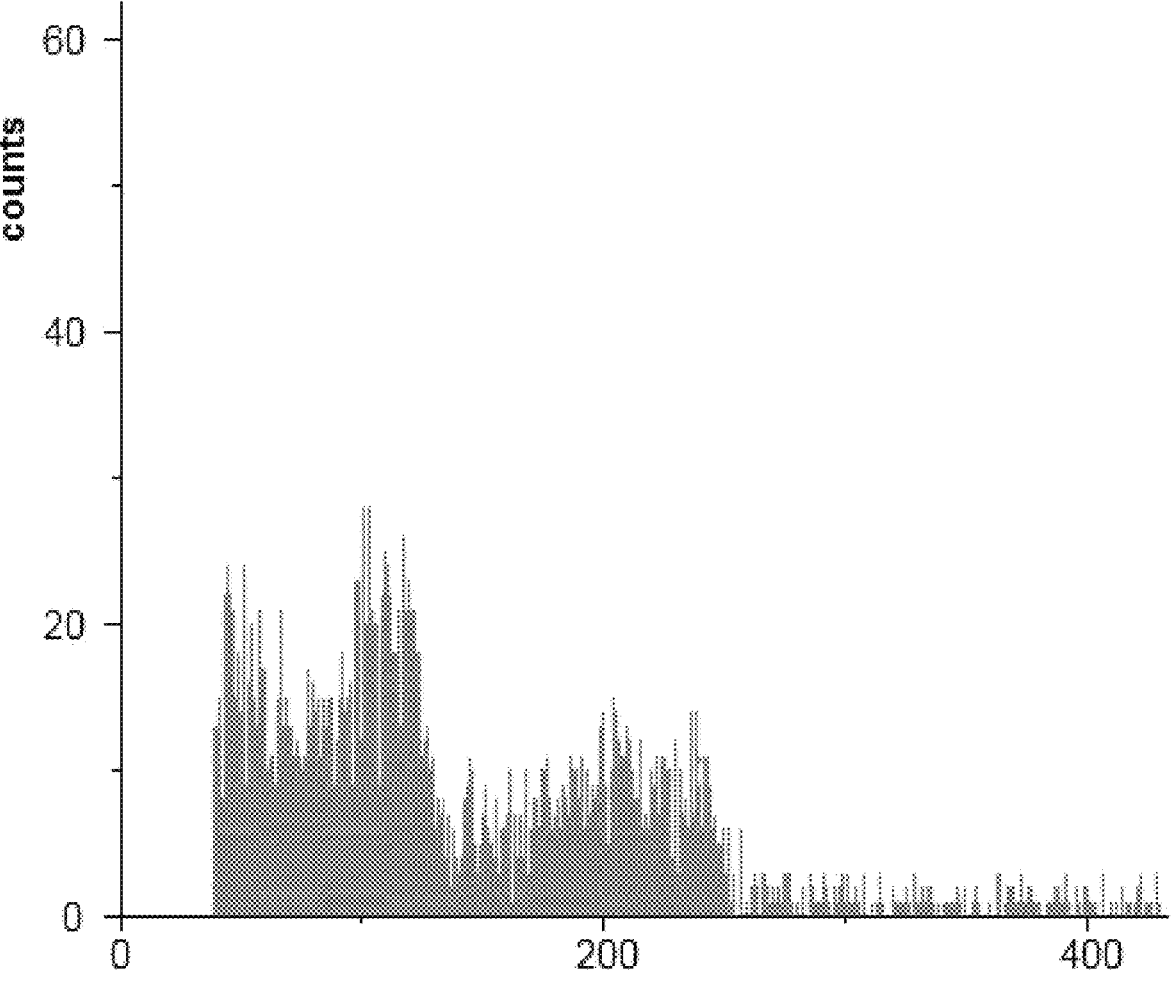
FIG. 2 shows the ploidy analysis (flow cytometry) data for USR01350333-3: HAPLOID (major peak at 100, secondary peak at 200).
Figure 3:
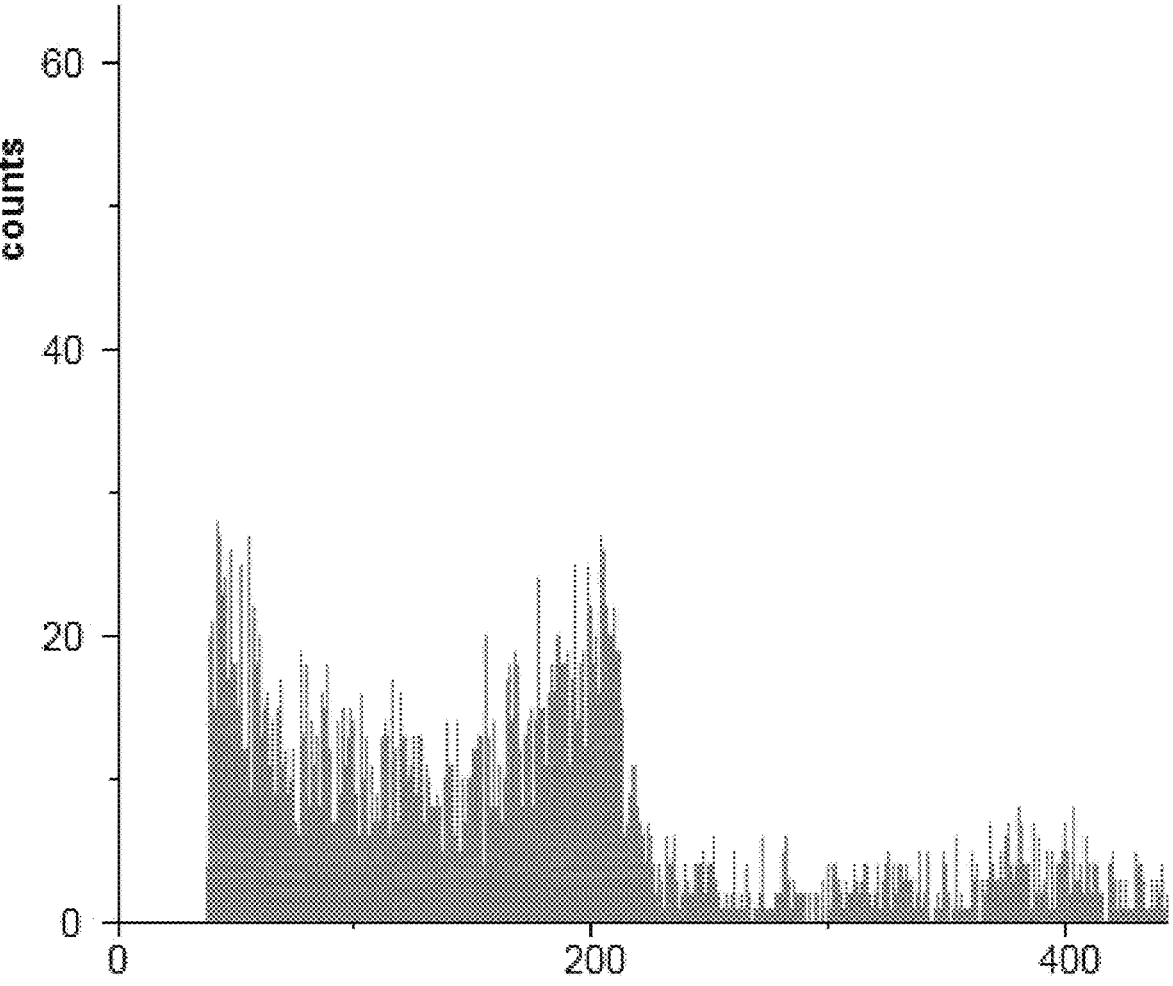
FIG. 3 shows the ploidy analysis (flow cytometry) data for USR01350333-10: DIPLOID (major peak at 200, secondary peak at 400).
Figure 4:
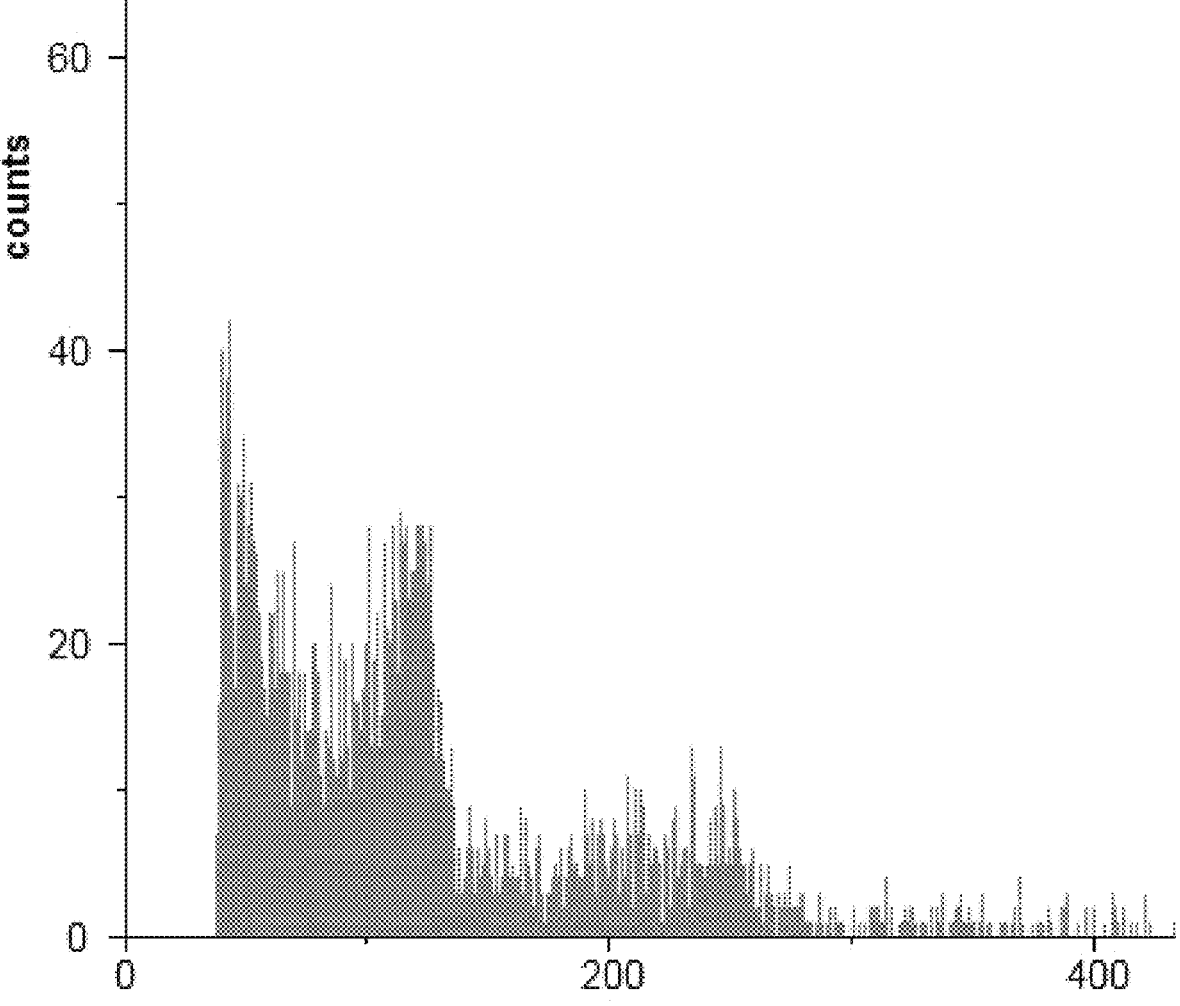
FIG. 4 shows the ploidy analysis (flow cytometry) data for USR01350344-2: HAPLOID (major peak at 100, secondary peak at 200).
Figure 5:
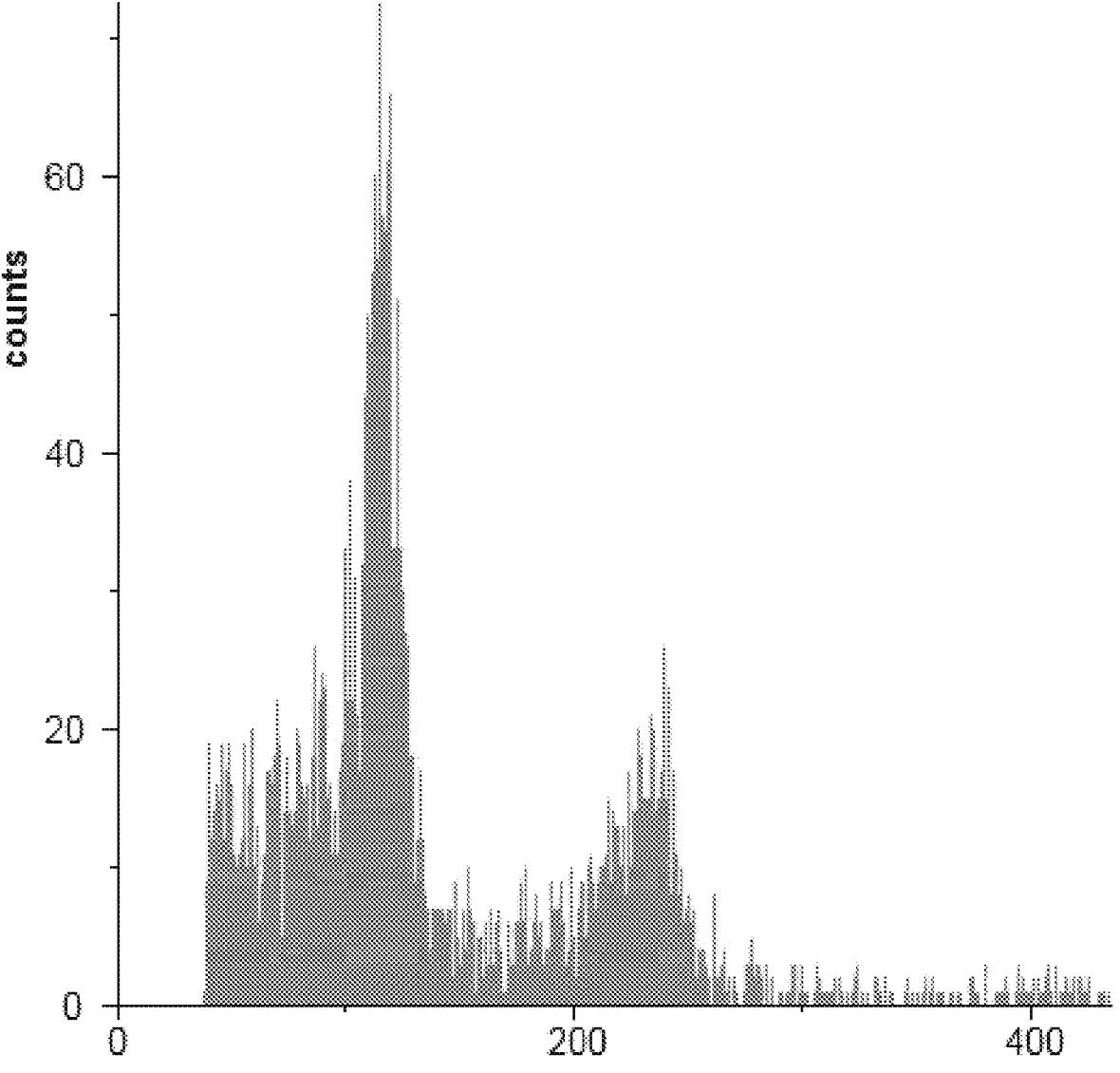
FIG. 5 shows the ploidy analysis (flow cytometry) data for USR01350343-1: HAPLOID (major peak at 100, secondary peak at 200).
Figure 6:
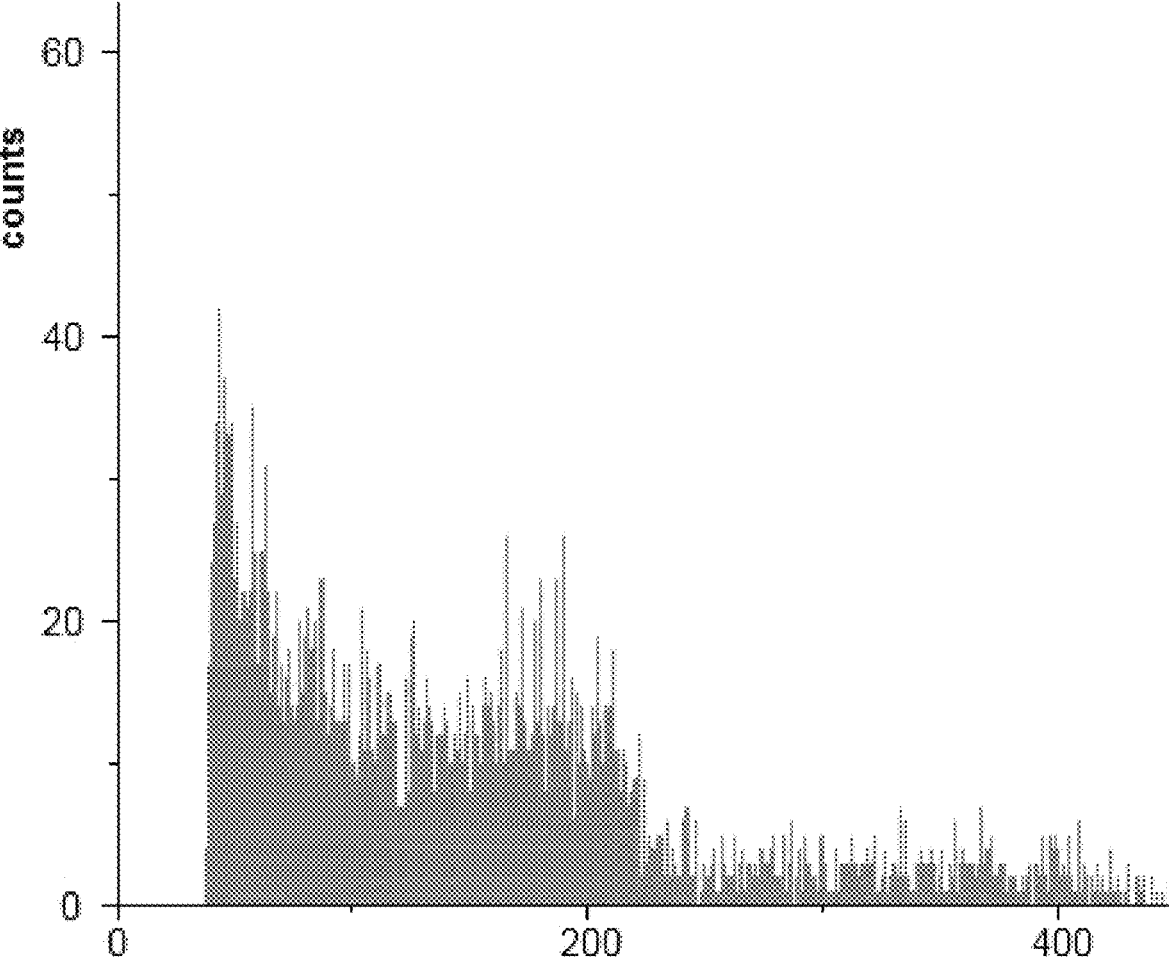
FIG. 6 shows the ploidy analysis (flow cytometry) data for USR01350341-1: DIPLOID (major peak at 200, secondary peak at 400).
Figure 7:
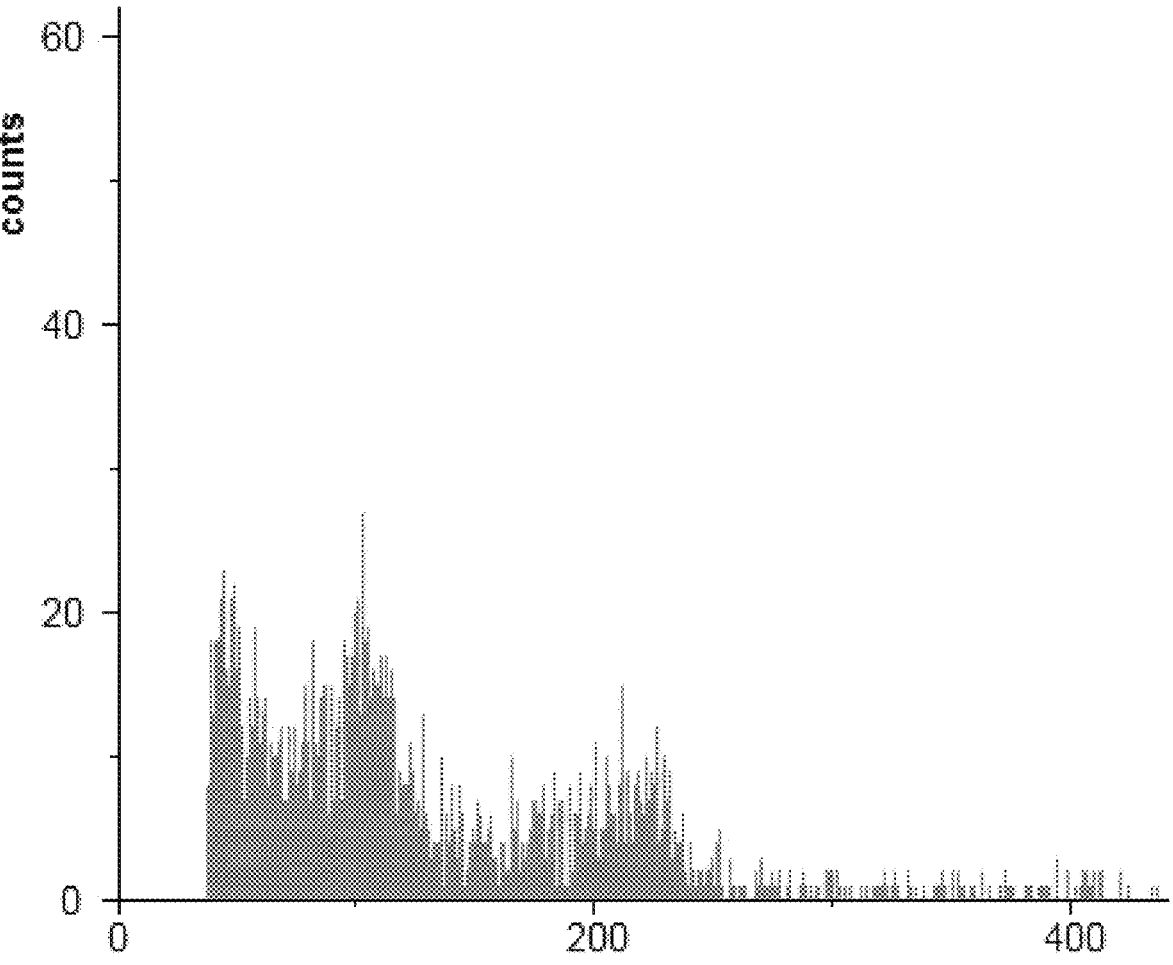
FIG. 7 shows the ploidy analysis (flow cytometry) data for USR01350328-1: HAPLOID (major peak at 100, secondary peak at 200).
Figure 8:
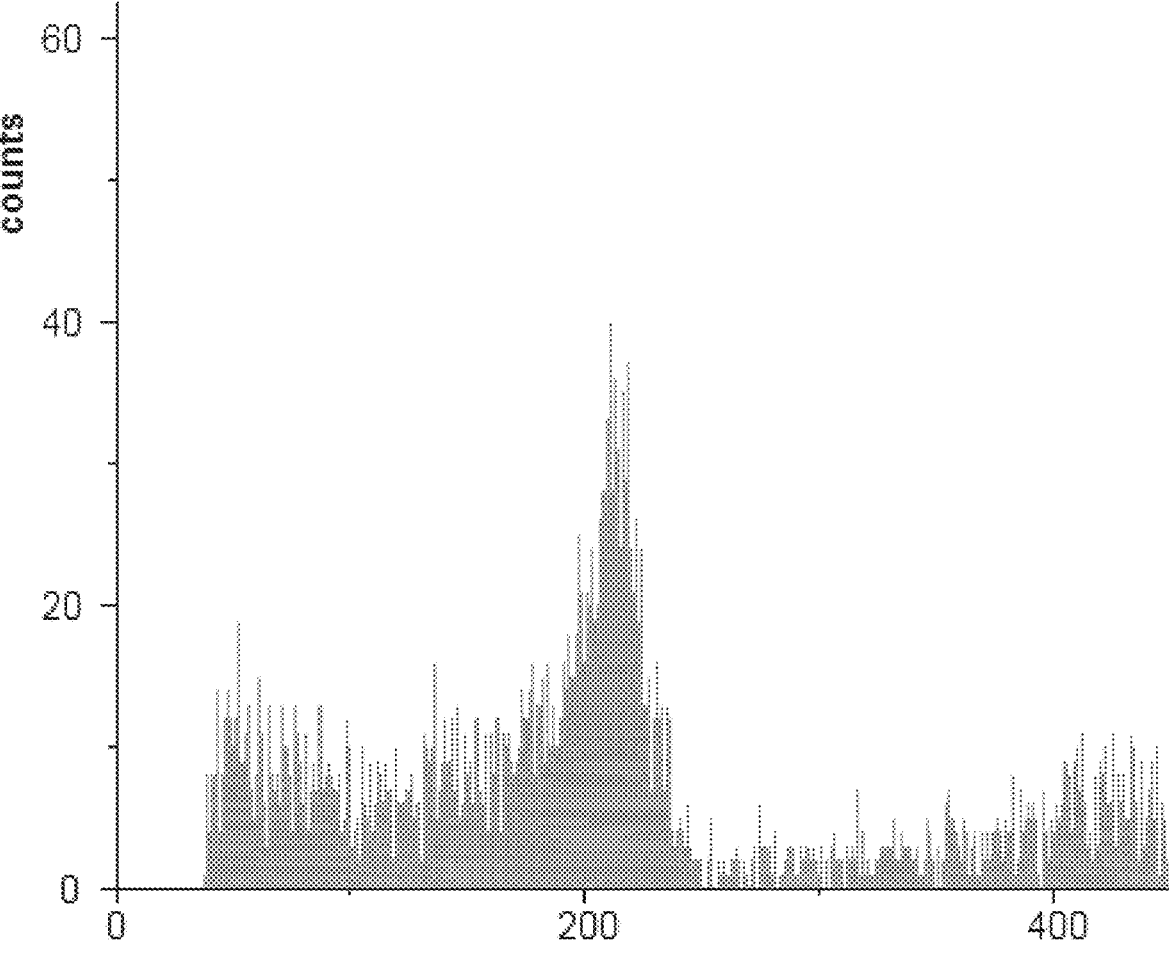
FIG. 8 shows the ploidy analysis (flow cytometry) data for USR01350321-3: DIPLOID (major peak at 200, secondary peak at 400).

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a," "an," and "the" refer to "one or more" when used in this application, including the claims. For example, the phrase "a cell" refers to one or more cells, and in some embodiments can refer to a tissue and/or an organ. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to all whole number values between 1 and 100 as well as whole numbers greater than 100.

Unless otherwise indicated, all numbers expressing quantities of ingredients, reaction conditions, and so forth used in the specification and claims are to be understood as being modified in all instances by the term "about." The term "about," as used herein when referring to a measurable value such as an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the discloses compositions, nucleic acids, polypeptides, etc. Accordingly, unless indicated to the contrary, the numerical parameters set forth in this specification and attached claims are approximations that can vary depending upon the desired properties sought to be obtained by the presently disclosed subject matter.

As used herein, the term "allele" refers to a variant or an alternative sequence form at a genetic locus. In diploids, a single allele is inherited by a progeny individual separately from each parent at each locus. The two alleles of a given locus present in a diploid organism occupy corresponding places on a pair of homologous chromosomes, although one of ordinary skill in the art understands that the alleles in any particular individual do not necessarily represent all of the alleles that are present in the species.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D (e.g., AB, AC, AD, BC, BD, CD, ABC, ABD, and BCD). In some embodiments, one of more of the elements to which the "and/or" refers can also individually be present in single or multiple occurrences in the combinations(s) and/or subcombination(s).

As used herein, the phrase "associated with" refers to a recognizable and/or assayable relationship between two entities. For example, the phrase "associated with HI" refers to a trait, locus, gene, allele, marker, phenotype, etc., or the expression thereof, the presence or absence of which can influence an extent and/or degree at which a plant or its progeny exhibits HI. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with HI" refers to a marker whose presence or absence can be used to predict whether and/or to what extent a plant will display haploid induction.

The term "comprising," which is synonymous with "including," "containing," and "characterized by," is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter.

With respect to the terms "comprising," "consisting essentially of," and "consisting of," where one of these three terms is used herein, the presently disclosed and claimed subject matter can include in some embodiments the use of either of the other two terms. For example, if a subject matter relates in some embodiments to nucleic acids that encode polypeptides comprising amino acid sequences that are at least 95% identical to a SEQ ID NO: 9 or 19. It is understood that the disclosed subject matter thus also encompasses nucleic acids that encode polypeptides that in some embodiments consist essentially of amino acid sequences that are at least 95% identical to that SEQ ID NO: 9 or 19 as well as nucleic acids that encode polypeptides that in some embodiments consist of amino acid sequences that are at least 95% identical to that SEQ ID NO: 9 or 19. Similarly, it is also understood that in some embodiments the methods for the disclosed subject matter comprise the steps that are disclosed herein, in some embodiments the methods for the presently disclosed subject matter consist essentially of the steps that are disclosed, and in some embodiments the methods for the presently disclosed subject matter consist of the steps that are disclosed herein.

As used herein, the term "de novo haploid induction" refers to the triggering of haploid induction by the introduction of a spontaneous haploid inducing agent. Such introduction can be achieved by topical spray, hand-pollination, mutagenesis, or transgenic methods. The terms "de novo haploid induction," "de novo HI," and "haploid induction de novo" are used interchangeably throughout this specification.

As used herein, the term "gene" refers to a hereditary unit including a sequence of DNA that occupies a specific location on a chromosome and that contains the genetic instruction for a particular characteristic or trait in an organism.

A "genetic map" is a description of genetic linkage relationships among loci on one or more chromosomes within a given species, generally depicted in a diagrammatic or tabular form.

As used herein, a plant referred to as "haploid" has a reduced number of chromosomes (n) in the haploid plant, and its chromosome set is equal to that of the gamete. In a haploid organism, only half of the normal number of chromosomes are present. Thus haploids of diploid organisms (e.g., maize) exhibit monoploidy; haploids of tetraploid organisms (e.g., ryegrasses) exhibit diploidy; haploids of hexaploid organisms (e.g., wheat) exhibit triploidy; etc. As used herein, a plant referred to as "doubled haploid" is developed by doubling the haploid set of chromosomes. A plant or seed that is obtained from a doubled haploid plant that is selfed to any number of generations may still be identified as a doubled haploid plant. A doubled haploid plant is considered a homozygous plant. A plant is considered to be doubled haploid if it is fertile, even if the entire vegetative part of the plant does not consist of the cells with the doubled set of chromosomes; that is, a plant will be considered doubled haploid if it contains viable gametes, even if it is chimeric in vegetative tissues.

As used herein, the term "human-induced mutation" refers to any mutation that occurs as a result of either direct or indirect human action. This term includes, but is not limited to, mutations obtained by any method of targeted mutagenesis.

As used herein, "introduced" means delivered, expressed, applied, transported, transferred, permeated, or other like term to indicate the delivery, whether of nucleic acid or protein or combination thereof, of a desired object to an object. For example, nucleic acids encoding a site directed nuclease and optionally at least one guide RNA may be introduced into a haploid embryo upon haploid induction. Likewise, extant editing machinery (comprising a site directed nuclease protein and optionally at least one guide RNA) may be introduced to a haploid embryo upon application of appropriate cell-penetrating peptides.

As used herein, the terms "marker probe" and "probe" refer to a nucleotide sequence or nucleic acid molecule that can be used to detect the presence or absence of a sequence within a larger sequence, e.g., a nucleic acid probe that is complementary to all of or a portion of the marker or marker locus, through nucleic acid hybridization. Marker probes comprising about 8, 10, 15, 20, 30, 40, 50, 60, 70, 80, 90, 100 or more contiguous nucleotides can be used for nucleic acid hybridization.

As used herein, the term "molecular marker" can be used to refer to a genetic marker, as defined above, or an encoded product thereof (e.g., a protein) used as a point of reference when identifying the presence/absence of a HI-associated locus. A molecular marker can be derived from genomic nucleotide sequences or from expressed nucleotide sequences (e.g., from an RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution (e.g., according to Watson-Crick base pairing rules). This term also refers to the genetic markers that indicate a trait by the absence of the nucleotide sequences complementary to or flanking the marker sequences, such as nucleotide sequences used as probes and/or primers capable of amplifying the marker sequence.

As used herein, the terms "nucleotide sequence," "polynucleotide," "nucleic acid sequence," "nucleic acid molecule," and "nucleic acid fragment" refer to a polymer of RNA or DNA that is single- or double-stranded, optionally containing synthetic, non-natural, and/or altered nucleotide bases. A "nucleotide" is a monomeric unit from which DNA or RNA polymers are constructed and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, the term "nucleotide sequence identity" refers to the presence of identical nucleotides at corresponding positions of two polynucleotides. Polynucleotides have "identical" sequences if the sequence of nucleotides in the two polynucleotides is the same when aligned for maximum correspondence (e.g., in a comparison window). Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence identity" for polynucleotides, such as about 50, 55, 60, 65, 70, 75, 80, 85, 90, 95, 98, 99 or 100 percent sequence identity, can be determined by comparing two optimally aligned sequences over a comparison window, wherein the portion of the polynucleotide sequence in the comparison window can include additions or deletions (i.e., gaps) as compared to the reference sequence for optimal alignment of the two sequences. In some embodiments, the percentage is calculated by: (a) determining the number of positions at which the identical nucleic acid base occurs in both sequences; (b) dividing the number of matched positions by the total number of positions in the window of comparison; and (c) multiplying the result by 100. Optimal alignment of sequences for comparison can also be conducted by computerized implementations of known algorithms, or by visual inspection. Readily available sequence comparison and multiple sequence alignment algorithms are, respectively, the Basic Local Alignment Search Tool (BLAST) and ClustalW/ClustalW2/Clustal Omega programs available on the Internet (e.g., the website of the EMBL-EBI). Other suitable programs include, but are not limited to, GAP, BestFit, Plot Similarity, and FASTA, which are part of the Accelrys GCG Package available from Accelrys, Inc. of San Diego, California, United States of America. See also Smith & Waterman, 1981; Needleman & Wunsch, 1970; Pearson & Lipman, 1988; Ausubel et al., 1988; and Sambrook & Russell, 2001.

One example of an algorithm that is suitable for determining percent sequence identity and sequence similarity is the BLAST algorithm, which is described in Altschul et al., 1990. In some embodiments, a percentage of sequence identity refers to sequence identity over the full length of one of the gDNA, cDNA, or the predicted protein sequences in the largest ORF of SEQ ID No: 1 being compared. In some embodiments, a calculation to determine a percentage of nucleic acid sequence identity does not include in the calculation any nucleotide positions in which either of the compared nucleic acids includes an "N" (i.e., where any nucleotide could be present at that position).

The term "open reading frame" (ORF) refers to a nucleic acid sequence that encodes a polypeptide. In some embodiments, an ORF comprises a translation initiation codon (i.e., start codon), a translation termination (i.e., stop codon), and the nucleic acid sequence there between that encodes the amino acids present in the polypeptide. The terms "initiation codon" and "termination codon" refer to a unit of three adjacent nucleotides (i.e., a codon) in a coding sequence that specifies initiation and chain termination, respectively, of protein synthesis (mRNA translation).

Patatin-like phospholipase A2a may also be known as PLA, pPLA, pPLAIIA pPLAIIa, PLA2alpha, or PLA2, or other similar variation. Patatin-like phospholipase AIIα is also referred to as MATRILINEAL (MATL). These terms are used interchangeably throughout. A MATRILINEAL gene comprising a four basepair frameshift mutation is referred to as matrilineal (matl).

As used herein, the terms "phenotype," "phenotypic trait" or "trait" refer to one or more traits of a plant or plant cell. The phenotype can be observable to the naked eye, or by any other means of evaluation known in the art, e.g., microscopy, biochemical analysis, or an electromechanical assay. In some cases, a phenotype is directly controlled by a single gene or genetic locus (i.e., corresponds to a "single gene trait"). In the case of haploid induction use of color markers, such as R Navajo, and other markers including transgenes visualized by the presences or absences of color within the seed evidence if the seed is an induced haploid seed. The use of R Navajo as a color marker and the use of transgenes is well known in the art as means to detect induction of haploid seed on the female plant. In other cases, a phenotype is the result of interactions among several genes, which in some embodiments also results from an interaction of the plant and/or plant cell with its environment.

As used herein, the term "plant" can refer to a whole plant, any part thereof, or a cell or tissue culture derived from a plant. Thus, the term "plant" can refer to any of: whole plants, plant components or organs (e.g., leaves, stems, roots, etc.), plant tissues, seeds and/or plant cells.

A plant cell is a cell of a plant, taken from a plant, or derived through culture from a cell taken from a plant. Thus, the term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "primer" refers to an oligonucleotide which is capable of annealing to a nucleic acid target (in some embodiments, annealing specifically to a nucleic acid target) allowing a DNA polymerase and/or reverse transcriptase to attach thereto, thereby serving as a point of initiation of DNA synthesis when placed under conditions in which synthesis of a primer extension product is induced (e.g., in the presence of nucleotides and an agent for polymerization such as DNA polymerase and at a suitable temperature and pH). In some embodiments, one or more pluralities of primers are employed to amplify plant nucleic acids (e.g., using the polymerase chain reaction; PCR).

As used herein, the term "probe" refers to a nucleic acid (e.g., a single stranded nucleic acid or a strand of a double stranded or higher order nucleic acid, or a subsequence thereof) that can form a hydrogen-bonded duplex with a complementary sequence in a target nucleic acid sequence. Typically, a probe is of sufficient length to form a stable and sequence-specific duplex molecule with its complement, and as such can be employed in some embodiments to detect a sequence of interest present in a plurality of nucleic acids.

As used herein, the terms "progeny" and "progeny plant" refer to a plant generated from vegetative or sexual reproduction from one or more parent plants. In gynogenesis-mediated haploid induction, the haploid embryo on the female parent comprises female chromosomes to the exclusion of male chromosomes—thus it is not a progeny of the male haploid-inducing line. The haploid corn seed typically still has normal triploid endosperm that contains the male genome. The edited haploid progeny and subsequent edited doubled haploid plants and subsequent seed is not the only desired progeny. There is also the seed from the haploid inducer line itself, often carrying the Cas9 transgene, and subsequent plant and seed progeny of the haploid inducing plant. Both the haploid seed and the haploid inducer (self-pollination-derived) seed can be progeny. A progeny plant can be obtained by cloning or selfing a single parent plant, or by crossing two or more parental plants. For instance, a progeny plant can be obtained by cloning or selfing of a parent plant or by crossing two parental plants and include selfings as well as the $F_1$ or $F_2$ or still further generations. An $F_1$ is a first-generation progeny produced from parents at least one of which is used for the first time as donor of a trait, while progeny of second generation (F2) or subsequent generations ($F_3$, $F_4$, and the like) are specimens produced from selfings, intercrosses, backcrosses, and/or other crosses of $F_1$s, $F_2$s, and the like. An $F_1$ can thus be (and in some embodiments is) a hybrid resulting from a cross between two true breeding parents (i.e., parents that are true-breeding are each homozygous for a trait of interest or an allele thereof), while an $F_2$ can be (and in some embodiments is) a progeny resulting from self-pollination of the $F_1$ hybrids.

As used herein, the phrase "recombination" refers to an exchange of DNA fragments between two DNA molecules or chromatids of paired chromosomes (a "crossover") over in a region of similar or identical nucleotide sequences. A "recombination event" is herein understood to refer in some embodiments to a meiotic crossover.

As used herein, the term "reference sequence" refers to a defined nucleotide sequence used as a basis for nucleotide sequence comparison. In some embodiments, any of SEQ ID NOs: 2, 4, 8, 21, 23, 25, 29, 32, and 33 can serve as a reference sequence for comparing to other sequences obtained from plants.

As used herein, the term "regenerate," and grammatical variants thereof, refers to the production of a plant from tissue culture.

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances.

Longer sequences typically hybridize specifically at higher temperatures. An extensive guide to the hybridization of nucleic acids is found in Sambrook & Russell, 2001. Generally, stringent conditions are selected to be about 5-10° C. lower than the thermal melting point ($T_m$) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Exemplary stringent conditions are those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

Stringent conditions can also be achieved with the addition of destabilizing agents such as formamide. Additional exemplary stringent hybridization conditions include 50% formamide, 5×SSC, and 1% SDS incubating at 42° C.; or SSC, 1% SDS, incubating at 65° C.; with one or more washes in 0.2×SSC and 0.1% SDS at 65° C. For PCR, a temperature of about 36° C. is typical for low stringency amplification, although annealing temperatures can vary between about 32° C. and 48° C. (or higher) depending on primer length. Additional guidelines for determining hybridization parameters are provided in numerous references (see e.g., Ausubel et al., 1999).

As used herein, the term "trait" refers to a phenotype of interest, a gene that contributes to a phenotype of interest, as well as a nucleic acid sequence associated with a gene that contributes to a phenotype of interest. For example, a "HI trait" refers to a haploid induction phenotype as well as a gene (e.g., matl in maize or Os03g27610 in rice) that contributes to a haploid induction and a nucleic acid sequence (e.g., a HI-associated gene product) that is associated with the presence or absence of the haploid induction phenotype.

As used herein, the term "transgene" refers to a nucleic acid molecule introduced into an organism or one or more of its ancestors by some form of artificial transfer technique. The artificial transfer technique thus creates a "transgenic organism" or a "transgenic cell." It is understood that the artificial transfer technique can occur in an ancestor organism (or a cell therein and/or that can develop into the ancestor organism) and yet any progeny individual that has the artificially transferred nucleic acid molecule or a fragment thereof is still considered transgenic even if one or more natural and/or assisted breedings result in the artificially transferred nucleic acid molecule being present in the progeny individual.

As used herein, the term "targeted mutagenesis" or "mutagenesis strategy" refers to any method of mutagenesis that results in the intentional mutagenesis of a chosen gene. Targeted mutagenesis includes the methods CRISPR, TILLING, TALEN, and other methods not yet discovered but which may be used to achieve the same outcome.

As used herein, haploid induction rate ("HIR") means the number of surviving haploid kernels over the total number of kernels after an ear is pollinated with haploid inducer pollen.

Particular problems plague that haploid induction: increased embryo abortion rates and increased fertilization failure rates (reduced seed set rates). For these reasons, there exists a need to successfully determine the cause of HI, and to use that knowledge to determine methods of stably or increasingly creating haploid plants while simultaneously reducing fertilization failure and embryo abortions.

It is specifically contemplated that one could mutagenize a promoter to potentially improve the utility of the elements for the expression of transgenes in plants. The mutagenesis of these elements can be carried out at random and the mutagenized promoter sequences screened for activity in a trial-by-error procedure. Alternatively, particular sequences which provide the promoter with desirable expression characteristics, or the promoter with expression enhancement activity, could be identified and these or similar sequences introduced into the promoter via mutation. It is further contemplated that one could mutagenize these sequences in order to enhance their expression of transgenes in a particular species. The means for mutagenizing a DNA segment encoding a promoter sequence of the current invention are well-known to those of skill in the art. As indicated, modifications to promoter or other regulatory element may be made by random, or site-specific mutagenesis procedures. The promoter and other regulatory element may be modified by altering their structure through the addition or deletion of one or more nucleotides from the sequence which encodes the corresponding unmodified sequences.

Mutagenesis may be performed in accordance with any of the techniques known in the art, such as, and not limited to, synthesizing an oligonucleotide having one or more mutations within the sequence of a particular regulatory sequence. In particular, site-specific mutagenesis is a technique useful in the preparation of promoter mutants, through specific mutagenesis of the underlying DNA. RNA-guided endonucleases ("RGEN," e.g., CRISPR/Cas9) may also be used. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

Where a clone comprising a promoter has been isolated in accordance with the instant invention, one may wish to delimit the essential promoter regions within the clone. One efficient, targeted means for preparing mutagenized promoters relies upon the identification of putative regulatory elements within the promoter sequence. This can be initiated by comparison with promoter sequences known to be expressed in similar tissue specific or developmentally unique patterns. Sequences which are shared among promoters with similar expression patterns are likely candidates for the binding of transcription factors and are thus likely elements which confer expression patterns. Confirmation of these putative regulatory elements can be achieved by deletion analysis of each putative regulatory sequence followed by functional analysis of each deletion construct by assay of a reporter gene which is functionally attached to each construct. As such, once a starting promoter sequence is provided, any of a number of different deletion mutants of the starting promoter could be readily prepared.

The invention disclosed herein provides polynucleotide molecules comprising regulatory element fragments that may be used in constructing novel chimeric regulatory elements. Novel combinations comprising fragments of these polynucleotide molecules and at least one other regulatory element or fragment can be constructed and tested in plants and are considered to be within the scope of this invention. Thus the design, construction, and use of chimeric regulatory elements is one embodiment of this invention. Promoters of the present invention include homologues of cis elements known to affect gene regulation that show homology with the promoter sequences of the present invention.

Functional equivalent fragments of one of the transcription regulating nucleic acids described herein comprise at least 50, 100, 150, 200, 250, 300, 350, 400, 450, 500, 550, 600, 650, 700, 750, 800, 850, 900, 950, or 1000 base pairs of a transcription regulating nucleic acid. Equivalent fragments of transcription regulating nucleic acids, which are obtained by deleting the region encoding the 5'-untranslated region of the mRNA, would then only provide the (untranscribed) promoter region. The 5'-untranslated region can be easily determined by methods known in the art (such as 5'-RACE analysis). Accordingly, some of the transcription regulating nucleic acids, described herein, are equivalent fragments of other sequences.

As indicated above, deletion mutants of the promoter of the invention also could be randomly prepared and then assayed. Following this strategy, a series of constructs are prepared, each containing a different portion of the promoter (a subclone), and these constructs are then screened for activity. A suitable means for screening for activity is to attach a deleted promoter or intron construct which contains a deleted segment to a selectable or screenable marker, and to isolate only those cells expressing the marker gene. In this way, a number of different, deleted promoter constructs are identified which still retain the desired, or even enhanced, activity. The smallest segment which is required for activity is thereby identified through comparison of the selected constructs. This segment may then be used for the construction of vectors for the expression of exogenous genes.

An expression cassette as described herein may comprise further regulatory elements. The term in this context is to be understood in the broad meaning comprising all sequences which may influence construction or function of the expression cassette. Regulatory elements may, for example, modify transcription and/or translation in prokaryotic or eukaryotic organisms. The expression cassette described herein may be downstream (in 3' direction) of the nucleic acid sequence to be expressed and optionally contain additional regulatory elements, such as transcriptional or translational enhancers. Each additional regulatory element may be operably liked to the nucleic acid sequence to be expressed (or the transcription regulating nucleotide sequence). Additional regulatory elements may comprise additional promoters, minimal promoters, promoter elements, or transposon elements which may modify or enhance the expression regulating properties. The expression cassette may also contain one or more introns, one or more exons and one or more terminators.

Furthermore, it is contemplated that promoters combining elements from more than one promoter may be useful. For example, U.S. Pat. No. 5,491,288 discloses combining a Cauliflower Mosaic Virus promoter with a histone promoter. Thus, the elements from the promoters disclosed herein may be combined with elements from other promoters. Promoters which are useful for plant transgene expression include those that are inducible, viral, synthetic, constitutive (Odell Nature 313: 810-812 (1985)), temporally regulated, spatially regulated, tissue specific, and spatial temporally regulated. Using the regulatory elements described herein, numerous agronomic genes can be expressed in transformed plants. More particularly, plants can be genetically engineered to express various phenotypes of agronomic interest.

DETAILED DESCRIPTION

One embodiment of the invention provides a method of editing plant genomic DNA, comprising: (i) obtaining a first plant, wherein the first plant is a haploid inducer line of the plant, and wherein said first plant is capable of expressing a DNA modification enzyme and optionally a guide nucleic acid; (ii) obtaining a second plant, wherein the second plant comprises the plant genomic DNA which is to be edited; (iii) pollinating the second plant with pollen from the first plant; and (iv) selecting at least one haploid progeny produced by the pollination of step (c) wherein the haploid progeny comprises the genome of the second plant but not the first plant, and the genome of the haploid progeny has been modified by the DNA modification enzyme and optional guide nucleic acid delivered by the first plant.

In one aspect of the method, the DNA modification enzyme is a site-directed nuclease selected from the group consisting of meganucleases (MNs), zinc-finger nucleases (ZFNs), transcription-activator like effector nucleases (TALENs), Cas9 nuclease, Cfp1 nuclease, dCas9-FokI, dCpf1-FokI, chimeric Cas9-cytidine deaminase, chimeric Cas9-adenine deaminase, chimeric FEN1-FokI, and Mega-TALs, a nickase Cas9 (nCas9), chimeric dCas9 non-FokI nuclease and dCpf1 non-FokI nuclease; and further wherein the guide nucleic acid is a guide RNA.

In another aspect of the method, the edited haploid progeny is treated with a chromosome doubling agent, thereby creating an edited doubled haploid progeny. For example, the chromosome doubling agent is colchicine, pronamide, dithipyr, trifluralin, or another known anti-microtubule agent.

In another aspect of the method, the first plant is a monocot or a dicot. For example, the first plant is a monocot selected from the group consisting of maize, wheat, rice, barley, oats, triticale, sorghum, pearl millet, teosinte, bamboo, sugar cane, asparagus, onion, and garlic. In another aspect, the second plant is a monocot or a dicot. For example the second plant is a monocot selected from the group consisting of maize, wheat, rice, barley, oats, triticale, sorghum, pearl millet, teosinte, bamboo, sugar cane, asparagus, onion, and garlic.

In another aspect of the method, the optional guide RNA is an 18-21 nucleotide sequence and is homologous to a sequence selected from the group consisting of SEQ ID NOs: 2, 4, 8, 21, 23, 25, 29, 32, and 33. In another aspect, the first plant expresses a marker gene. For example, the marker gene is selected from the group consisting of GUS, PMI, PAT, GFP, RFP, CFP, B1, C1, R-nj, anthocyanin pigments, and any other marker gene.

In another aspect of the method, the first plant is a maize plant selected and/or derived from the lines Stock 6, RWK, RWS, UH400, AX5707RS, NP2222-matl, or any of the several other known HI lines.

In one embodiment, the first plant and the second plant are different species. In one aspect, first plant is a wheat plant and the second plant is a maize plant. In another aspect, the first plant is a maize plant and the second plant is a wheat plant.

One object of the invention is a gene-edited plant produced by the method provided.

In another embodiment, the invention provides a method of editing plant genomic DNA, comprising: (i) obtaining a first plant, wherein said first plant is capable of expressing a DNA modification enzyme and optionally a guide nucleic acid; (ii) obtaining a second plant, wherein the second plant comprises the plant genomic DNA which is to be edited; (iii) pollinating the second plant with pollen from the first plant; (iv) applying a composition comprising a lipid or a phospholipase inhibitor immediately preceding, during, or following the pollination of step (iii); and (v) selecting at least one haploid progeny produced by the pollination of step (iii) wherein the haploid progeny comprises the genome of the second plant but not the first plant, and the genome of the haploid progeny has been modified by the DNA modification enzyme and optional guide nucleic acid delivered by the first plant. In one aspect, the composition comprises methyl alpha-linolenoyl fluorophosphonate (MALFP), linoleic acid ethyl ester (LLAEE), linoleic acid (LLA), corn oil, distearoyl-phosphatidyl choline (DSPC), methyl arachidonyl fluorophosphonate (MAFP), Palmityl trifluoromethylketone (PACOCF3), Arachidonyl trifluoromethylketone (AA-COCF3), Manoalide, Linolenic acid ethyl ester (LNAEE), Linolenic acid ethyl ester (LNAEE), Oleic acid methyl ester (OAME), Oleic acid ethyl ester (OAEE), Palmitic acid ethyl ester (PAEE), Palmitoleic acid ethyl ester (PLAEE), Linseed oil, corn oil, alpha-Linolenic acid (aLNA), gamma-Linolenic acid (gLNA), Oleic acid, Arachidonic acid, Stearic Acid, 9(Z)-11(E)-conjugated Linoleic acid, or 2-oleoyl-1-palmitoyl-sn-glycero-3-phospho-ethanolamine.

In another embodiment, the invention provides a method of editing plant genomic DNA, comprising: (i) obtaining a first plant, wherein said first plant is capable of expressing a DNA modification enzyme and optionally a guide nucleic acid; (ii) obtaining a second plant, wherein the second plant comprises the plant genomic DNA which is to be edited; (iii)

crossing the first plant with the second plant; and (iv) selecting at least one haploid progeny produced by the crossing of step (iii) wherein the haploid progeny comprises the genome of the second plant but not the first plant, and the genome of the haploid progeny has been modified by the DNA modification enzyme and optional guide nucleic acid delivered by the first plant. In one aspect, the first plant acts as the female parent in the cross of step (iii). In another aspect, the first plant comprises a mutation in a CENH3 gene, an ig1 gene, or another mutation conferring paternal-haploid inducing systems.

EXAMPLES

I. Producing New Haploid Inducer Lines Comprising the Editing Machinery.

We transformed a transformable line of maize called NP2222 with a TALEN construct, and separately transformed this line with a Cas9 and guide RNA construct. The TALEN construct (pBSC22808 (SEQ ID NO: 5), with TALENs targeting cleavage within target sequence,

```
                                    SEQ ID NO: 6;
5'-TCCAGGGTCAACGTGGAGACAGGGAGGTACGAACCGGTGACTGGCGA

AGGAAGCA-3',
```

TALEN recognition sequence underlined) and the Cas9 construct (pBSC23123 (SEQ ID NO: 7) with guide RNA sequence of xZmPLAIIA, 5'-GGGTCAACGTGGA-GACAGGG-3', SEQ ID NO: 8) were designed to target mutations into the fourth exon of maize gene called MATRI-LINEAL (MATL; GRAMENE ID: GRMZM2G471240). This gene, when mutated at the target site by the TALEN or by the Cas9 and guide RNA, is knocked out, resulting in a loss of function of the protein product. We previously established that lines that are homozygous for loss of function mutations in MATL are haploid inducer lines, meaning that when they are used as pollen donors in crosses, they induce the formation of haploids on the resulting ears (see P.C.T. Patent Application No. PCT/US2016/62548, filed Nov. 17, 2016, incorporated herein by reference in its entirety).

We produced several events and self-pollinated them to make T1 seed. We grew up T1 individuals from event MZET152408A042A. We recovered five T1 progeny that retained two copies of the Cas9 and guide RNA editing machinery stably transformed, and were also homozygous mutant for the MATL gene. See Table 1.

TABLE 1

| New HI lines comprising the genome editing machinery. | | | |
|---|---|---|---|
| New HI Line Individual ID | wt MATL Presence | Cas9 Presence | Mutation in MATL |
| USR01283349 | – | + | 13 bp deletion, homozygous |
| USR01283378 | – | + | 13 bp deletion, homozygous |
| USR01283388 | – | + | 8 bp deletion, homozygous |
| USR01283391 | – | + | 8 bp deletion, homozygous |
| USR01283398 | – | + | 13 bp deletion, homozygous |

The MATL mutations are detected using a TaqMan assay, which amplifies the wildtype copy of MATL (referred to herein as MATL or wt-MATL; these terms are used interchangeably throughout). When both copies of MATL are mutated, this assays reads negative (i.e., "–"). The Cas9 and guide RNA editing machinery were stably inserted via Construct 23123 (SEQ ID NO: 7). We sequenced the mutations in MATL via PCR and subcloning. Four colonies of each PCR product was sequenced, and all of the colonies for a given individual had the same sequence, indicating these plants are all homozygous mutant for the MATL allele (also referred to herein as matl when referencing the 4 basepair insertion in MATRILINEAL found in Stock6 and other Stock6-derived lines, or μMATL when referencing any other human-induced mutation in MATRILINEAL). There were two plants that had 8 bp deletions, and three plants that had 13 bp deletions.

II. Using the New HI Lines as Male Parents and Progeny Analysis.

We crossed the above new HI plants as male pollen donors to a female tester line, which contained a recessive color marker but were wild type for the MATL gene. The male haploid inducer line is homozygous wild type for the same color marker. This female line was thus a non-haploid inducer and were homozygous wild-type for the MATL gene but homozygous mutant for the color marker. We recovered seeds from the crosses, and germinated seedlings therefrom.

Progeny seedlings were subjected to several assays. Progeny seedlings were scored as diploids if they do not exhibit the color marker (because the recessive marker is complemented by the male inducer DNA). Progeny seedlings were scored as putative haploids if they do exhibit the color marker because the recessive marker is not complemented. Of the 2656 seeds planted, we used the color assay and identified 90 seedlings as putative haploids.

We further analyzed the 90 putative haploids for presence of the wildtype MATL gene using a Taqman marker assay. Of these, 82 were positive for MATL, meaning they were not edited by the editing machinery provided by the male parent.

The remaining 8 putative haploid seedlings were negative for wildtype MATL using the Taqman marker, indicating that they may have been edited by the editing machinery provided by the male parent.

We performed ploidy analysis via Flow Cytometry on these 8 putative, edited haploid seedlings using leaf tissue in a ploidy analyzer. See FIGS. 1-8. We found that four of them were true haploids, while the others were actually diploids. As we discuss below, we ran PCR and sequenced the mutations in the MATL gene in these four true haploids as well as for plant USR01350337-2 which, according to the MATL Taqman assay, was not edited by the genome editing machinery.

The finding that there were four diploids among the 90 putative haploids was not unexpected—the seedling assay is not perfect and there are occasional false positives. We tested the 90 haploids for the presence of the Cas9 construct (Construct 23123), and found it was missing in 86 out of 90, including the four true haploids above. In contrast, the four edited diploids that we found during the ploidy analysis all had the Cas9 construct present, confirming their status as hybrid diploids that were falsely identified by the haploid seedling assay as being haploids.

We then used the leaf tissue to isolate genomic DNA and ran a PCR reaction to sequence the MATL gene in those four true haploid, putative edited individuals, specifically focusing on the sequence flanking the guide RNA target mutagenesis site. This was to determine the nature of the edits that may or may not have occurred there. We sub-cloned the PCR fragment using commercially-available TOPO Blunt IV kit, and sequenced at least four colonies each (forward and reverse sequencing). See Table 2, below, for comparisons of the edited alleles and the reference wt-MATL allele.

TABLE 2

| | Comparing the Edited Alleles against wt-MATL. | | |
|---|---|---|---|
| Individual ID | Allele Type | Sequence (corresponds to 1116-1166 of SEQ ID NO: 19) | SEQ ID NO: |
| NP2222 | wt-MATL | AGGGTCAACGTGGAGACAGGGAGGTACGAACCGGTGACTGG | 9 |
| Stock6 | matl | AGGGTCAACGTGGAGACAGGCGAGGAGGTACGAACCGGTGACTGG | 10 |
| USR01350333-3 | edited Allele 1 | AGGGTCAACGTGGAGACAAGGGAGGTACGAACCGGTGACTGG | 11 |
| USR01350333-3 | PCR contamination Allele 2 | AGGGTCAACGTGGA:::::::::::::GAACCGGTGACTGG | 12 |
| USR01350344-2 | edited Allele 1 | AGGGTCAACGTGGAGAC:GGGAGGTACGAACCGGTGACTGG | 13 |
| USR01350344-2 | PCR contamination Allele 2 | AGGGTCAACGTGGA:::::::::::::GAACCGGTGACTGG | 14 |
| USR01350343-1 | edited Allele 1 | AGGGTCAACGTGGAGACAAGGGAGGTACGAACCGGTGACTGG | 15 |
| USR01350328-1 | edited Allele 1 | AGGGTCAACGTGGAGAC:GGGAGGTACGAACCGGTGACTGG | 16 |
| USR01350337-2 | not edited Allele 1 | AGGGTCAACGTGGAGACAGGGAGGTACGAACCGGTGACTGG | 17 |
| USR01350337-2 | PCR contamination Allele 2 | AGGGTCAACGTGGA:::::::::::::GAACCGGTGACTGG | 18 |

Individual USR01350333-3 produced an edited MATL allele with an insertion of alanine at basepair 1143 of the cDNA sequence (underlined in Table 2). This would be sufficient to cause a frameshift in the coding sequence, which would produce a premature STOP codon. What we previously thought was Edited Allele #2 of USR01350333-3 (a 13 basepair deletion of GACAAGGGAGGTAC) was actually the result of PCR contamination. After resequencing, we confirmed that this plant only has one edited allele, and it was found in 6 out of 6 colonies.

This alleles is novel in that it is not in either the male or the female parent plant of this individual. The male parent ID for this individual was USR01283391, and that plant was found to be homozygous for an 8 bp deletion.

Individual USR01350344-2 provides a deletion of A (a deletion of basepair 1143 of the wild type cDNA sequence). This mutation would be sufficient to cause a frame-shift in the coding sequence, and produce a premature STOP codon. After resequencing and discovering the PCR contamination, we confirmed this was found in 6 out of 6 colonies. Previously identified as Edited Allele #2 of USR01350344-2, this was identified as PCR contamination.

Individual USR01350343-1 provides an insertion of A at basepair 1143 of the cDNA sequence. This would be sufficient to cause a frame-shift in the coding sequence, and produce a premature STOP codon. This was found in 4 out of 4 colonies.

Individual USR01350328-1 provides a deletion of A (a deletion of basepair 1143 from the wild type cDNA sequence). This mutation would be sufficient to cause a frame-shift in the coding sequence, and produce a premature STOP codon. It was found in 4 out of 4 colonies.

Individual USR01350337-2 had no change: its sequence was 100% identical to that of wt-MATL.

In summary, we found that 4 out of 86 confirmed haploids had mutations in the MATL gene. We have confirmed that these plants are haploids and do not contain any Cas9 DNA. It is clear that the Cas9 transgene has been eliminated along with the rest of the male-derived DNA during embryogenesis, and that edits have occurred to the female (egg cell-derived) genome in the process of embryogenesis.

We know that the edits are novel and occurred in the female genome in the process of embryogenesis because the haploid inducer line typically makes maternal haploids and we have confirmed that these are indeed haploids. One might try to argue that there is a chance that these are actually paternal haploids, and that the edits we are seeing are actually edits that were already present in the paternal DNA. However, we can prove that this is not the case. First, the mutations do not match those of the paternal parent. This can clearly be seen in Table 3 and 4 (shown below). The edited haploid plant USR01350343-1 was homozygous for an insertion of a single nucleotide (an "A"), but the male parent plant had a deletion of 13 nucleotides. Similarly, plant USR01350328-1 was homozygous for a deletion of an A, but the male parent had a deletion of 13 nucleotides. These examples, taken together, prove that during the haploid induction process, it is possible to have editing of the maternal genome occur, resulting in the formation of edited maternal haploids. According to these and based on the assay detecting MATL presence and the confirmation via ploidy analysis, and using the Cas9 transgene on the male side under control of the maize ubiquitin promoter, the rate of editing during the haploid induction process is about 4/86, or 4.65%.

Furthermore, the rate of editing during haploid induction may be very different when using different haploid inducer lines or using wide crosses. It appears that both haploid induction in maize using MATL mutant lines and wide crosses in barley, wheat, or other crops all work via similar mechanisms: fertilization is followed by genome elimination. It also appears that the time period between fertilization and genome elimination is long enough for the editing machinery to edit the target gene in the genome of the line to which the inducer line has been hybridized (the target germplasm). It is noted that the choice of promoter driving expression of the stably transformed editing proteins system may have a large impact on the rate of editing in haploids. We used a constitutive sugarcane promoter (prSoUbi4) but other promoters driving high or specific expression in the embryo sac, the egg cell, in the pollen, or in sperm cells might be more effective, particularly in the case of wide crosses, in which the male DNA is eliminated in a much more robust and rapid fashion than in intraspecific haploid inducer systems like the maize haploid inducer system or CENH3 type haploid inducer systems. In other words, during a wide cross, for instance when crossing maize pollen on to wheat ears, which is done in order to induce wheat maternal haploids, it might work best to have the editing machinery in the maize pollen driven by a promoter that has strong pollen or sperm cell expression, perhaps in addition to zygote expression, so that abundant editing machinery (RNA and protein) is delivered and present in the zygote cell and during the subsequent two, four, or eight cell embryo stage, even if the male DNA is eliminated or lost very quickly.

TABLE 3

| Haploid Progeny Produced | | | | |
|---|---|---|---|---|
| Individual Progeny ID code | wt MATL Presence | Ploidy Analysis | Cas9 Presence | Allele 1 |
| USR01350333-3 | − | Haploid | − | insertion of A |
| USR01350344-2 | − | Haploid | − | deletion of A |
| USR01350343-1 | − | Haploid | − | insertion of an A |
| USR01350328-1 | − | Haploid | − | deletion of A |
| USR01350337-2 | + | Haploid | − | no mutation |
| USR01350334-3 | − | Diploid | + | |
| USR01350333-10 | − | Diploid | + | |
| USR01350341-1 | − | Diploid | + | |
| USR01350321-3 | − | Diploid | + | |

TABLE 4

| Male Parent Information and Their Progeny | | | | |
|---|---|---|---|---|
| Male Parent ID | wt MATL Presence | Sequencing (# colonies) | Cas9 Presence | Progeny ID |
| USR01283391 | − | deletion of 8 nt (4) | + | USR01350333-3 and USR01350333-10 |
| USR01283349 | − | deletion of 13 nt (4) | + | USR01350344-2, USR01350328-1 and USR01350321-3 |
| USR01283378 | − | deletion of 13 nt (4) | + | USR01350343-1 and USR01350341-1 |
| USR01283398 | − | deletion of 13 nt (4) | + | USR01350337-2 |
| USR01283388 | − | deletion of 8 nt (4) | + | USR01350334-3 |

III. Simultaneous Haploid Induction and Editing in Elite Maize Inbred Lines.

A transformable haploid inducer line, NP2222-HI, RWK, RWS, or UH400 or Stock6 or any other haploid inducer line, all of which already have the mutant versions of MATL, is stably transformed with construct expressing genome modification system such as Cas9+guide RNA (Cong, L. et al. 2013. Multiplex genome engineering using CRISPR/Cas systems. Science 339, 819-823), dCas9-FokI+ guide RNA (Tsai, S. Q. et al. 2014, Dimeric CRISPR RNA-guided FokI nucleases for highly specific genome editing. *Nature Biotechnol.* 32, 569-576), TALEN (Li et al., 2012, High-efficiency TALEN-based gene editing produces disease-resistant rice. Nature Biotech. 30, 390-392), engineered meganuclease (Gao et al., 2010, Heritable targeted mutagenesis in maize using a designed endonuclease. *Plant Journal.* 61:176-187), zinc finger nuclease (Shukla et al. 2009. Precise genome modification in the crop species *Zea mays* using zinc-finger nucleases. Nature 459, 437-441), dCas9-cytidine deaminase (Komor et al. 2016, Programmable editing of a target base in genomic DNA without double-stranded DNA cleavage. Nature doi:10.1038/nature17946) or any other genome modification system. The transgenic haploid inducer line also expressing the editing machinery is then used as pollen donor to create mutations and haploids in target lines via outcrossing. Haploid embryos or seeds are then recovered, identified as haploids, and tested for the edits at the target site (whatever target site is chosen by virtue of the TALEN construct design or the Cas9 guide RNA design). Haploids containing the desired edits is chromosomally doubled using standard procedures using standard means such as colchicine, trifluralin or other chromosome doubling agent. Identification of the induced haploids can be simplified by using a color marker as is typically done in corn doubled haploid production—this color marker can display in the resulting embryos, seeds, seedlings, or adult plant. Presence of mutations at the target site can be checked by sequence analysis (DNA sequencing), by marker analysis, or by phenotype. Because there is only one copy of the DNA to mutate in haploid plants, recessive phenotypes should display so that could be another way to identify the haploids that were edited.

A. Mutagenesis of VLHP Targets in Elite Maize Inbred Line with Transgenic Editing Locus Generated Directly in a Haploid Inducer Line.

VLHP1 and VLHP2 are homeodomain-leucine zipper I-class homeobox genes and members of a class of proteins that is unique to plants. The HD domain is involved in DNA binding whereas the Zip domain is involved in protein homo- and hetero-dimerization. HD-Zip I proteins are generally involved in responses related to abiotic stress, abscisic acid (ABA), blue light, de-etiolation and embryogenesis (Elhiti and Stasolla, 2009. Structure and function of homodomain-leucine zipper (HD-Zip) proteins. *Plant Signal Behav.* 4: 86-88). VLHP1 and VLHP2 are in the same gene family as Grassy Tillers1 (GT1). GT1 promotes lateral bud dormancy and suppresses elongation of lateral ear branches in maize.

Figure 9:
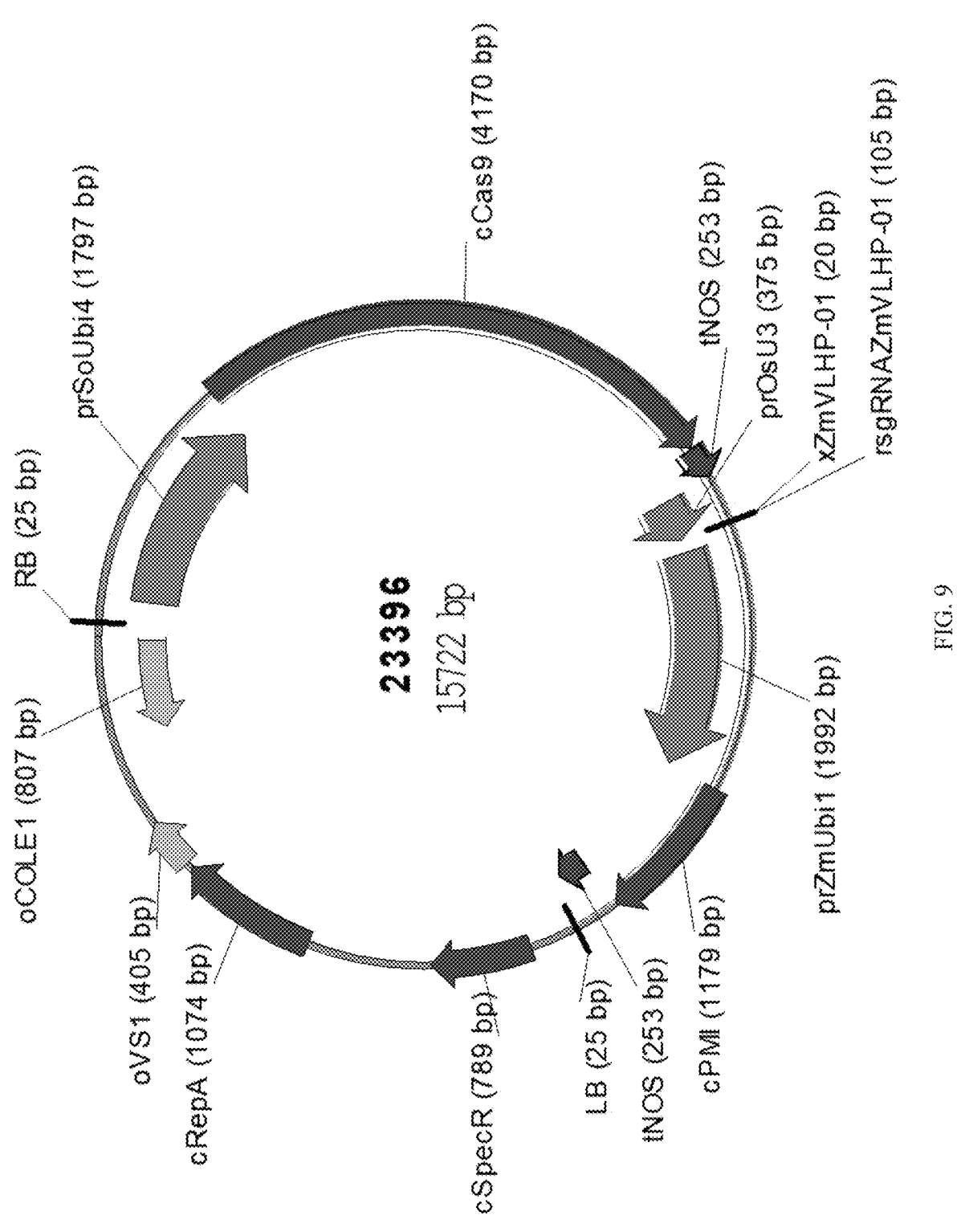
FIG. 9 is a schematic drawing of vector 23396 (SEQ ID NO: 1) used for *Agrobacterium*-mediated transformation of maize immature embryos to generate targeted mutations in ZmVLHP1 genes. xZmVLHP-01: guide RNA (gRNA) sequence (5'-GCAGGAGGCGTCGAGCAGCG-3', SEQ ID NO: 2); rsgRNAZmVLHP-01: single guide RNA (sgRNA) comprising of gRNA, tracRNA and PolIII termination sequences. cPMI: PMI selectable marker gene; cCas9: Cas9 nuclease gene; RB: T-DNA right border; LB: T-DNA left border; tNOS: Nopaline synthetase terminator. cSpec: Spectinomycin resistance gene.

In this example, vector 23396 (SEQ ID NO: 1; see also FIG. 9) for expressing Cas9 and single guide RNA (sgRNA) was made to target maize VLHP1 (GRMZM2G104204) and its homolog VLHP2 (GRMZM2G062244) genes. Vector 23396 expresses a sgRNA with 20-nucleotide targeting sequence xZmVLHP-01 (5'-GCAGGAGGCGTCGAGCAGCG-3', SEQ ID NO: 2). xZmVLHP-01 targets both VLHP1 and VLHP2 genes at the second exon. Vector 23396 was introduced into a transformable haploid inducer line NP2222-HI using *Agrobacterium*-mediated transformation with mannose selection. NP2222-HI was derived from crossing of transformable maize inbred line NP2222 with Stock 6 derivative line RWKS to introgress the haploid induction (HI) locus. NP2222-HI has an average haploid induction rate of about 9.2%.

NP2222-HI transformants from vector 23396 were assayed for modification of genomic VLHP target sequences (5'-GCAGGAGGCGTCGAGCA/GCG-3'; SEQ ID NO: 2). The slash ("/") represents the Cas9 cleavage position. Target locus editing activity was determined using quantitative PCR Taqman method as described before (WO2016106121, incorporated herein by reference). Transgenic lines with high target site modification activities—i.e., both VLHP1 and VLHP2 genes were modified, and preferably containing single copy transgene—were selected for further studies and used for crossing or progeny production.

Pollen from T0 transformants of 23396 is used directly to pollinate ears of elite inbred line ID5829 or other maize lines including sweet corn lines to induce production of haploid embryos. Alternatively, T0 transformants of 23396 in NP2222-HI background are selfed to produce progeny lines carrying homozygous transgene and pollen from the progeny plants are used to pollinate other corn lines to induce haploid embryo formation. The induced haploid embryos are extracted from kernels and placed on embryo rescue media for direct germination or allowed to mature to form seeds. Tissues from the induced haploid embryos and the resulting plants are assayed to determine if editing has occurred in the VLHP target sequences. If the induced haploid embryos or plants contain desired mutations, chromosome doubling treatment is applied to produce doubled haploid lines from them. For example, using embryo rescue method, embryos are extracted from elite line ID5829 ears pollinated with transgenic haploid inducer line carrying 23396 editing locus at 18-22 days after pollination ("DAP," extraction between 10-25 DAP is theoretically possible). DNA is isolated from germinated haploid seedlings and used for assay. Colchicine treatment is applied to seedling for chromosome doubling. Alternatively, chromosome doubling agent can be applied to the isolated embryos during germination. DNA is extracted from germinated seedlings and used for determining that mutation has occurred at the xZmVLHP-01 target sequence.

Alternate methods are available. One could allow the seed to mature and select haploids later by another phenotype. One could let the seed dry down and at a later date germinate the seeds to determine haploids without a marker (e.g., using plant size rather than a gene conferring a color marker), at which point one would test for edits and apply chromosome doubling agents where appropriate. This method may have its advantages in that embryo screening and/or rescue is avoided.

B. Mutagenesis of GW2 Targets in Elite Maize Inbred Line with Transgenic Editing Locus Introduced Directly in a Haploid Inducer Line.

A mutation in DA2, an E3-ubiquitin ligase gene, in rice resulted in larger seeds (Song et al., 2007). Rice DA2 has 2 maize homologs, GW2-1 (GRMZM2G170088) and GW2-2 (GRMZM2G007288). The maize genes are 94% identical at the protein level and 90% identical at the DNA level. GRMZM2G170088 has a large 177 bp insert (59 aa) in comparison with GRMZM2G007288.

Figure 10:
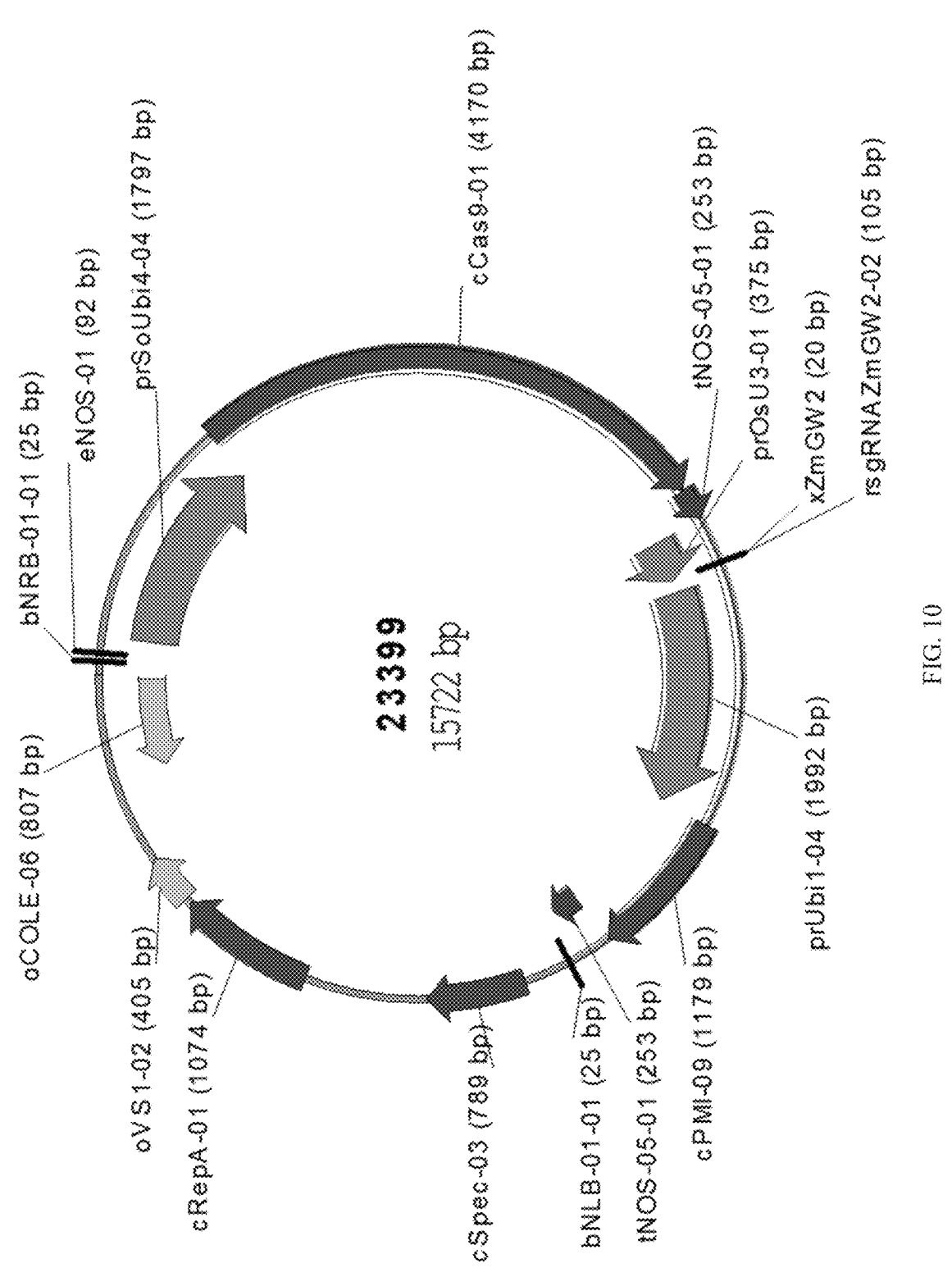
FIG. 10 is a schematic drawing of vector 23399 (SEQ ID NO: 3) used for *Agrobacterium*-mediated transformation of maize immature embryos to generate targeted mutations in ZmGW2 genes. xZmGW2-02: guide RNA (gRNA) sequence (5'-AAGCTCGCGCCCTGCTACCC-3', SEQ ID NO: 4); rsgRNAZmGW2-02: single guide RNA (sgRNA) comprising of gRNA, tracrRNA and PolIII termination sequences. cPMI-09: PMI selectable marker gene; cCas9-01: Cas9 nuclease gene; RB: T-DNA right border; LB: T-DNA left border; tNOS: Nopaline synthetase terminator. cSpec: Spectinomycin resistance gene.

In this example, vector 23399 (SEQ ID NO: 3, see also FIG. 10) was made for expression of Cas9 and sgRNA to target both maize GW2-1 (GRMZM2G170088) and its homolog GW2-2 (GRMZM2G007288) genes. Both GW2-1 and GW2-2 genes contain target sequence xZmGW2-02 (5'-AAGCTCGCGCCCTGCTACCC-3', SEQ ID NO: 4) in exon 1 and this sequence was used to design sgRNA expressed from vector 23399. Binary vector 23399 expresses single guide RNA (sgRNA) with 20-nucleotide targeting sequence xZmGW2-02 fused to single guide RNA scaffold comprising of both crRNA and tracrRNA. Vector 23399 was introduced into a transformable haploid inducer line NP2222-HI using *Agrobacterium*-mediated transformation with mannose selection. NP2222-HI was derived from crossing of transformable maize inbred line NP2222 with Stock 6 derivative line RWKS to introgress the haploid induction (HI) locus.

NP2222-HI transformants of vector 23399 were assayed for modification of genomic GW2-2 target sequences (5'-AAGCTCGCGCCCTGCTA/CCC-3', SEQ ID NO: 4; the slash ("I") indicates the Cas9 cleavage position). Target sequence editing activity was determined using quantitative PCR Taqman method as described before (WO2016106121). Transgenic lines with high target site modification activities—i.e. both GW2-1 and GW2-2 genes were modified, and preferably containing single copy transgene—were selected for further studies and used for crossing or progeny production.

Pollen from T0 transformants of 23399 is used directly to pollinate ears of elite inbred line ID5829 or other maize line including sweet corn lines to induce production of haploid embryos. Alternatively, T0 transformants of 23399 in NP2222-HI background are selfed to produce progeny lines carrying homozygous transgene and pollen from the progeny plants are used to pollinate other corn lines to induce haploid embryo formation. The induced haploid embryos are extracted from kernels and placed on embryo rescue media for direct germination or allowed to mature to form seeds. Tissues from the induced haploid embryos and the resulting plants are assayed to determine if editing has occurred in the maize GW2 target sequences. If the induced haploid embryos or plants contain desired mutations, chromosome doubling treatment is applied to produce doubled haploid lines from them. For example, using embryo rescue method, embryos are extracted from elite line ID5829 ears pollinated with transgenic haploid inducer line carrying 23396 editing locus at 18-22 days after pollination. DNA is isolated from germinated haploid seedlings and used for assay. Colchicine treatment is applied to seedling for chromosome doubling. Alternatively, chromosome doubling agent can be applied to the isolated embryos during germination. DNA is extracted from germinated seedlings and used for determining if mutation has occurred at the xZmGW2-02 target sequence. Alternately, one could allow the seed to mature and select haploids later by another phenotype. One could even let the seed dry down and at a later date germinate the seeds to determine haploids without a marker (e.g., using plant size rather than a gene conferring a color marker), at which point one would test for edits and apply chromosome doubling agents where appropriate. This method may have its advantages in that embryo screening and/or rescue is avoided.

IV. Simultaneous Haploid Induction and Editing in Corn, Rice, Sunflower, or any Other Crop Via Chemical-Based Haploid Induction Any line of corn, rice, wheat, tomato, sunflower, barley, or any other crop is transformable with the editing construct (Cas9 plus guide RNAs designed to mutate a particular target site) and then optionally make the editing construct either heterozygous or homozygous (via self-pollination of the transformed event), and then using lipid or oil applications during outcrossing (pollination onto target lines) in order to induce de novo haploids and simultaneously edit the target sites in the target genomes. These lipid applications have the ability to induce haploids when applied to pollen, silks, flowers, or tassels of any plant—regardless of male parent. In particular, the male parent is not required to have any mutations in the MATL gene (i.e., it can be homozygous wild type for the MATRILINEAL gene). These lipid applications induce haploids de novo, without any genetic requirement on behalf of either parent. See P.C.T. Patent Application No. PCT/US2016/62548, incorporated herein by reference in its entirety. The mechanism of de novo haploid induction via lipid spray apparently works the same way as it does in matl mutant (genetic haploid inducer) lines: via chromosome elimination post-fertilization. Haploid progeny are isolated and checked for the induced mutations (caused via the editing process) and then doubled to make edited, doubled haploid plants.

V. Mutagenesis of Target Sequences in Elite Field Corn and Sweet Corn Inbred Lines with Transgenic Editing Locus Introgressed into a Haploid Inducer Line.

Transgenic locus expressing genome editing machinery can also be generated in conventional transformable maize line without haploid inducing activity such as A188, Hi-II or NP2222 and then introgressed into haploid inducer line such as NP2222-HI, RWK, RWKS, RWS, or UH400 or Stock6 or any other haploid inducer line.

In this example, maize inbred line NP2222 is transformed with VLHP Cas9-sgRNA vectors (23396 and 23397) and GW2 Cas9-sgRNA vectors (23398 and 23399). Vectors 23396 and 23399 have been described in previous examples (Example IIIA and Example IIIB). Vector 23397 (SEQ ID NO: 20) is identical to 23396 except the gRNA-coding sequence xZmVLHP-01 (5'-GCAG-GAGGCGTCGAGCAGCG-3', SEQ ID NO: 2) is replaced with xZmVLHP-02 (5'-GCTGGAGCTGAGCTTCCGGG-3', SEQ ID NO: 21). Vector 23398 (SEQ ID NO: 23) is identical to 23399 except the gRNA-coding sequence xZmGW2-02 (5'-AAGCTCGCGCCCTGCTACCC-3', SEQ ID NO: 4) in 23399 is replaced by xZmGW2-01 (5'-GAGCGGTTCACGCGGCCGCA-3', SEQ ID NO: 23). These vectors were introduced into *Agrobacterium* strain LBA4404 (pVGW7). The resulting *Agrobacterium* strain containing vector 23396, 23397, 23398, or 23399 was used to transform immature embryos of transformable elite inbred line NP2222. Calli were induced from infected immature embryos and selected on mannose media to recover transgenic calli. Transgenic calli were placed on regeneration and rooting media to recover transgenic plants expressing the CRISPR-Cas9 editing machinery. Transgenic plants were assayed for transgene copy number and moved to greenhouse for seed production.

Single copy transformants of vector 23396 (MZET154902A004A, MZET154902B006A), 23397 (MZET154903B009A, MZET154903B012A), 23398 (MZET154904B005A, MZET154904B014A) and 23399 (MZET154905A002A, MZET154905A010A) were identified and backcrossed with non-transgenic NP2222. Ears of transgenic progeny plants containing T-DNA insert of each of the above vectors were pollinated with pollen of haploid inducer line RWKS to produce F1 progeny. F1 progeny containing transgenic locus and haploid induction locus were identified by genotyping assays and self-pollinated to produce F2 progeny seeds. F2 progeny seeds were planted and seedling plants assayed to identify plants homozygous for transgenic Cas9-sgRNA locus (assay #2540) and haploid induction locus (assay #2827) with qPCR Taqman assays.

Lines homozygous for the haploid induction locus and preferably homozygous transgenic 23396, 23397, 23398, and 23399 Cas9-sgRNA editing locus were used to pollinate ears from target elite field corn line ID5829 and sweet corn lines (SWC726 or SWC412F) for haploid induction. Induced haploid embryos were isolated from pollinated haploid inducer locus will have copy call of "2" for assay #2826 and "0" for assay #2827 (haploid inducer variant). If a corn plant line is a diploid between sweet corn and transgenic inducer, it will be heterozygous for the haploid inducer gene and thus have copy call of "1" for both assay #2826 and assay #2827.

TABLE 5

Progeny zygosity analysis from crosses. Taqman analysis results showing the lines do not contain transgene or haploid inducer locus from pollen donor, but have edits in GW2-01 and/or GW2-02 targets.

| | | | | Allele: | | | |
|---|---|---|---|---|---|---|---|
| | | cCas9-01 | cPMI-09 | CRISPR target in GW2-01 (23399) | CRISPR target in GW2-02 (23399) | pPLAIIa WT allele | RWK (Haploid Inducer) allele of pPLAIIa |
| | | | | Assay ID: | | | |
| Plant ID | Construct ID | 2540 Copy# level | 1750 Copy# level | 3065 Copy# level | 3095 Copy# level | 2826 Copy# level | 2827 Copy# level |
| 1-copy control | | + | 1 | ND | ND | 1 | 1 |
| wild type control | | 0 | 0 | 2 | 2 | 2 | 0 |
| JSER82A056 | 23399 | 0 | 0 | 0 | 0 | 2 | 0 |
| JSER82A063 | 23399 | 0 | 0 | 1 or 2 | 0 | 2 | 0 |
| JSER85A021 | 23399 | 0 | 0 | 0 | >2 | 2 | 0 |
| JSER85A022 | 23399 | 0 | 0 | 0 | >2 | 2 | 0 |
| JSER85A024 | 23399 | 0 | 0 | 0 | >2 | 2 | 0 |
| JSER85A027 | 23399 | 0 | 0 | 0 | >2 | 2 | 0 |
| JSER85A037 | 23399 | 0 | 0 | 0 | >2 | 2 | 0 |
| JSER85A039 | 23399 | 0 | 0 | 0 | >2 | 2 | 0 |
| JSER85A044 | 23399 | 0 | 0 | 0 | >2 | 2 | 0 |
| JSER85A055 | 23399 | 0 | 0 | 0 | >2 | 2 | 0 |

ID5829, SWC412F, SWC726 ears and geminated on embryo rescue media. Alternatively, pollinated ears were allowed to mature and kernels with haploid embryos were germinated. Leaf samples were collected and analyzed with Taqman assay to identify plants containing mutations in VLHP and GW2 genes but absence of genetic components from induction line such as transgenic Cas9-sgRNA or other non-transgenic marker gene sequences. Identified haploid plants with targeted GW2 or VLHP gene mutations were treated with colchicine for chromosome doubling to recover doubled haploid plants for seed production. Alternatively, extracted haploid embryos can be treated with chromosome doubling agent such as colchicine and the resulting plants are analyzed for ploidy level and presence of targeted mutations in GW2 or VLHP genes. Plants with targeted GW2 and VLHP gene mutations are grown to maturity for seed production and further progeny evaluation.

Figure 11:
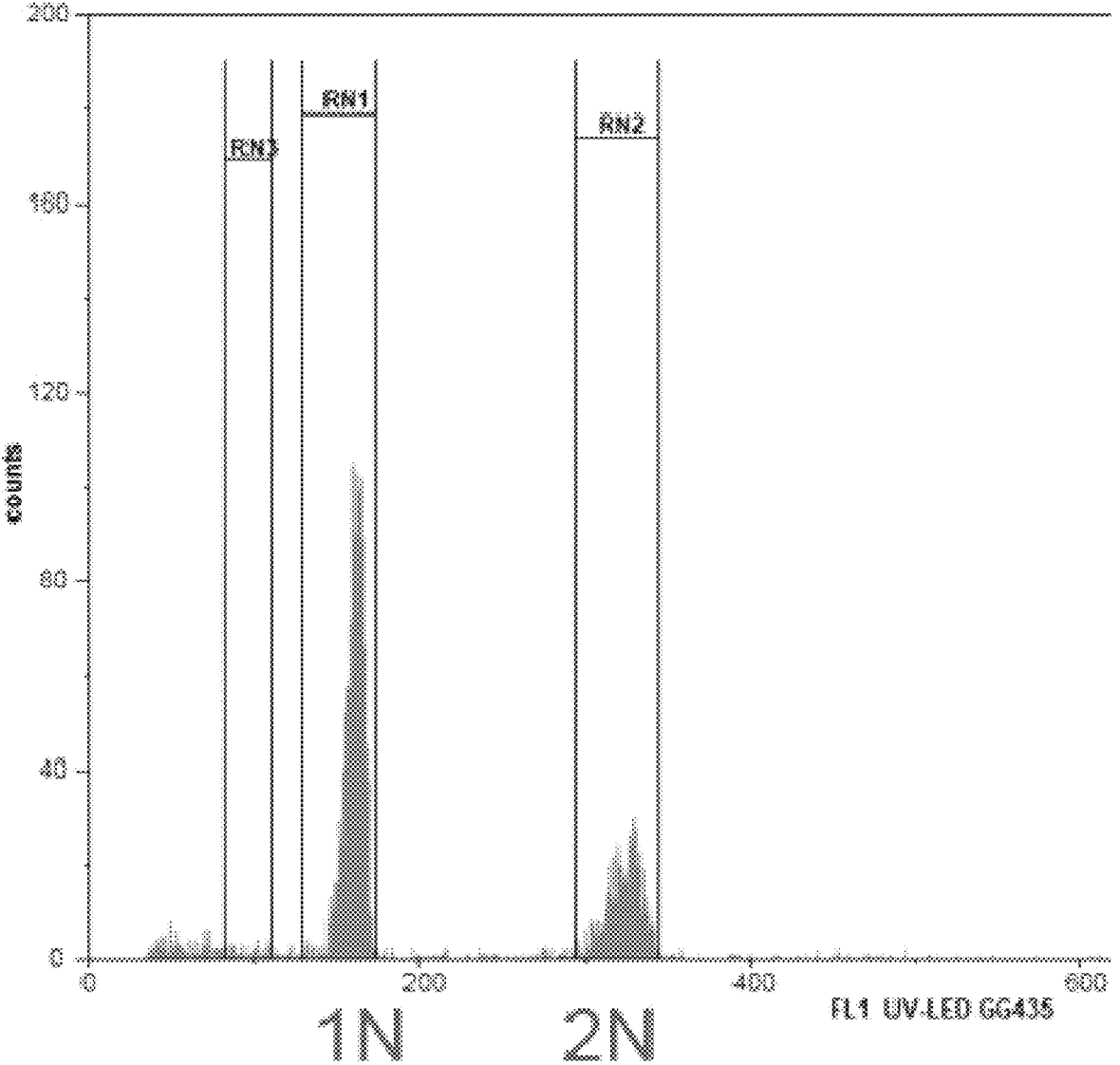
FIG. 11 shows ploidy assay of edited haploid sweet corn line JSER82A056.
Figure 12:
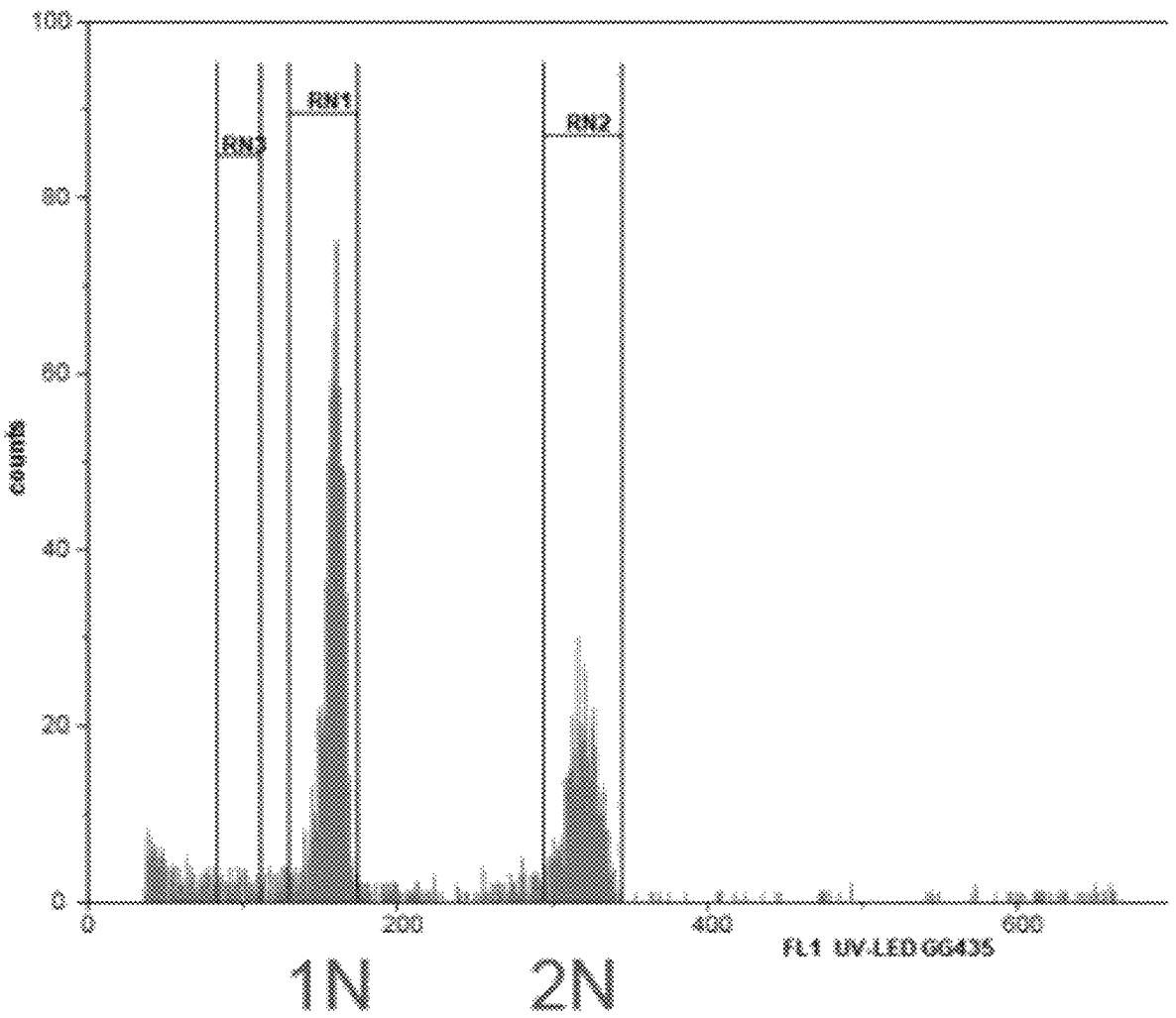
FIG. 12 shows the same for edited haploid sweet corn line JSER82A063. These lines were obtained through crossing with RWKS haploid induction line carrying transgene locus of CRISPR-Cas9 expression vector 23399.
Figure 13:
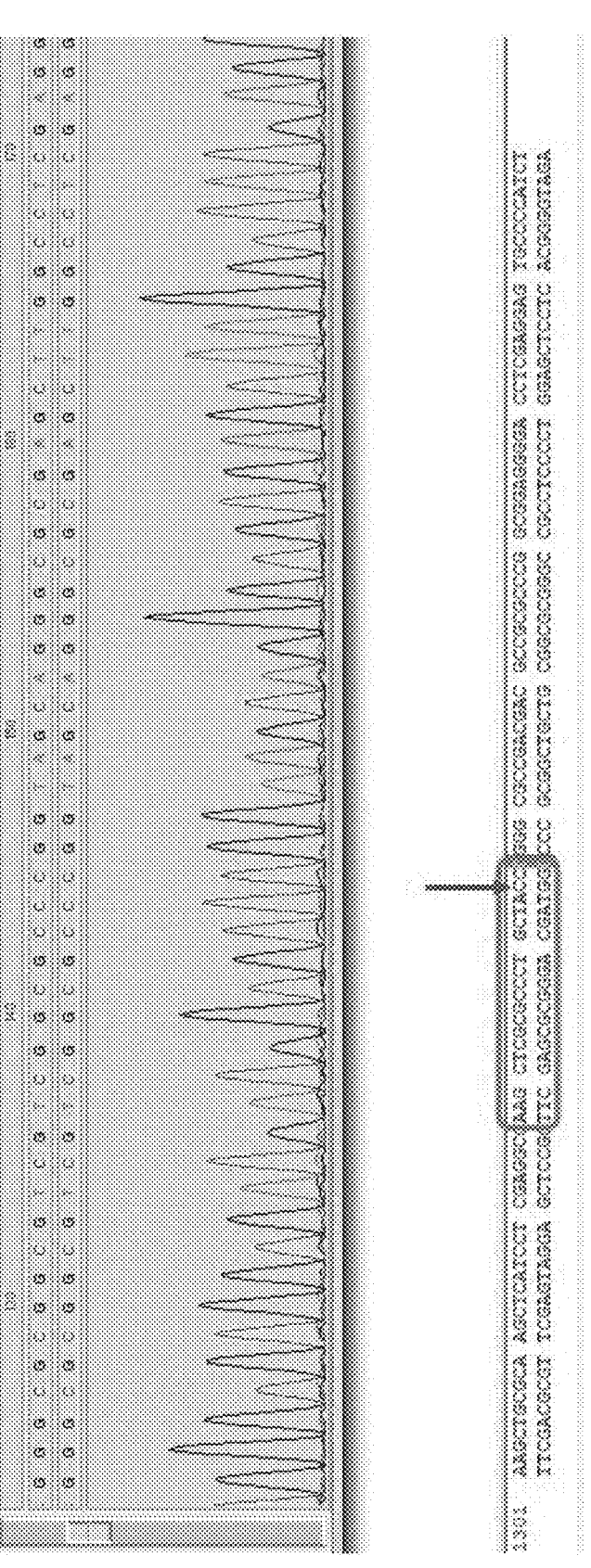
FIG. 13 shows sequencing confirmation of GW2-02 target site editing in haploid sweet corn line JSER82A063. A single base C next to the predicted Cas9 cleavage site was deleted. The sequence presented within the box is identical to SEQ ID NO: 4. The top-line sequence presented at the bottom of the figure is represented by SEQ ID NO: 99. The bottom-line sequence is represented by SEQ ID NO: 100 and is the reverse complement of SEQ ID NO: 99.

For example, edited haploid lines (JSER82A056 and JSER82A063) were identified from crosses between sweet corn line SWC412F ears pollinated with haploid inducer containing 23399 Cas9-sgRNA transgene. Line JSER82A056 has both GW2-01 and GW2-02 target genes mutated, whereas line JSER82A063 only has GW2-02 gene mutated (See Table 5). Neither of these lines contain Cas9 transgene (assay #2540 for Cas9 or #1750 for PMI selectable marker gene) or haploid inducer gene (assay #2827) as the male genome has been eliminated from the haploids. Ploidy level analysis confirmed that both lines are haploids (FIGS. 11 and 12). Note that wildtype ("WT") genes in the haploids have a copy number of "2" and mutant will be "0" since the copy call is relative to the endogenous ADH gene copy number. Therefore, haploid lines carrying WT unedited GW2-01 or GW2-02 genes will have a copy call of "2." WT To further confirm target-specific editing in these haploid lines, GW2-02 target region was amplified from JSER82A063 by PCR and the PCR product was sequenced. A single base C was deleted in JSER82A063 in comparison with the WT sequence precisely at the Cas9 cleavage site (FIG. 13). These results clearly demonstrated that editing machinery brought into the egg cell from the male gametophyte can edit the female genome before the male genome is eliminated after double fertilization to form haploid embryo. Candidate edited haploid lines without transgene were treated with injection of 0.125% colchicine in 0.5% DMSO or seedling drenching in 0.06% colchicine solution (Eder and Chalyk, 2002, In vivo haploid induction in maize. Theor. Appl. Genetics 104:703-708). Treated lines were planted in soil and grown in greenhouse for progeny seed production.

VI. Simultaneous Haploid Induction and Editing in Wheat and Other Monocots Via Wide Cross.

Haploid induction is also achieved using interspecific or intergeneric wide crosses (Kasha and Kao, 1970, High frequency haploid production in barley (*Hordeum vulgare* L.). Nature 225:874-886). For example, wheat haploids can be obtained by pollination with various intergeneric crosses with maize (Suenaga and Nakajima 1989), pearl millet (Inagaki and Mujeeb-Kazi 1995), teosinte (Ushiyama et al. 1991), *H. bulbosum* (Barclay 1975), and sorghum (Ohkawa et al. 1992). Barley haploids are obtained by pollination with *Hordeum bulbosum* pollen. Tobacco haploids can be obtained by crossing with *N. africana* pollen. Many other examples exist in other crops.

Similar to examples above in introducing transgenic editing locus into Stock6 induction line, transgenic editing locus can be introduced into these lines used for wide crosses to induce haploid induction and targeted sequence mutation. Transgenic lines expressing editing machinery can be generated in any line of corn, wheat, barley, rye, pearl millet, rice, *brassica*, lettuce, tomato, or any other crop by direct transformation or outcrossing. Preferably the transgenic locus is made homozygous and then the line is used as pollen donor in a wide cross with other compatible recipient crops to induce haploids to produce desired edits. The process of post-fertilization genome elimination in wide crosses is basically the same as the process in the maize MATL mutant system, although in some cases the foreign pollen-derived DNA and editing machinery may be eliminated slightly earlier in embryo development, which is why this method is preferably practiced using a promoter that drives expression of the editing machinery in the pollen, sperm cells, and/or zygote cell, so that the editing RNA and protein is present and able to edit the target genome even though the male DNA is eliminated rather quickly after fertilization.

To demonstrate feasibility of simultaneous haploid induction and editing via wide crosses, maize transgenic lines expressing Cas9 and sgRNA targeting wheat VLHP gene sequences were generated. Vector 23763 (SEQ ID NO: 24) contains expression cassettes for Cas9 and sgRNA containing protospacer sequence xTaVLHP1 (5'-GACGAGCAGGCGCAGTTCC-3', SEQ ID NO: 25) for guiding Cas9-mediated cleavage of TaVLHP1 target sites in wheat. The wheat genome has three xTaVLHP1 targets in total (TaVLHP1-4A, TaVLHP1-4B and TaVLHP1-4D), with each one in its three sub-genomes. The guide sequence in 23397 (SEQ ID NO: 20), xZmVLHP (5'-GCTGGAGCT-GAGCTTCCGGG-3', SEQ ID NO: 21) will also direct cleavage of wheat VLHP target sequences, xTaVLHP2-1A (5'-GCTGGAGCTGAGCTTCCGGG-3', SEQ ID NO: 26) or xTaVLHP2-1B (5'-TCTGGAGCTGAGCTTCCGGG-3', SEQ ID NO: 27). There are three VLHP2A genes containing xTaVLHP2-1A and 3 VLHP2B genes containing xTaVLHP2-1B sequences in the Chinese Spring wheat genome. Vectors 23397 and 23763 were transformed into maize inbred line NP2222 using *Agrobacterium*-mediated transformation to generate transgenic lines expressing Cas9 and sgRNA. Transgenic maize lines were grown in greenhouse and selfed to produce T1 plants.

Pollen collected from transgenic maize T0 or progeny T1 plants carrying T-DNA of vector 23397 or 23763 were used to pollinate emasculated spring wheat line AC-Nanda. At one to two days before anthesis, wheat florets were emasculated and two days later are pollinated with fresh maize pollen carrying the editing machinery. For convenience, spikelets from a Syngenta elite cytoplasmic male sterile ("CMS") wheat line (16A300292) were also directly used as female donors to induce haploid embryo formation with transgenic maize pollen expressing 23397 or 23763 Cas9-sgRNA. Embryos were extracted from pollinated florets at 14-20 days after pollination for embryo rescue to recover haploid plantlets from the wheat×maize haploid induction system. Excised embryos were cultured on either full strength MS (Murashige and Skoog 1962) or ½ MS or B5 basal medium containing various modifications of organic supplements and grown in vitro for 3-5 weeks at 20-25° C. and 16-hour day length.

Figure 14:
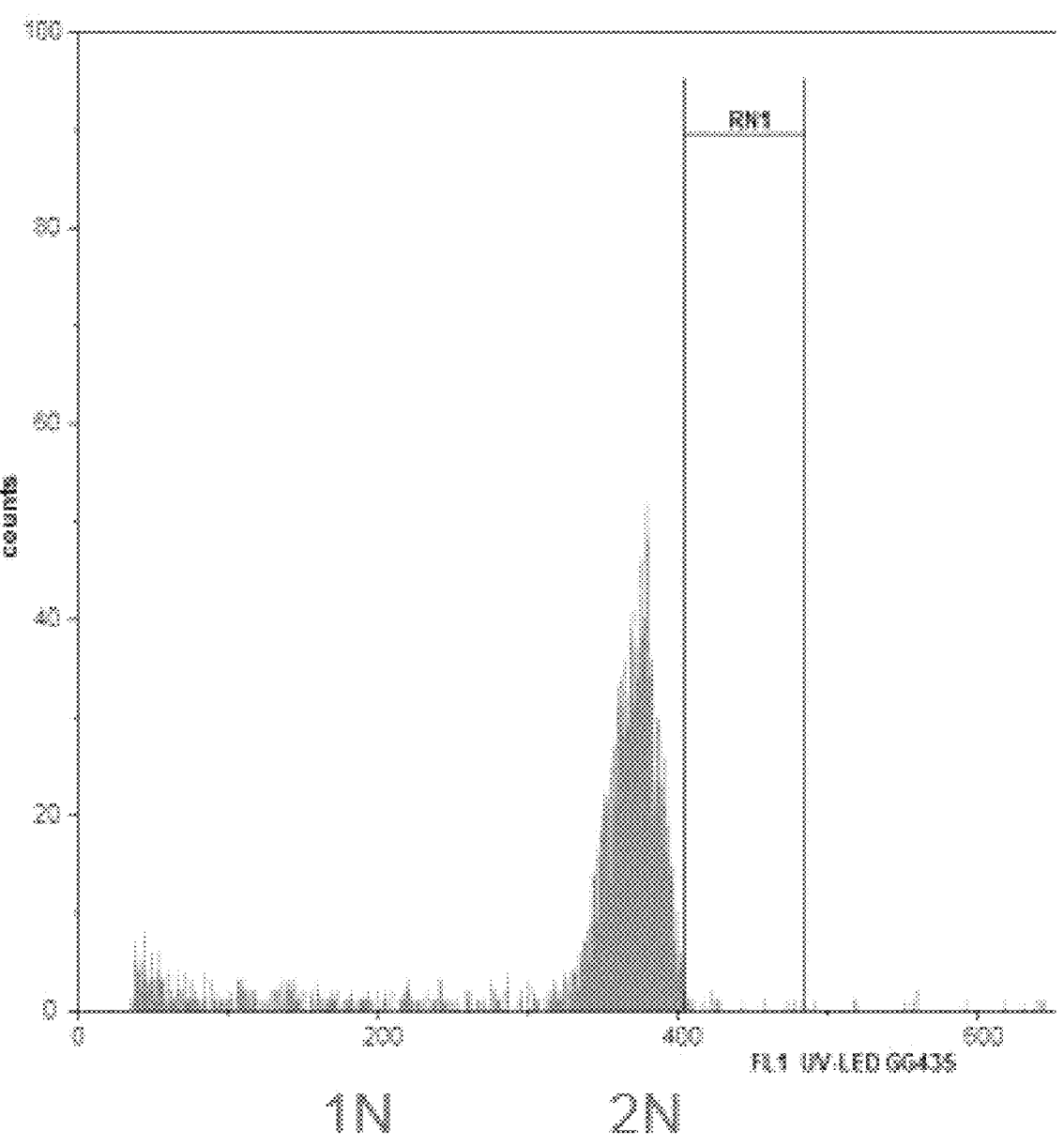
FIG. 14 shows ploidy analysis of wild type control.
Figure 15:
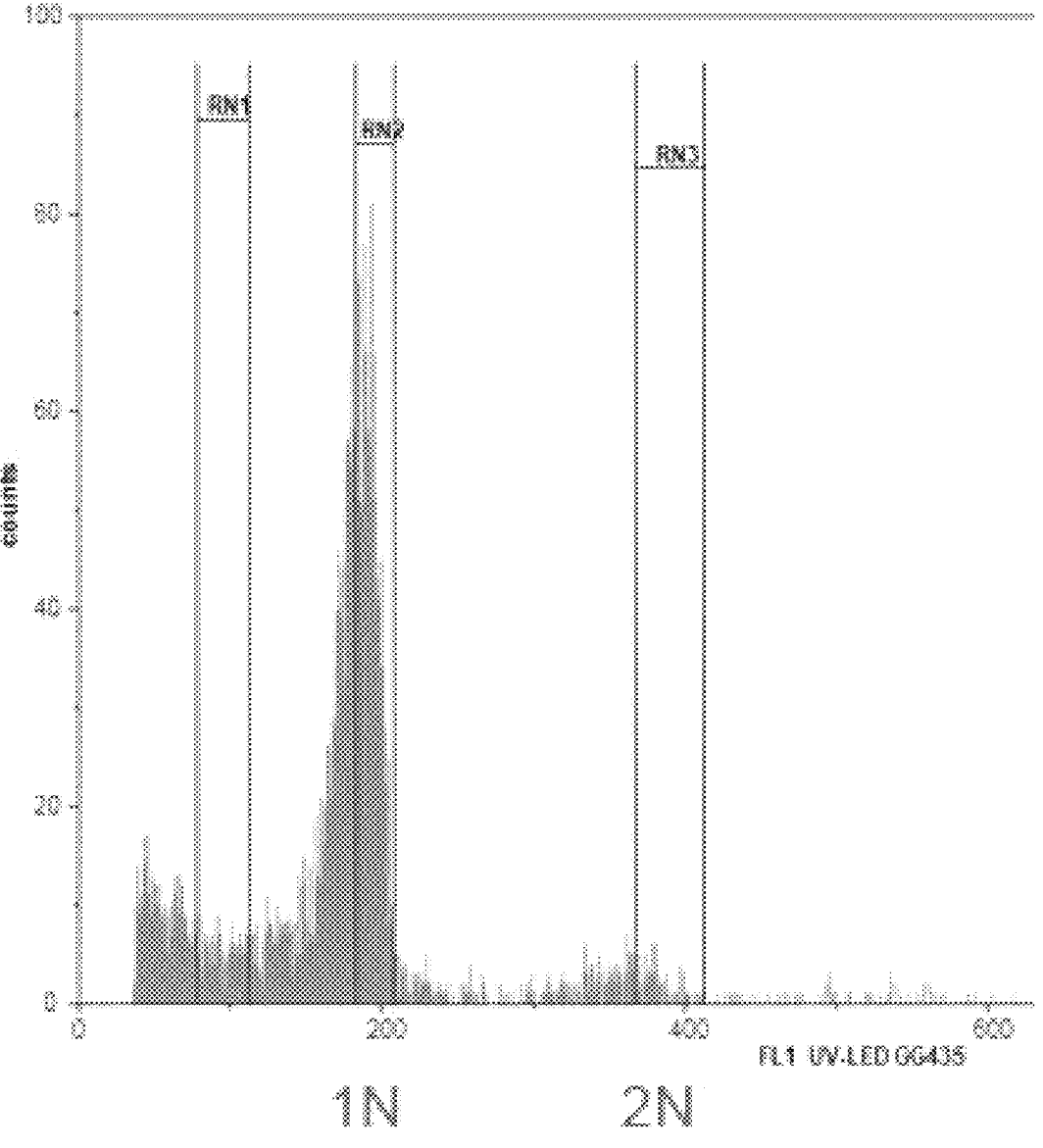
FIG. 15 shows ploidy analysis of edited haploid wheat line JSWER30A22.
Figure 16:
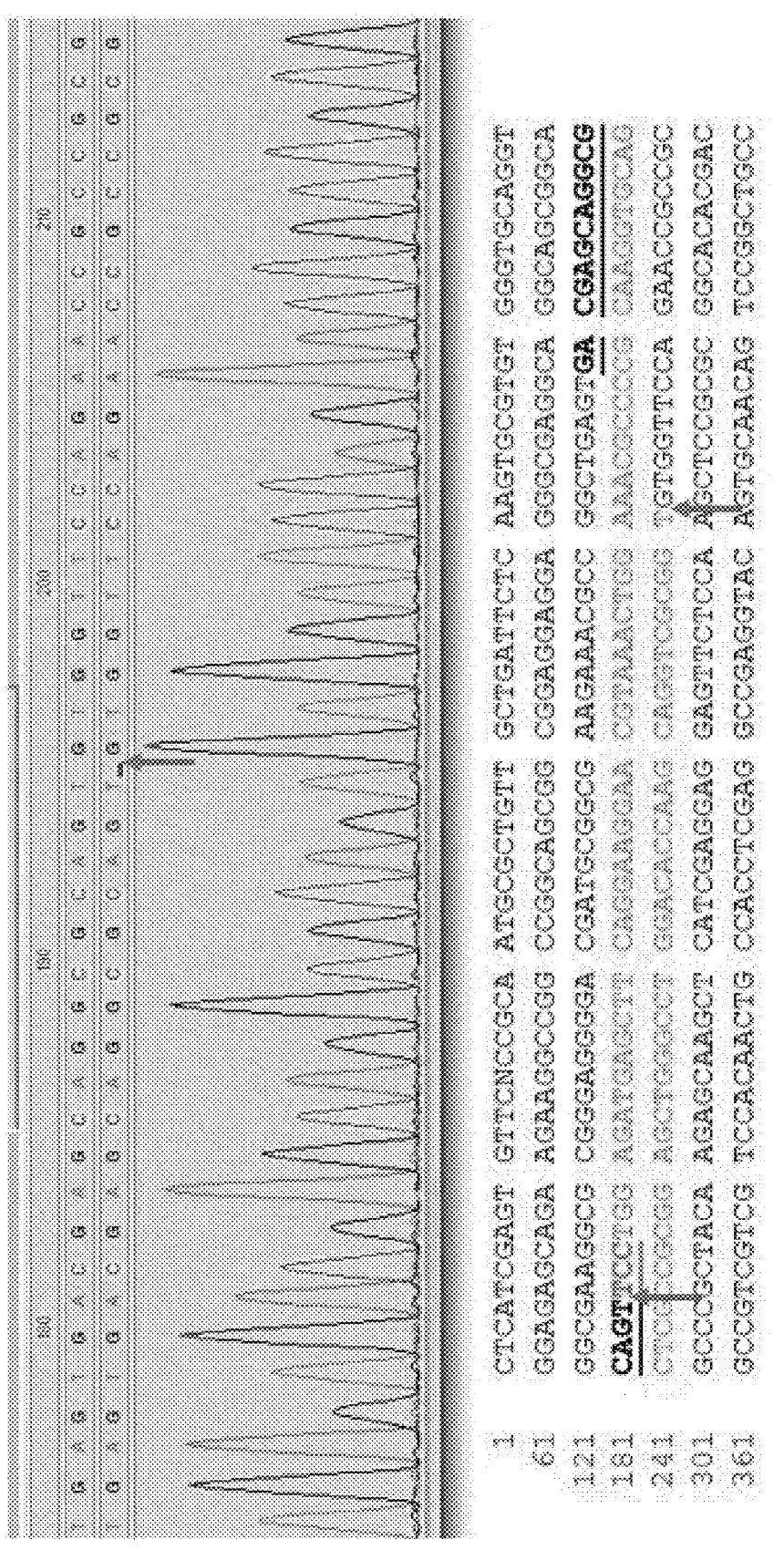
FIG. 16 shows sequencing confirmation of TaVLHP1-4B target site editing in haploid wheat line JSWER30A22. Lower panel showing 97 bp of TaVLHP1-4B sequence was deleted immediately downstream of the predicted Cas9 cleavage site. The 97 bp deleted sequences were marked by 2 arrows. The underlined sequence matches the gRNA sequence of SEQ ID NO: 25. The entire sequence is represented by SEQ ID NO: 101.

For example, pollen of T1 progeny from transgenic maize line MZET164902A044A containing vector 23763 was used to pollinate spikes of CMS line 16A300292 to induce wheat haploids. Haploid embryos were rescued and the resulting wheat haploid seedling were sampled for qPCR analysis to determine the copy number of VLHP target sequences (See Table 6). One of the haploid lines (JSWER30A22) was found to contain mutation in TaVLHP1-4B gene, but not in its orthologs TaVLHP1-4A and TaVLHP1-4D in the A and D sub-genomes. Ploidy level analysis confirmed that JSWER30A22 is a true haploid (See FIGS. 14 and 15). The mutation within the TaVLHP1-4B target region was further characterized by sequencing and was found to contain 97 bp deletion starting from the predicted Cas9 cleavage site (FIG. 16). We also identified another line JSW16A07 with "0" copy in TaVLHP1-4A gene (assay #3252), suggesting targeted editing in the target sequence. However, the deletion in this target gene is probably quite large in deleting the primer binding site(s) since we were not able to recover PCR product for sequencing. Haploid seedlings with an edited target site were transplanted to soil after 3-5 weeks in vitro culture. The transplanted seedlings were hardened for one week in a growth chamber under the same environmental regime. Colchicine was added after shoots had formed. However, the chromosome doubling treatment can be done earlier at embryo rescue in vitro culture stage or later after transplanting. When whole wheat seedlings are treated for doubling, roots of the haploid seedling are trimmed leaving a zone of 2-3 cm and then submerged in a 0.1% colchicine solution with 2% dimethyl sulfoxide (DMSO) and ca. 0.05% Tween-20 at 20° C. for 5 hours. After this treatment, the roots are washed to remove residual colchicine and potted in peat soil. Plant tissue samples can be removed from haploid seedlings for mutation detection to identify plants containing mutations in TaVLHP target gene sequences but with the maize chromosomes including sequences encoding the transgenic editing machinery completely eliminated. Since JSWER30A22 is from a CMS line, the plant is pollinated with a restorer to produce progeny seeds.

TABLE 6

Taqman analysis for wheat progeny from wide crosses. Line JSW30A22 is edited.

| | | Allele: | | | | |
|---|---|---|---|---|---|---|
| | | TAV_4A | TAV_4B | TAV_4D | PMI | CAS 9 |
| | | | | Assay ID: | | |
| Plant ID | Construct ID | 3252 Copy# level | 3253 Copy# level | 3254 Copy# level | 1750 Copy# level | 2540 Copy# level |
| WT, AC-Nanda | N/A | >2 | 2 | >2 | 0 | 0 |
| WT, AC-Nanda | N/A | 2 | 2 | 2 | 0 | 0 |
| WT, CMS | N/A | 2 | 2 | 2 | 0 | 0 |
| WT, CMS | N/A | 2 | 2 | 2 | 0 | 0 |
| JSW29A01 | 23763 | 2 | 2 | 2 | 0 | 0 |
| JSW29A02 | 23763 | 2 | 2 | 2 | 0 | 0 |

TABLE 6-continued

Taqman analysis for wheat progeny from wide crosses. Line JSW30A22 is edited.

| | | Allele: | | | | |
| | | TAV_4A | TAV_4B | TAV_4D | PMI | CAS 9 |
| | | | | Assay ID: | | |
| Plant ID | Construct ID | 3252 Copy# level | 3253 Copy# level | 3254 Copy# level | 1750 Copy# level | 2540 Copy# level |
|---|---|---|---|---|---|---|
| JSW29A03 | 23763 | 2 | 2 | 2 | 0 | 0 |
| JSW29A04 | 23763 | 2 | 2 | 2 | 0 | 0 |
| JSW29A05 | 23763 | 1 or 2 | 2 | 2 | 0 | 0 |
| JSW29A06 | 23763 | 2 | 2 | 2 | 0 | 0 |
| JSW29A07 | 23763 | 2 | 2 | 2 | 0 | 0 |
| JSW29A08 | 23763 | 2 | 2 | 2 | 0 | 0 |
| JSW29A09 | 23763 | 2 | 2 | 2 | 0 | 0 |
| JSW29A10 | 23763 | 2 | 2 | 2 | 0 | 0 |
| JSW29A11 | 23763 | 2 | 2 | 2 | 0 | 0 |
| JSW29A12 | 23763 | 2 | 2 | 2 | 0 | 0 |
| JSW29A13 | 23763 | 2 | 2 | 2 | 0 | 0 |
| JSW29A14 | 23763 | 2 | 2 | 2 | 0 | 0 |
| JSW29A15 | 23763 | 2 | 2 | 2 | 0 | 0 |
| JSW29A16 | 23763 | 2 | 2 | 2 | 0 | 0 |
| JSW30A01 | 23763 | 2 | 2 | 2 | 0 | 0 |
| JSW30A02 | 23763 | 2 | 1 or 2 | 2 | 0 | 0 |
| JSW30A03 | 23763 | 2 | 2 | 2 | 0 | 0 |
| JSW30A04 | 23763 | 2 | 2 | 2 | 0 | 0 |
| JSW30A05 | 23763 | 2 | 2 | 2 | 0 | 0 |
| JSW30A06 | 23763 | 2 | 2 | 2 | 0 | 0 |
| JSW30A07 | 23763 | 2 | 2 | 2 | 0 | 0 |
| JSW30A08 | 23763 | 2 | 2 | 2 | 0 | 0 |
| JSW30A09 | 23763 | 2 | 2 | 2 | 0 | 0 |
| JSW30A10 | 23763 | 2 | 2 | 2 | 0 | 0 |
| JSW30A11 | 23763 | 2 | 2 | 2 | 0 | 0 |
| JSW30A12 | 23763 | 2 | 2 | 2 | 0 | 0 |
| JSW30A13 | 23763 | 2 | 2 | 2 | 0 | 0 |
| JSW30A14 | 23763 | 2 | 2 | 2 | 0 | 0 |
| JSW30A15 | 23763 | 2 | 2 | 2 | 0 | 0 |
| JSW30A16 | 23763 | 2 | 2 | 2 | 0 | 0 |
| JSW30A17 | 23763 | 2 | 2 | 2 | 0 | 0 |
| JSW30A18 | 23763 | 2 | 2 | 2 | 0 | 0 |
| JSW30A19 | 23763 | >2 | 2 | 2 | 0 | 0 |
| JSW30A20 | 23763 | 2 | 2 | 2 | 0 | 0 |
| JSW30A21 | 23763 | 2 | 2 | 2 | 0 | 0 |
| JSW30A22 | 23763 | 2 | 0 | 2 | 0 | 0 |
| JSW30A23 | 23763 | 2 | 2 | 1 or 2 | 0 | 0 |
| JSW30A24 | 23763 | 2 | 2 | 2 | 0 | 0 |
| JSW30A25 | 23763 | 2 | 2 | 2 | 0 | 0 |
| JSW30A26 | 23763 | 2 | 2 | 2 | 0 | 0 |
| JSW30A27 | 23763 | 2 | 2 | 2 | 0 | 0 |
| JSW30A28 | 23763 | 2 | 2 | 2 | 0 | 0 |
| JSW30A29 | 23763 | 2 | 2 | 2 | 0 | 0 |
| JSW30A30 | 23763 | 2 | 1 or 2 | 1 or 2 | 0 | 0 |
| JSW30A31 | 23763 | 2 | 2 | 2 | 0 | 0 |

To further demonstrate feasibility of simultaneous haploid induction and editing via wide crosses, maize transgenic lines expressing Cas9 from five promoters that have high and/or specific expression in pollen, along with sgRNA targeting wheat VLHP gene sequences, were generated. These five vectors were 24038 (SEQ ID NO: 34), 24039 (SEQ ID NO: 35), 24079 (SEQ ID NO: 36), 24091 (SEQ ID NO: 37), and 24094 (SEQ ID NO: 38). All five of these vectors utilized the same sgRNA containing protospacer sequence xTaVLHP2 (5'-GCTGGAGCT-GAGCTTCCGGG-3', SEQ ID NO: 21) for guiding Cas9-mediated cleavage of TaVLHP2 target sites in wheat. The wheat genome has three xTaVLHP2 targets in total (TaV-LHP2-2A, TaVLHP2-2B and TaVLHP2-2D), with each one in its three sub-genomes. The guide sequence in these five constructs also directs cleavage of wheat VLHP target sequences, xTaVLHP2 (5'-GCTGGAGCT-GAGCTTCCGGG-3', SEQ ID NO: 26) or xTaVLHP3 (5'-

TCTGGAGCTGAGCTTCCGGG-3', SEQ ID NO: 27). There are three TaVLHP2 genes containing xTaVLHP2 and 3 TaVLHP3 genes containing xTaVLHP2-1B sequences in the Chinese Spring wheat genome.

Vector 24038 (SEQ ID NO: 34) contains expression cassettes for Cas9 under control of a pollen-preferred high expression promoter prZmGRMZM5G876285 and terminator tZmGRMZM5G876285 from the maize prf3 (profilin homolog3) gene, which has an extremely high native expression at the RNA and protein level in pollen and which has evidence of high sperm cell expression.

Vector 24039 (SEQ ID NO: 35) contains expression cassettes for Cas9 under control of a pollen-preferred high expression promoter prZmGRMZM2G020852 and terminator tZmGRMZM2G020852 from the maize EXPB2 (BETA EXPANSIN2) gene, which has an extremely high native expression at the RNA and protein level in pollen and which has evidence of sperm cell expression.

Vector 24079 (SEQ ID NO: 36) contains expression cassettes for Cas9 under control of a pollen-preferred high expression promoter prZmGRMZM2G146551 and terminator tZmGRMZM2G146551 from the maize EXPB1 (BETA EXPANSIN1) gene, which has an extremely high native expression at the RNA and protein level in pollen and which has evidence of sperm cell expression.

Vector 24091 (SEQ ID NO: 37) contains expression cassettes for Cas9 under control of a pollen-preferred promoter prZmGRMZM2G471240 and terminator tZmGMRMZM2G471240 from the maize MATL (MATRI-LINEAL) gene, which shows evidence of pollen and possibly sperm cell expression at the RNA and protein level.

Vector 24094 (SEQ ID NO: 38) contains expression cassettes for Cas9 under control of a pollen-preferred promoter prZmGRMZM2G471240 and terminator tZmGMRMZM2G471240 from the maize MATL (MATRI-LINEAL) gene, which shows evidence of pollen and possibly sperm cell expression at the RNA and protein level. This construct additionally has an N-terminal fusion of AmCyan fluorescent protein on the Cas9 molecule for imaging and visualization of the Cas9 localization in pollen.

These five vectors (24038, 24039, 24079, 24091, and 24094) were transformed into maize inbred line NP2222 using *Agrobacterium*-mediated transformation to generate transgenic lines expressing Cas9 and sgRNA.

Figure 17:
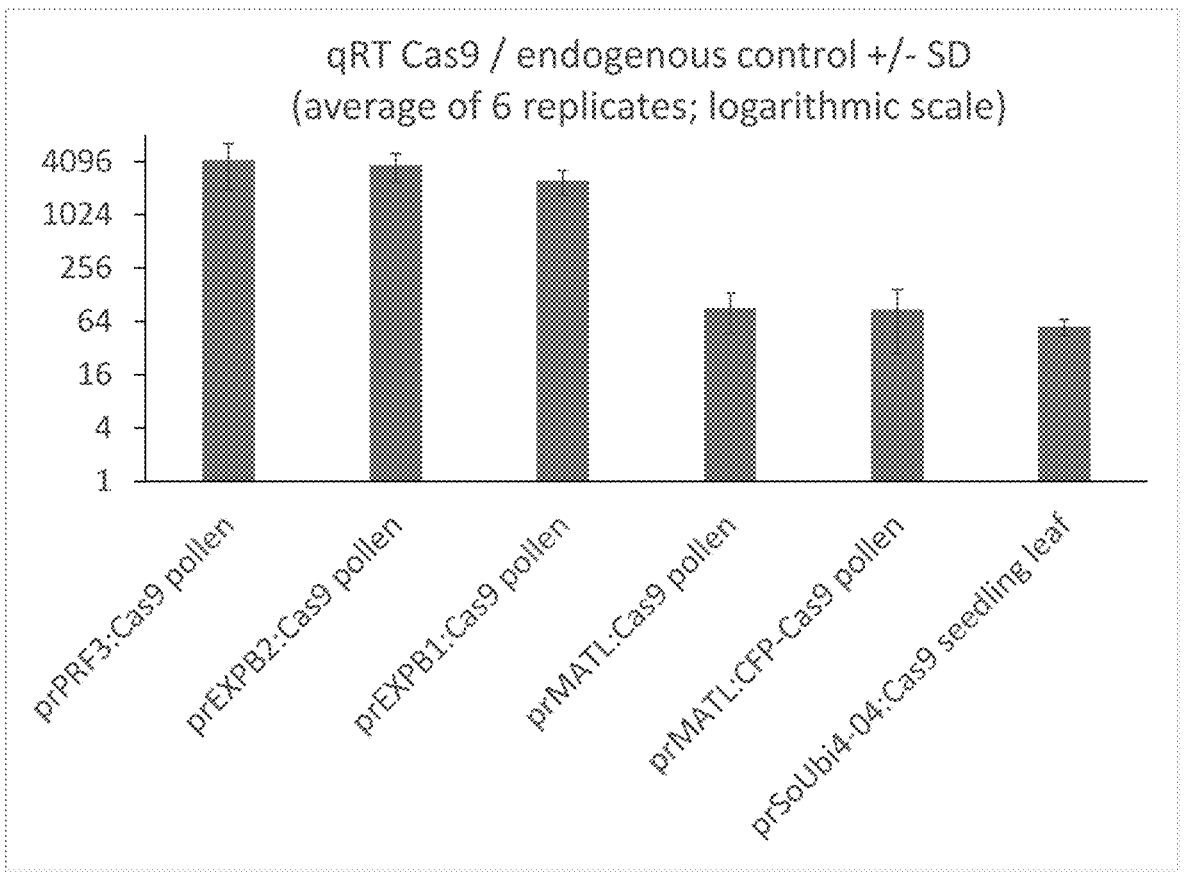
FIG. 17 shows pollen expression as measured by pollen collected from transgenic maize T0 plants carrying T-DNA of vector 24038, 24039, 24079, 24091, and 24094, which were used to pollinate emasculated spring wheat line AC-Nanda. The expression was high in the pollen, averaging about 100 fold higher in plants carrying T-DNA vectors 24038, 24039, and 24079 compared to the sugar cane ubiquitin promoter used in many of the corn and wheat examples. The expression was also higher in pollen from plants containing vactors 24038, 24039, and 24079 when compared to the pollen carrying the MATRILINEAL promoter constructs (24094 and 24091).
Figure 18:
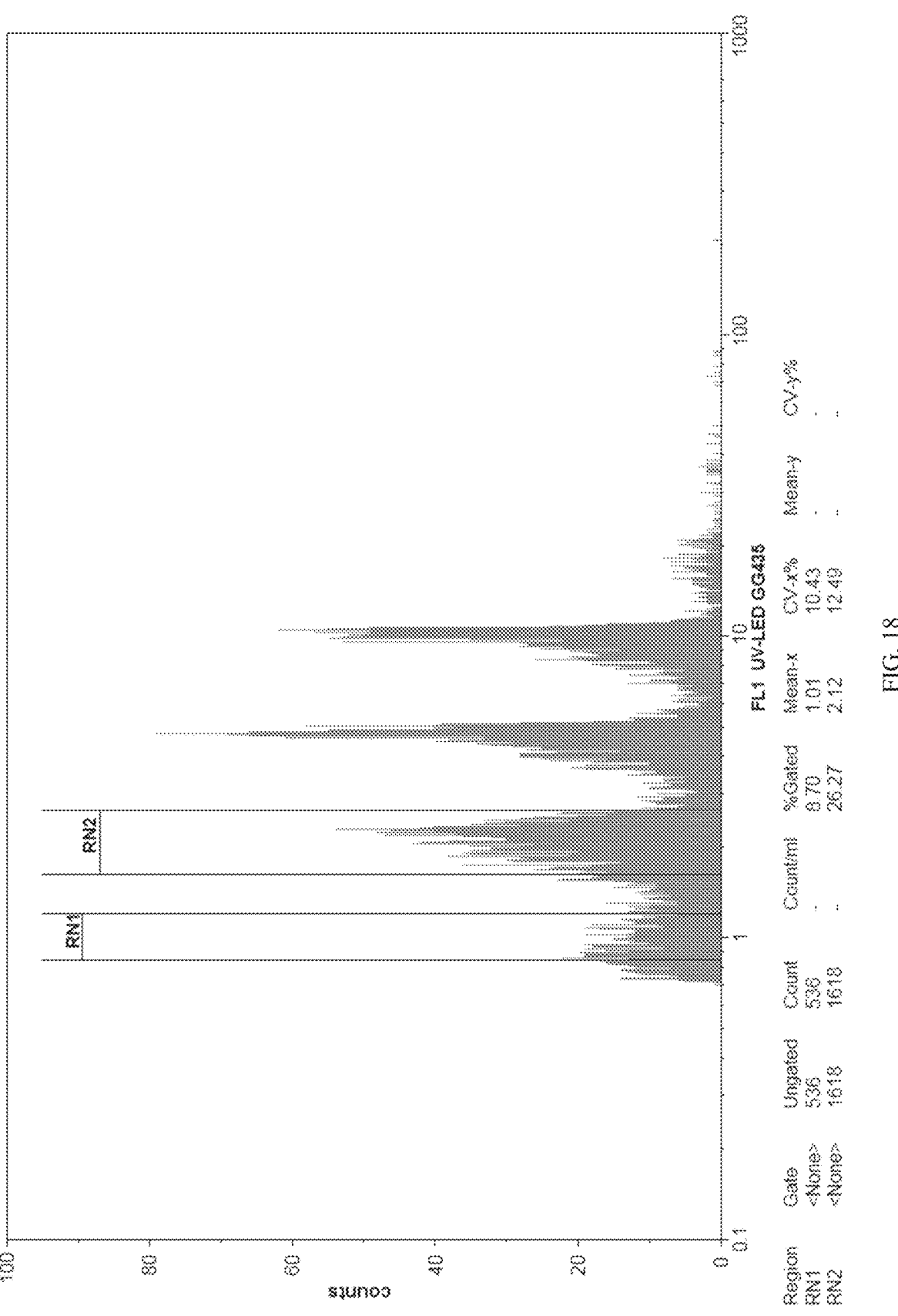
FIG. 18 shows the ploidy analysis histogram of a diploid control (parent USR01424135). The first peak is located at the "2" position on the logarithmic X-axis. Because this is leaf tissue from *Arabidopsis*, we see multiple peaks indicating the normal level of endoreduplication.
Figure 19:
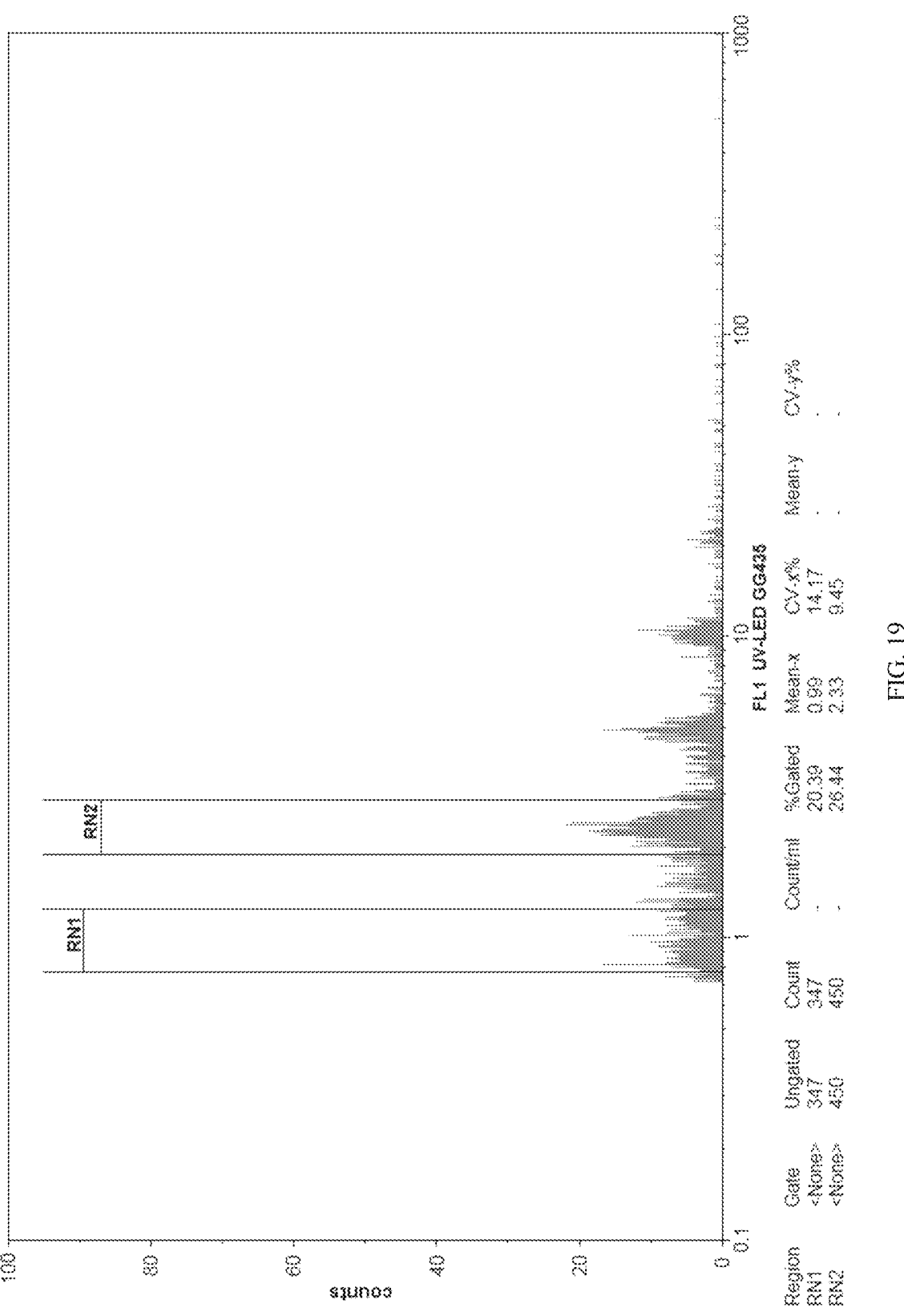
FIG. 19 shows the ploidy analysis histogram of a diploid control (parent USR01431603). The first peak is located at the "2" position on the logarithmic X-axis. Because this is leaf tissue from *Arabidopsis*, we see multiple peaks indicating the normal level of endoreduplication.
Figure 20:
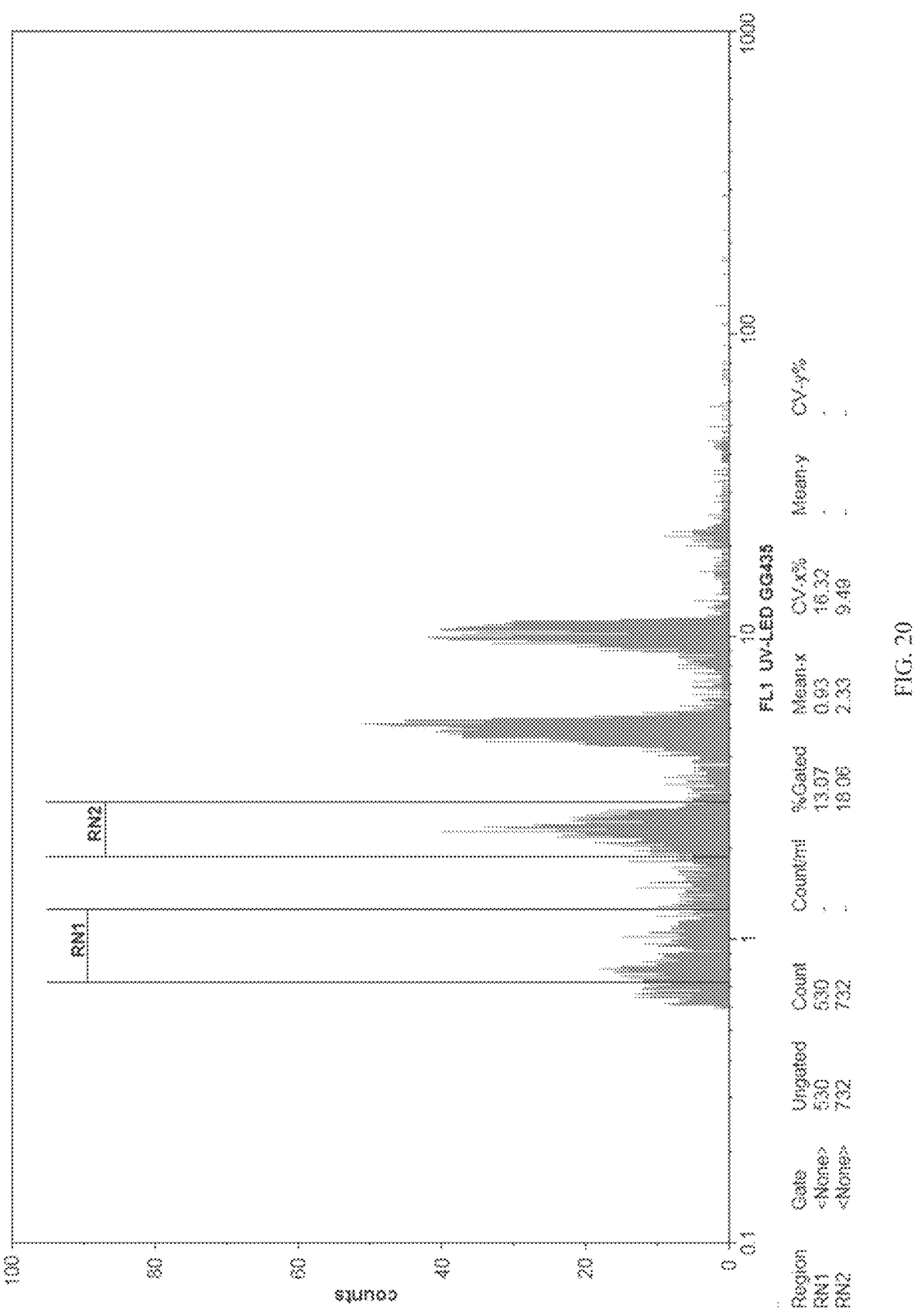
FIG. 20 shows the ploidy analysis histogram of a diploid control (parent USR01431609). The first peak is located at the "2" position on the logarithmic X-axis. Because this is leaf tissue from *Arabidopsis*, we see multiple peaks indicating the normal level of endoreduplication.
Figure 21:
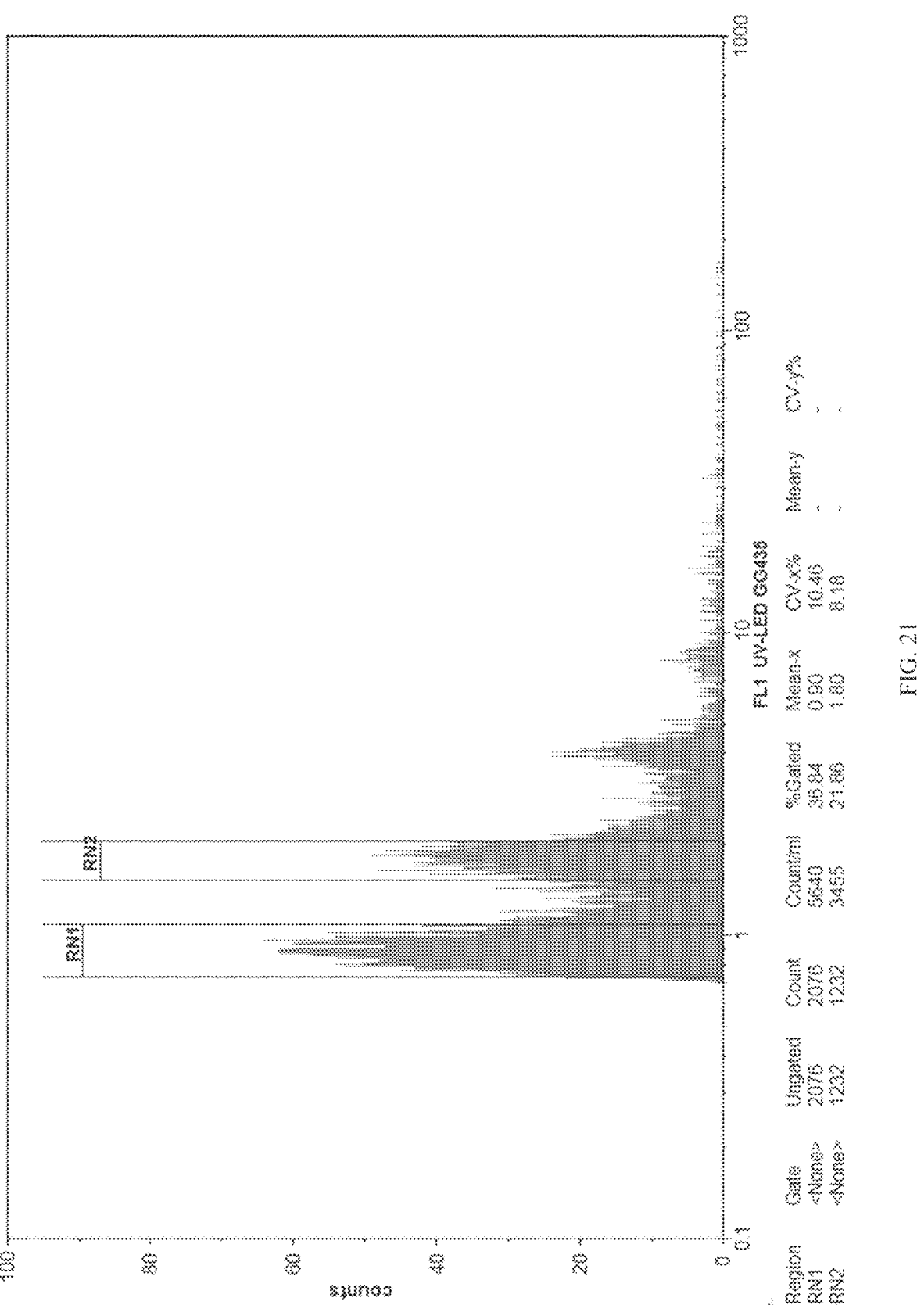
FIG. 21 shows the ploidy analysis histogram of an edited haploid from plate 1033, well C3 (USR01424135 X Ler-427). The first peak is located at the "1" position on the logarithmic X-axis, indicating it is a haploid. Because this is leaf tissue from *Arabidopsis*, we see multiple peaks indicating the normal level of endoreduplication.
Figure 22:
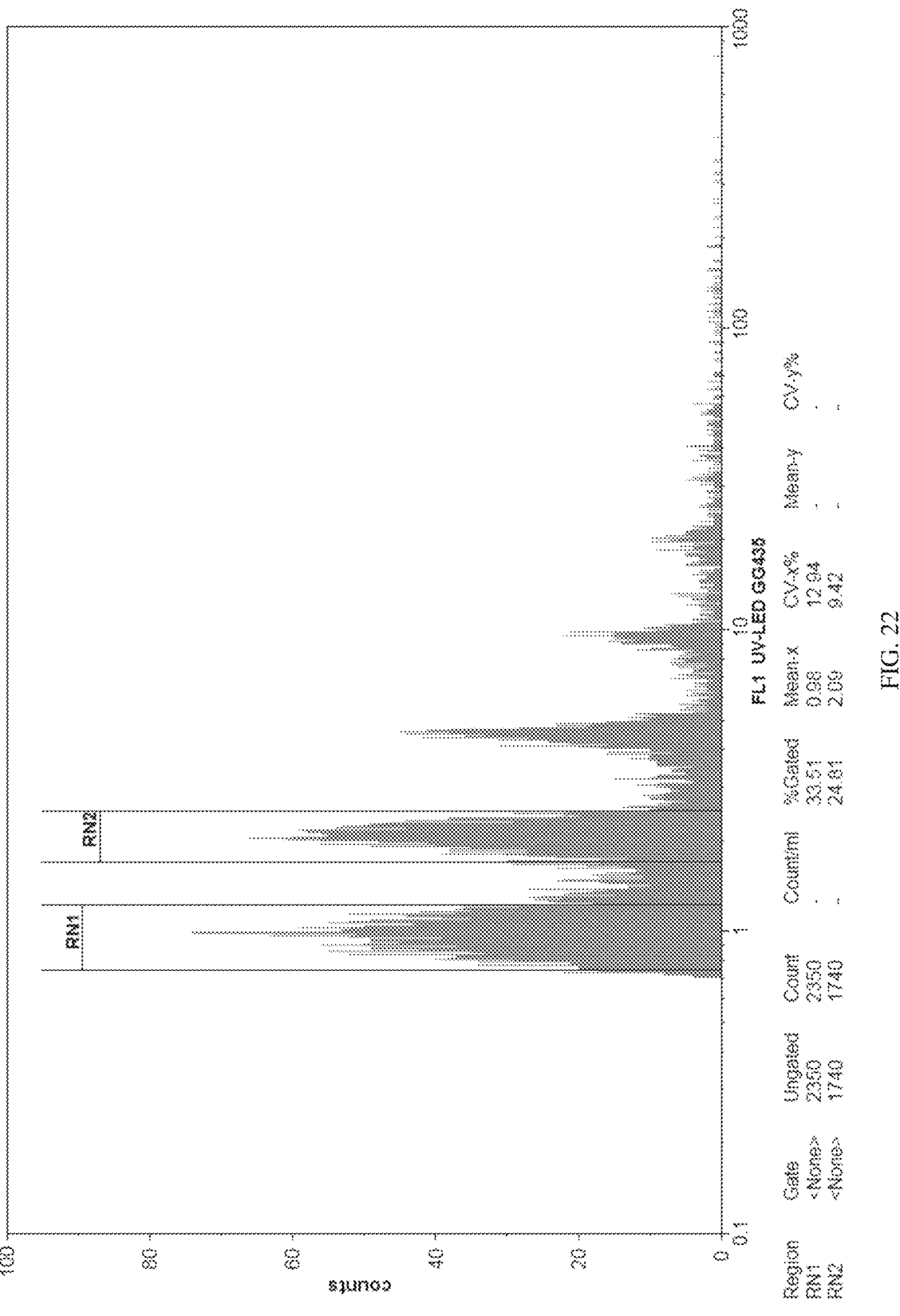
FIG. 22 shows the ploidy analysis histogram of an edited haploid from plate 1033, well E4 (USR01424135 X Ler-437). The first peak is located at the "1" position on the logarithmic X-axis, indicating it is a haploid. Because this is leaf tissue from *Arabidopsis*, we see multiple peaks indicating the normal level of endoreduplication.
Figure 23:
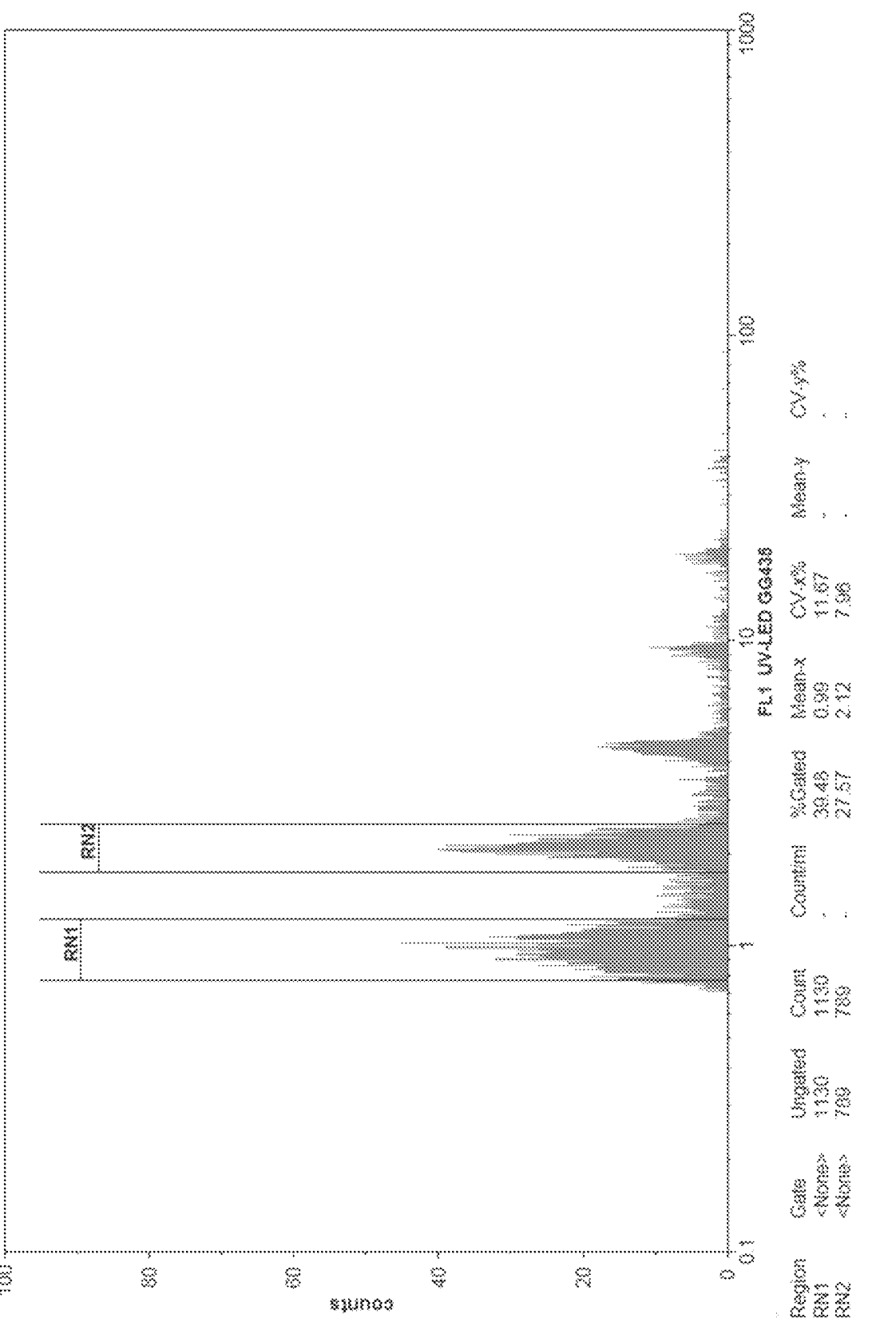
FIG. 23 shows the ploidy analysis histogram of an edited haploid from plate 1046, well H12 (USR01431609 X Ler-123). The first peak is located at the "1" position on the logarithmic X-axis, indicating it is a haploid. Because this is leaf tissue from *Arabidopsis*, we see multiple peaks indicating the normal level of endoreduplication.

Transgenic maize lines were grown in greenhouse and single and two-copy transgenic plants were outcrossed onto spring wheat and a CMS wheat line. Pollen collected from transgenic maize T0 plants carrying T-DNAs of one of the vectors 24038, 24039, 24079, 24091, and 24094 were used to pollinate emasculated spring wheat line AC-Nanda. Pollen was also used for a qRT experiment, in which the expression of the Cas9 was measured at the RNA level and compared to Cas9 expression in leaf samples when the Cas9 was driven by a sugar cane ubiquitin promoter used in many of the corn and wheat examples given above. As you can see in FIG. 17, the expression was high in the pollen, averaging about 100 fold higher in plants carrying the T-DNA vectors 24038, 24039, and 24079 compared to the Ubiquitin promoter. The expression was also higher in pollen from plants containing vectors 24038, 24039, and 24079 when compared to the pollen carrying the MATRILINEAL promoter constructs (24094 and 24091), which is known to have lower native gene expression. All five of these promoters have expression patterns that are restricted to pollen. As an indication that the promoters were working properly, we observed no T0 expression of Cas9 in callus seedling leaves, and there was no editing of the VLHP target sites in the T0 maize leaves (without wishing to be bound by theory, editing may happen at the maize target sites, in all likelihood, at the mature pollen stage, when the Cas9 is expressed for the first time).

At one to two days before anthesis, wheat florets were emasculated from the CMS line and the AC Nanda line. Two days later the florets were pollinated with fresh maize pollen carrying the editing machinery, Cas9-sgRNA, from either construct 24038, 24039, 24091, or 24094 (T0 plants transformed with construct 24079 were delayed, and not crossed to wheat in this manner). Wheat embryos were extracted from pollinated florets at 14-20 days after pollination for embryo rescue to recover haploid plantlets from the wheat× maize haploid induction system. Excised embryos were cultured on either full strength MS (Murashige and Skoog 1962) or ½ MS or B5 basal medium containing various modifications of organic supplements and grown in vitro for 1-5 weeks at 20-25° C. and 16-hour day length. For example, pollen of T0 progeny from transgenic maize line MZKE172601A100A containing vector 24039 was used to pollinate spikes of CMS line 16A300292 to induce wheat haploids. Haploid embryos were rescued and the resulting wheat haploid seedlings were sampled for qPCR analysis to determine the copy number of VLHP target sequences (Table 7). In this analysis, we tested for the Cas9 transgene using assay #2540. All wheat embryos rescued and tested lacked this transgene and gave scores of "0" for Cas9, because they do not have any corn DNA in the developing embryo and therefore do not have the transgene. The corn DNA is totally eliminated, kicked out or fails to be fully delivered in the first place during the haploid induction process, taking place during and/or after fertilization). In addition to Cas9, we test for assays #3332 and #3333, which give non-specific amplification of both VLHP2-2A and -2D alleles. These assays typically read as "2" or ">2" in haploid wheat, and the majority of the haploids we produced using the transgenic maize pollen scored 2 or >2 for these assays. We used these assays to look for putative edited haploids, by looking for scores of 0 or 1. A call of "1" might indicate that one of the two alleles, either VLHP2-2A, or -2D, was edited. Finally, we tested for assay 3255 in AC Nanda haploids, which detects VLHP2-2B specifically. The CMS line does not amplify this assay, even when it is wild-type, so we did not use it for the CMS haploids. The unedited haploids give a score of a "2," while putative edited haploids are found because they have a score of "0." A score of "1" might indicate a faulty reading or a chimeric, partially-edited sample.

As an example, one of the AC Nanda haploid plants 440-A5 was found to contain mutation in TaVLHP2-2B gene, but not in its orthologs TaVLHP2-2A and TaVLHP2-2D in the A and D sub-genomes (Table 7). The Taqman data also showed that it lacked the Cas9 transgene. The mutation within the TaVLHP2-2B target region was further characterized by sequencing, but although we were able to amplify the A and D alleles, we could no longer amplify the B allele, suggesting that there is a larger edit present, likely a large deletion, that results in the PCR product no longer amplifying.

As another example, one of the CMS haploid plants 450-D11 was found to contain mutation in either the TaVLHP2-2D or -2A homologues, according to the score of "1" for both assays 3332 and 3333. (Table 7). The taqman data showed that it lacked the Cas9 transgene. The TaVLHP2-2A, 2B and 2D target regions were further characterized by sequencing, but although we were able to amplify the A and B alleles, we could no longer amplify the D allele, suggesting that there is a larger edit present that led to PCR failure.

Considering the 2295 wheat haploids produced from crosses to maize pollen carrying one of the following five preferred-pollen expression constructs (24038, 24039, 24091, and 24094), we found 15 haploids that gave Taqman assay data that indicated possible editing at either the VLHP2-2A, VLHP2-2D, or VLHP2-2B target sites. After sequencing, seven of those haploids were found to have wild-type sequences at the target sites, and were called false positives due to Taqman error. These errors are thought to be either due to the fact that assays #3332 and #3333 gave non-specific amplification of both VLHP-2A and -2D alleles, leading to some missed calls, or due to low DNA quantity.

Of the remaining 8 putative edited haploids, six were AC Nanda (440-B3, 440-D3, 440-A5, 447-G8, 456-G9, 459-A2) where the editing transgene was from construct 24038. Four of those (440-B3, 440-D3, 440-A5, and 456-G9) contained edits in VLHP2-2B. These were found because they had a Taqman score of "0" for assay 3255. These plants lacked Cas9 (score of "0") but had wild-type "2" scores for VLHP2-2A or VLHP2-2D (assays #3332 and #3333) indicating they were not edited that those sites. These six plants were confirmed to be haploids by ploidy analysis. We attempted to sequence the edited alleles, but while the PCR and sequencing reactions worked well for 2A and 2D, we were not able to obtain a PCR product for 2B. We repeated the PCR several times using a range of reaction conditions but could not amplify the 2B homeologs from these haploid plants. This may indicate that the editing caused a large change in the 2B gene in these plants that may end up deleting the primer annealing site. We expect that many of the CMS plants also have edits at the VLHP2-2B target site, but we did not have an assay to detect the VLHP2-2B allele from the CMS line.

Considering AC Nanda alone, we calculate an overall editing rate at that allele of 0.7% for all constructs, but a particularly high editing rate of 1.4% for construct 24038.

In addition to these four edited haploids with scores of "0" for 3255, several other plants gave scores of "0 or 1" or "1" for 3255, which indicates possible chimerism (partial editing in certain cell lineages of the embryo or plantlet), but we did not follow up on those plants. For AC Nanda homolog VLHP2-2A, plant 447-G8 contained an edit which we were also not able to sequence because the PCR reaction failed, even though 2B and 2D did amplify and contained wild-type sequence. We repeated the PCR several times using a range of reaction conditions but could not amplify the 2A homolog. Similarly, for VLHP2-2D, plant 459-A2 contained an edit which we were not able to sequence because the PCR reaction failed. We repeated the PCR several times using a range of reaction conditions but could not amplify the 2D homolog. We also found putative edits in 447-H12 and 440-G6, but upon sequencing we found that these were false positives.

For the CMS haploids, plant 450-D11 gave scores of "1" for both assay #3332 and 3333 (Table 7). Upon sequencing, we found that the 2A homolog had wild-type sequence, but we could not PCR-amplify the 2D homolog, suggesting that a large edit had occurred. We repeated the PCR several times using a range of reaction conditions but could not amplify the 2D homolog. For plant 452-B11, the Taqman score was "0" for #3332 (VLHP2-2A), and we could not amplify that allele for sequencing, even though the 2D and 2B PCR products and sequences were normal. We repeated the PCR several times using a range of reaction conditions but could not amplify the 2A homolog. We also found five plants that had putative edits according to the Taqman data for assays 3332 and 3333, but PCR-sequencing showed these to be false positives; the sequence was wild-type (unedited).

In total, we found two edited CMS haploids and six edited AC Nanda haploids. There may be many more edited haploids that we were not able to detect because we did not have assays for the 2B gene for the CMS plants, nor for the VLHP3 gene target sites of the guide RNA in these five constructs.

The sequencing data from these edited haploids are consistent with the concept of a large deletion, inversion or rearrangement around the guide RNA target site, and extending far enough away to possibly include removal of one of the primer binding sites. This type of large change is not uncommon during editing by Cas9, especially in tissues where DNA repair via non-homologous end-joining is slower or inhibited—which may be the case in the just-fertilized zygote or early haploid wheat embryo.

TABLE 7

| | | | | | | | | | | | | |
|---|---|---|---|---|---|---|---|---|---|---|---|---|
| Sequencing data from edited wheat haploids. | | | | | | | | | | | | |
| | | | | | | | | CMS | | | | |
| | | | TAV_2A 3332 | | TAV_2D 3333 | | TAV_2B 3255 | | PMI 1750 | | Cas9 2540 | |
| Plant ID | Construct ID | copy # | Raw Copy # | Copy # level | Raw Copy # | Copy # level | Raw Copy # | Copy # level | Raw Copy # | Copy # level | Raw Copy # | Copy # level | Sequencing result |
| 427-A2 | WT | N/A | 2.44 | >2 | 2.38 | 2 | Not tested | | 0.00 | 0 | 0.00 | 0 | not sequenced |
| 427-B2 | WT | N/A | 1.99 | 2 | 1.99 | 2 | Not tested | | 0.00 | 0 | 0.00 | 0 | not sequenced |
| 427-C2 | WT | N/A | 2.02 | 2 | 2.07 | 2 | Not tested | | 0.00 | 0 | 0.00 | 0 | not sequenced |
| 427-D2 | WT | N/A | 2.31 | 2 | 2.16 | 2 | Not tested | | 0.00 | 0 | 0.00 | 0 | not sequenced |
| 427-A10 | 24091 | 2 | 2.07 | 2 | 1.66 | 2 | Not tested | | 0.00 | 0 | 0.00 | 0 | not sequenced |
| 427-B10 | 24091 | 2 | 1.95 | 2 | 1.84 | 2 | Not tested | | 0.00 | 0 | 0.00 | 0 | not sequenced |
| 427-C10 | 24091 | 2 | 1.93 | 2 | 2.28 | 2 | Not tested | | 0.00 | 0 | 0.00 | 0 | not sequenced |
| 427-D10 | 24091 | 2 | 2.59 | >2 | 2.48 | >2 | Not tested | | 0.00 | 0 | 0.00 | 0 | not sequenced |
| 427-E10 | 24091 | 2 | 1.90 | 2 | 1.78 | 2 | Not tested | | 0.00 | 0 | 0.00 | 0 | not sequenced |
| 427-F10 | 24091 | 2 | 2.03 | 2 | 1.96 | 2 | Not tested | | 0.00 | 0 | 0.00 | 0 | not sequenced |
| 427-G10 | 24091 | 2 | 2.08 | 2 | 2.25 | 2 | Not tested | | 0.00 | 0 | 0.00 | 0 | not sequenced |
| 427-H10 | 24091 | 2 | 0.58 | 1 | 0.81 | 1 | Not tested | | 0.00 | 0 | 0.00 | 0 | A and D were both WT |
| 427-A11 | 24091 | 2 | 1.57 | 1 or 2 | 1.93 | 2 | Not tested | | 0.00 | 0 | 0.00 | 0 | not sequenced |
| 427-B11 | 24091 | 2 | 1.41 | 1 or 2 | 1.63 | 2 | Not tested | | 0.00 | 0 | 0.00 | 0 | not sequenced |
| 427-C11 | 24091 | 2 | 1.06 | 1 | 1.21 | 1 | Not tested | | 0.01 | 0 | 0.01 | 0 | not sequenced |
| 427-D11 | 24091 | 2 | 1.98 | 2 | 2.03 | 2 | Not tested | | 0.00 | 0 | 0.00 | 0 | not sequenced |
| 427-E11 | 24091 | 2 | 1.94 | 2 | 1.94 | 2 | Not tested | | 0.00 | 0 | 0.00 | 0 | not sequenced |
| 427-F11 | 24091 | 2 | 1.84 | 2 | 1.84 | 2 | Not tested | | 0.00 | 0 | 0.00 | 0 | not sequenced |
| 427-G11 | 24091 | 2 | 1.54 | 1 or 2 | 1.76 | 2 | Not tested | | 0.00 | 0 | 0.00 | 0 | not sequenced |
| 427-H11 | 24091 | 2 | 1.75 | 2 | 1.76 | 2 | Not tested | | 0.00 | 0 | 0.00 | 0 | not sequenced |
| 427-A12 | 24091 | 2 | 1.99 | 2 | 2.15 | 2 | Not tested | | 0.00 | 0 | 0.00 | 0 | not sequenced |
| 427-B12 | 24091 | 2 | 0.72 | 1 | 1.26 | 1 | Not tested | | 0.00 | 0 | 0.00 | 0 | A and D were both WT |
| 427-C12 | 24091 | 2 | 1.69 | 2 | 1.50 | 1 or 2 | Not tested | | 0.00 | 0 | 0.01 | 0 | not sequenced |
| 427-D12 | 24091 | 1 | 2.34 | 2 | 2.03 | 2 | Not tested | | 0.00 | 0 | 0.00 | 0 | not sequenced |

TABLE 7-continued

Sequencing data from edited wheat haploids.

| Plant ID | construct ID | copy # | TAV_2A 3332 Raw Copy # | TAV_2A Copy # level | TAV_2D 3333 Raw Copy # | TAV_2D Copy # level | TAV_2B 3255 Raw Copy # | TAV_2B Copy # level | PMI 1750 Raw Copy # | PMI Copy # level | Cas9 2540 Raw Copy # | Cas9 Copy # level | Sequencing result |
|---|---|---|---|---|---|---|---|---|---|---|---|---|---|
| 427-E12 | 24091 | 1 | 1.98 | 2 | 2.04 | 2 | Not tested | | 0.00 | 0 | 0.00 | 0 | not sequenced |
| 427-F12 | 24091 | 1 | 1.89 | 2 | 1.97 | 2 | Not tested | | 0.00 | 0 | 0.00 | 0 | not sequenced |
| 427-G12 | 24091 | 1 | 1.56 | 1 or 2 | 1.77 | 2 | Not tested | | 0.00 | 0 | 0.00 | 0 | not sequenced |
| 427-H12 | 24091 | 1 | 1.57 | 1 or 2 | 2.36 | 2 | Not tested | | 0.00 | 0 | 0.00 | 0 | not sequenced |
| 428-A3 | 24091 | 1 | 2.12 | 2 | 1.75 | 2 | Not tested | | 0.00 | 0 | 0.00 | 0 | not sequenced |
| 428-B3 | 24091 | 1 | 2.69 | >2 | 1.89 | 2 | Not tested | | 0.00 | 0 | 0.00 | 0 | not sequenced |
| 428-C3 | 24091 | 1 | 2.09 | 2 | 2.44 | >2 | Not tested | | 0.00 | 0 | 0.00 | 0 | not sequenced |
| 428-D3 | 24091 | 1 | 2.05 | 2 | 2.39 | 2 | Not tested | | 0.00 | 0 | 0.00 | 0 | not sequenced |
| 428-E3 | 24091 | 1 | 2.48 | >2 | 2.87 | >2 | Not tested | | 0.00 | 0 | 0.00 | 0 | not sequenced |
| 428-F3 | 24091 | 1 | 2.33 | 2 | 2.76 | >2 | Not tested | | 0.00 | 0 | 0.00 | 0 | not sequenced |
| 428-G3 | 24091 | 1 | 2.84 | >2 | 0.22 | 0 | Not tested | | 0.00 | 0 | 0.00 | 0 | A and D were both WT |
| 428-H3 | 24091 | 1 | 2.83 | >2 | 2.60 | >2 | Not tested | | 0.00 | 0 | 0.00 | 0 | not sequenced |
| 450-A11 | 24094 | 1 | 1.97 | 2 | 2.24 | 2 | Not tested | | 0.00 | 0 | 0.00 | 0 | not sequenced |
| 450-B11 | 24094 | 1 | 2.13 | 2 | 2.04 | 2 | Not tested | | 0.00 | 0 | 0.00 | 0 | not sequenced |
| 450-C11 | 24094 | 1 | 2.15 | 2 | 2.18 | 2 | Not tested | | 0.00 | 0 | 0.00 | 0 | not sequenced |
| 450-D11 | 24094 | 1 | 1.04 | 1 | 0.99 | 1 | Not tested | | 0.00 | 0 | 0.00 | 0 | A & B were WT; D failed |
| 450-E11 | 24094 | 1 | 2.35 | 2 | 2.01 | 2 | Not tested | | 0.00 | 0 | 0.00 | 0 | not sequenced |
| 450-F11 | 24094 | 1 | 2.02 | 2 | 1.90 | 2 | Not tested | | 0.00 | 0 | 0.00 | 0 | not sequenced |
| 450-G11 | 24039 | 1 | 1.76 | 2 | 1.72 | 2 | Not tested | | 0.00 | 0 | 0.00 | 0 | not sequenced |
| 450-H11 | 24039 | 1 | 2.07 | 2 | 2.04 | 2 | Not tested | | 0.00 | 0 | 0.00 | 0 | not sequenced |
| 452-H4 | 24038 | 2 | 2.62 | >2 | 0.01 | 0 | Not tested | | 0.00 | 0 | 0.00 | 0 | A and D were both WT |
| 452-A11 | 24038 | 2 | 2.24 | 2 | 2.28 | 2 | Not tested | | 0.00 | 0 | 0.00 | 0 | not sequenced |
| 452-B11 | 24038 | 2 | 0.00 | 0 | 2.22 | 2 | Not tested | | 0.00 | 0 | 0.00 | 0 | B & D were WT; A failed |
| 452-C11 | 24038 | 2 | 2.55 | >2 | 2.22 | 2 | Not tested | | 0.00 | 0 | 0.00 | 0 | not sequenced |
| 452-D11 | 24038 | 2 | 0.82 | 1 | 1.26 | 1 | Not tested | | 0.00 | 0 | 0.00 | 0 | A and D were both WT |
| 452-E11 | 24038 | 2 | 2.43 | >2 | 2.36 | 2 | Not tested | | 0.00 | 0 | 0.00 | 0 | not sequenced |
| 452-F11 | 24038 | 2 | 2.12 | 2 | 2.21 | 2 | Not tested | | 0.00 | 0 | 0.00 | 0 | not sequenced |
| 452-G11 | 24038 | 2 | 2.38 | 2 | 1.99 | 2 | Not tested | | 0.00 | 0 | 0.00 | 0 | not sequenced |
| 452-H11 | 24038 | 2 | 1.82 | 2 | 1.83 | 2 | Not tested | | 0.00 | 0 | 0.00 | 0 | not sequenced | z

NANDA

| Plant ID | construct ID | copy # | TAV_2A 3332 Raw Copy # | TAV_2A Copy # level | TAV_2D 3333 Raw Copy # | TAV_2D Copy # level | TAV_2B 3255 Raw Copy # | TAV_2B Copy # level | PMI 1750 Raw Copy # | PMI Copy # level | Cas9 2540 Raw Copy # | Cas9 Copy # level | Sequencing result |
|---|---|---|---|---|---|---|---|---|---|---|---|---|---|
| 425-A2 | WT | N/A | 2.30 | 2 | 2.62 | >2 | 1.908 | 2 | 0.00 | 0 | 0.00 | 0 | not sequenced |
| 425-B2 | WT | N/A | 2.28 | 2 | 2.41 | >2 | 2.274 | 2 | 0.00 | 0 | 0.00 | 0 | not sequenced |
| 425-C2 | WT | N/A | 2.47 | >2 | 1.92 | 2 | 1.962 | 2 | 0.00 | 0 | 0.00 | 0 | not sequenced |
| 425-D2 | WT | N/A | 2.10 | 2 | 2.11 | 2 | 1.772 | 2 | 0.00 | 0 | 0.00 | 0 | not sequenced |
| 447-A12 | 24038 | 2 | 1.72 | 2 | 1.90 | 2 | 2.02 | 2 | 0.00 | 0 | 0.00 | 0 | not sequenced |
| 447-B12 | 24039 | 2 | 2.18 | 2 | 1.62 | 2 | 1.47 | 1 or 2 | 0.00 | 0 | 0.00 | 0 | not sequenced |
| 447-C12 | 24039 | 2 | 1.78 | 2 | 2.40 | 2 | 1.90 | 2 | 0.00 | 0 | 0.00 | 0 | not sequenced |
| 447-D12 | 24039 | 2 | 1.58 | 1 or 2 | 1.70 | 2 | 2.18 | 2 | 0.00 | 0 | 0.00 | 0 | not sequenced |
| 447-E12 | 24039 | 2 | 2.13 | 2 | 1.82 | 2 | 2.14 | 2 | 0.00 | 0 | 0.00 | 0 | not sequenced |
| 447-F12 | 24039 | 2 | 2.25 | 2 | 1.78 | 2 | 2.15 | 2 | 0.00 | 0 | 0.00 | 0 | not sequenced |
| 447-G12 | 24039 | 2 | 1.90 | 2 | 2.30 | 2 | 2.23 | 2 | 0.00 | 0 | 0.00 | 0 | not sequenced |
| 447-H12 | 24039 | 1 | 2.34 | 2 | 1.95 | 2 | 0.89 | 1 | 0.00 | 0 | 0.00 | 0 | A, B, and D were all WT |
| 440-A2 | 24039 | 1 | 1.72 | 2 | 1.71 | 2 | 1.24 | 1 | 0.00 | 0 | 0.00 | 0 | not sequenced |
| 440-B2 | 24039 | 1 | 2.30 | 2 | 2.56 | >2 | 1.77 | 2 | 0.00 | 0 | 0.00 | 0 | not sequenced |
| 440-C2 | 24039 | 1 | 3.05 | >2 | 1.85 | 2 | 2.01 | 2 | 0.00 | 0 | 0.00 | 0 | not sequenced |
| 440-D2 | 24039 | 1 | 1.66 | 2 | 1.70 | 2 | 1.44 | 1 or 2 | 0.00 | 0 | 0.00 | 0 | not sequenced |
| 440-E2 | 24039 | 1 | 2.23 | 2 | 1.91 | 2 | 2.04 | 2 | 0.00 | 0 | 0.00 | 0 | not sequenced |
| 440-F2 | 24039 | 1 | 2.63 | >2 | 2.07 | 2 | 2.28 | 2 | 0.00 | 0 | 0.00 | 0 | not sequenced |
| 440-G2 | 24038 | 11 | 1.91 | 2 | 1.87 | 2 | 2.10 | 2 | 0.00 | 0 | 0.00 | 0 | not sequenced |
| 440-H2 | 24038 | 1 | 1.85 | 2 | 1.80 | 2 | 1.97 | 2 | 0.00 | 0 | 0.00 | 0 | not sequenced |
| 440-A3 | 24038 | 1 | 2.52 | >2 | 2.05 | 2 | 1.99 | 2 | 0.00 | 0 | 0.00 | 0 | not sequenced |
| 440-B3 | 24038 | 1 | 2.16 | 2 | 2.19 | 2 | 0.00 | 0 | 0.00 | 0 | 0.00 | 0 | A & D were WT; B failed |
| 440-C3 | 24038 | 1 | 2.58 | >2 | 2.02 | 2 | 2.78 | >2 | 0.00 | 0 | 0.00 | 0 | not sequenced |
| 440-D3 | 24038 | 1 | 2.34 | 2 | 2.32 | 2 | 0.00 | 0 | 0.00 | 0 | 0.00 | 0 | A& D were WT; B failed |
| 440-E3 | 24038 | 1 | 2.49 | >2 | 2.23 | 2 | 2.47 | >2 | 0.00 | 0 | 0.00 | 0 | not sequenced |
| 440-F3 | 24038 | 1 | 2.08 | 2 | 2.10 | 2 | 2.17 | 2 | 0.00 | 0 | 0.00 | 0 | not sequenced |
| 440-F4 | 24038 | 1 | 1.73 | 2 | 1.47 | 1 or 2 | 1.41 | 1 or 2 | 0.00 | 0 | 0.00 | 0 | not sequenced |
| 440-G4 | 24038 | 1 | 1.53 | 1 or 2 | 2.02 | 2 | 1.99 | 2 | 0.00 | 0 | 0.00 | 0 | not sequenced |
| 440-H4 | 24038 | 1 | 2.22 | 2 | 1.90 | 2 | 0.00 | 0 | 0.00 | 0 | 0.00 | 0 | not sequenced |
| 440-A5 | 24038 | 1 | 2.22 | 2 | 1.90 | 2 | 0.00 | 0 | 0.00 | 0 | 0.00 | 0 | A & D were WT; B failed |

TABLE 7-continued

Sequencing data from edited wheat haploids.

| | | | | | | | | | | | | | |
|---|---|---|---|---|---|---|---|---|---|---|---|---|---|
| 440-A6 | 24039 | 2 | 2.49 | >2 | 2.32 | 2 | 1.84 | 2 | 0.00 | 0 | 0.00 | 0 | not sequenced |
| 440-B6 | 24039 | 2 | 2.12 | 2 | 2.03 | 2 | 2.21 | 2 | 0.00 | 0 | 0.00 | 0 | not sequenced |
| 440-C6 | 24039 | 2 | 2.63 | >2 | 2.07 | 2 | 2.28 | 2 | 0.00 | 0 | 0.00 | 0 | not sequenced |
| 440-D6 | 24039 | 2 | 2.49 | >2 | 2.23 | 2 | 2.47 | >2 | 0.00 | 0 | 0.00 | 0 | not sequenced |
| 440-E6 | 24039 | 2 | 2.45 | >2 | 2.20 | 2 | 2.32 | 2 | 0.00 | 0 | 0.00 | 0 | not sequenced |
| 440-F6 | 24039 | 2 | 2.10 | 2 | 1.92 | 2 | 1.91 | 2 | 0.00 | 0 | 0.00 | 0 | not sequenced |
| 440-G6 | 24039 | 2 | 0.57 | 1 | 0.66 | 1 | 0.53 | 1 | 0.00 | 0 | 0.00 | 0 | A, B & D were all WT |
| 440-H6 | 24039 | 2 | 1.81 | 2 | 1.96 | 2 | 2.51 | >2 | 0.00 | 0 | 0.00 | 0 | not sequenced |
| 447-A8 | 24038 | 1 | 2.42 | >2 | 2.21 | 2 | 2.10 | 2 | 0.00 | 0 | 0.00 | 0 | not sequenced |
| 447-B8 | 24038 | 1 | 2.46 | >2 | 2.32 | 2 | 2.09 | 2 | 0.00 | 0 | 0.00 | 0 | not sequenced |
| 447-C8 | 24038 | 1 | 2.09 | 2 | 2.08 | 2 | 2.29 | 2 | 0.00 | 0 | 0.00 | 0 | not sequenced |
| 447-D8 | 24038 | 1 | 2.13 | 2 | 2.14 | 2 | 2.34 | 2 | 0.00 | 0 | 0.00 | 0 | not sequenced |
| 447-E8 | 24038 | 11 | 2.36 | 2 | 2.31 | 2 | 2.44 | >2 | 0.00 | 0 | 0.00 | 0 | not sequenced |
| 447-F8 | 24038 | 1 | 2.72 | >2 | 2.28 | 2 | 2.00 | 2 | 0.00 | 0 | 0.00 | 0 | not sequenced |
| 447-G8 | 24038 | 1 | 0.71 | 1 | 1.34 | 1 or 2 | 2.33 | 2 | 0.00 | 0 | 0.00 | 0 | B & D were WT; A failed |
| 447-H8 | 24038 | 1 | 2.25 | 2 | 2.29 | 2 | 2.01 | 2 | 0.00 | 0 | 0.00 | 0 | not sequenced |
| 456-A9 | 24038 | 2 | 2.19 | 2 | 1.59 | 1 or 2 | 2.03 | 2 | 0.00 | 0 | 0.00 | 0 | not sequenced |
| 456-B9 | 24038 | 2 | 2.13 | 2 | 2.11 | 2 | 2.02 | 2 | 0.00 | 0 | 0.00 | 0 | not sequenced |
| 456-C9 | 24038 | 2 | 2.16 | 2 | 1.85 | 2 | 1.45 | 1 or | 0.00 | 0 | 0.00 | 0 | not sequenced |
| 456-D9 | 24038 | 2 | 2.56 | >2 | 2.18 | 2 | 1.76 | 2 | 0.00 | 0 | 0.00 | 0 | not sequenced |
| 456-E9 | 24038 | 2 | 2.29 | 2 | 2.03 | 2 | 1.65 | 2 | 0.00 | 0 | 0.00 | 0 | not sequenced |
| 456-F9 | 24038 | 2 | 2.24 | 2 | 2.02 | 2 | 2.05 | 2 | 0.00 | 0 | 0.00 | 0 | not sequenced |
| 456-G9 | 24038 | 2 | 2.49 | >2 | 2.03 | 2 | 0.00 | 0 | 0.00 | 0 | 0.00 | 0 | A & D were WT; B failed |
| 456-H9 | 24038 | 2 | 1.78 | 2 | 1.62 | 2 | 1.38 | 1 or 2 | 0.00 | 0 | 0.00 | 0 | not sequenced |
| 459-A2 | 24038 | 2 | 1.38 | 1 or 2 | 1.11 | 1 | 0.94 | 1 | 0.00 | 0 | 0.00 | 0 | A & B were WT; D failed |
| 459-B2 | 24038 | 2 | 1.86 | 2 | 1.91 | 2 | 2.12 | 2 | 0.00 | 0 | 0.00 | 0 | not sequenced |
| 459-C2 | 24038 | 2 | 1.94 | 2 | 2.09 | 2 | 1.42 | 1 or 2 | 0.00 | 0 | 0.00 | 0 | not sequenced |
| 459-D2 | 24038 | 2 | 2.09 | 2 | 2.05 | 2 | 1.91 | 2 | 0.00 | 0 | 0.00 | 0 | not sequenced |
| 459-E2 | 24038 | 2 | 2.18 | 2 | 2.12 | 2 | 2.12 | 2 | 0.00 | 0 | 0.00 | 0 | not sequenced |

Overall, we found that the editing frequency (number of edited haploids identified divided by the total number of haploids) for construct 24038 was 0.79%; for construct 24039 it was 0%; for construct 24091 it was 0%, and for construct 24094 it was 0.75%. However, this editing rate is certainly an under-estimate because we did not have assays to detect edits at many of the guide RNA target sites. Additionally, because we used T0 pollen that was either 1 or 2 copy, we know that with the 1-copy pollen, only 50% of the fertilizing pollen grains will contain the Cas9, and so only half of the embryos have the opportunity to be edited; similarly, for 2 copy parents, assuming random segregation of the transgenes in the male meiosis, we would expect about 75% of the pollen to contain Cas9, so 25% of the embryos cannot be edited. It is reasonable to conclude that, when one is trying to use this simultaneous editing plus haploid induction technology with the editing machinery carried by the pollen, it may in some cases be more optimal to use a promoter that express specifically or highly in pollen and in sperm cells, so that the Cas9 can be expressed at a higher level. In cases where the gene target might impact development of the haploid inducer plant, having a pollen or sperm-preferred promoter that does not express in leaves might be useful because it would avoid editing the target gene in the haploid inducer plant during development—perhaps editing it for the first time in pollen.

Because the sperm cells fertilize the egg, they have the potential to deliver Cas9 RNA and protein (as well as the transgene DNA itself, integrated into one of the male chromosomes that will be eliminated). As we demonstrated in the wide-cross work in this example, it may work well to have the Cas9 and/or guide RNA under the control of a promoter that specifically or highly expresses in pollen, and in particular in sperm cells, when using a haploid inducer as the male to edit elite lines. We do not know exactly whether MATRILINEAL, EXPB1, EXPB2, and PRF3 express in the vegetative nucleus, the sperm cells, or both, and whether there might be any expression in a zygote cell type, but these were chosen because they are supposedly highly and/or specifically expressed in pollen. The PRF3 promoter has a DUO1 binding motif in the promoter, which may indicate it expresses in sperm cells. This is consistent with that promoter having higher editing frequency. The fact that we found many edited wheat haploids after the wide cross makes it clear that when there is high expression of Cas9 in pollen, using these or any other promoter, that expression can lead to editing in the wheat embryos after the wide cross. There is a strong possibility that these promoters, as well as other promoters that drive expression in pollen, or in particular in the sperm cells, might increase the efficiency of the editing process during corn haploid induction, or rice haploid induction.

Similarly, in the next example below, we show haploid editing in a dicot using a CENH3-modified-haploid inducer line, and we use constitutive promoter to drive the Cas9. But in an attempt to increase the efficiency of the haploid editing, we could opt to use a promoter that drives high and/or specific expression in egg cells, such as the EGG APPARATUS1 gene's promoter ("prEA1") (see, e.g., Gray-Mitsumune, M. and Matton, D. P., *The Egg apparatus 1 gene from maize is a member of a large gene family found in both monocots and dicots*, PLANTA 223(3):618-625 (February 2006)) or EGG CELL1 (EC1) (see, e.g., Sprunck S, et al., *Egg cell-secreted EC1 triggers sperm cell activation during double fertilization*. Science 2012; 338:1093-97; PMID: 23180860; http://dx.doi.org/10.1126/science.1223944).

As an example of this, one could use a sperm-cell expressed promoter, such as the *Arabidopsis* sperm-specific DUO1 promoter (see, e.g., Engel, et al., *Green Sperm. Identification of Male Gamete Promoters in Arabidopsis,*

PLANT PHYSIOLOGY August 2005, 138 (4) 2124-2133; DOI: 10.1104/pp. 104.054213), or homologs of DUO1 from other species (for instance, the maize genes GRMZM2G105137 and GRMZM2G046443 are both DUO1 homologs that share a similar pollen-specific expression pattern). If one used any of these to drive Cas9 expression in the sperm cells of a haploid inducer line like RWK, NP2222-HI, or an mat1 mutant, it might make a highly efficient haploid editor line for use in editing diverse elite maize or wheat germplasm, via intraspecific or wide cross, respectively.

Other suitable sperm-expressed promoters for this concept of driving high Cas9 expression in sperm cells would include the DUO1 homologs in wheat, rice, barley, tomato, sunflower, or other monocots or dicots. Other suitable promoters for this concept are shown in Table 8 below. These promoters, or their homologs in crop species—might be very useful for this concept. The principal at work is that gamete cell expression of the editing machinery can increase the rate or efficiency of this invention because it means that there will be abundant editing protein or RNA present or delivered to the embryo during fertilization so that editing can happen rapidly.

TABLE 8

Promoters List: promoters one can use in a transgene to drive high sperm cell expression of editing machinery to boost the efficiency of simultaneous editing and doubled-haploid induction ("SEDHI").

| Gene Name | Gene ID | Maize Ortholog | Rice Ortholog |
|---|---|---|---|
| DUO1 | At3G60460 | GRMZM2G105137, GRMZM2G046443 | LOC_Os04g46384 |
| MGH3 | At1G19890 | NA | NA |
| GEX1 | At5G55490 | GRMZM2G388045 | LOC_Os09g27040 LOC_Os07g47194 |
| GEX2 | At5G49150 | GRMZM2G036832 | LOC_Os09g25650 |
| GEX3 | At5G16020 | GRMZM2G458159 | LOC_Os01g42060 |
| HAP2/GSC1 | At4G11720 | GRMZM2G412911 | LOC_Os05g18730 |
| CycB1 | At4G37490 | NA | NA |
| DAZ1 | At2G17180 | GRMZM2G132057 | NA |
| DAZ2 | At4G35280 | NA | LOC_Os02g19180 |
| DAZ3 | At4G35700 | NA | NA |
| PCR11 | At1G68610 | NA | NA |
| DAN1 | At3G04620 | NA | NA |
| TIP1 | AT3G47440 | NA | LOC_Os04g46490 |
| MKKK20 | AT3G50310 | NA | NA |
| DAF1 | At3G62230 | NA | NA |
| DAW1 | At4G35560 | GRMZM2G176647 | NA |
| DAU2/DMP9 | At5G39650 | NA | NA |

VII. Simultaneous Haploid Induction and Editing in Dicots Via Wide Cross or Via Crosses to CENH3-Altered Lines or Other Haploid Inducing Lines.

In vivo haploid induction can also be achieved using interspecific or intergeneric wide crosses on dicot plant species, for example, in cotton (Turcotte et al. 1969, Semigametic production of haploids in pima cotton. Crop Sci. 9:653-655) and tobacco (Burke et al, 1979, Maternal haploids of *Nicotiana tabacum* L. Science 206:585; Wernsman et al. 1989, Androgenetic vs. gynogenetic doubled haploids of tobacco. Crop Sci. 29:1151-1155). Haploid *Arabidopsis* plants can be obtained by crossing with pollen from mutant CENH3 plant, or by crossing said plants as females to wild type pollen (Ravi and Chan, 2010, Haploid plants produced by centromere-mediated genome elimination. Nature 464: 615-618). Other candidate genes which may be modified to generate a haploid inducer and SEDHI editing line include KNL2 and CENPC (both of which may operate via centromere-mediated uniparental genome elimination) as well as MSI2 and sunflower PLA2. In this case, the haploid-inducing genome (be it the male or female in the cross) also contains the editing machinery, so that the editing can be achieved during the haploid induction process, with the result being an edited maternal or paternal haploid progeny plant without altered CENH3 or editing transgenes. See, e.g., WO 2017/004375, incorporated herein by reference in its entirety. Transgenic locus expressing editing machinery can be introduced into any dicot crops or their wild relatives of *Brassica*, tomato, pepper, lettuce, eggplant, soybean, sunflower, sugar beet, cotton, alfalfa, tobacco, and others. The transgenic lines expressing editing machinery are then used as pollen donors, or in the case of CENH3, either pollen donors or acceptors, in interspecific or intergeneric wide crosses for haploid induction and simultaneous genome editing. For example, *N. africana* transgenic CRISPR-Cas9 lines expressing sgRNA targeting tobacco gibberellin 20-oxidase are created through *Agrobacterium*-mediated transformation and used to pollinate emasculated tobacco flowers to induce haploid plants with their genome edited at the gibberellin 20-oxidase locus. Preferably, an easily transformable line with large number of pollen is used as pollen donor for haploid induction and to provide the editing machinery transiently. The recipient plant for haploid production has flowers that are easy to emasculate or is male sterile. More preferably, a color or other visual marker is present in the induction line or is included in the editing locus to easily differentiate haploid embryos or plants from diploids resulted from normal zygote development.

We exemplified this by utilizing an *Arabidopsis* haploid inducer line in the Columbia ecotype, and transforming it with a construct encoding expression of Cas9 and a single guide RNA targeting the GLABROUS1 gene (GL1) which, when knocked out, gives a trichome-less phenotype. We crossed the T0s as females by Landsberg *Erecta* (Ler) ecotype pollen, and recovered gl1 edited haploid progeny.

The haploid inducer materials were obtained from the Comai lab at UC Davis. These materials are typically utilized as paternal haploid inducer lines (causing androgenesis, when crossed as females to wild-type males) but can also act as maternal haploid inducers (causing gynogenesis, when crossed as males to wild-type females). These lines have been altered to become haploid inducers by replacing the native CENH3 gene with a *Zea Mays* CENH3 transgene as reported in (Maheshwari, et al, 2017, Centromere location in *Arabidopsis* is unaltered by extreme divergence in CENH3 protein sequence. Genome Research 27(3)).

In particular, both copies of the native AtCENH3 gene was knocked out and complemented with the stably inserted ZmCENH3 transgene, which did not impact normal plant development, and did not produce haploids upon self-pollination, but did produce about 10% haploids upon outcross. This is a modification to the original concept of CENH3-tailswap described in detail in (Ravi and Chan, 2010, Haploid plants produced by centromere-mediated genome elimination. Nature 464: 615-618) and many subsequent publications.

After we obtained the CENH3* lines from UC Davis, we grew them up, confirmed that they had the ZmCENH3 transgene and were homozygous "null" for the native AtCENH3 gene. We did this by designing a taqman qPCR assay for ZmCENH3 (assay #2298) and by using PCR and gel electrophoresis to test 183 seedlings for the zygosity of the AtCENH3 genotype by running PCR using the Xbal forward and reverse primers (SEQ NO TKX and TKY) and Reddy mix at 60° C. annealing temperature and cutting with the Xbal restriction enzyme overnight at 37° C. The wild-type allele would be cut by this enzyme and produce two bands (189 bp, 25 bp) while the mutant would remain at 215 bp. These tests showed that all of the seed that UC Davis sent were homozygous for the mutant allele Atcenh3-1, and that there were multiple copies of the ZmCENH3 transgene present.

Confident that these acquired seeds were indeed haploid inducers, we kept 100 plants and initiated floral dip transformation with binary vector 24075 (SEQ ID NO: 98) containing a sgRNA cassette targeting the *Arabidopsis* (GL1) gene (AT3G27920) at two target sites. The target sequences are 5'-GGAAAAGTTGTAGACTGAGA-3', and 5'-GCAGTGATGAACAATGACGG-3' (complementary strand). The disruption of the GL1 gene produces visible phenotypes of partially or completely glabrous plants (glabrous plants lack trichomes). The Cas9 gene (cCas9-05) in this vector was driven by the *Arabidopsis thaliana* elongation factor promoter. The vector also contains two selectable marker cassettes conferring Kan resistance and AmCyan florescence driven by the CMP-02 promoter and *Glycine max* UBI-01 promoter respectively. The vector was moved into the *agrobacterium* strain EHA101 and then floral dip transformed into the haploid inducer *Arabidopsis* plants.

The transformation protocol was as follows: In the morning we spread 24075 EHA101 RecA *Agrobacterium* obtained from plates to YPSpec100Kan50 plates. We cultured these in 28° C. dark for 24 hours. We prepared infiltration medium (4 L): ½ XMS salts (8.66 g), 1× Gamborg's B5 vitamins (4 ml), 5% (W/V) sucrose (200 g), 0.044 μM BAP (12.5 mg-12.5 mlDMSO) 40 μL, followed by filter sterilization. We then added 250 μl 40 mg/ml AS (20 mg/L) and 25 μl SIlwet L-77 (50 μl/L) to 500 ml Infiltration media. Using a loop to collect the *Agrobacterium* and put in 50 ml tube with ~10 ml of the filter sterilization, we suspended the *Agrobacterium* until it produced 1 L with an optical density 600 of 0.54. We dipped the inflorescence shoot in to the suspension medium for 20-30 seconds and used the lid to cover the tray. We repeated this for a second time with another suspension of OD600 of 0.552.

About 4 weeks after transformation, approximately 100,000 self-pollinated seeds were harvested and incubated at 4° C. for two days vernalization, and then the seeds were sterilized by soaking in 70% ethanol for 1 minute and then soaking in 50% (V/V) bleach with 0.05% (v/v) Triton X-100 for a further 10 minutes, then washing the seeds in four changes of sterile water. The seeds were then placed on kanamycin (50 μg/ml) plates for germination-screening/ selection in a plant tissue culture room (23° C. day, 24° C. night, 16 hours lighting). 38 positive transformants were identified because they were resistant to the kanamycin selection, and they were grown into seedlings before being transferred onto soil and sampled to test for the presence of the Cas9 T-DNA (assay #3049) as well as the status of the two guide RNA cut sites (assays #3321 and #3322). 10 single copy and 15 2-copy events were identified that had both alleles of GL1 mutated and that had a trichomeless phenotype. These plants were prioritized because they had shown evidence of Cas9 activity (by virtue of the mutated GL1 and the glabrous phenotype), they had the Cas9 transgene and they had the ZmCENH3 transgene by qPCR assay. These plants were induced to flower for a long period of time by keeping them in the following growth conditions: 16 hours light, 23° C. Day 20° C. night temperature, not >60% relative humidity.

At the same time as these haploid inducer plants that were transformed with the Cas9 construct were being identified, we were sowing and growing a population of Landsberg *Erecta* (Ler) seed obtained from the *Arabidopsis* Biological Resource Center at Ohio State University (line #CS20). These are wild type seed and the sequence of the GL1 guide RNA target sites in CS20 match that of the guide RNA in our construct. We allowed both populations to flower and made about 2000 controlled crosses, using the wild-type Ler plants as the male pollen-donor, crossing onto the approximately 25 haploid inducers with the Cas9 construct, which was used as the female. We made up to 100 crosses per female, marking the crossed flowers with a black marker and removing flowers that we did not cross so as to limit the potential of harvesting self-pollinated siliques. In most cases, we emasculated the female flowers prior to pollination by removing the anthers with forceps, again to avoid contamination with self-pollinated seed, but in some cases this was not necessary because the anthers were young or mal-developed.

About 15 days we harvested the siliques which had developed a light brown color. Then we opened the siliques and planted the seeds in the soil. Then put them in the 6° C. (day and light), 8 hours day length, 200 umal/m²s lighting, 60% relative humidity growth chamber for 4 days. Then we transferred them to 16 hours light, 23° C. Day, 20° C. night temperature, not >60% humidity growth chamber for 7-10 days. We observed a high frequency of aborted seed in almost all of the siliques, averaging about 40-50% of the total seeds. This number of aborted embryos is very consistent with the performance of this haploid inducer material in published reports. Without wishing to be constrained by this theory, it has been speculated that the aborted seed is most likely caused by partial or complete genome elimination in the endosperm leading to endosperm imbalance and failure. This is a natural phenomenon in CENH3-type haploid inducer lines during outcross and is likely not connected with the presence of the Cas9 transgene. These aborted embryos do not germinate. Because of the steady and reliable rate of embryo abortion in every outcrossed silique, we ended up using the absence of that phenotype to screen away siliques that were accidental self-pollinations. That way we germinated siliques that had been outcrossed.

In total we recovered approximately 2000 germinated progeny, the majority of which were outcrossed. We identified the edited haploids via a combination of qPCR marker assays and/or phenotypic screening. The markers that we used to detect the edited haploids were as follows.

First, we looked for a "0" score for the ZmCENH3 assay. This indicates that the plant is a haploid because the maternal genome has been lost, and so the ZmCENH3 transgene, which is present in multiple copies of the mother haploid inducer plant, has also been lost. The diploids, in contrast, will be hybrids between the maternal and paternal genome, and will have a "1" or "2" or higher Taqman score for this assay, depending on the copy number of the mother plant. The key is that all diploids will show evidence of this transgene, but paternal haploids, having only the Ler genome, will not and will thus be a "0."

Second, we looked for a "0" score for the Cas9 assay, which indicates that it is non-transgenic. This can also be seen visually by using a fluorescent light and looking for the CFP fluorescent marker.

Third, we looked for a "0" score for one of the GL1 target site assays, which indicates that the plant has been edited. The diploid plants might show a "0," "1" or "2" for those assays, but the haploids either showed a "2" or a "0." The first of the two GL1 guide RNAs apparently had a much higher editing efficiency than the second, because assay 3321 had a high preponderance of "0"s and "F" s in the haploid inducer T0s, but 3322 had mostly "2" s.

Using these assays, we were able to identify unedited haploids (which were "0" for ZmCENH3 and Cas9, but had "2" scores for both GL1 target sites) and also edited haploids (which had a "0" for the ZmCENH3, Cas9 and GL1 (3321) assays). We were also able to identify diploid hybrids that had Cas9 (and often were edited at the GL1 sites) and diploid hybrids that did not have Cas9 (and often had one copy of GL1 edited (from the maternal parent) but not the other, and thus had a score of "1" for the GL1 assay. We were also able to identify several putative edited haploids because they had a score of "0" for the target site assay (3321), the ZmCENH3 (2298) and the Cas9 (3049). See Table 9 below for an example of progeny Taqman data from parent USR01424136 containing three putative edited haploids (plant 254 in well F2, plant 260 in well D3, and plant 261 in plant E3).

We were aware of the fact that it is possible that some of these glabrous plants that lack CFP were false positives, either because the CFP was silent or because of self-pollination of the fully-edited mother plant and production of null segregant, fully edited (and thus glabrous) progeny. The Taqman assays were able to detect and screen out these false positives, because they directly tested for the presence of not only the Cas9 transgene, but also the ZmCENH3 allele, which would certainly be present in any self-pollinated contaminating seed. We found several examples of self-pollinated seed that all came from one mother plant. The pollination notes for that mother indicated that there was highly abundant pollen that may have resulted in some self-pollination. We excluded these progeny from the total analysis.

TABLE 9

Progeny analysis from parent USR01424136.

PLATE 1045 HI parent was single copy Cas9

| | | AtGL1-1 cut site 3321 | | AtGL1-2 cut site 3322 | | ZmCENH3 2298 | | Cas9 3049 | | | |
|---|---|---|---|---|---|---|---|---|---|---|---|
| Well | Plant ID | Raw Copy # | Copy# level | Raw Copy # | Copy# level | Raw Copy # | Copy# level | Raw Copy # | Copy# level | Putative Haploid | Putative Edited |
| E2 | USR01424136 × Ler-253 | 0.06 | 0 | 0.87 | 1 | 4.30 | >2 | 2.93 | >2 | | x |
| F2 | USR01424136 × Ler-254 | 0.00 | 0 | 0.32 | 0 or 1 | 0.00 | 0 | 0.00 | 0 | x | x |
| G2 | USR01424136 × Ler-255 | 1.32 | 1 or 2 | 2.06 | 2 | 3.16 | >2 | 0.00 | 0 | | |
| H2 | USR01424136 × Ler-256 | 0.02 | 0 | 0.99 | 1 | 2.51 | >2 | 2.99 | >2 | | x |
| A3 | USR01424136 × Ler-257 | 0.04 | 0 | 0.87 | 1 | 2.40 | 2 | 2.84 | >2 | | x |
| B3 | USR01424136 × Ler-258 | 0.03 | 0 | 1.64 | 2 | 2.99 | >2 | 3.17 | >2 | | x |
| C3 | USR01424136 × Ler-259 | 0.03 | 0 | 1.21 | 1 | 5.28 | >2 | 5.28 | >2 | | x |
| D3 | USR01424136 × Ler-260 | 0.06 | 0 | 2.01 | 2 | 0.00 | 0 | 0.00 | 0 | x | x |
| E3 | USR01424136 × Ler-261 | 0.00 | 0 | 2.01 | 2 | 0.01 | 0 | 0.00 | 0 | x | x |
| F3 | USR01424136 × Ler-262 | 2.04 | 2 | 2.10 | 2 | 0.00 | 0 | 0.00 | 0 | x | |
| G3 | USR01424136 × Ler-263 | 1.36 | 1 or 2 | 1.25 | 1 | 0.00 | 0 | 0.00 | 0 | x | |
| H3 | USR01424136 × Ler-264 | 1.75 | 2 | 1.71 | 2 | 0.00 | 0 | 0.00 | 0 | x | |
| A4 | USR01424136 × Ler-265 | 0.00 | 0 | 1.67 | 2 | 3.06 | >2 | 3.16 | >2 | | x |
| B4 | USR01424136 × Ler-266 | 1.66 | 2 | 2.32 | 2 | 0.00 | 0 | 0.00 | 0 | x | |
| C4 | USR01424136 × Ler-267 | 2.09 | 2 | 1.94 | 2 | 3.99 | >2 | 0.00 | 0 | | |
| D4 | USR01424136 × Ler-268 | 1.47 | 1 or 2 | 2.08 | 2 | 6.34 | >2 | 1.51 | 1 or 2 | | |
| E4 | USR01424136 × Ler-269 | 1.95 | 2 | 1.76 | 2 | 3.19 | >2 | 0.00 | 0 | | |
| F4 | USR01424136 × Ler-270 | 1.92 | 2 | 2.17 | 2 | 4.28 | >2 | 0.02 | 0 | | |
| G4 | USR01424136 × Ler-271 | 2.02 | 2 | 1.85 | 2 | 4.31 | >2 | 0.00 | 0 | | |
| H4 | USR01424136 × Ler-272 | 0.00 | 0 | 1.71 | 2 | 1.65 | 2 | 1.12 | 1 | | x |

Simply by germinating seeds and sampling for qPCR Taqman analysis, we were able to identify 8 putative edited haploids. Edited haploids were also identified by phenotypic visual screening, and then confirmed later by Taqman assay. We screened for the edited haploids by looking for trichome-less, or glabrous, plants, which indicated that they did not have any wild-type alleles for the GL1 gene, and by looking for a lack of cyan fluorescent protein ("CFP") expression in the embryo or seedling root. This indicated that they lacked the Cas9 T-DNA. We observed several of these plants, and submitted them for Taqman assays. For three such plants that we identified phenotypically, we were able to confirm that they were truly edited haploids by the Taqman assays.

Figure 24:
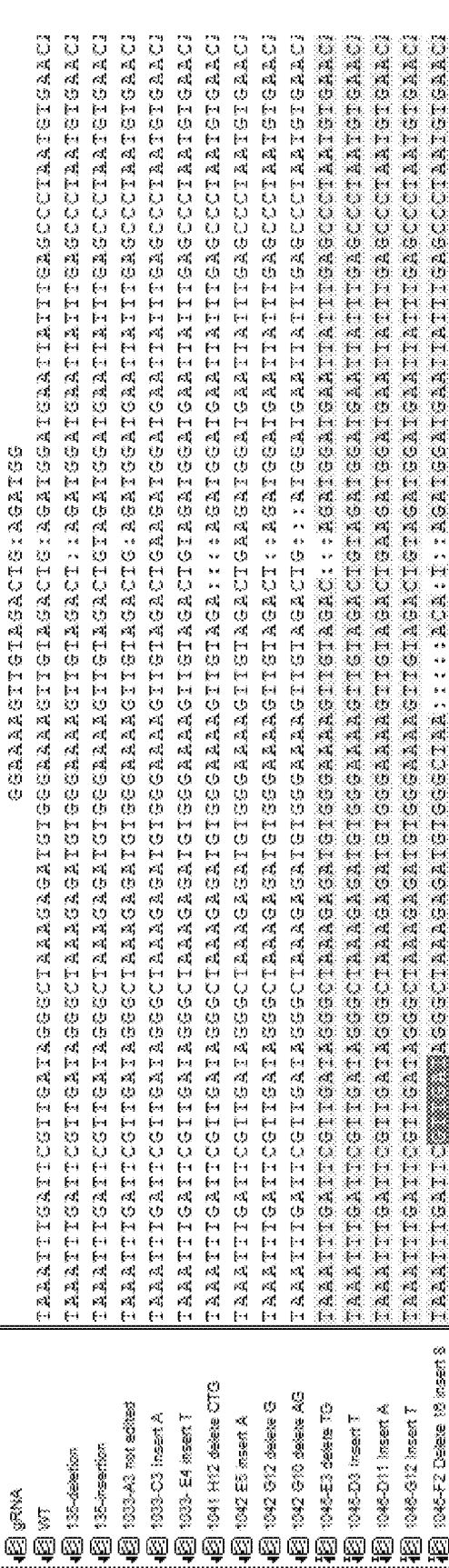
FIG. 24 shows the GL1 target site sequence mutations in the parent #USR01424135 and all of the sequenced edited haploids from outcrosses by Landsberg erecta pollen. It is clear that the precise edit made is different in the different haploids. From top to bottom, the sequences shown are represented by SEQ ID NOs: 102-117, respectively.

All of the putative edited haploids identified by Taqman assay were sequenced. We used PCR to amplify the edited alleles, and then subcloned and sequenced at least 8 colonies for each putative edited allele. See Table 10 for the sequence changes we found in the edited haploids at the first guide RNA (assay #3321) target site, as well as the Taqman data from the T0 parents. In total, we found 19 putative edited haploids, and we confirmed that the 3321 target sites had mutations in 11 of the 12 edited haploids that we attempted to sequence. Whether the other 7 would also have mutations will be confirmed upon sequencing. See the sequence alignment for these edits in FIG. 24.

TABLE 10

Taqman and sequence data from 19 edited haploids.

| Plate | Well | Plant ID | AtGL1-1 cut site 3321 | | AtGL1-2 cut site 3322 | | ZmCENH3 2298 | | Cas9 3049 | | Target site mutation | PA confirm? |
|---|---|---|---|---|---|---|---|---|---|---|---|---|
| | | | Raw Copy # | Copy # level | Raw Copy # | Copy # level | Raw Copy # | Copy # level | Raw Copy # | Copy # level | | |
| 1033 | A3 | USR01424135 × Ler-425 | 0.00 | 0 | 1.67 | 2 | 0.04 | 0 | 0.00 | 0 | wild type | Not done |
| 1033 | C3 | USR01424135 × Ler-427 | 0.21 | 0 | 2.43 | >2 | 0.01 | 0 | 0.00 | 0 | insert A | Yes |
| 1033 | E4 | USR01424135 × Ler-437 | 0.08 | 0 | 2.04 | 2 | 0.00 | 0 | 0.00 | 0 | insert T | Yes |
| 1042 | E5 | USR01424136 × Ler-25 | 0.16 | 0 | 2.95 | >2 | 0.00 | 0 | 0.00 | 0 | insert A | Not done |
| 1042 | G10 | USR01424136 × Ler-67 | 0.00 | 0 | 2.19 | 2 | 0.00 | 0 | 0.00 | 0 | delete AG | Not done |
| 1042 | G12 | USR01424136 × Ler-83 | 0.00 | 0 | 1.86 | 2 | 0.00 | 0 | 0.00 | 0 | delete G | Not done |
| 1043 | B11 | USR01424136 × Ler-154 | 0.16 | 0 | 1.59 | 1 or 2 | 0.01 | 0 | 0.00 | 0 | Not done | Not done |
| 1045 | F2 | USR01424136 × Ler-254 | 0.00 | 0 | 0.32 | 0 or 1 | 0.00 | 0 | 0.00 | 0 | delete 8nt* | Not done |
| 1045 | D3 | USR01424136 × Ler-260 | 0.06 | 0 | 2.01 | 2 | 0.00 | 0 | 0.00 | 0 | insert T | Not done |
| 1045 | E3 | USR01424136 × Ler-261 | 0.00 | 0 | 2.01 | 2 | 0.01 | 0 | 0.00 | 0 | delete TG | Not done |
| 1046 | D11 | USR01431609 × Ler-111 | 0.09 | 0 | 1.59 | 1 or 2 | 0.02 | 0 | 0.01 | 0 | insert A | Not done |
| 1046 | G12 | USR01431609 × Ler-122 | 0.02 | 0 | 1.62 | 2 | 0.00 | 0 | 0.00 | 0 | insert T | Not done |
| 1046 | H12 | USR01431609 × Ler-123 | 0.00 | 0 | 0.00 | 0 | 0.00 | 0 | 0.00 | 0 | delete CTG | Yes |
| 0583 | D12 | USR01431603 × Ler-80 | 0.00 | 0 | 1.50 | 1 or 2 | 0.00 | 0 | 0.00 | 0 | Not done | Not done |
| 0584 | A9 | USR01431603 × Ler-137 | 0.00 | 0 | 1.87 | 2 | 0.00 | 0 | 0.00 | 0 | Not done | Not done |
| 0584 | C11 | USR01431603 × Ler-155 | 0.05 | 0 | 2.06 | 2 | 0.00 | 0 | 0.17 | 0 | Not done | Not done |
| 0584 | G11 | USR01431603 × Ler-159 | 0.09 | 0 | 2.15 | 2 | 0.00 | 0 | 0.00 | 0 | Not done | Not done |
| 0584 | C12 | USR01431603 × Ler-163 | 0.00 | 0 | 1.35 | 1 or 2 | 0.00 | 0 | 0.11 | 0 | Not done | Not done |
| 0584 | F12 | USR01431603 × Ler-166 | 0.00 | 0 | 1.65 | 2 | 0.00 | 0 | 0.00 | 0 | Not done | Not done |
| 0585 | H7 | USR01431603 × Ler-212 | 0.06 | 0 | 2.05 | 2 | 0.00 | 0 | 0.01 | 0 | Not done | Not done |
| Female | | USR01424135 | 0.03 | 0 | 1.42 | 1 or 2 | 4.46 | >2 | 2.98 | >2 | ΔG, +T chimera | Diploid |
| Parent | | USR01424136 | 0.03 | 0 | 1.13 | 1 | 3.59 | >2 | 2.76 | >2 | Not done | Diploid |
| T0 | | USR01431603 | 0.14 | 0 | 1.25 | 1 | 2.48 | >2 | 3.42 | >2 | Not done | Diploid |
| Plants | | USR01431609 | 0.18 | 0 | 1.1 | 1 | 4.75 | >2 | 5.57 | >2 | Not done | Diploid |

*delete 16 nt insert CTAAACAT

We further ran leaf samples from three edited haploid plants through ploidy analysis, along with three diploid controls (tissue sampled from the maternal parent plants), which showed that they were true haploids (FIGS. 18-23). This served to reconfirm their status as edited haploids.

In three parental lines where we were confident that there was no self-pollination contamination, we did not do any phenotypic pre-screening, but instead sampled all germinated progeny for Taqman analysis (Table 11). The three female parents for these progeny were USR01431603, USR01431609, and USR01431604. We found a haploid induction rate of about 9.7% calculated by dividing the number of progeny that lack the ZmCENH3 and Cas9 transgenes (59) by the total number of progeny sampled (605). Of the 59 haploids we found that 10 were edited. That means 16.9% of haploids, on average, were edited by the maternal Cas9, prior to elimination of the maternal genome. Without wishing to be constrained by this final number, this means that, using this system, as a percentage of total progeny, 9.7%*16.9%=1.64% of all germinated progeny were edited haploids.

The rate of CENH3* type haploid editing or other paternal haploid editing (using a maternal haploid inducer line) might be increased through the use of a promoter that drives the expression of Cas9 and/or the guide RNA to a higher level in the egg cell before fertilization and/or in the zygote cell during or after fertilization. An example of such a promoter would the promoter for EA1 (EGG APPARATUS1) (GRMZM2G456746), although there are many other examples. One could also express the Cas9 in the context of an egg apparatus-specific enhancer (EASE), which is a 77-bp sequence that stimulates expression of adjoining genes in the egg cell or the very early zygote (see, e.g., Yang, et al. *An Egg Apparatus-Specific Enhancer of Arabidopsis, Identified by Enhancer Detection*, PLANT PHYSIOLOGY November 2005, 139 (3) 1421-1432; DOI: https://doi.org/10.1104/pp.105.068262).

VIII. Simultaneous Haploid Induction and Editing by Directly Modifying a Target Base in Genomic DNA Sequence.

Targeted mutagenesis of DNA sequence can also be achieved through direct conversion of one DNA base to

TABLE 11

Haploid induction rate and editing rate data from three sets of progeny, each derived from a different SEDHI inducer female parent crossed by Landsberg erecta pollen.

| ID | Parent plant Cas9-05 | Parent plant CNpt2-10 | Total samples | Haploid number | Haploid rate | Edited Haploid | Edited Haploid rate |
|---|---|---|---|---|---|---|---|
| USR01431603 × Landsberg erecta | >2 | >2 | 230 | 36 | 15.65 | 7 | 19.44 |
| USR01431609 × Landsberg erecta | >2 | >2 | 123 | 14 | 11.38 | 3 | 21.43 |
| USR01431604 × Landsberg erecta | 2 | 1 | 252 | 9 | 3.57 | 0 | 0.00 | another without requiring double stranded breaks (DSBs). For example, cytidine deaminase APOBEC1, adenine deaminase, and other enhancing components like Uracil DNA glycosylase (UDG) can be fused to Cas9 (A840H) nickase or nuclease-inactivated dead Cas9 (dCa9) to direct editing of DNA sequence without introducing double strand DNA breaks (Komor et al. 2016. Programmable editing of a target base in genomic DNA without double-stranded DNA cleavage. Nature doi:10.1038/nature17946; Gaudelli et al. 2017. Programmable base editing of A:T to G:C in genomic DNA without DNA cleavage. Nature doi:10.1038/nature24644; Komor et al. 2017. Improved base excision repair inhibition and bacteriophage Mu Gam protein yields C:G-to-T:A base editors with higher efficiency and product purity. *Science Advances*, Vol. 3, no. 8, eaao4774, DOI: 10.1126/sciadv.aao4774). This kind of base editor machinery can also be delivered through haploid induction line to induce base editing in target sequences directly in other varieties. For example, a guide RNA sequence, xZmVLHP-03 (5'-AGGCGTCGAGCAGCGAGGTG-3', SEQ ID NO: 28) is designed to target the cytidine deaminase base editor system to convert ZmVLHP gene exon 2 genomic sequence 5'-AGGCGTCGAGCAGCGAGGTG-3' (SEQ ID NO: 28) into 5'-AGGCGTTGAGCAGCGAGGTG-3' (SEQ ID NO: 29), thus changing the arginine codon CGA into a stop codon (TGA) in the coding sequence and causing premature termination of the protein sequence and functional gene knock-out. The C to T mutation is underlined. Similarly, chimeric nCas9- or dCas9-adenine deaminase base editing system can be used to mutate the coding region, splicing junction or promoter sequence of ZmVLHP or other genes to generate variants that have altered gene activity. Both cytidine and adenine deaminase are particularly useful for altering transcript splicing site since canonical splicing junction has 5'- . . . AG/GT . . . 3' sequence (or 5'- . . . AC/CT . . . 3' in the opposite strand).

IX. Simultaneous Haploid Induction and Editing by Allele Replacement with DNA Template Not only can in vivo haploid induction system be used to introduce protein, RNA or DNA for cleavage or conversion of target sequence, it can also be used to deliver DNA template for homology-dependent repair for precise sequence replacement in the target region in the form of transgenic DNA. The template DNA can be inserted into the inducer line genome carrying genome editing machinery such as CRISPR-Cas9 system, either in the same transgenic locus or different locus. When both Cas9-sgRNA and template DNA are present in the induced haploid embryos, cleavage of the target sequence will result in repair of the chromosomal break with the homologous transgenic DNA sequence as template. For example, for creating E149L mutation in ZmPYL-D gene (GRMZM2G048733_P02) (see WO16033230, incorporated herein by reference), DNA fragment containing donor sequence (5'-CCTTGGTGTTGCCGTCGG GGACGTCGACGACGAATGACAG-GATGACGAGCGTCC CTGGCCGGCCGTC-GATGACCT-3', SEQ ID NO: 30) is used as repair donor. It should be noted that additional homology sequences can be added to flank this core repair donor sequence. One or more copies of this repair donor sequence are inserted into Cas9-sgRNA expression vector 23136 (SEQ ID NO: 31) which expresses guide RNA 5'-GTCGGGGACGTCGACGACGA-3' (SEQ ID NO: 32) to form allele modification vector pBSC23136-AMD. It should be noted that the potential PAM site has been removed from the donor DNA sequences so that the integrated donor sequence will not be cleaved by the Cas9-sgRNA complex expressed from pBSC23136-AMD. pBSC23136-AMD is transformed into haploid inducer line NP2222-HI to generate transgenic editing line. Transgenic editing-haploid induction lines are selfed to produce progeny lines homozygous editing loci. These homozygous lines are used to pollinate target elite maize inbred lines to induce haploid formation and also introduce modified alleles by expressed Cas9-sgRNA using donor DNA present transiently before pollen donor chromosomes are eliminated.

X. Inducing Haploids and Simultaneous Gene Editing in Rice

A HI-rice line is obtained. For example, the rice MATL ortholog, Os03g27610 (SEQ ID NO: 33, is mutated to create a new rice HI line. This line is transformed with a vector comprising a site-directed mutagenesis system for editing the rice genome, for example the CRISPR/Cas9 system.

The rice HI line is crossed with a different rice line, preferably an elite line, to produce at least one progeny haploid embryo. During the cross to produce at least one progeny haploid embryo, the HI parent rice plant also causes the genome editing machinery, e.g., Cas9 plus a guide RNA, to be delivered to the embryo. At that point, the editing machinery operates to edit the genome of the haploid embryo, and thus an edited, haploid progeny plant is obtained.

XI. Taqman Assays and Conditions.

Several assays are mentioned by number or by target name. Provided below is a table of assays mentioned above and the sequences of the relevant primers and probes. Conditions for PCR are standard for all assays and are as follows: Denature at 98° C. for 2 minutes; followed by 35 cycles of (i) denature at 98° C. for 30 seconds, (ii) anneal at 60° C. for 30 seconds, (iii) extension at 72° C. for 1 minute; followed by final extension at 72° C. for 10 minutes with a hold at 4° C. until ready. Assays are carried out at these conditions unless otherwise noted below.

TABLE 11

Assay primers and probes.

| Target Assay No. | Cas9-in corn 2540 | Sequence | SEQ ID NO: |
|---|---|---|---|
| Forward Primer | FE09340 | TTGTGCTGCTCCACGAACA | 39 |
| Reverse Primer | FE09341 | GCCAGCCACTACGAGAAGCT | 40 |
| Probe | FE09342 | CTGCTTCTGCTCGTTGTCCTCCGG | 41 |

TABLE 11-continued

Assay primers and probes.

| Target | mat1 | | |
|---|---|---|---|
| Assay No. | 2827 | Sequence | SEQ ID NO: |
| Forward Primer | FE10299 | GCGGATGCTGGCACAGC | 42 |
| Reverse Primer | FE10300 | GGCATTGCTTCCTTCTCCG | 43 |
| Probe | FE10301 | CAGGGAGCGAGGTAC | 44 |
| Target | PMI | | |
| Assay No. | 1750 | Sequence | SEQ ID NO: |
| Forward Primer | FE07390 | CTGGTGGCCAACGTGAAGTT | 45 |
| Reverse Primer | FE07391 | GCTTCACGGGCTGGGTC | 46 |
| Probe | FE07392 | AGGCCAAGCCCGCCAACCAG | 47 |
| Target | MATL-WT | | |
| Assay No. | 2826 | Sequence | SEQ ID NO: |
| Forward Primer | FE10297 | GCGGATGCTGGCACAGA | 48 |
| Reverse Primer | FE10298 | GCATTGCTTCCTTCGCCA | 49 |
| Probe | FE10299 | CAGGGAGGTACGAACC | 50 |
| Target | TAV_4A | | |
| Assay No. | 3252 | Sequence | SEQ ID NO: |
| Forward Primer | FE11306 | GCGGCGAAGAAGCGAA | 51 |
| Reverse Primer | FE11307 | GCGGCGTCTCCAGCTTC | 52 |
| Probe | FE11308 | CCAGGAACTGCG | 53 |
| Target | TAV_4B | | |
| Assay No. | 3253 | Sequence | SEQ ID NO: |
| Forward Primer | FE11309 | AAGAAACGCCGGCTGAGT | 54 |
| Reverse Primer | FE11310 | ACCTTGCGGGGCGTT | 55 |
| Probe | FE11308 | CCAGGAACTGCG | 56 |
| Target | TAV_4D | | |
| Assay No. | 3254 | Sequence | SEQ ID NO: |
| Forward Primer | FE11309 | AAGAAACGCCGGCTGAGT | 57 |
| Reverse Primer | FE11311 | CCTTGCGCGGCGTC | 58 |
| Probe | FE11308 | CCAGGAACTGCG | 59 |
| Target | GW2-01 | | |
| Assay No. | 3065 | Sequence | SEQ ID NO: |
| Forward Primer | FE10799 | TGATCCTCGAGGCCAAGCT | 60 |
| Reverse Primer | FE10800 | AGGTCGAGGTCCCCTCCA | 61 |
| Probe | FE10801 | CCTGCTACCCGGGC | 62 |
| Target | GW2-02 | | |
| Assay No. | 3095 | Sequence | SEQ ID NO: |
| Forward Primer | FE10991 | CGCGCCCTGCTACCC | 63 |
| Reverse Primer | FE10992 | GCGCGTGCTTACCAGGA | 64 |
| Probe | FE10993 | TCGAGGAGTGCCC | 65 |
| Target | TaVHLP2-2A | | |
| Assay No. | 3332 | Sequence | SEQ ID NO: |
| Forward Primer | FE11312 | CACCGATGAGCAGGCG | 66 |
| Reverse Primer | FE11313 | AGATACACCTTCCGGCCG | 67 |
| Probe | FE11314 | TTCCTCCCGGAAGC | 68 |
| Target | TaVHLP2-2D | | |
| Assay No. | 3333 | Sequence | SEQ ID NO: |
| Forward Primer | FE11312 | CACCGATGAGCAGGCG | 69 |
| Reverse Primer | FE11313 | AGATACACCTTCCGGCCAGT | 70 |
| Probe | FE11314 | CTCCTCCCGGAAGC | 71 |
| Target | | | |
| Assay No. | 3049 | Sequence | SEQ ID NO: |
| Forward Primer | FE10730 | CAAGTTTCTGGACAAGGAGATTCTC | 72 |
| Reverse Primer | FE10731 | AAGAATTCCCTTCTTAATAGCTGGAGA | 73 |
| Probe | FE10732 | CACGAGCACATTGCTAACCTTGCTGG | 74 |

TABLE 11-continued

Assay primers and probes.

| Target | TaVHLP2-2B | | |
|---|---|---|---|
| Assay No. | 3255 | Sequence | SEQ ID NO: |
| Forward Primer | FE11315 | TCACCGATGAGCAGGCA | 75 |
| Reverse Primer | FE11316 | ATACACCTTCCGGCCAGC | 76 |
| Probe | FE11317 | TTCCTCCCGGAAGC | 77 |

| Target | | | |
|---|---|---|---|
| Assay No. | 3321 | Sequence | SEQ ID NO: |
| Forward Primer | FE11540 | GATAGGGCTAAAGAGATGTGGGAA | 78 |
| Reverse Primer | FE11541 | CTTTGTTCACATTAGGGCTCAAATAA | 79 |
| Probe | FE11542 | TAGACTGAGATGGATG | 80 |

| Target | | | |
|---|---|---|---|
| Assay No. | 3322 | Sequence | SEQ ID NO: |
| Forward Primer | FE11543 | AAAACCACCGGAGAAGACGA | 81 |
| Reverse Primer | FE11544 | AGGTGTGGCGGCAGTGA | 82 |
| Probe | FE11545 | CACCGTCATTGTTC | 83 |

| Target | Cas9-in | | |
|---|---|---|---|
| Assay No. | *Arabidopsis* | Sequence | SEQ ID NO: |
| Forward Primer | FE10730 | CAAGTTTCTGGACAAGGAGATTCTC | 84 |
| Reverse Primer | FE10731 | AAGAATTCCCTTCTTAATAGCTGGAGA | 85 |
| Probe | FE10732 | CACGAGCACATTGCTAACCTTGCTGG | 86 |

| Target | ZmCENH3 | | |
|---|---|---|---|
| Assay No. | 2298 | Sequence | SEQ ID NO: |
| Forward Primer | FE08737 | GCGACGCCGGAAAGG | 87 |
| Reverse Primer | FE08738 | TGGCGTGGTTTCGTCTTCTTA | 88 |
| Probe | FE08739 | AAGAGCGGCGTCTGGAGGTGACTCA | 89 |

| Target | GL1 3321 target | | |
|---|---|---|---|
| Assay No. | site (PCR) | Sequence | SEQ ID NO: |
| Forward Primer | 3321F | AACCGCATCGTCAGAAAAC | 90 |
| Reverse Primer | 3321R | TCAACTTAACCGGCCAAATC | 91 |
| Annealing Temp. | 60° C. | | |

| Target | VLHP2-2A target | | |
|---|---|---|---|
| Assay No. | site (PCR) | Sequence | SEQ ID NO: |
| Forward Primer | FE4117 | CATCCCTTCTCTTCCCTCCTG | 92 |
| Reverse Primer | FE4118 | GCCAGTGTGAGTGTGTATGAGCA | 93 |
| Annealing Temp. | 61° C. | | |

| Target | VLHP2-2B target | | |
|---|---|---|---|
| Assay No. | site (PCR) | Sequence | SEQ ID NO: |
| Forward Primer | FE4120 | CATCGTTTTCTCCCCTCCTCA | 94 |
| Reverse Primer | FE4121 | ACTGATATGCACGGCGCCA | 95 |
| Annealing Temp. | 62° C. | | |

| Target | VLHP2-2D target | | |
|---|---|---|---|
| Assay No. | site (PCR) | Sequence | SEQ ID NO: |
| Forward Primer | FE4121 | TGCAGTAGCTTCATTTTCACCG | 96 |
| Reverse Primer | FE4122 | AGGAATTGATATGTACGCCCGT | 97 |
| Annealing Temp. | 61° C. | | |

What is claimed is:

1. A method of editing rice plant genomic DNA, comprising:

a) obtaining a first rice plant, wherein the first rice plant comprises a loss-of function mutation in a wildtype patatin-like phospholipase A2α gene encoding a polypeptide having at least 95% identity to SEQ ID NO:118; and the loss-of function mutation is a frameshift mutation or insertion or deletion mutation that prevents expression of an active protein product from the wildtype patatin-like phospholipase A2α gene; and wherein said first rice plant expresses a DNA modification enzyme and optionally at least one guide nucleic acid that targets the genome of a second rice plant at a site to be edited;

b) pollinating the second rice plant with pollen from the first rice plant; and c) selecting at least one haploid progeny produced by the pollination of step (b) wherein the haploid progeny comprises the genome of the second rice plant but not the first rice plant, and the genome of the haploid progeny has been modified by the DNA modification enzyme and optional at least one guide nucleic acid delivered by the first rice plant.

2. The method of claim 1, wherein the DNA modification enzyme is a site-directed nuclease selected from the group consisting of meganucleases (MNs), zinc-finger nucleases (ZFNs), transcription-activator like effector nucleases (TALENs), Cas9 nuclease, Cpf1 nuclease, dCas9-FokI, dCpf1-FokI, chimeric Cas9-cytidine deaminase, chimeric Cas9-adenine deaminase, chimeric FEN1-FokI, Mega-TALs, nickase Cas9 (nCas9), chimeric dCas9 non-FokI nuclease, and dCpf1 non-FokI nuclease.

3. The method of claim 1, wherein the at least one guide nucleic acid is a guide RNA.

4. The method of claim 1, wherein the edited haploid progeny is treated with a chromosome doubling agent, thereby creating an edited doubled haploid progeny.

5. The method of claim 4, wherein the chromosome doubling agent is colchicine, pronamide, dithipyr, or trifluralin.

6. The method of claim 1, wherein the first rice plant expresses a marker gene.

7. The method of claim 6, wherein the marker gene is selected from the group consisting of GUS, PMI, PAT, GFP, RFP, CFP, B1, C1, and R-nj; or is an anthocyanin pigment.

8. The method of claim 1, wherein the wildtype patatin-like phospholipase A2α gene comprises SEQ ID NO:33.

9. The method of claim 1, wherein the wildtype patatin-like phospholipase A2α gene encodes SEQ ID NO:118.

10. The method of claim 1, wherein the wildtype patatin-like phospholipase A2α gene encodes SEQ ID NO:119.

* * * * *